United States Patent
Rancati et al.

(10) Patent No.: US 9,453,013 B2
(45) Date of Patent: *Sep. 27, 2016

(54) COMPOUNDS HAVING MUSCARINIC RECEPTOR ANTAGONIST AND BETA2 ADRENERGIC RECEPTOR AGONIST ACTIVITY

(71) Applicant: CHIESI FARMACEUTICI S.p.A., Parma (IT)

(72) Inventors: Fabio Rancati, Parma (IT); Ian Linney, Saffron Walden (GB); Chris Knight, Saffron Walden (GB); Wolfgang Schmidt, Saffron Walden (GB)

(73) Assignee: CHIESI FARMACEUTICI S.p.A., Parma (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/609,524

(22) Filed: Jan. 30, 2015

(65) Prior Publication Data

US 2015/0139916 A1 May 21, 2015

Related U.S. Application Data

(63) Continuation of application No. 14/098,662, filed on Dec. 6, 2013, now Pat. No. 8,980,913.

(30) Foreign Application Priority Data

Dec. 6, 2012 (EP) .................... 12195898

(51) Int. Cl.
| | |
|---|---|
| *C07D 453/02* | (2006.01) |
| *A61K 31/496* | (2006.01) |
| *A61K 31/4709* | (2006.01) |
| *A61K 45/06* | (2006.01) |
| *A61M 15/00* | (2006.01) |
| *A61M 16/14* | (2006.01) |
| *A61K 9/00* | (2006.01) |

(52) U.S. Cl.
CPC ........... *C07D 453/02* (2013.01); *A61K 9/0073* (2013.01); *A61K 31/4709* (2013.01); *A61K 31/496* (2013.01); *A61K 45/06* (2013.01); *A61M 15/009* (2013.01); *A61M 15/0045* (2013.01); *A61M 16/14* (2013.01)

(58) Field of Classification Search
CPC ............ C07D 453/02; A61K 31/496; A61K 31/4709; A61K 45/06; A61K 9/0073; A61M 16/14
See application file for complete search history.

(56) References Cited

U.S. PATENT DOCUMENTS

| | | | | |
|---|---|---|---|---|
| 8,877,774 B2* | 11/2014 | Rancati | ................ | A61K 9/0075 514/305 |
| 8,980,913 B2* | 3/2015 | Rancati | ............. | A61K 31/4709 514/305 |
| 8,987,299 B2* | 3/2015 | Rancati | ................ | A61K 31/439 514/305 |
| 2009/0181935 A1 | 7/2009 | Villetti et al. | | |
| 2013/0034504 A1 | 2/2013 | Rancati et al. | | |
| 2013/0045169 A1 | 2/2013 | Rancati et al. | | |
| 2014/0161736 A1 | 6/2014 | Rancati et al. | | |

FOREIGN PATENT DOCUMENTS

| | | |
|---|---|---|
| WO | 2005/115467 | 12/2005 |
| WO | 2012/168359 | 12/2012 |

OTHER PUBLICATIONS

U.S. Appl. No. 14/603,926, filed Jan. 23, 2015, Rancati, et al.
European Search Report in Application No. 12195898.7 issued Mar. 1, 2013.
Hughes et al., Bioorganic & Medicinal Chemistry Letters, vol. 21, No. 5 (2011) pp. 1354-1358.

* cited by examiner

*Primary Examiner* — D M Seaman

(74) *Attorney, Agent, or Firm* — Oblon, McClelland, Maier & Neustadt, L.L.P.

(57) ABSTRACT

Compounds of formula (I) defined herein act both as muscarinic receptor antagonists and beta2 adrenergic receptor agonists and are useful for the prevention and/or treatment of broncho-obstructive or inflammatory diseases.

16 Claims, No Drawings

COMPOUNDS HAVING MUSCARINIC RECEPTOR ANTAGONIST AND BETA2 ADRENERGIC RECEPTOR AGONIST ACTIVITY

CROSS REFERENCES TO RELATED APPLICATIONS

This application is a continuation of U.S. patent application Ser. No. 14/098,662, filed on Dec. 6, 2013, now U.S. Pat. No. 8,980,913, and claims priority to European Patent Application No. 12195898.7 filed on Dec. 6, 2012, which is incorporated herein by reference in its entirety.

BACKGROUND OF THE INVENTION

1. Field of the Invention

The present invention relates to compounds which act both as muscarinic receptor antagonists and beta2 adrenergic receptor agonists. The present invention also relates to processes for preparing such a compound, compositions which contain such a compound, therapeutic uses of such a compound, and combinations of such a compound with other pharmaceutical active ingredients.

2. Discussion of the Background

Pulmonary disorders, such as asthma and chronic obstructive pulmonary disease (COPD), are commonly treated with bronchodilators. A known class of bronchodilators consists of beta-2 adrenergic receptor agonists, such as salbutamol, fenoterol, formoterol and salmeterol. These compounds are generally administered by inhalation.

Another known class of bronchodilators consists of muscarinic receptor antagonists (anticholinergic compounds), such as ipratropium and tiotropium. These compounds are also typically administered by inhalation.

Inhaled formulations of both beta-2 agonists and muscarinic receptor antagonists are valuable agents in the treatment of asthma and COPD, with both classes of agents providing symptomatic relief due to their ability to relax constricted airways. Observations that the bronchodilator effects of the two classes of agents were additive, prompted studies with combinations of the two agents. In 1975, it was shown that beneficial effects could be achieved by combining two ingredients such as fenoterol and ipratropium bromide in a single aerosol. This prompted the development of fixed dose combinations of ipratropium bromide firstly with fenoterol (Berodual, introduced in 1980), and then with salbutamol (Combivent, introduced in 1994).

More recently the availability of both long-acting muscarinic antagonists and long-acting beta-2 agonists prompted to the development of combinations of these agents. For example, WO 00/69468, which is incorporated herein by reference in its entirety, discloses medicament compositions containing a muscarinic receptor antagonist, such as tiotropium bromide, and beta-2 adrenergic receptor agonists, such as formoterol fumarate or salmeterol, and WO 2005/115467, which is incorporated herein by reference in its entirety, discloses a combination which comprises a beta-2 agonist and an antagonist of M3 muscarinic receptors which is a salt of 3(R)-(2-hydroxy-2,2-dithien-2-ylacetoxy)-1-(3-phenoxypropyl)-1-azoniabicyclo[2.2.2]octane.

An alternative approach to the development of fixed dose combinations is the identification of molecules that combine both activities of muscarinic antagonism and beta-2 agonism. In fact compounds possessing both beta-2 adrenergic receptor agonist and muscarinic receptor antagonist activity are highly desirable since such bifunctional compounds would provide bronchodilation through two independent mechanisms of action while having a single molecule pharmacokinetics.

Such kind of compounds was described in some patent applications, such as WO 2004/074246, WO 2004/074812, WO 2005/051946, WO 2006/023457, WO 2006/023460, WO 2010/123766, WO 2011/048409, and co-pending patent application WO 2012/168359, all of which are incorporated herein by reference in their entireties.

SUMMARY OF THE INVENTION

Accordingly, it is one object of the present invention to provide novel compounds which act both as muscarinic receptor antagonists and beta2 adrenergic receptor agonists.

It is another object of the present invention to provide novel processes for preparing such a compound.

It is another object of the present invention to provide novel compositions which contain such a compound.

It is another object of the present invention to provide novel methods for treating and/or preventing certain diseases and conditions by administering such a compound.

It is another object of the present invention to provide novel combinations of such a compound with other pharmaceutical active ingredients among which are, for instance, those currently used in the treatment of respiratory disorders, among which beta2-agonists, antimuscarinic agents, mitogen-activated protein kinases (P38 MAP kinase) inhibitors, nuclear factor kappa-B kinase subunit beta (IKK2) inhibitors, human neutrophil elastase (HNE) inhibitors, phosphodiesterase 4 (PDE4) inhibitors, leukotriene modulators, non-steroidal anti-inflammatory agents (NSAIDs), antitussive agents, mucus regulators, mucolytics, expectorant/mucokinetic modulators, peptide mucolytics, antibiotics, inhibitors of JAK, SYK inhibitors, inhibitors of PI3Kdelta or PI3Kgamma, corticosteroids, and M3-antagonists/PDE4-inhibitors (MAPI).

These and other objects, which will become apparent during the following detailed description, have been achieved by the inventors' discovery of compounds of general formula (I), described below.

It has now been found that some particular carbamate derivatives, besides possessing both beta-2 adrenergic receptor agonist and muscarinic receptor antagonist activity, possess elevated affinity for the M3 muscarinic receptors and long lasting bronchodilating activity.

DETAILED DESCRIPTION OF THE PREFERRED EMBODIMENTS

In particular, the present invention provides compounds of general formula (I)

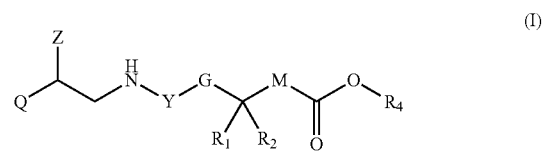

(I)

wherein
Q is a group of formula Q1, Q2, or Q3

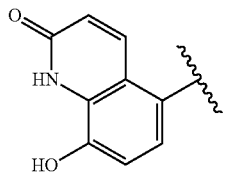
Q1

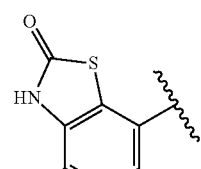
Q2

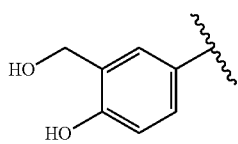
Q3

Z is H or OH;
Y is Y' or Y1 which are divalent groups of formula

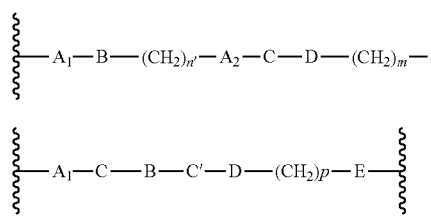
Y'
or
Y1 wherein
A1 and A2 are independently absent or are selected from the group consisting of ($C_1$-$C_6$)alkylene, ($C_3$-$C_8$)cycloalkylene, and ($C_3$-$C_8$)heterocycloalkylene optionally substituted by one or more substituents selected from the group consisting of ($C_1$-$C_6$)alkyl, aryl($C_1$-$C_6$)alkyl and heteroaryl($C_1$-$C_6$)alkyl;
B is absent or is selected from the group consisting of ($C_3$-$C_8$)cycloalkylene, ($C_3$-$C_8$)heterocycloalkylene, arylene, and heteroarylene, optionally substituted by one or more groups selected from halogen, nitrile, linear or branched ($C_1$-$C_6$)alkyl, linear or branched ($C_1$-$C_6$)haloalkyl, ($C_1$-$C_6$)alkoxy, aryl, aryl($C_1$-$C_6$)alkyl, —NR$_7$(R$_8$), and heteroaryl;
C and C' are absent or are independently selected from the group consisting of —O—, —CO—, —OC(O)— and —C(OO)— or is one of the following groups C1-C14

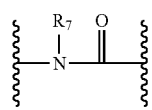
C1

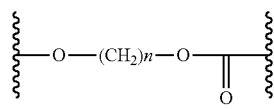
C2

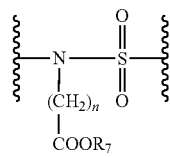
C3

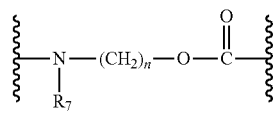
C4

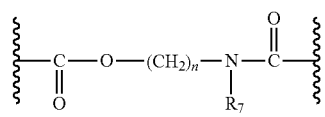
C5

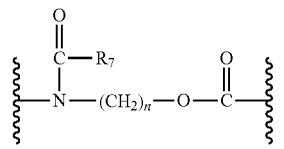
C6

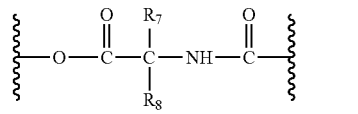
C7

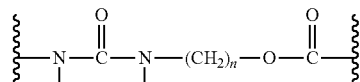
C8

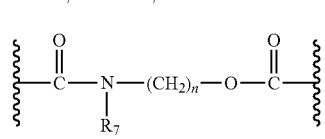
C9

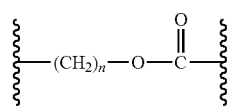
C10

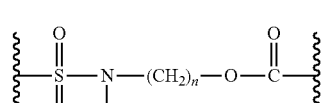
C11

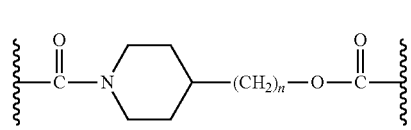
C12

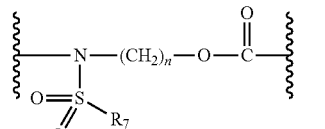
C13

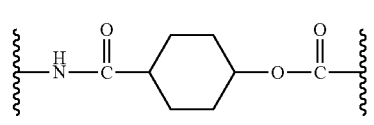
C14 wherein R$_7$, R$_{7'}$ and R$_8$ are independently H or selected from the group consisting of linear or branched ($C_1$-

$C_6$)alkyl, $(C_3-C_8)$cycloalkyl, $(C_3-C_8)$cycloalkyl$(C_1-C_6)$ alkyl, $(C_3-C_8)$heterocycloalkyl$(C_1-C_6)$alkyl, aryl, and aryl$(C_1-C_6)$alkyl, optionally substituted by one or more substituents selected from the group consisting of $(C_1-C_6)$alkyl, halo$(C_1-C_6)$alkyl, halogen atoms, $(C_1-C_6)$ alkoxy, and halo$(C_1-C_6)$alkoxy;

D is absent or is selected from the group consisting of $(C_1-C_6)$alkylene, arylene, heteroarylene, and $(C_3-C_8)$ heterocycloalkylene, optionally substituted by one or more $(C_1-C_6)$alkyl groups;

n, n', m and p are independently 0 or an integer from 1 to 3;

E is absent or is selected from —O— and —OC(O)—;

G is arylene optionally substituted by one or more substituents selected from the group consisting of halogen atom, —OH, oxo (=O), —SH, —$NO_2$, —CN, and —$NH_2$;

$R_1$ and $R_2$ are independently H or selected from the group consisting of $(C_1-C_6)$alkyl and aryl, optionally substituted by one or more halogen atoms;

M is —N($R_3$)—;

$R_3$ is H or $(C_1-C_6)$alkyl;

$R_4$ is a group of formula J1

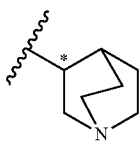

J1 and pharmaceutically acceptable salts and solvates thereof.

The expression "$(C_1-C_x)$alkyl" refers to straight or branched chain alkyl groups wherein the number of carbon atoms is from 1 to x. Examples of groups are methyl, ethyl, n-propyl, isopropyl, t-butyl, pentyl, hexyl, octyl, nonyl, decyl, undecyl, dodecyl, and the like.

In an analogous manner, the expression "$(C_1-C_x)$alkylene" refers to divalent groups, such as methylene, ethylene, n-propylene, isopropylene, t-butylene, pentylene, hexylene, octylene, nonylene, decylene, undecylene, dodecylene, and the like.

The expression "$(C_1-C_6)$haloalkyl" refers to the above "$(C_1-C_6)$alkyl" group wherein one or more hydrogen atoms are replaced by one or more halogen atoms, which can be the same or different from each other. Examples of said $(C_1-C_6)$haloalkyl groups include halogenated, poly-halogenated and fully halogenated alkyl groups wherein one or more of the hydrogen atoms are replaced by halogen atoms, e.g. trifluoromethyl group.

The expression "$(C_1-C_6)$alkoxy" refers to alkyl-oxy (e.g. alkoxy) groups, with the alkyl portion as above defined. Examples of said groups comprise methoxy, ethoxy, n-propoxy, isopropoxy, n-butoxy, isobutoxy, sec-butoxy, tert-butoxy, pentoxy, hexoxy, and the like.

The expression "halo$(C_1-C_6)$alkoxy" include halogenated, poly-halogenated and fully halogenated alkyl-oxy (e.g. alkoxy) groups, being the alkoxy portion as above defined wherein one or more of the hydrogen atoms are replaced by halogen atoms, e.g. trifluoromethoxy group.

The expression "$(C_3-C_8)$cycloalkyl" refers to mono or bi-cycloaliphatic hydrocarbon groups with 3 to 8 carbon atoms. Examples include cyclopropyl, cyclobutyl, cyclopentyl, cyclohexyl, cycloheptyl, bicyclo[2.2.1]hept-2-yl, and the like.

The expression "$(C_3-C_8)$heterocycloalkyl" refers to $(C_3-C_8)$cycloalkyl groups, in which at least one ring carbon atom is replaced by a heteroatom or heteroaromatic group (e.g. N, NH, S or O). Examples include quinuclidinyl, pyrrolidinyl, piperidinyl, azabicyclo[3.2.1]octan-3-yl and azoniabicyclo [2.2.2]octanyl, and the like.

In an analogous manner, the expressions "$(C_3-C_8)$cycloalkylene" and "$(C_3-C_8)$heterocycloalkylene" refer to divalent groups, such as, respectively, cyclopropylene, cyclobutylene, cyclopentylene, cyclohexylene, cycloheptylene, bicyclo[2.2.1]hept-2-ylene and quinuclidinylene, pyrrolidinylene, piperidinylene, azabicyclo[3.2.1]octan-3-ylene, azoniabicyclo[2.2.2]octanylene, and the like.

The expression "aryl" refers to mono, bi- or tricyclic ring systems having 5 to 20, preferably from 5 to 15, ring atoms, and wherein at least one ring is aromatic.

The expression "heteroaryl" refers to mono, bi- or tricyclic systems with 5 to 20 ring atoms, preferably from 5 to 15, in which at least one ring is aromatic and in which at least one carbon ring atom is a heteroatom or heteroaromatic group (e.g. N, NH, S or O).

Examples of suitable aryl or heteroaryl monocyclic systems include, for instance, thiophene (thiophenyl), benzene (phenyl), pyrrole (pyrrolyl), pyrazole (pyrazolyl), imidazole (imidazolyl), isoxazole (isoxazolyl), oxazole (oxazolyl), isothiazole (isothiazolyl), thiazole (thiazolyl), pyridine (pyridinyl), imidazolidine (imidazolidinyl), furan (furanyl) radicals and the like.

Examples of suitable aryl or heteroaryl bicyclic systems include naphthalene (naphthyl), biphenylene (biphenylenyl), purine (purinyl), pteridine (pteridinyl), benzotriazole (benzotriazolyl), quinoline (quinolinyl), isoquinoline (isoquinolinyl), indole (indolyl), isoindole (isoindolyl), benzothiophene (benzothiophenyl), dihydrobenzo dioxin, dihydro-indene, dihydrobenzo dioxepin, benzo oxazin radicals and the like.

Examples of suitable aryl or heteroaryl tricyclic systems include fluorene radicals as well as benzocondensed derivatives of the aforementioned heteroaryl bicyclic systems. In an analogous manner, the expressions "arylene" and "heteroarylene" refer to divalent groups, such a phenylene, biphenylene and thienylene.

The expressions "aryl$(C_1-C_6)$alkyl," "heteroaryl$(C_1-C_6)$ alkyl," "$(C_3-C_8)$heterocycloalkyl$(C_1-C_6)$alkyl," and "$(C_3-C_8)$cycloalkyl$(C_1-C_6)$alkyl" refer to a $(C_1-C_6)$alkyl respectively substituted by one or more aryl, heteroaryl, $(C_3-C_8)$ heterocycloalkyl or $(C_3-C_8)$cycloalkyl groups, as defined above. Examples of aryl$(C_1-C_6)$alkyl include triphenylmethyl.

Whenever basic amino or quaternary ammonium groups are present in the compounds of formula I, physiological acceptable anions, selected among chloride, bromide, iodide, trifluoroacetate, formate, sulfate, phosphate, methanesulfonate, nitrate, maleate, acetate, citrate, fumarate, tartrate, oxalate, succinate, benzoate, p-toluenesulfonate, pamoate and naphthalene disulfonate may be present. Likewise, in the presence of acidic groups such as COOH groups, corresponding physiological cation salts may be present as well, for instance including alkaline or alkaline earth metal ions.

It will be apparent that the compounds of general formula I may contain asymmetric centers. Therefore, the invention also includes any of the optical stereoisomers, diastereoisomers and mixtures thereof, in any proportion.

In particular, the carbon atom linked to $R_1$, $R_2$, G and M groups, depending on the meanings provided to $R_1$ and $R_2$ among those formerly reported, may represent a chiral center.

In an embodiment, the configuration is (S).

In another embodiment, the absolute configuration of this chiral center is preferably (R).

In another preferred embodiment, the compounds of general formula I described in the present invention are present as mixtures of diastereoisomers.

In another embodiment, when in the compounds of general formula I, $R_4$ is a group of formula J1

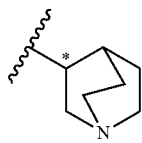

J1 the carbon atom marked with an asterisk represents a chiral center.

In a preferred embodiment, this chiral center has (R) configuration.

It is apparent for the skilled in the art that compounds of general formula I wherein $R_4$ is J1 contain three stereogenic centers, as indicated below with the asterisk (*). This means that the structure of formula I is characterized by eight different stereoisomers.

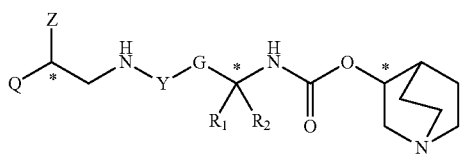

(I)

It is to be understood that all preferred groups or embodiments described below for compounds of formula I may be combined among each other and apply as well mutatis mutandis.

A first preferred group of compounds is that of general formula I wherein Q is a group of formula Q1, Q2 and Q3

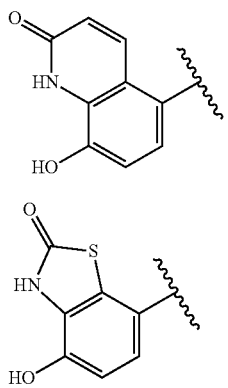

Q1

Q2

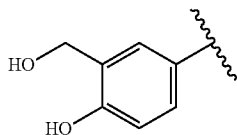

Q3

Z is H or OH;

Y is Y' or Y1 which are divalent groups of formula

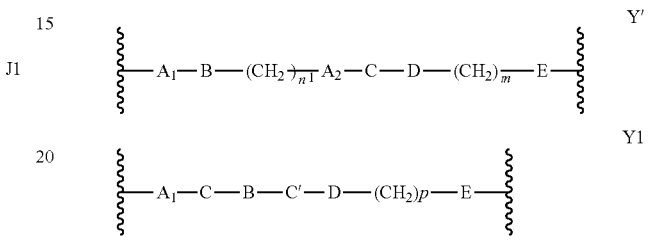

Y'

Y1 wherein

A1 and A2 are independently absent or are selected from the group consisting of $(C_1-C_6)$alkylene, $(C_3-C_8)$cycloalkylene, and $(C_3-C_8)$heterocycloalkylene, optionally substituted by one or more substituents selected from the group consisting of $(C_1-C_6)$alkyl, aryl$(C_1-C_6)$alkyl, and heteroaryl$(C_1-C_6)$alkyl;

B is absent or is selected from the group consisting of $(C_3-C_8)$cycloalkylene, $(C_3-C_8)$heterocycloalkylene, arylene, and heteroarylene, optionally substituted by one or more groups selected from halogen, nitrile, linear or branched $(C_1-C_6)$alkyl, linear or branched $(C_1-C_6)$haloalkyl, $(C_1-C_6)$alkoxy, aryl, aryl$(C_1-C_6)$alkyl, —$NR_7(R_8)$, and heteroaryl;

C and C' are absent or are independently selected from the group consisting of —O—, —CO—, —OC(O)— and —C(OO)— or is one of the following groups C1-C14

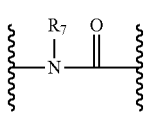

C1

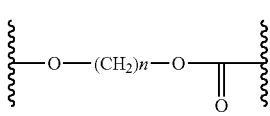

C2

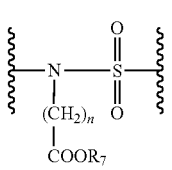

C3

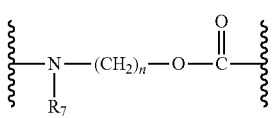

C4

-continued

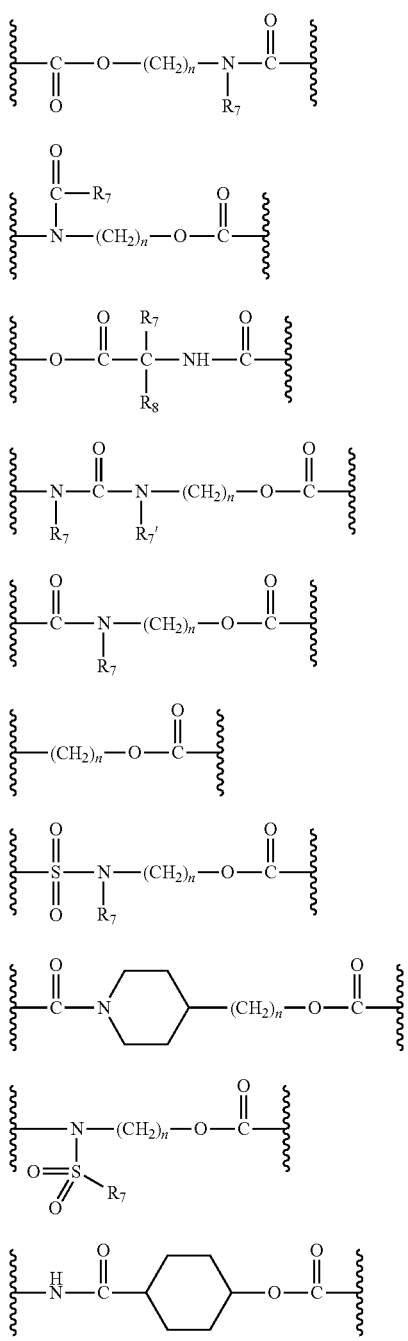

C5

C6

C7

C8

C9

C10

C11

C12

C13

C14 wherein $R_7$, $R_{7'}$ and $R_8$ are independently H or selected from the group consisting of linear or branched ($C_1$-$C_6$)alkyl, ($C_3$-$C_8$)cycloalkyl, ($C_3$-$C_8$)cycloalkyl($C_1$-$C_6$)alkyl, ($C_3$-$C_8$)heterocycloalkyl($C_1$-$C_6$)alkyl, aryl, and aryl($C_1$-$C_6$)alkyl, optionally substituted by one or more substituents selected from the group consisting of ($C_1$-$C_6$)alkyl, halo($C_1$-$C_6$)alkyl, halogen atoms, ($C_1$-$C_6$)alkoxy, and halo($C_1$-$C_6$)alkoxy;

D is absent or is selected from the group consisting of ($C_1$-$C_6$)alkylene, arylene, heteroarylene, and ($C_3$-$C_8$)heterocycloalkylene, optionally substituted by one or more ($C_1$-$C_6$)alkyl groups;

n, n', m and p are independently 0 or an integer from 1 to 3;

E is absent or is selected from —O— and —OC(O)—;

G is arylene optionally substituted by one or more substituents selected from the group consisting of halogen atom, —OH, oxo (=O), —SH, —$NO_2$, —CN, and —$NH_2$;

$R_1$, $R_2$, M, $R_4$ and $R_6$ are as defined above.

Still more preferred within this first group, are the compounds of general formula I, wherein Q is Q1

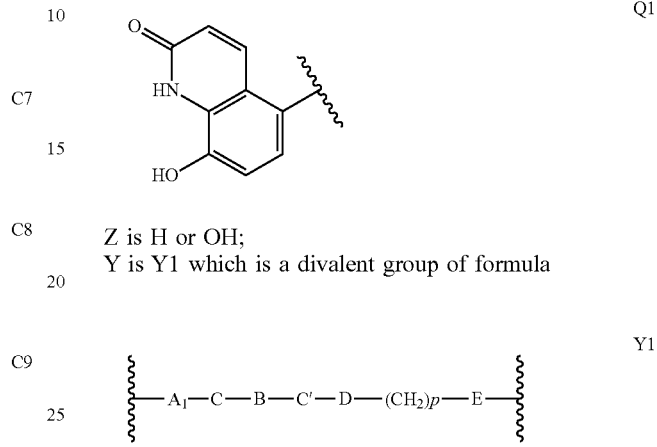

Z is H or OH;

Y is Y1 which is a divalent group of formula

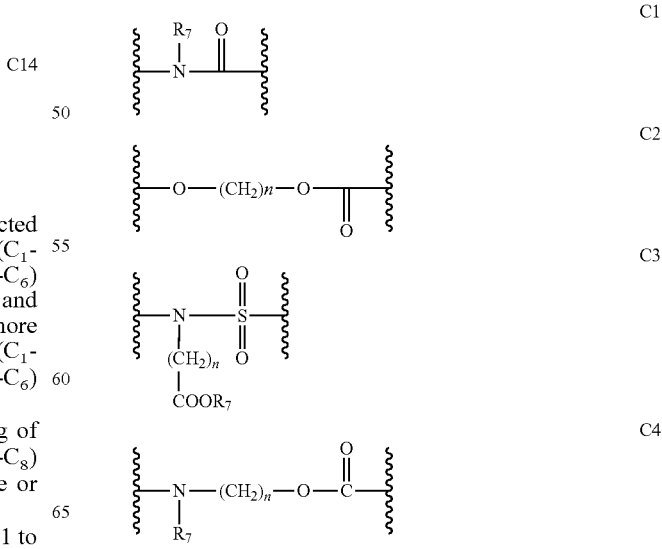

wherein

A1 is absent or is selected from the group consisting of ($C_1$-$C_6$)alkylene, ($C_3$-$C_8$)cycloalkylene, and ($C_3$-$C_8$)heterocycloalkylene, optionally substituted by one or more substituents selected from the group consisting of ($C_1$-$C_6$)alkyl, aryl($C_1$-$C_6$)alkyl, and heteroaryl($C_1$-$C_6$)alkyl;

B is absent or is selected from the group consisting of ($C_3$-$C_8$)cycloalkylene, ($C_3$-$C_8$)heterocycloalkylene, arylene, and heteroarylene, optionally substituted by one or more groups selected from halogen, nitrile, linear or branched ($C_1$-$C_6$)alkyl, linear or branched ($C_1$-$C_6$)haloalkyl, ($C_1$-$C_6$)alkoxy, aryl, and heteroaryl;

C and C' are absent or are independently selected from the group consisting of —O—, —CO—, —OC(O)— and —C(OO)— or is one of the following groups C1-C14

C1

C2

C3

C4

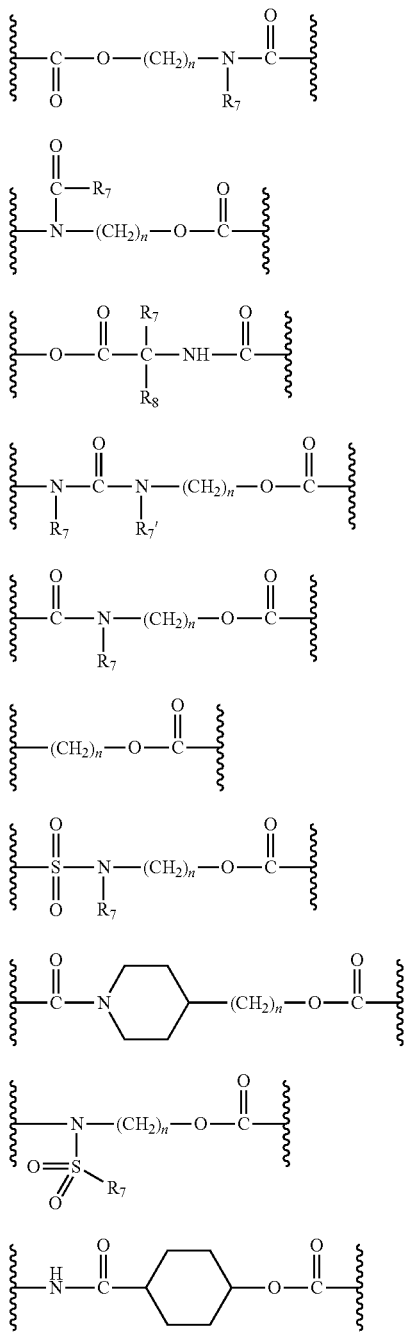

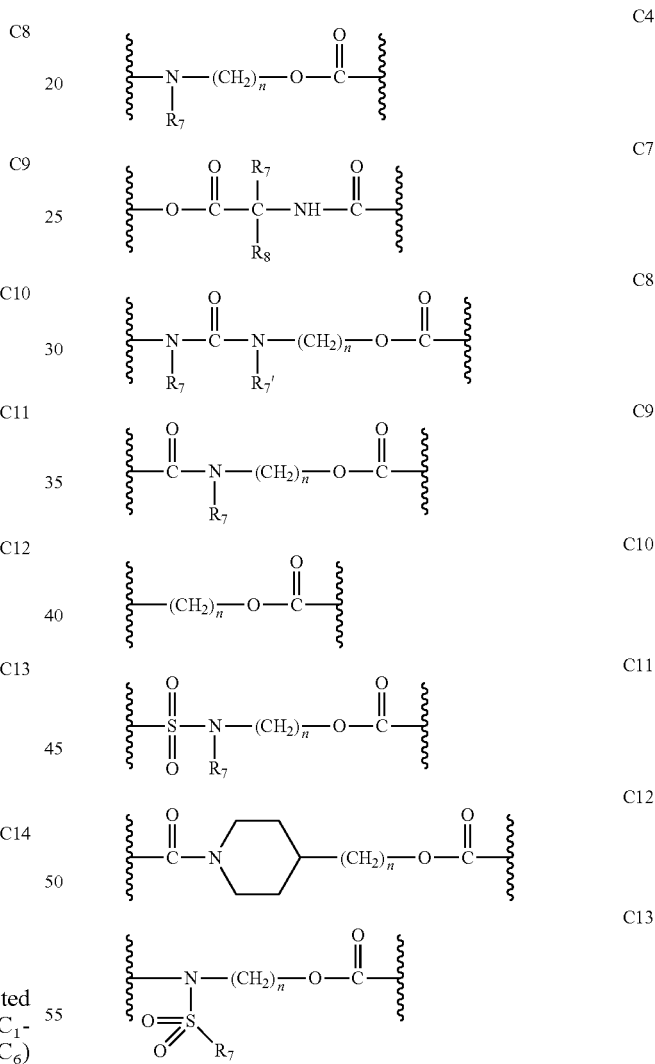

wherein $R_7$, $R_{7'}$ and $R_8$ are independently H or selected from the group consisting of linear or branched ($C_1$-$C_6$)alkyl, ($C_3$-$C_8$)cycloalkyl, ($C_3$-$C_8$)cycloalkyl($C_1$-$C_6$)alkyl, ($C_3$-$C_8$)heterocycloalkyl($C_1$-$C_6$)alkyl, aryl, and aryl($C_1$-$C_6$)alkyl, optionally substituted by one or more substituents selected from the group consisting of ($C_1$-$C_6$)alkyl, halo($C_1$-$C_6$)alkyl, halogen atom, ($C_1$-$C_6$)alkoxy, and halo($C_1$-$C_6$)alkoxy;

D is absent or is selected from the group consisting of ($C_1$-$C_6$)alkylene and arylene, optionally substituted by one or more ($C_1$-$C_6$)alkyl groups;

n and p are independently 0 or an integer from 1 to 3;

E is absent or is selected from —O— and —OC(O)—;

G is arylene optionally substituted by one or more substituents selected from the group consisting of halogen atom, —OH, oxo (=O), —SH, —$NO_2$, —CN, and —$NH_2$.

Still more preferred within this first group, are the compounds of general formula I, wherein A1 is ($C_1$-$C_6$)alkylene; B is absent or is selected from the group consisting of ($C_3$-$C_8$)cycloalkylene, ($C_3$-$C_8$)heterocycloalkylene, arylene, and heteroarylene, optionally substituted by one or more groups selected from halogen, nitrile, linear or branched ($C_1$-$C_6$)alkyl, linear or branched ($C_1$-$C_6$)haloalkyl, and ($C_1$-$C_6$)alkoxy; C and C' are absent or are independently selected from the group consisting of —O—, —CO—, —OC(O)— and —C(OO)— or is one of the following groups C4, C7-C13 wherein $R_7$, $R_{7'}$ and $R_8$ are independently H or selected from the group consisting of linear or branched ($C_1$-$C_6$)alkyl, ($C_3$-$C_8$)cycloalkyl, aryl, and aryl($C_1$-$C_6$)alkyl, optionally substituted by one or more substituents selected from the group consisting of halogen atoms and ($C_1$-$C_6$)alkoxy;

D is absent or is selected from the group consisting of ($C_1$-$C_6$)alkylene and arylene, optionally substituted by one or more ($C_1$-$C_6$)alkyl groups;

n and p are independently 0 or an integer from 1 to 3;
E is absent or is —O—;
G is arylene optionally substituted by one or more substituents selected from the group consisting of halogen atom, —OH, oxo (=O), —SH, —NO$_2$, —CN, and —NH$_2$.

Even still more preferred within this first group are the compounds of general formula I, wherein A1 is selected from the group consisting of methylene, propylene, and butylene; B is absent or is selected from the group consisting of piperidinylene, phenylene, pyridinediyl, furanediyl, thiophenediyl, and cyclohexylene, optionally substituted by one or more groups selected from methoxy, trifluoromethyl, fluorine, and chlorine; C is absent or is selected from the group consisting of —OC(O)—, C4, C7-C13

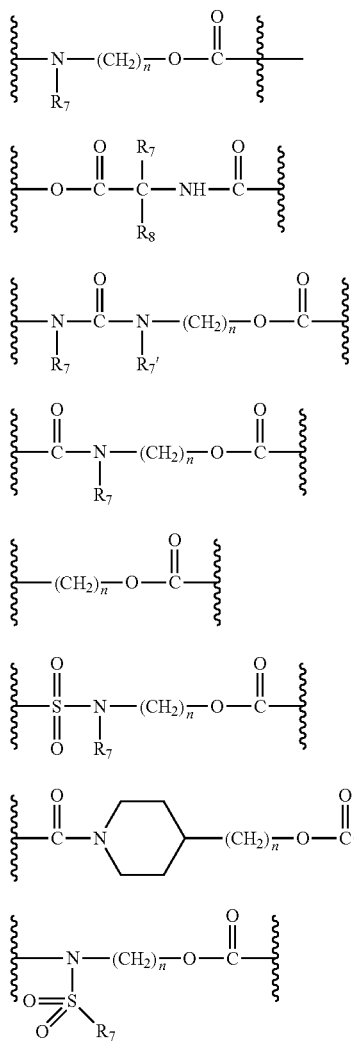

and C' is absent or —CO—; $R_7$, $R_{7'}$ and $R_8$ are independently H or selected from the group consisting of linear or branched (C$_1$-C$_6$)alkyl, (C$_3$-C$_8$)cycloalkyl, aryl, and aryl (C$_1$-C$_6$)alkyl, optionally substituted by one or more substituents selected from the group consisting of halogen atom and (C$_1$-C$_6$)alkoxy; D is absent or is selected from the group consisting of (C$_1$-C$_6$)alkylene and arylene; n is 2 or 3 and p is 1; E is —O—; G is phenylene.

A second group of preferred compounds of general formula I is that wherein Q is a group of formula Q1, Q2 and Q3

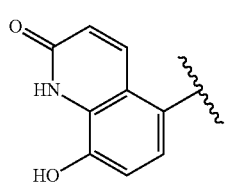

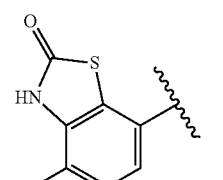

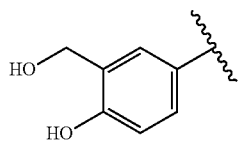

Z is H or OH;
Y is Y' which is a divalent group of formula

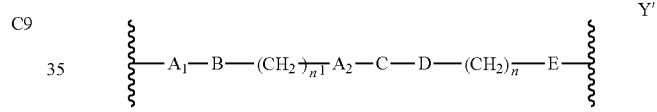

wherein
A1 and A2 are independently absent or are selected from the group consisting of (C$_1$-C$_6$)alkylene, (C$_3$-C$_8$)cycloalkylene, and (C$_3$-C$_8$)heterocycloalkylene, optionally substituted by one or more substituents selected from the group consisting of (C$_1$-C$_6$)alkyl, aryl(C$_1$-C$_6$)alkyl, and heteroaryl(C$_1$-C$_6$)alkyl;
B is absent or is selected from the group consisting of (C$_3$-C$_8$)cycloalkylene, (C$_3$-C$_8$)heterocycloalkylene, arylene, and heteroarylene, optionally substituted by one or more groups selected from halogen, nitrile, linear or branched (C$_1$-C$_6$)alkyl, linear or branched (C$_1$-C$_6$)haloalkyl, (C$_1$-C$_6$)alkoxy, aryl, aryl(C$_1$-C$_6$)alkyl, —NR$_7$(R$_8$), and heteroaryl;
C and C' are absent or are independently selected from the group consisting of —O—, —CO—, —OC(O)— and —C(OO)— or is one of the following groups C1-C14

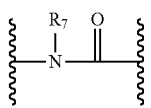

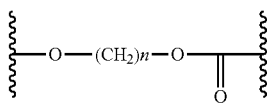

-continued

C3: [structure: N(CH₂)ₙCOOR₇ — SO₂]

C4: [structure: N(R₇)—(CH₂)ₙ—O—C(O)—]

C5: [structure: —C(O)—O—(CH₂)ₙ—N(R₇)—C(O)—]

C6: [structure: C(O)R₇ / N(—(CH₂)ₙ—O—C(O)—)]

C7: [structure: —O—C(O)—C(R₇)(R₈)—NH—C(O)—]

C8: [structure: —N(R₇)—C(O)—N(R₇')—(CH₂)ₙ—O—C(O)—]

C9: [structure: —C(O)—N(R₇)—(CH₂)ₙ—O—C(O)—]

C10: [structure: —(CH₂)ₙ—O—C(O)—]

C11: [structure: —S(O)₂—N(R₇)—(CH₂)ₙ—O—C(O)—]

C12: [structure: —C(O)—N(piperidine)—(CH₂)ₙ—O—C(O)—]

C13: [structure: —N(SO₂R₇)—(CH₂)ₙ—O—C(O)—]

C14: [structure: —NH—C(O)—cyclohexyl—O—C(O)—]

wherein $R_7$, $R_{7'}$ and $R_8$ are independently H or selected from the group consisting of linear or branched ($C_1$-$C_6$)alkyl, ($C_3$-$C_8$)cycloalkyl, aryl, and aryl($C_1$-$C_6$)alkyl, optionally substituted by one or more substituents selected from the group consisting of halogen atom and ($C_1$-$C_6$)alkoxy;

D is absent or is selected from the group consisting of ($C_1$-$C_6$)alkylene, arylene, heteroarylene, and ($C_3$-$C_8$)heterocycloalkylene, optionally substituted by one or more ($C_1$-$C_6$)alkyl groups;

n, n' and m are independently 0 or an integer from 1 to 3;

E is absent or is selected from —O— and —OC(O)—;

G is arylene optionally substituted by one or more substituents selected from the group consisting of halogen atoms, —OH, oxo (=O), —SH, —NO₂, —CN, and —NH₂;

$R_1$, $R_2$, M and $R_4$ are as defined above.

Still more preferred within this second group, are the compounds of general formula I, wherein Q is a group of formula Q1

Q1: [structure: 2-oxo-8-hydroxyquinoline with attachment at position 5]

Z is H or OH;
Y is Y' which is a divalent group of formula

Y': [structure: —A₁—B—(CH₂)ₙ'—A₂—C—D—(CH₂)ₘ—E—]

wherein

A1 and A2 are independently absent or are selected from the group consisting of ($C_1$-$C_6$)alkylene and ($C_3$-$C_8$)heterocycloalkylene, optionally substituted by one or more ($C_1$-$C_6$)alkyl;

B is absent or is selected from the group consisting of ($C_3$-$C_8$)heterocycloalkylene, arylene, and heteroarylene, optionally substituted by one or more groups selected from halogens, linear or branched ($C_1$-$C_6$)alkyl, linear or branched ($C_1$-$C_6$)haloalkyl, ($C_1$-$C_6$)alkoxy, and aryl;

C is selected from the group consisting of —O—, —CO—, —OC(O)— and —C(OO)— or is one of the following groups C4, C8-C12

C4: [structure: —N(R₇)—(CH₂)ₙ—O—C(O)—]

C8: [structure: —N(R₇)—C(O)—N(R₇')—(CH₂)ₙ—O—C(O)—]

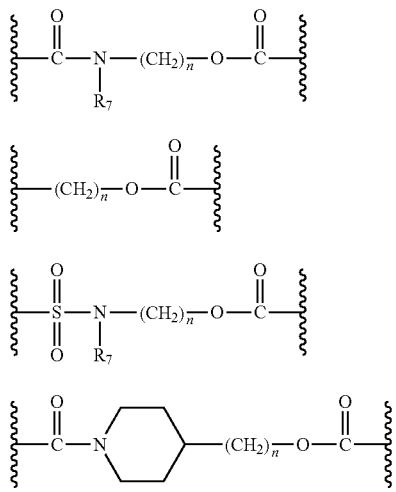

C9

C10

C11

C12 wherein $R_7$ and $R_{7'}$ are independently H or selected from the group consisting of linear or branched $(C_1$-$C_6)$alkyl, $(C_3$-$C_8)$cycloalkyl, aryl, and aryl$(C_1$-$C_6)$alkyl, optionally substituted by one or more substituents selected from the group consisting of halogen atom and $(C_1$-$C_6)$alkoxy;

D is absent or is selected from the group consisting of $(C_1$-$C_6)$alkylene and arylene;

n, n' and m are independently 0 or an integer from 1 to 3;

E is absent or is selected from —O— and —OC(O)—;

G is arylene;

$R_1$, $R_2$, M, $R_4$ and $R_6$ are as defined above.

Even still more preferred within this second group, are the compounds of general formula I, wherein A1 is $(C_1$-$C_6)$alkylene and A2 is absent or is $(C_3$-$C_8)$heterocycloalkylene;

B is absent or is selected from the group consisting of $(C_3$-$C_8)$heterocycloalkylene, arylene and heteroarylene, optionally substituted by one or more groups selected from halogen, linear or branched $(C_1$-$C_6)$alkyl, linear or branched $(C_1$-$C_6)$haloalkyl, and $(C_1$-$C_6)$alkoxy;

C is selected from the group consisting of —O—, —CO—, —OC(O)— and —C(OO)— or is one of the following groups C4, C8-C12

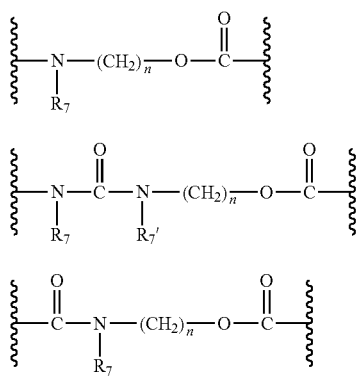

C4

C8

C9

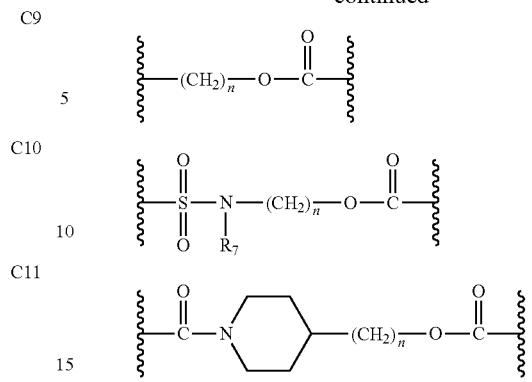

C10

C11

C12 wherein $R_7$ and $R_{7'}$ are independently H or selected from the group consisting of linear or branched $(C_1$-$C_6)$alkyl, $(C_3$-$C_8)$cycloalkyl, aryl, and aryl$(C_1$-$C_6)$alkyl, optionally substituted by one or more substituents selected from the group consisting of halogen atom and $(C_1$-$C_6)$alkoxy;

D is absent or is selected from the group consisting of $(C_1$-$C_6)$alkylene and arylene;

n, n' and m are independently 0 or an integer from 1 to 3;

E is absent or is selected from —O— and —OC(O)—; and

G is arylene.

Even still more preferred within this second group, are the compounds of general formula I, wherein A1 is selected from the group consisting of methylene, propylene, and butylene, $(C_1$-$C_6)$alkylene and A2 is absent or is selected from the group consisting of methylene and piperidinylene; B is absent or is selected from the group consisting of phenylene, pyridinediyl, furanediyl, thiophenediyl, and cyclohexylene, optionally substituted by one or more groups selected from methoxy, trifluoromethyl, fluorine and chlorine; C is selected from the group consisting of —O— and —OC(O)— or is one of the following groups C4, C8-C12

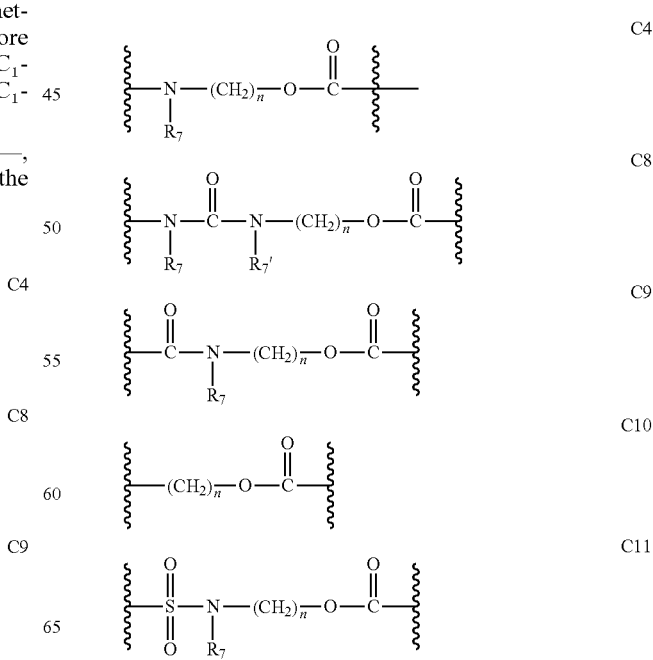

C4

C8

C9

C10

C11

-continued

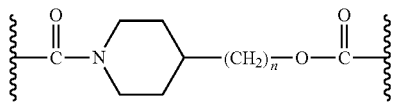

C12 wherein $R_7$ and $R_{7'}$ are independently H or selected from the group consisting of methyl, ethyl, benzyl, phenyl, isopropyl, cyclohexyl, chloro-benzyl, and fluoro-benzyl; D is absent or is phenyl; n is 2 or 3; n' is 1, m is; E is absent or is —O—; and G is phenylene.

The present invention also provides pharmaceutical compositions of compounds of formula I alone or in combination with or in admixture with one or more pharmaceutically acceptable carriers and/or excipients.

The present invention also provides the use of compounds of formula I for preparing a medicament.

In a further aspect, the invention provides the use of compounds of formula I for the prevention and/or treatment of any broncho-obstructive or inflammatory disease, preferably asthma or chronic bronchitis or chronic obstructive pulmonary disease (COPD).

In a further aspect, the invention provides the use of compounds of formula I for the manufacture of a medicament for the prevention and/or treatment of any broncho-obstructive or inflammatory disease, preferably asthma or chronic bronchitis or chronic obstructive pulmonary disease (COPD).

The present invention further provides a method for prevention and/or treatment of any broncho-obstructive or inflammatory disease, preferably asthma or chronic bronchitis or chronic obstructive pulmonary disease (COPD), which comprises administering to a subject in need thereof a therapeutically effective amount of a compound of general formula I.

The present invention also provides pharmaceutical compositions suitable for administration by inhalation.

Inhalable preparations include inhalable powders, propellant-containing metering aerosols or propellant-free inhalable formulations.

The present invention also provides devices which may be a single- or multi-dose dry powder inhaler, a metered dose inhaler and a soft mist nebulizer comprising the compounds of formula I.

The present invention is also directed to a kit comprising the pharmaceutical compositions of compounds of formula I alone or in combination with or in admixture with one or more pharmaceutically acceptable carriers and/or excipients and a device which may be a single- or multi-dose dry powder inhaler, a metered dose inhaler and a soft mist nebulizer comprising the compounds of general formula I.

According to specific embodiments, the present invention provides the compounds reported below:

| Cpd. | Chemical Name |
|---|---|
| 1 | 4-(((R)-2-Hydroxy-2-(8-hydroxy-2-oxo-1,2-dihydroquinolin-5-yl)ethyl)amino)butyl 1-(4-((3-((S)-phenyl((((R)-quinuclidin-3-yloxy)carbonyl)amino)methyl)phenoxy)methyl)benzoyl)piperidine-4-carboxylate |
| 2 | (S)-4-(((R)-2-Hydroxy-2-(8-hydroxy-2-oxo-1,2-dihydroquinolin-5-yl)ethyl)amino)butyl 2-(4-((3-((S)-phenyl((((R)-quinuclidin-3-yloxy)carbonyl)amino)methyl)phenoxy)methyl)benzamido)propanoate |
| 3 | (S)-4-(((R)-2-Hydroxy-2-(8-hydroxy-2-oxo-1,2-dihydroquinolin-5-yl)ethyl)amino)butyl 3-methyl-2-(4-((3-((S)-phenyl((((R)-quinuclidin-3-yloxy)carbonyl)amino)methyl)phenoxy)methyl)benzamido)butanoate |
| 4 | (S)-4-(((R)-2-Hydroxy-2-(8-hydroxy-2-oxo-1,2-dihydroquinolin-5-yl)ethyl)amino)butyl 4-methyl-2-(4-((3-((S)-phenyl((((R)-quinuclidin-3-yloxy)carbonyl)amino)methyl)phenoxy)methyl)benzamido)pentanoate |
| 5 | 4-(((R)-2-Hydroxy-2-(8-hydroxy-2-oxo-1,2-dihydroquinolin-5-yl)ethyl)amino)butyl 2-methyl-2-(4-((3-((S)-phenyl((((R)-quinuclidin-3-yloxy)carbonyl)amino)methyl)phenoxy)methyl)benzamido)propanoate |
| 6 | (S)-4-(((R)-2-Hydroxy-2-(8-hydroxy-2-oxo-1,2-dihydroquinolin-5-yl)ethyl)amino)butyl 3-cyclohexyl-2-(4-((3-((S)-phenyl((((R)-quinuclidin-3-yloxy)carbonyl)amino)methyl)phenoxy)methyl)benzamido)propanoate |
| 7 | (R)-4-(((R)-2-Hydroxy-2-(8-hydroxy-2-oxo-1,2-dihydroquinolin-5-yl)ethyl)amino)butyl 4-methyl-2-(4-((3-((S)-phenyl((((R)-quinuclidin-3-yloxy)carbonyl)amino)methyl)phenoxy)methyl)benzamido)pentanoate |
| 8 | (S)-4-(((R)-2-Hydroxy-2-(8-hydroxy-2-oxo-1,2-dihydroquinolin-5-yl)ethyl)amino)butyl 3-(4-methoxyphenyl)-2-(4-((3-((S)-phenyl((((R)-quinuclidin-3-yloxy)carbonyl)amino)methyl)phenoxy)methyl)benzamido)propanoate |
| 9 | 4-(((R)-2-Hydroxy-2-(8-hydroxy-2-oxo-1,2-dihydroquinolin-5-yl)ethyl)amino)butyl 2-(4-((3-((S)-phenyl((((R)-quinuclidin-3-yloxy)carbonyl)amino)methyl)phenoxy)methyl)benzamido)acetate |
| 9A | (R)-Quinuclidin-3-yl ((S)-(3-((4-(4-(((R)-2-hydroxy-2-(8-hydroxy-2-oxo-1,2-dihydroquinolin-5-yl)ethyl)amino)piperidine-1-carbonyl)benzyl)oxy)phenyl)(phenyl)methyl)carbamate |
| 9B | (R)-Quinuclidin-3-yl ((S)-(3-((4-(4-((((R)-2-hydroxy-2-(8-hydroxy-2-oxo-1,2-dihydroquinolin-5-yl)ethyl)amino)methyl)piperidine-1-carbonyl)benzyl)oxy)phenyl)(phenyl)methyl)carbamate |
| 9C | 4-(((R)-2-Hydroxy-2-(8-hydroxy-2-oxo-1,2-dihydroquinolin-5-yl)ethyl)amino)butyl 1-(3-((3-((S)-phenyl((((R)-quinuclidin-3-yloxy)carbonyl)amino)methyl)phenoxy)methyl)benzoyl)piperidine-4-carboxylate |
| 9D | 4-(((R)-2-Hydroxy-2-(8-hydroxy-2-oxo-1,2-dihydroquinolin-5-yl)ethyl)amino)butyl 1-(5-((3-((S)-phenyl((((R)-quinuclidin-3-yloxy)carbonyl)amino)methyl)phenoxy)methyl)furan-2-carbonyl)piperidine-4-carboxylate |

| Cpd. | Chemical Name |
|---|---|
| 9E | 4-(((R)-2-Hydroxy-2-(8-hydroxy-2-oxo-1,2-dihydroquinolin-5-yl)ethyl)amino)butyl 1-(1-methyl-5-((3-((S)-phenyl((((R)-quinuclidin-3-yloxy)carbonyl)amino)methyl)phenoxy)methyl)-1H-pyrazole-3-carbonyl)piperidine-4-carboxylate |
| 9F | Quinuclidin-3-yl ((S)-(3-((3-(4-((((R)-2-hydroxy-2-(8-hydroxy-2-oxo-1,2-dihydroquinolin-5-yl)ethyl)amino)methyl)piperidine-1-carbonyl)-1-methyl-1H-pyrazol-5-yl)methoxy)phenyl)(phenyl)methyl)carbamate |
| 9G | (R)-Quinuclidin-3-yl ((3-((3-(4-((((R)-2-hydroxy-2-(8-hydroxy-2-oxo-1,2-dihydroquinolin-5-yl)ethyl)amino)methyl)piperidine-1-carbonyl)benzyl)oxy)phenyl)(phenyl)methyl)carbamate |
| 10 | 2-(N-Ethyl-4-((((R)-2-hydroxy-2-(8-hydroxy-2-oxo-1,2-dihydroquinolin-5-yl)ethyl)amino)methyl)benzamido)ethyl 4-((3-((S)-phenyl((((R)-quinuclidin-3-yloxy)carbonyl)amino)methyl)phenoxy)methyl)benzoate |
| 11 | 2-(4-((((R)-2-Hydroxy-2-(8-hydroxy-2-oxo-1,2-dihydroquinolin-5-yl)ethyl)amino)methyl)-N-methylbenzamido)ethyl 4-((3-((S)-phenyl((((R)-quinuclidin-3-yloxy)carbonyl)amino)methyl)phenoxy)methyl)benzoate |
| 12 | 2-(N-Benzyl-4-((((R)-2-hydroxy-2-(8-hydroxy-2-oxo-1,2-dihydroquinolin-5-yl)ethyl)amino)methyl)benzamido)ethyl 4-((3-((S)-phenyl((((R)-quinuclidin-3-yloxy)carbonyl)amino)methyl)phenoxy)methyl)benzoate |
| 13 | 2-(4-((((R)-2-Hydroxy-2-(8-hydroxy-2-oxo-1,2-dihydroquinolin-5-yl)ethyl)amino)methyl)-N-iso-propylbenzamido)ethyl 4-((3-((S)-phenyl((((R)-quinuclidin-3-yloxy)carbonyl)amino)methyl)phenoxy)methyl)benzoate |
| 14 | 2-(N-Cyclohexyl-4-((((R)-2-hydroxy-2-(8-hydroxy-2-oxo-1,2-dihydroquinolin-5-yl)ethyl)amino)methyl)benzamido)ethyl 4-((3-((S)-phenyl((((R)-quinuclidin-3-yloxy)carbonyl)amino)methyl)-phenoxy)methyl)benzoate |
| 15 | 2-(N-(4-Chlorobenzyl)-4-((((R)-2-hydroxy-2-(8-hydroxy-2-oxo-1,2-dihydroquinolin-5-yl)ethyl)amino)methyl)benzamido)ethyl 4-((3-((S)-phenyl((((R)-quinuclidin-3-yloxy)carbonyl)amino)methyl)phenoxy)-methyl)benzoate |
| 16 | 2-(3-((((R)-2-Hydroxy-2-(8-hydroxy-2-oxo-1,2-dihydroquinolin-5-yl)ethyl)amino)methyl)-N-methylbenzamido)ethyl 4-((3-((S)-phenyl((((R)-quinuclidin-3-yloxy)carbonyl)amino)methyl)phenoxy)methyl)benzoate |
| 17 | 2-(4-((((R)-2-Hydroxy-2-(8-hydroxy-2-oxo-1,2-dihydroquinolin-5-yl)ethyl)amino)methyl)benzamido)ethyl 4-((3-((S)-phenyl((((R)-quinuclidin-3-yloxy)carbonyl)amino)methyl)phenoxy)methyl)benzoate |
| 18 | 2-(4-((((R)-2-Hydroxy-2-(8-hydroxy-2-oxo-1,2-dihydroquinolin-5-yl)ethyl)amino)methyl)-3-methoxybenzamido)ethyl 4-((3-((S)-phenyl((((R)-quinuclidin-3-yloxy)carbonyl)amino)methyl)phenoxy)methyl)benzoate |
| 19 | 2-(6-((((R)-2-Hydroxy-2-(8-hydroxy-2-oxo-1,2-dihydroquinolin-5-yl)ethyl)amino)methyl)nicotinamido)ethyl 4-((3-((S)-phenyl((((R)-quinuclidin-3-yloxy)carbonyl)amino)methyl)phenoxy)methyl)benzoate |
| 20 | 2-(5-((((R)-2-Hydroxy-2-(8-hydroxy-2-oxo-1,2-dihydroquinolin-5-yl)ethyl)amino)methyl)furan-2-carboxamido)ethyl 4-((3-((S)-phenyl((((R)-quinuclidin-3-yloxy)carbonyl)amino)methyl)phenoxy)methyl)benzoate |
| 21 | 2-(5-((((R)-2-Hydroxy-2-(8-hydroxy-2-oxo-1,2-dihydroquinolin-5-yl)ethyl)amino)methyl)thiophene-2-carboxamido)ethyl 4-((3-((S)-phenyl((((R)-quinuclidin-3-yloxy)carbonyl)amino)methyl)phenoxy)methyl)benzoate |
| 21A | 3-(5-((((R)-2-Hydroxy-2-(8-hydroxy-2-oxo-1,2-dihydroquinolin-5-yl)ethyl)amino)methyl)isoxazole-3-carboxamido)propyl 4-((3-((S)-phenyl((((R)-quinuclidin-3-yloxy)carbonyl)amino)methyl)phenoxy)methyl)benzoate |
| 21B | 3-(5-((((R)-2-Hydroxy-2-(8-hydroxy-2-oxo-1,2-dihydroquinolin-5-yl)ethyl)amino)methyl)-1-methyl-1H-pyrazole-3-carboxamido)propyl 4-((3-((S)-phenyl((((R)-quinuclidin-3-yloxy)carbonyl)amino)methyl)phenoxy)-methyl)benzoate |
| 22 | 4-(((R)-2-Hydroxy-2-(8-hydroxy-2-oxo-1,2-dihydroquinolin-5-yl)ethyl)amino)butyl 2-methoxy-4-((3-((S)-phenyl((((R)-quinuclidin-3-yloxy)carbonyl)amino)methyl)phenoxy)methyl)benzoate |
| 23 | 4-(((R)-2-Hydroxy-2-(8-hydroxy-2-oxo-1,2-dihydroquinolin-5-yl)ethyl)amino)butyl 4-((3-((S)-phenyl((((R)-quinuclidin-3-yloxy)carbonyl)amino)methyl)phenoxy)methyl)-2-(trifluoromethyl)benzoate |
| 24 | 4-(((R)-2-Hydroxy-2-(8-hydroxy-2-oxo-1,2-dihydroquinolin-5-yl)ethyl)amino)butyl 3-fluoro-5-((3-((S)-phenyl((((R)-quinuclidin-3-yloxy)carbonyl)amino)methyl)phenoxy)methyl)benzoate |
| 25 | 4-(((R)-2-Hydroxy-2-(8-hydroxy-2-oxo-1,2-dihydroquinolin-5-yl)ethyl)amino)butyl 3-chloro-5-((3-((S)-phenyl((((R)-quinuclidin-3-yloxy)carbonyl)amino)methyl)phenoxy)methyl)benzoate |
| 26 | 2-(N-(3-(((R)-2-Hydroxy-2-(8-hydroxy-2-oxo-1,2-dihydroquinolin-5-yl)ethyl)amino)propyl)acetamido)ethyl 4-((3-((S)-phenyl((((R)-quinuclidin-3-yloxy)carbonyl)amino)methyl)phenoxy)methyl)benzoate |
| 27 | 2-(N-(3-(((R)-2-Hydroxy-2-(8-hydroxy-2-oxo-1,2-dihydroquinolin-5-yl)ethyl)amino)propyl)benzamido)ethyl 4-((3-((S)-phenyl((((R)-quinuclidin-3-yloxy)carbonyl)amino)methyl)phenoxy)methyl)benzoate |

| Cpd. | Chemical Name |
|---|---|
| 28 | 2-(N-(3-(((R)-2-Hydroxy-2-(8-hydroxy-2-oxo-1,2-dihydroquinolin-5-yl)ethyl)amino)propyl)phenylsulfonamido)ethyl 4-((3-((S)-phenyl((( ®-quinuclidin-3-yloxy)carbonyl)amino)methyl)phenoxy)methyl)benzoate |
| 29 | 3-(N-(3-(((R)-2-Hydroxy-2-(8-hydroxy-2-oxo-1,2-dihydroquinolin-5-yl)ethyl)amino)propyl)benzamido)propyl 4-((3-((S)-phenyl((((R)-quinuclidin-3-yloxy)carbonyl)amino)methyl)phenoxy)methyl)benzoate |
| 30 | 3-(N-(3-(((R)-2-Hydroxy-2-(8-hydroxy-2-oxo-1,2-dihydroquinolin-5-yl)ethyl)amino)propyl)cyclohexanecarboxamido)propyl 4-((3-((S)-phenyl((((R)-quinuclidin-3-yloxy)carbonyl)amino)methyl)phenoxy)-methyl)benzoate |
| 31 | 3-(N-(3-(((R)-2-Hydroxy-2-(8-hydroxy-2-oxo-1,2-dihydroquinolin-5-yl)ethyl)amino)propyl)phenylsulfonamido)propyl 4-((3-((S)-phenyl((((R)-quinuclidin-3-yloxy)carbonyl)amino)methyl)phenoxy)methyl)benzoate |
| 32 | 3-(N-(3-(((R)-2-Hydroxy-2-(8-hydroxy-2-oxo-1,2-dihydroquinolin-5-yl)ethyl)amino)propyl)-2-phenylacetamido)propyl 4-((3-((S)-phenyl((((R)-quinuclidin-3-yloxy)carbonyl)amino)methyl)phenoxy)methyl)benzoate |
| 33 | Trans-4-(((R)-2-Hydroxy-2-(8-hydroxy-2-oxo-1,2-dihydroquinolin-5-yl)ethyl)amino)butyl 4-((3-((S)-phenyl((((R)-quinuclidin-3-yloxy)carbonyl)amino)methyl)phenoxy)methyl)cyclohexanecarboxylate |
| 33A | (R)-Quinuclidin-3-yl ((S)-(3-(((1R,4S)-4-(3-(((R)-2-hydroxy-2-(8-hydroxy-2-oxo-1,2-dihydroquinolin-5-yl)ethyl)amino)propyl)(methyl)carbamoyl)-cyclohexyl)methoxy)phenyl)(phenyl)methyl)carbamate |
| 33B | (R)-Quinuclidin-3-yl ((S)-(3-(((1R,4S)-4-(3-(((R)-2-hydroxy-2-(8-hydroxy-2-oxo-1,2-dihydroquinolin-5-yl)ethyl)amino)propyl)carbamoyl)cyclohexyl)-methoxy)phenyl)(phenyl)methyl)carbamate |
| 34 | 2-(3-(4-((((R)-2-Hydroxy-2-(8-hydroxy-2-oxo-1,2-dihydroquinolin-5-yl)ethyl)amino)methyl)phenyl)-1-methylureido)ethyl 4-((3-((S)-phenyl((((R)-quinuclidin-3-yloxy)carbonyl)amino)methyl)phenoxy)-methyl)benzoate |
| 35 | 2-(3-(4-((((R)-2-Hydroxy-2-(8-hydroxy-2-oxo-1,2-dihydroquinolin-5-yl)ethyl)amino)methyl)phenyl)ureido)ethyl 4-((3-((S)-phenyl((((R)-quinuclidin-3-yloxy)carbonyl)amino)methyl)phenoxy)methyl)benzoate |
| 36 | 2-(3-(4-((((R)-2-Hydroxy-2-(8-hydroxy-2-oxo-1,2-dihydroquinolin-5-yl)ethyl)amino)methyl)phenyl)-1-phenylureido)ethyl 4-((3-((S)-phenyl((((R)-quinuclidin-3-yloxy)carbonyl)amino)methyl)phenoxy)methyl)benzoate |
| 37 | 2-(1-Ethyl-3-(4-((((R)-2-hydroxy-2-(8-hydroxy-2-oxo-1,2-dihydroquinolin-5-yl)ethyl)amino)methyl)phenyl)ureido)ethyl 4-((3-((S)-phenyl((((R)-quinuclidin-3-yloxy)carbonyl)amino)methyl)phenoxy)methyl)benzoate |
| 38 | 2-(3-(4-((((R)-2-Hydroxy-2-(8-hydroxy-2-oxo-1,2-dihydroquinolin-5-yl)ethyl)amino)methyl)phenyl)-1-isopropylureido)ethyl 4-((3-((S)-phenyl((((R)-quinuclidin-3-yloxy)carbonyl)amino)methyl)phenoxy)methyl)benzoate |
| 39 | 2-(1-Cyclohexyl-3-(4-((((R)-2-hydroxy-2-(8-hydroxy-2-oxo-1,2-dihydroquinolin-5-yl)ethyl)amino)methyl)phenyl)ureido)ethyl 4-((3-((S)-phenyl((((R)-quinuclidin-3-yloxy)carbonyl)amino)methyl)phenoxy)methyl)benzoate |
| 40 | 2-(1-Benzyl-3-(4-((((R)-2-hydroxy-2-(8-hydroxy-2-oxo-1,2-dihydroquinolin-5-yl)ethyl)amino)methyl)phenyl)ureido)ethyl 4-((3-((S)-phenyl((((R)-quinuclidin-3-yloxy)carbonyl)amino)methyl)phenoxy)methyl)benzoate |
| 41 | 2-(1-(4-Fluorobenzyl)-3-(4-((((R)-2-hydroxy-2-(8-hydroxy-2-oxo-1,2-dihydroquinolin-5-yl)ethyl)amino)methyl)phenyl)ureido)ethyl 4-((3-((S)-phenyl((((R)-quinuclidin-3-yloxy)carbonyl)amino)methyl)phenoxy)methyl)benzoate |
| 42 | 2-((4-((((R)-2-Hydroxy-2-(8-hydroxy-2-oxo-1,2-dihydroquinolin-5-yl)ethyl)amino)methyl)phenyl)(methyl)amino)ethyl 4-((3-((S)-phenyl((((R)-quinuclidin-3-yloxy)carbonyl)amino)methyl)phenoxy)methyl)benzoate |
| 43 | 1-(4-((((R)-2-Hydroxy-2-(8-hydroxy-2-oxo-1,2-dihydroquinolin-5-yl)ethyl)amino)methyl)phenyl)piperidin-4-yl 4-((3-((S)-phenyl((((R)-quinuclidin-3-yloxy)carbonyl)amino)methyl)phenoxy)methyl)benzoate |
| 44 | (1-(4-((((R)-2-Hydroxy-2-(8-hydroxy-2-oxo-1,2-dihydroquinolin-5-yl)ethyl)amino)methyl)phenyl)piperidin-4-yl)methyl 4-((3-((S)-phenyl((((R)-quinuclidin-3-yloxy)carbonyl)amino)methyl)phenoxy)methyl)benzoate |
| 45 | 2-(4-((((R)-2-Hydroxy-2-(8-hydroxy-2-oxo-1,2-dihydroquinolin-5-yl)ethyl)amino)methyl)-N-methylphenylsulfonamido)ethyl 4-((3-((S)-phenyl((((R)-quinuclidin-3-yloxy)carbonyl)amino)methyl)phenoxy)methyl)benzoate |
| 46 | 2-(4-(4-((((R)-2-Hydroxy-2-(8-hydroxy-2-oxo-1,2-dihydroquinolin-5-yl)ethyl)amino)methyl)benzyl)piperazin-1-yl)ethyl 4-((3-((S)-phenyl((((R)-quinuclidin-3-yloxy)carbonyl)amino)methyl)phenoxy)methyl)benzoate |
| 47 | 2-((4-((((R)-2-Hydroxy-2-(8-hydroxy-2-oxo-1,2-dihydroquinolin-5-yl)ethyl)amino)methyl)benzyl)(methyl)amino)ethyl 4-((3-((S)-phenyl((((R)-quinuclidin-3-yloxy)carbonyl)amino)methyl)phenoxy)methyl)benzoate |
| 48 | (R)-Quinuclidin-3-yl ((S)-(3-((4-(benzyl(3-(((R)-2-hydroxy-2-(8-hydroxy-2-oxo-1,2-dihydroquinolin-5-yl)ethyl)amino)propyl)carbamoyl)benzyl)oxy)-phenyl)(phenyl)methyl)carbamate |

-continued

| Cpd. | Chemical Name |
|---|---|
| 48A | (R)-Quinuclidin-3-yl ((S)-(3-((3-(benzyl(3-(((R)-2-hydroxy-2-(8-hydroxy-2-oxo-1,2-dihydroquinolin-5-yl)ethyl)amino)propyl)carbamoyl)benzyl)oxy)-phenyl)(phenyl)methyl)carbamate |
| 48B | (R)-Quinuclidin-3-yl ((S)-(3-((5-(benzyl(3-(((R)-2-hydroxy-2-(8-hydroxy-2-oxo-1,2-dihydroquinolin-5-yl)ethyl)amino)propyl)carbamoyl)furan-2-yl)methoxy)phenyl)(phenyl)methyl)carbamate |
| 49 | (R)-Quinuclidin-3-yl ((S)-(3-((4-((3-(((R)-2-hydroxy-2-(8-hydroxy-2-oxo-1,2-dihydroquinolin-5-yl)ethyl)amino)propyl)(2-methoxyethyl)carbamoyl)benzyl)oxy)phenyl)(phenyl)methyl)carbamate |
| 50 | (R)-Quinuclidin-3-yl ((S)-(3-((4-((3-(((R)-2-hydroxy-2-(8-hydroxy-2-oxo-1,2-dihydroquinolin-5-yl)ethyl)amino)propyl)((tetrahydro-2H-pyran-4-yl)methyl)carbamoyl)benzyl)oxy)phenyl)(phenyl)methyl)carbamate |
| 51 | (R)-Quinuclidin-3-yl ((S)-(3-((4-((cyclopentylmethyl)(3-(((R)-2-hydroxy-2-(8-hydroxy-2-oxo-1,2-dihydroquinolin-5-yl)ethyl)amino)propyl)carbamoyl)-benzyl)oxy)phenyl)(phenyl)methyl)carbamate |
| 52 | (R)-Quinuclidin-3-yl ((S)-(3-((4-((3-(((R)-2-hydroxy-2-(8-hydroxy-2-oxo-1,2-dihydroquinolin-5-yl)ethyl)amino)propyl)(3-methoxybenzyl)carbamoyl)-benzyl)oxy)phenyl)(phenyl)methyl)carbamate |
| 53 | (R)-Quinuclidin-3-yl ((S)-(3-((4-((3-(((R)-2-hydroxy-2-(8-hydroxy-2-oxo-1,2-dihydroquinolin-5-yl)ethyl)amino)propyl)(3-methylbenzyl)carbamoyl)-benzyl)oxy)phenyl)(phenyl)methyl)carbamate |
| 54 | (R)-Quinuclidin-3-yl ((S)-(3-((4-((3-(((R)-2-hydroxy-2-(8-hydroxy-2-oxo-1,2-dihydroquinolin-5-yl)ethyl)amino)propyl)(4-trifluoromethoxybenzyl)-carbamoyl)benzyl)oxy)phenyl)(phenyl)methyl)carbamate |
| 55 | (R)-Quinuclidin-3-yl ((S)-(3-((4-((3-(((R)-2-hydroxy-2-(8-hydroxy-2-oxo-1,2-dihydroquinolin-5-yl)ethyl)amino)propyl)(3-trifluoromethylbenzyl)-carbamoyl)benzyl)oxy)phenyl)(phenyl)methyl)carbamate |
| 56 | (R)-Quinuclidin-3-yl ((S)-(3-((4-((3-(((R)-2-hydroxy-2-(8-hydroxy-2-oxo-1,2-dihydroquinolin-5-yl)ethyl)amino)propyl)(2-methylbenzyl)carbamoyl)-benzyl)oxy)phenyl)(phenyl)methyl)carbamate |
| 57 | (R)-Quinuclidin-3-yl ((S)-(3-((4-((3-(((R)-2-hydroxy-2-(8-hydroxy-2-oxo-1,2-dihydroquinolin-5-yl)ethyl)amino)propyl)(2-trifluromethylbenzyl)-carbamoyl)benzyl)oxy)phenyl)(phenyl)methyl)carbamate |
| 58 | (R)-Quinuclidin-3-yl ((S)-(3-((4-((3-(((R)-2-hydroxy-2-(8-hydroxy-2-oxo-1,2-dihydroquinolin-5-yl)ethyl)amino)propyl)(4-methoxybenzyl)carbamoyl)-benzyl)oxy)phenyl)(phenyl)methyl)carbamate |
| 59 | (R)-Quinuclidin-3-yl ((S)-(3-((4-((3-(((R)-2-hydroxy-2-(8-hydroxy-2-oxo-1,2-dihydroquinolin-5-yl)ethyl)amino)propyl)(3-chlorobenzyl)carbamoyl)-benzyl)oxy)phenyl)(phenyl)methyl)carbamate |
| 60 | (R)-Quinuclidin-3-yl ((S)-(3-((4-((3-(((R)-2-hydroxy-2-(8-hydroxy-2-oxo-1,2-dihydroquinolin-5-yl)ethyl)amino)propyl)(2-methoxybenzyl)carbamoyl)-benzyl)oxy)phenyl)(phenyl)methyl)carbamate |
| 61 | (R)-Quinuclidin-3-yl ((S)-(3-((4-((3-(((R)-2-hydroxy-2-(8-hydroxy-2-oxo-1,2-dihydroquinolin-5-yl)ethyl)amino)propyl)(2-trifluoromethoxybenzyl)-carbamoyl)benzyl)oxy)phenyl)(phenyl)methyl)carbamate |
| 62 | (R)-Quinuclidin-3-yl ((S)-(3-((4-((3-(((R)-2-hydroxy-2-(8-hydroxy-2-oxo-1,2-dihydroquinolin-5-yl)ethyl)amino)propyl)(2-fluorobenzyl)carbamoyl)-benzyl)oxy)phenyl)(phenyl)methyl)carbamate |
| 63 | (R)-Quinuclidin-3-yl ((S)-(3-((4-((3-(((R)-2-hydroxy-2-(8-hydroxy-2-oxo-1,2-dihydroquinolin-5-yl)ethyl)amino)propyl)(4-fluorobenzyl)carbamoyl)-benzyl)oxy)phenyl)(phenyl)methyl)carbamate |
| 64 | (R)-Quinuclidin-3-yl ((S)-(3-((4-((3-(((R)-2-hydroxy-2-(8-hydroxy-2-oxo-1,2-dihydroquinolin-5-yl)ethyl)amino)propyl)(2-chlorobenzyl)carbamoyl)-benzyl)oxy)phenyl)(phenyl)methyl)carbamate |
| 65 | (R)-Quinuclidin-3-yl ((S)-(3-((4-((3-(((R)-2-hydroxy-2-(8-hydroxy-2-oxo-1,2-dihydroquinolin-5-yl)ethyl)amino)propyl)(4-chlorobenzyl)carbamoyl)-benzyl)oxy)phenyl)(phenyl)methyl)carbamate |
| 66 | (R)-Quinuclidin-3-yl ((S)-(3-((4-((3-(((R)-2-hydroxy-2-(8-hydroxy-2-oxo-1,2-dihydroquinolin-5-yl)ethyl)amino)propyl)(4-trifluoromethylbenzyl)-carbamoyl)benzyl)oxy)phenyl)(phenyl)methyl)carbamate |
| 67 | (R)-Quinuclidin-3-yl ((S)-(3-((4-((3-(((R)-2-hydroxy-2-(8-hydroxy-2-oxo-1,2-dihydroquinolin-5-yl)ethyl)amino)propyl)(4-methylbenzyl)carbamoyl)-benzyl)oxy)phenyl)(phenyl)methyl)carbamate |
| 68 | (R)-Quinuclidin-3-yl ((S)-(3-((4-((3-(((R)-2-hydroxy-2-(8-hydroxy-2-oxo-1,2-dihydroquinolin-5-yl)ethyl)amino)propyl)(2,4-dimethoxybenzyl)-carbamoyl)benzyl)oxy)phenyl)(phenyl)methyl)carbamate |
| 69 | (R)-Quinuclidin-3-yl ((S)-(3-((4-(cyclopentyl(3-(((R)-2-hydroxy-2-(8-hydroxy-2-oxo-1,2-dihydroquinolin-5-yl)ethyl)amino)propyl)carbamoyl)-benzyl)oxy)phenyl)(phenyl)methyl)carbamate |
| 70 | (R)-Quinuclidin-3-yl ((S)-(3-((4-((cyclohexylmethyl)(3-(((R)-2-hydroxy-2-(8-hydroxy-2-oxo-1,2-dihydroquinolin-5-yl)ethyl)amino)propyl)carbamoyl)-benzyl)oxy)phenyl)(phenyl)methyl)carbamate |
| 71 | (R)-quinuclidin-3-yl ((S)-(3-((4-((cyclopropylmethyl)(3-(((R)-2-hydroxy-2-(8-hydroxy-2-oxo-1,2-dihydroquinolin-5-yl)ethyl)amino)propyl)carbamoyl)-benzyl)oxy)phenyl)(phenyl)methyl)carbamate |

| Cpd. | Chemical Name |
|---|---|
| 72 | (R)-quinuclidin-3-yl ((S)-(3-((4-((3-(((R)-2-hydroxy-2-(8-hydroxy-2-oxo-1,2-dihydroquinolin-5-yl)ethyl)amino)propyl)(isobutyl)carbamoyl)-benzyl)oxy)phenyl)(phenyl)methyl)carbamate |
| 73 | (R)-quinuclidin-3-yl ((S)-(3-((1-(4-((((R)-2-hydroxy-2-(8-hydroxy-2-oxo-1,2-dihydroquinolin-5-yl)ethyl)amino)methyl)benzoyl)piperidin-4-yl)methoxy)phenyl)(phenyl)methyl)carbamate |
| 74 | (R)-Quinuclidin-3-yl ((S)-(3-((1-(4-((((R)-2-hydroxy-2-(8-hydroxy-2-oxo-1,2-dihydroquinolin-5-yl)ethyl)amino)methyl)-3-methoxybenzoyl)piperidin-4-yl)methoxy)phenyl)(phenyl)methyl)carbamate |
| 75 | (R)-Quinuclidin-3-yl ((S)-(3-((1-(4-(2-(((R)-2-hydroxy-2-(8-hydroxy-2-oxo-1,2-dihydroquinolin-5-yl)ethyl)amino)ethyl)benzoyl)piperidin-4-yl)methoxy)phenyl)(phenyl)methyl)carbamate |
| 76 | (R)-quinuclidin-3-yl ((S)-(3-((1-(4-((3-(((R)-2-hydroxy-2-(8-hydroxy-2-oxo-1,2-dihydroquinolin-5-yl)ethyl)amino)propyl)(methyl)carbamoyl)-benzoyl)piperidin-4-yl)methoxy)phenyl)(phenyl)methyl)carbamate |
| 77 | (R)-Quinuclidin-3-yl ((S)-(3-((1-(4-((3-(((R)-2-hydroxy-2-(8-hydroxy-2-oxo-1,2-dihydroquinolin-5-yl)ethyl)amino)propyl)carbamoyl)benzoyl)-piperidin-4-yl)methoxy)phenyl)(phenyl)methyl)carbamate |
| 78 | (R)-Quinuclidin-3-yl ((S)-(3-(2-(4-((((R)-2-hydroxy-2-(8-hydroxy-2-oxo-1,2-dihydroquinolin-5-yl)ethyl)amino)methyl)phenoxy)ethoxy)phenyl)-(phenyl)methyl)carbamate |
| 79 | (R)-Quinuclidin-3-yl ((S)-(3-(2-(3-((((R)-2-hydroxy-2-(8-hydroxy-2-oxo-1,2-dihydroquinolin-5-yl)ethyl)amino)methyl)phenoxy)ethoxy)phenyl)-(phenyl)methyl)carbamate |
| 80 | (R)-Quinuclidin-3-yl ((S)-(3-(2-((3-((((R)-2-hydroxy-2-(8-hydroxy-2-oxo-1,2-dihydroquinolin-5-yl)ethyl)amino)methyl)phenyl)amino)-2-oxoethoxy)phenyl)(phenyl)methyl)carbamate |

The present invention also provides pharmaceutical compositions comprising a compound of the invention, either as such or as pharmaceutically acceptable salt, and one or more pharmaceutically acceptable carriers and/or excipients.

The compounds of the invention may be administered as the sole active agent or in combination with other pharmaceutical active ingredients including those currently used in the treatment of respiratory disorders e.g. beta2-agonists, antimuscarinic agents, mitogen-activated protein kinases (P38 MAP kinase) inhibitors, nuclear factor kappa-B kinase subunit beta (IKK2) inhibitors, human neutrophil elastase (HNE) inhibitors, phosphodiesterase 4 (PDE4) inhibitors, leukotriene modulators, non-steroidal anti-inflammatory agents (NSAIDs), antitussive agents, mucus regulators, mucolytics, expectorant/mucokinetic modulators, peptide mucolytics, antibiotics, inhibitors of JAK, SYK inhibitors, inhibitors of PI3Kdelta or PI3Kgamma, corticosteroids, and M3-antagonists/PDE4-inhibitors (MAPI).

The present invention also provides combinations of a compound of the invention, either as such or as pharmaceutically acceptable salt, with a corticosteroid selected from the group consisting of dexamethasone, fluticasone, fluticasone furoate, fluticasone propionate, prednisolone, betamethasone, budesonide, mometasone, mometasone furoate, triamcinolone acetonide, ciclesonide, TPI-1020, beclomethasone, beclomethasone dipropionate, prednisone, deflazacort, hydrocortisone, QAE-397, and flunisolide.

The present invention also provides combinations of a compound of the invention, either as such or as pharmaceutically acceptable salt, with a β2-agonist selected from the group consisting of carmoterol, GSK-642444, indacaterol, milveterol, arformoterol, arformoterol tartrate, formoterol, formoterol fumarate, salmeterol, salmeterol xinafoate, salbutamol, albuterol, levalbuterol, terbutaline, indacaterol (QAB-149), AZD-3199, BI-1744-CL, LAS-100977, GSK159797, GSK59790, GSK159802, GSK642444, GSK678007, GSK96108, bambuterol, isoproterenol, procaterol, clenbuterol, reproterol, fenoterol, bitolterol, brodxatelor, and ASF-1020 and salts thereof.

The present invention also provides combinations of a compound of the invention, either as such or as pharmaceutically acceptable salt, with an antimuscarinic agent selected from the group consisting of aclidinium, tiotropium, tiotropium bromide (Spiriva®), ipratropium, ipratropium bromide, trospium, glycopyrrolate, NVA237, LAS34273, GSK656398, GSK233705, GSK57319, LAS35201, QAT370 and oxitropium salts.

The present invention also provides combinations of a compound of the invention, either as such or as pharmaceutically acceptable salt, with a PDE4 inhibitor selected from the group consisting of AN-2728, AN-2898, CBS-3595, apremilast, ELB-353, KF-66490, K-34, LAS-37779, IBFB-211913, AWD-12-281, cipamfylline, cilomilast, roflumilast, BAY19-8004 and SCH-351591, AN-6415, indus-82010, TPI-PD3, ELB-353, CC-11050, GSK-256066, oglemilast, OX-914, tetomilast, MEM-1414, and RPL-554.

The present invention also provides combinations of a compound of the invention, either as such or as pharmaceutically acceptable salt, with a P38 MAP kinase inhibitor selected from the group consisting of semapimod, talmapimod, pirfenidone, PH-797804, GSK-725, GSK856553, GSK681323, minokine, and losmapimod and salts thereof.

In a preferred embodiment, the present invention provides combinations of a compound of the invention with an IKK2 inhibitor.

The invention also provides combinations of a compound of the invention with a HNE inhibitor selected from the group consisting of AAT, ADC-7828, aeriva, TAPI, AE-3763, KRP-109, AX-9657, POL-6014, AER-002, AGTC-0106, respriva, AZD-9668, zemaira, AAT IV, PGX-100, elafin, SPHD-400, prolastin C and prolastin inhaled.

The invention also provides combinations of a compound of the invention, either as such or as pharmaceutically acceptable salt, with a leukotriene modulator selected from the group consisting of montelukast, zafirlukast, and pranlukast.

The invention also provides combinations of a compound of the invention, either as such or as pharmaceutically acceptable salt, with a NSAID selected from the group consisting of ibuprofen and ketoprofen.

The invention also provides combinations of a compound of the invention, either as such or as pharmaceutically acceptable salt, with an antitussive agent, selected from the group consisting of codeine and dextramorphan.

The invention also provides combinations of a compound of the invention, either as such or as pharmaceutically acceptable salt, with a mucolytic, selected from the group consisting of N acetyl cysteine and fudostein.

The invention also provides combinations of a compound of the invention, either as such or as pharmaceutically acceptable salt, with an expectorant/mucokinetic modulator, selected from the group consisting of ambroxol, hypertonic solutions (e.g. saline or mannitol) and surfactant.

The invention also provides combinations of a compound of the invention, either as such or as pharmaceutically acceptable salt, with a peptide mucolytic, selected from the group consisting of recombinant human deoxyribonuclease I (dornase-alfa and rhDNase) and helicidin.

The invention also provides combinations of a compound of the invention, either as such or as pharmaceutically acceptable salt, with an antibiotic, selected from the group consisting of azithromycin, tobramycin, and aztreonam.

The invention also provides combinations of a compound of the invention, either as such or as pharmaceutically acceptable salt, with a mucus regulator selected from the group consisting of INS-37217, diquafosol, sibenadet, CS-003, talnetant, DNK-333, MSI-1956, and gefitinib.

The invention also provides combinations of a compound of the invention, either as such or as pharmaceutically acceptable salt, with an inhibitor of JAK, selected from the group consisting of CP-690550 and GLPG0634.

The invention also provides combinations of a compound of the invention, either as such or as pharmaceutically acceptable salt, with a SYK inhibitor selected from the group consisting of R406, R343, and PRT062607.

The compounds of the invention can be prepared from readily available starting materials using the following general methods and procedures or by using other information readily available to those of ordinary skill in the art. Although a particular embodiment of the present invention may be shown or described herein, the skilled in the art will recognize that all embodiments or aspects of the present invention can be prepared using the methods described herein or by using other methods, reagents and starting materials known to the skilled in the art. It will also be appreciated that where typical or preferred process conditions (i.e., reaction temperatures, times, mole ratios of reactants, solvents, pressures, etc.) are given, other process conditions can also be used unless otherwise stated. While the optimum reaction conditions may vary depending on the particular reactants or solvent used, such conditions can be readily determined by one skilled in the art by routine optimisation procedures.

Compounds of general formula I may be prepared according to the following synthetic Scheme.

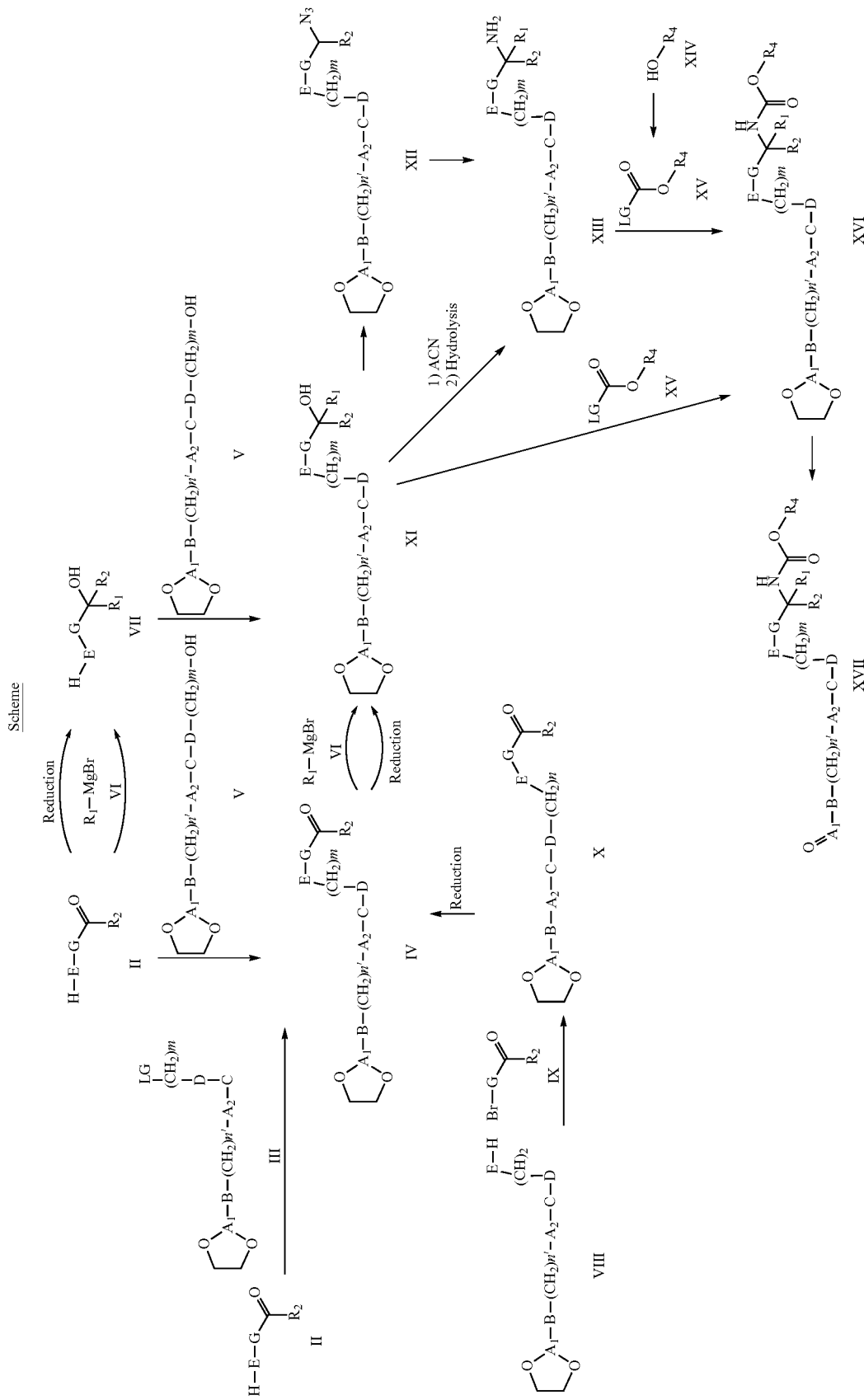

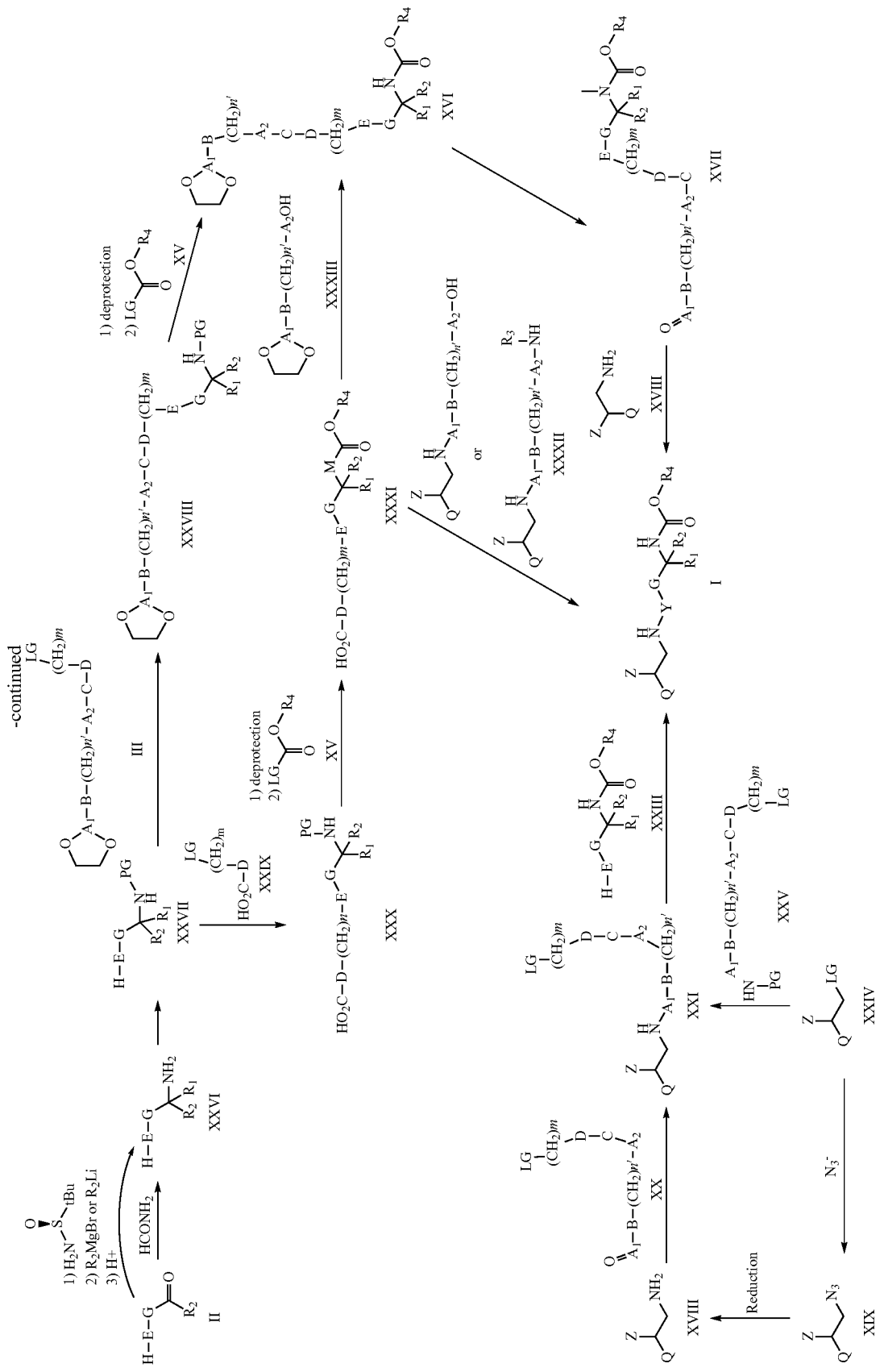

General Procedure for the Preparation of Compounds of Formula I:

The compounds of general formula VIII represent a compound wherein A1 is alkylene substituted with oxo, leading to an aldehyde or ketone protected as cyclic acetal. The synthesis of compounds of general formula I may require the protection of potential reactive functionality in addition to those methods already described. In such a case, examples of compatible protecting groups (PG) and their particular methods of protection and deprotection are described in "Protecting groups in organic Synthesis" by T. W. Green and P. Wutz (Wiley-Interscience publication, 1999), which is incorporated herein by reference in its entirety. Compounds of general formula I can be prepared for example by reaction of a compound of general formula XVII with a compound of general formula XVIII. This reductive amination reaction can be performed following several different protocols described in the literature and known for the skilled in the art. For example, it can be performed in solvent such as methanol, ethanol, tetrahydrofuran (THF) or dichloromethane (DCM) using a reducing agent such as $NaBH_4$, $NaCNBH_3$ or $NaBAcO_3H$. It could be useful to obtain the imine before adding the reducing agent. The reaction proceeds smoothly at room temperature (RT) over 1 to 12 hours.

The intermediate of general formula XVII can be easily prepared by reaction of a compound of general formula XIII with a compound of general formula XV. The reaction occurs smoothly at RT or lower temperature in a solvent such as DCM or pyridine over 1-16 hours leading to compounds of formula XVI that can be easily deprotected in aqueous acidic solution, leading to a compound of general formula XVII.

Compounds of general formula XV are either commercially available or can be prepared by reacting an alcohol of general formula XIV with for example diphosgene in a solvent such as DCM, THF or acetonitrile (ACN) at RT or lower temperature, over a period of time ranging from 0.5 to 12 hours, leading to a compound of general formula XV wherein the leaving group LG is chlorine. Alternatively alcohol of general formula XIV can be reacted with for example carbonyldiimidazole (CDI) leading to the same intermediate wherein LG is imidazole. Other possible intermediates with other known LGs can be prepared as described in the literature.

Compound of general formula XIII may be prepared from a compound of general formula XI via Ritter reaction (acetonitrile and sulfuric acid at RT) followed by hydrolysis of the intermediate acetamide performed under basic condition.

Alternatively compounds of general formula XIII can be prepared by reduction of azide formula XII via hydrogenation under hydrogen atmosphere or hydrogen transfer conditions. The reaction occurs in alcohols at RT or higher temperature and stops in 1 to 12 hours. An alternative reduction method could be the Staudinger reaction, which involves treatment of the azide, first with for example triphenylphosphine, followed by hydrolysis of the iminophosphorane intermediate with water. This reaction occurs at RT in a water miscible solvent such as for example THF. The use of a strong reducing agent such as for example $LiAlH_4$ in THF or ether at −40° C. or lower temperature could easily allow to perform the required conversion of compound XIV into XIII.

Azide XII is obtained from compound of formula XI by reaction with diphenyl phosphoryl azide. The reaction is performed in a high boiling point such as toluene or xylene in the presence of a strong base such as, but not limited to, 1,8-diazabicyclo[5.4.0]undec-7-ene (DBU) at a temperature ranging from 80 to 120° C. and it completes over 12 to 24 hours. Alternatively the hydroxyl moiety of intermediate of formula XI can be converted into a suitable leaving group (LG), such as for example mesyl, tosyl or halogen and then reacted with an alkaline azide in a polar solvent such as acetonitrile, DMF or N-Methyl-2-pyrrolidone (NMP) at RT or higher temperature.

Intermediates of general formula XI can be prepared in several different ways. For example they can be prepared from reaction of a compound of general formula VII, wherein E is —O—, and an aldehyde of general formula V featuring a suitable hydroxyl group that can conveniently react under standard Mitsunobu conditions. The reaction is done in solvents such as THF or N-methyl-morpholine (NMM) at a temperature from −10° C. to RT and completes in 1 to 24 hours. It occurs in the presence of diethyl azodicarboxylate (DEAD) or diisopropyl azodicarboxylate (DIAD) and an organic phosphine such as, but not limited to, triphenylphosphine.

Alcohol of general formula VII is either commercially available or it can be prepared from compound of formula II by addition of a Grignard reagent of formula VI. The reaction is normally done in an aprotic solvent such as ether or THF at RT or lower temperature and completes over 0.5 to 12 hours. Alternatively it can be prepared by reduction of a compound of general formula II, wherein $R_2$ is not hydrogen, with a reducing agent such as, but not limited to, $NaBH_4$, leading in this case to a compound of formula VII wherein $R_1$ is hydrogen. The reaction is performed in a solvent such as methanol, ethanol or THF and completes over a period of time ranging from 1 to 12 hours. A similar synthetic protocol can be used for the preparation of intermediate XI from compounds of general formula IV.

It is clear to a person skilled in the art that the preparation of compound of general formula VII or XI can be accomplished via inverse Grignard reaction in which Grignard of formula G-MgBr react with a compound of formula $R_1C(O)R_2$ under the same reaction conditions described above.

Compounds of general formula IV wherein E is —O—, can be prepared from a compound of general formula II, following an approach similar to that described for the preparation of compounds of formula XI from VII. Alternatively the compounds of general formula IV can be obtained by alkylation of a compound of general formula II, with a compound of general formula III wherein LG is a suitable leaving group such as tosylate, mesylate or halogen. The reaction is normally done in polar solvents such as acetonitrile or DMF, occurs in a presence of a base such as for example alkaline carbonate, bicarbonates or organic bases and completes over a period of time varying from 1 to 24 hours.

Preparation of compounds of formula X can be achieved by reaction of a compound of general formula IX, or the analogue wherein the bromine is substituted by iodine or triflate, with a compound of general formula VIII, wherein n is 2, under transition metal catalyzed cross-coupling reaction conditions. The terminal alkene VIII can be reacted under for example the heck reaction condition with IX, leading to an alkenylene intermediate X that can be easily reduced by mean of a classical catalytic hydrogenation of double bond to give compounds of formula IV. A great number of protocols, reagents and catalysts can be conveniently used to achieve the desired conversion, as it is known to a person skilled in the art.

Alternatively, compounds of general formula I featuring an ester moiety in the linker Y can be prepared by treating a compound of general formula XXXI with a compound of general formula XXXII, wherein A2 is functionalized with OH, under the condensation reaction condition for the preparation of esters. It is possible prepare a compound of general formula I, wherein C is equal to C1, reacting a compound of general formula XXXI with a compound XXXII wherein A2 is substituted with —NR3 under the known reaction condition for the preparation of amide starting from carboxylic acid and amines.

In another embodiment of the present invention, compounds of general formula I can be prepared by reaction of a compound of formula XXI with a compound of formula XXIII under the condition described above for the reaction of a compound of formula II with a compound of formula III.

Intermediates of formula XXI can be prepared by reaction of compound of formula XVIII under reductive amination conditions, described above for the reaction of compound of formula XVII with XVIII, starting from compound of formula XX.

Compounds of general formula XVIII can be obtained from by simple reduction of the azide of formula XIX. The reaction can be accomplished by mean of a catalytic hydrogenation in the presence Palladium catalyst. The reaction occurs, in polar solvent such as methanol or ethanol, under hydrogen atmosphere or under hydrogen transfer condition, using for example 1,4-cyclohexadiene or 1-methyl 1,4-cyclohexadiene as source of hydrogen. The reaction proceeds at RT. In case it is performed under hydrogen transfer conditions higher temperature can be required.

The azide XIX can be easily prepared from XXIV by the known nucleophilic substitution of alkyl bromide with alkaline azide. The reaction proceeds at a temperature ranging from 50 to 80° C. and in a polar solvent such as for example DMF of NMP and can be accelerated by the presence of alkaline iodide.

In another embodiment of the present invention, compounds of general formula XXI can be prepared by reacting an intermediate of general formula XXIV with an amine of general formula XXV. This reaction is a common alkylation of amine in which the leaving group LG (normally chlorine, bromine or sulfate) is displaced by a nucleophile like the amine XXV as such or protected at the amine moiety. Several methods to perform this reaction, that normally occurs in a polar solvent at a temperature higher than RT, are described in the literature. A similar reaction can be used for the preparation of a compound of general formula XXXII.

It is apparent for those skilled in the art that compounds of general formula I wherein $R_4$ is J1 contain three stereogenic centers, as indicated below with the symbol *. This means that the structure of formula I is characterized by eight different stereoisomers.

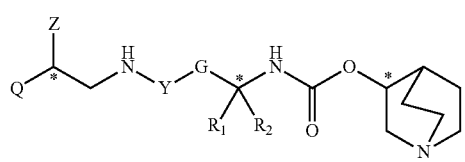

(I)

Each diastereoisomer can be obtained theoretically by chromatographic separation of the mixture obtained by reacting racemic mixtures of the required intermediates. It is clear that this approach it is not convenient and that it can be used only for the separation of mixtures containing few diastereoisomers.

In a more convenient approach, the synthesis of each single stereoisomer can be accomplished using, in the reactions described above, only enantiomerically pure intermediates.

The enantiomerically pure alcohols required for the preparation of compounds of general formula I wherein $R_4$ is J1 are commercially available.

The preparation of single enantiomerically pure compounds of general formula XXIV wherein LG is bromine are described in WO2005/080324, US2005-2222128, WO2004/032921, US2005/215590, and WO2005/092861 (cited by WO2007/107228), all of which are incorporated herein by reference in their entireties. Enantiomerically pure compounds of general formula XXVII can be obtained by chiral chromatographic separation of the racemic mixture or starting from enantiomerically pure amine compounds of general formula XXVI. Intermediate compounds of formula XXVI contains a basic group, it is possible to obtain the two enantiomers by mean of crystallization of the diastereomeric salt, obtained by salification of the racemic mixture with an enantiomerically pure carboxylic acid. Widely used carboxylic acids used for this purpose are for example mandelic acid, tartaric acid and its derivatives. The base XXVI is dissolved in a suitable polar solvent and then treated with enantiomerically pure carboxylic acid causing precipitation of one of the two diastereoisomeric salts. It could be required to repeat the procedure several times to obtain the desired level of enantiomeric excess.

Alternatively the amines of formula XXVI can be obtained via enantioselective synthesis following for example the approach described in the literature (Tetrahedron: *Asymmetry* 13 (2002) 303-310, which is incorporated herein by reference in its entirety) in which the aldehyde of formula II, wherein R2 is H, is treated first with a enantiomerically pure tert-butyl sulfonamide and then with $R_2MgBr$ or $R_2Li$ (wherein R2 is not H), followed by hydrolysis of the intermediate leading to the formation of enantiomerically enriched compounds of formula XXVI that can be used as such or further purified to increase the enantiomeric excess.

The racemic amine of general formula XXVI can be prepared in several different ways, for example by addition of hydroxylamine to a compound of general formula II followed by the reduction of the oxime intermediate obtained than can be performed under several reaction condition known for those skilled in the art. For example catalytic hydrogenation, or the use of reducing agent such as $LiAlH_4$ or Zinc in the presence of ammonium formate are all very efficient method to accomplished the reduction of oxime to amine.

The available amine of formula XXVI can be easily further derivatized under the reaction conditions described above. For example it can be treated with a protected aldehyde of formula III, under the conditions described for the alkylation of compounds of formula II with compounds of formula III, leading to compound or general formula XXVIII. Deprotection of the amino group and reaction of compounds of formula XV, lead to the preparation of a compound of general formula XVI.

Alternatively, compound of general formula I can be prepared coupling a compound of general formula XXXI with a compound of general formula XXXII leading to a compound of general formula I wherein C is —OCO— or Cl. This ester or amide can be obtained under different reaction condition known to those skilled in the art. The reaction requires the activation of the acid XXXI with reactant such as N,N'-Dicyclohexylcarbodiimide (DCC), 1-ethyl-3-(3-dimethylaminopropyl)carbodiimide (EDC), 2-(1H-Benzotriazole-1-yl)-1,1,3,3-Tetramethyluronium hexafluorophosphate (HBTU), (O-(7-azabenzotriazol-1-yl)-N,N,N',N'-tetramethyluronium hexafluorophosphate (HATU) or it may be converted into the corresponding acyl chloride. The activated ester can smoothly react, in DCM, pyridine or other aprotic solvents, with compound of formula XXXII.

Compound of formula XXXI can be prepared starting from XXVII via alkylation with compound of formula XXIX, deprotection and reaction with compound of formula XV. The reaction conditions for this conversion are described above and described in literature. Acid XXXI can be easily reacted with a compound of formula XXXIII, as described above.

A compound of general formula XXXII can be prepared by reaction of a compound of general formula XXIV with an amine of formula $NH_2$-$A_1$-$(CH_2)_{n'}$—B-$A_2$-OH or $NH_2$-$A_1$-$(CH_2)_{n'}$—B-$A_2$-$NHR_4$, under the reaction conditions described for the reaction of compounds of general formula XXIV with compounds of general formula XXV.

For all the above, the synthesis of compounds of general formula I can be performed following several different approaches. In particular it must be noted that the sequence of reaction required, strongly depends on the nature of the linkers Y and Y1 and on the functional groups present on the linker. The example given above for the preparation of compounds of formula I wherein C is —OCO— or Cl allows a person skilled in the art to appreciate this aspect of the invention.

The invention also provides pharmaceutical compositions of compounds of formula I in admixture with one or more pharmaceutically acceptable carriers, for example those described in Remington's Pharmaceutical Sciences Handbook, XVII Ed., Mack Pub., N.Y., U.S.A., which is incorporated herein by reference in its entirety.

Administration of the compounds of the present invention may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and known excipients, including suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering compounds of the invention, including aqueous and non-aqueous solutions, emulsions, suspensions, syrups, and elixirs. Such dosage forms can also contain suitable known inert diluents such as water and suitable known excipients such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the invention can be prepared by mixing the compound with a suitable excipient such as cocoa butter, salicylates and polyethylene glycols.

Formulations for vaginal administration can be in the form of cream, gel, paste, foam, or spray formula containing, in addition to the active ingredient, such as suitable carriers, are also known.

For topical administration the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

For the treatment of the diseases of the respiratory tract, the compounds according to the invention are preferably administered by inhalation.

Inhalable preparations include inhalable powders, propellant-containing metering aerosols or propellant-free inhalable formulations.

For administration as a dry powder, single- or multi-dose inhalers known from the prior art may be utilized. In that case the powder may be filled in gelatine, plastic or other capsules, cartridges or blister packs or in a reservoir.

A diluent or carrier, generally non-toxic and chemically inert to the compounds of the invention, e.g. lactose or any other additive suitable for improving the respirable fraction may be added to the powdered compounds of the invention.

Inhalation aerosols containing propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the invention may be in form of solutions or suspensions in an aqueous, alcoholic or hydroalcoholic medium and they may be delivered by jet or ultrasonic nebulizers known from the prior art or by soft-mist nebulizers such as Respimat®.

The compounds of the invention may be administered as the sole active agent or in combination with other pharmaceutical active ingredients including those currently used in the treatment of respiratory disorders, e.g. corticosteroids, P38 MAP kinase inhibitors, IKK2, HNE inhibitors, PDE4 inhibitors, leukotriene modulators, NSAIDs, and mucus regulators.

The dosages of the compounds of the invention depend upon a variety of factors including the particular disease to be treated, the severity of the symptoms, the route of administration, the frequency of the dosage interval, the particular compound utilized, the efficacy, toxicology profile, and pharmacokinetic profile of the compound.

Advantageously, the compounds of formula I can be administered for example, at a dosage comprised between 0.001 and 1000 mg/day, preferably between 0.1 and 500 mg/day.

When the compounds of formula I are administered by inhalation route, they are preferably given at a dosage comprised between 0.001 and 500 mg/day, preferably between 0.1 and 200 mg/day.

The compounds of formula I may be administered for the prevention and/or treatment of broncho-obstructive or inflammatory diseases, such as asthma, chronic bronchitis, chronic obstructive pulmonary disease (COPD), bronchial hyperreactivity, cough, emphysema or rhinitis; urological disorders such as urinary incontinence, pollakiuria, cystospasm, chronic cystitis and overactive bladder (OAB); gastrointestinal disorders such as bowel syndrome, spastic colitis, diverticulitis, peptic ulceration, gastrointestinal motility or gastric acid secretion; dry mouth; mydriasis, tachycardia; ophthalmic interventions cardiovascular disorders such as vagally induced sinus bradycardia.

Other features of the invention will become apparent in the course of the following descriptions of exemplary embodiments which are given for illustration of the invention and are not intended to be limiting thereof.

EXAMPLES

The LCMS methods A, B and C, used for the characterization of the compounds of the present invention, are described in the following:

Method A (10 cm_ESCI_FORMIC)
HPLC Setup
Solvents:—Acetonitrile (Far UV grade) with 0.1% (V/V) formic acid
Water (High purity via PureLab Option unit) with 0.1% formic acid
Column:—Phenomenex Luna 5μ C18 (2), 100×4.6 mm. (Plus guard cartridge)
Flow Rate:—2 ml/min

| Gradient:- | | |
|---|---|---|
| Time | A % | B % |
| 0.00 | 95 | 5 |
| 3.50 | 5 | 95 |
| 5.50 | 5 | 95 |
| 5.60 | 95 | 5 |
| 6.50 | 95 | 5 |

A: Water/formic
B: MeCN/formic

Typical Injections 2-7 ul (concentration ~0.2-1 mg/ml).
UV detection via HP or Waters DAD
Start Range (nm) 210 End Range (nm) 400 Range interval (nm) 4.0
Other wavelength traces are extracted from the DAD data.
Optional ELS detection using Polymer Labs ELS-1000.
MS detection: Micromass ZQ, single quadrapole LC-MS or Quattro Micro LC-MS-MS.
Flow splitter gives approximately 300 ul/min to mass spec
Scan range for MS Data (m/z)
Start (m/z) 100
End (m/z) 650 or 1500 when required
With +ve/−ve switching
Ionization is routinely ESCI an option which gives both ESI and APCI data from a single run.
Typical ESI voltages and temperatures are:

| Source 120-150 C. | 3.5 KV capillary | 25 V cone |
|---|---|---|

Typical APCI voltages and temperatures are:

| Source 140-160 C. | 17 uA corona | 25 V cone |
|---|---|---|

Method B (HPLC Conditions—15 cm_Formic_Ascentis_HPLC_CH$_3$CN)
HPLC Setup
Solvents:—Acetonitrile (Far UV grade) with 0.1% (V/V) formic acid
Water (High purity via PureLab Ultra unit) with 0.1% formic acid
Column:—Supelco, Ascentis® Express C18 or Hichrom Halo C18, 2.7 μm C18, 150×4.6 mm.
Flow Rate:—1 ml/min

| Gradient:- | | |
|---|---|---|
| Time | A % | B % |
| 0.00 | 96 | 4 |
| 3.00 | 96 | 4 |
| 9.00 | 0 | 100 |
| 13.6 | 0 | 100 |
| 13.7 | 96 | 4 |
| 15 | 96 | 4 |

A: Water/formic
B: MeCN/formic

Typical Injections 0.2-10 ul
Maximum pressure setting 400 bar.
Instrument: Agilent 1100, Binary Pump, Agilent Sampler and Agilent DAD detector
Diode array detection: (300 nm, Band Width 200 nm; Ref. 450 nm, Band Width 100 nm).
Method C(HPLC Conditions—10 cm_Formic_ACE-AR_HPLC_CH3CN)
HPLC Setup
Solvents:—Acetonitrile (Far UV grade) with 0.1% (V/V) formic acid
Water (High purity via PureLab Ultra unit) with 0.1% formic acid
Column:—Hichrom ACE 3 C18-AR mixed mode column 100×4.6 mm
Flow Rate:—1 ml/min

| Gradient:- | | |
|---|---|---|
| Time | A % | B % |
| 0.00 | 98 | 2 |
| 3.00 | 98 | 2 |
| 12.00 | 0 | 100 |
| 15.4 | 0 | 100 |
| 15.5 | 98 | 2 |
| 17 | 98 | 2 |

A: Water/formic
B: MeCN/formic

Typical Injections 0.2-10 ul
Maximum pressure setting 400 bar.
Instrument: Agilent 1100, Binary Pump, Agilent Sampler and Agilent DAD detector
Diode array detection: (300 nm, Band Width 200 nm; Ref 450 nm, Band Width 100 nm)
Method D (HPLC Conditions—25 cm_Acidic_Prodigy_HPLC)
HPLC Setup
Solvents:—Acetonitrile (Far UV grade) with 0.1% formic acid
Water (High purity via PureLab Option unit) with 0.1% formic acid Column:—Phenominex Prodigy 5 μm ODS 3, 250×4.6 mm.
Flow Rate:—1 ml/min

| Gradient:- | | |
|---|---|---|
| Time | A % | B % |
| 0.00 | 95.5 | 4.5 |
| 1.0 | 95.5 | 4.5 |
| 22 | 0 | 100 |
| 23 | 0 | 100 |
| 25 | 95.5 | 4.5 |
| 30 | 95.5 | 4.5 |

A: Water/formic
B: MeCN/formic

Typical Injections 2-7 ul
Instrument: Agilent 1100, Binary Pump, Agilent Sampler and Agilent DAD detector The intermediate compounds for the synthesis of final compounds of general formula (I) were obtained through the preparations herebelow described.

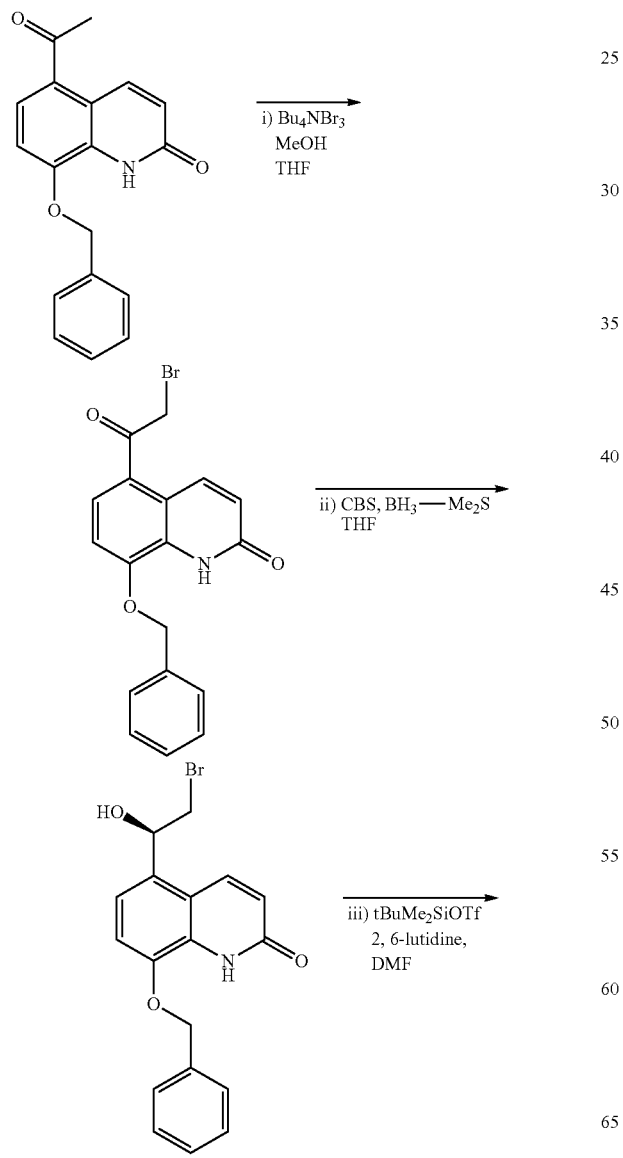

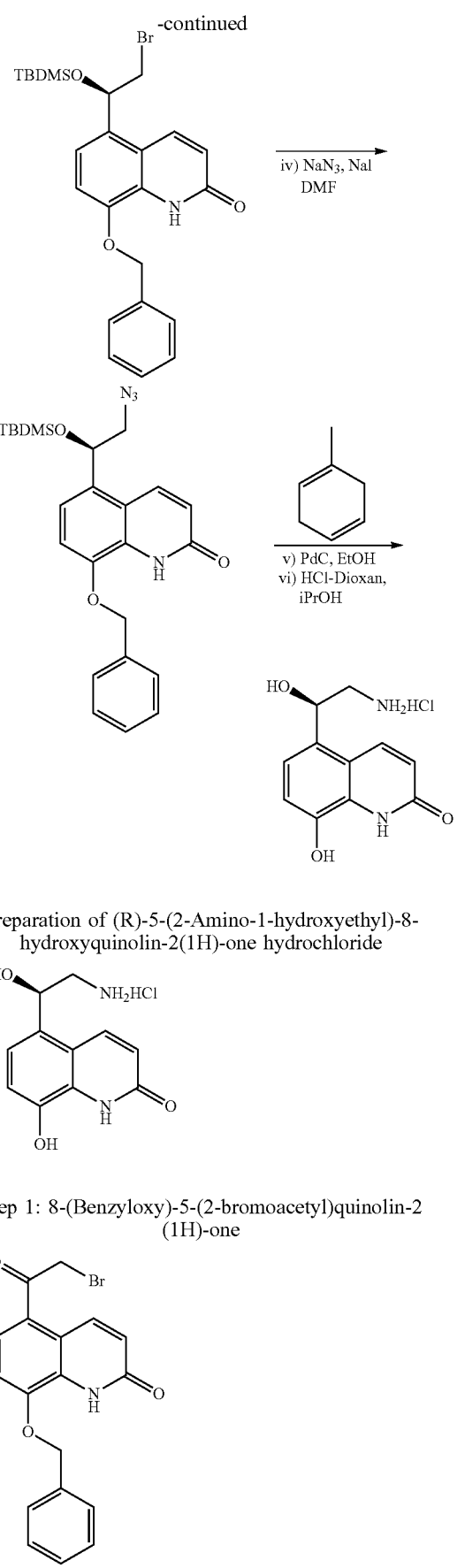

Preparation of (R)-5-(2-Amino-1-hydroxyethyl)-8-hydroxyquinolin-2(1H)-one hydrochloride Step 1: 8-(Benzyloxy)-5-(2-bromoacetyl)quinolin-2(1H)-one To a suspension of 5-acetyl-8-(benzyloxy)quinolin-2(1H)-one (19.4 g, 66.4 mmol) in anhydrous THF (240 mL) and anhydrous methanol (165 mL) was added a solution of tetra-n-butylammonium tribromide (54.5 g, 113.0 mmol) in anhydrous THF (130 mL) dropwise over 1.5 hours. The resulting solution was stirred at RT overnight before concentrating under reduced pressure without heating. The residue was re-dissolved in methanol (200 mL). Saturated aqueous ammonium chloride solution (390 mL) was added with ice-cooling. The resulting suspension was filtered and the solid washed with water and air-dried under vacuum. The solid was suspended in DCM and methanol (1:1 v/v, 100 mL) for 90 minutes. The solid was collected by filtration, washed with DCM and air-dried to afford the title compound (18.0 g, 73%).

$^1$H NMR (400 MHz, DMSO-$d_6$): δ 11.07 (s, 1H); 8.51 (d, J=10.0 Hz, 1H); 7.94-7.83 (m, 1H); 7.60 (d, J=7.5 Hz, 2H); 7.44-7.27 (m, 4H); 6.79-6.65 (m, 1H); 5.53-5.39 (s, 2H); 4.93 (s, 2H)

Step 2: (R)-8-(Benzyloxy)-5-(2-bromo-1-hydroxyethyl)quinolin-2(1H)-one

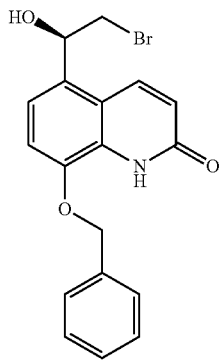 [SMILES: O=c1ccc2c([C@@H](O)CBr)ccc(OCc3ccccc3)c2[nH]1]

8-(Benzyloxy)-5-(2-bromoacetyl)quinolin-2(1H)-one (26.0 g, 69.9 mmol) and (R)-3,3-diphenyl-1-methyltetrahydro-3H-pyrrolo[1,2-c][1,3,2]oxazaborole (21.3 g, 76.8 mmol) were azeotroped with toluene (×3) then suspended in anhydrous THF (400 mL) under an atmosphere of nitrogen. The suspension was cooled to −20° C. (external temperature) and borane dimethyl sulfide complex solution (45.4 mL, 90.8 mmol, 2.0 M solution in THF) was added by syringe pump over 3 hours. After complete addition the reaction mixture was stirred for one hour before quenching with methanol (25 mL). The reaction was warmed to RT over 20 minutes. The mixture was concentrated under reduced pressure and the residue was suspended in aqueous hydrochloric acid (500 mL, 1 M solution) and stirred at RT for 18 hours. After this time the solid was collected by filtration and washed with water (3×100 mL). The solid was partially dissolved in ethyl acetate and heated at reflux for 2 hours. The remaining solid was removed by hot filtration and the filtrate was evaporated to afford the title compound. The solid collected from the hot ethyl acetate was again partially dissolved in ethyl acetate and heated at reflux for 2 hours then filtered to give filtrate containing pure product. This process was repeated four more times. The combined solid was recrystallised from ethyl acetate and petroleum ether to afford the title compound (20.0 g, 76%).

$^1$H NMR (400 MHz, DMSO-$d_6$): δ 10.68 (s, 1H); 8.19 (d, J=9.9 Hz, 1H); 7.58 (d, J=7.5 Hz, 2H); 7.41-7.36 (m, 2H); 7.34-7.29 (m, 1H); 7.23-7.19 (m, 2H); 6.57 (d, J=9.8 Hz, 1H); 5.94 (d, J=4.7 Hz, 1H); 5.31 (s, 2H); 5.25-5.19 (m, 1H); 3.71-3.58 (m, 2H).

Step 3: (R)-8-(Benzyloxy)-5-(2-bromo-1-((tert-butyldimethylsilyl)oxy)ethyl)quinolin-2(1H)-one

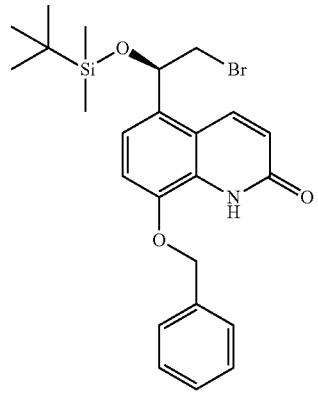 [SMILES: CC(C)(C)[Si](C)(C)O[C@@H](CBr)c1ccc(OCc2ccccc2)c2[nH]c(=O)ccc12]

2,6-Lutidine (6.9 mL, 59.5 mmol) was added to a solution of (R)-8-(benzyloxy)-5-(2-bromo-1-hydroxyethyl)quinolin-2(1H)-one (10.1 g, 27.0 mmol) in DCM (100 mL) at 0° C. The reaction mixture was stirred for 5 minutes then tert-butyldimethylsilyl trifluoromethanesulfonate (13.0 mL, 56.8 mmol) was added dropwise over 15 minutes. The mixture was stirred at 0° C. for 30 minutes, followed by RT overnight. After this time the reaction was quenched with saturated aqueous sodium bicarbonate solution and extracted with DCM (×3). The combined organic extracts were dried (magnesium sulfate), filtered and concentrated under reduced pressure. Iso-hexane (500 mL) was added to the crude material and the resulting solid collected by filtration. The solid was recrystallised from ethyl acetate and petroleum ether (40:60) to afford the title compound (11.3 g, 85%).

$^1$H NMR (400 MHz, CDCl$_3$): δ 9.19 (s, 1H); 8.23 (dd, J=9.9, 4.4 Hz, 1H); 7.43 (d, J=4.6 Hz, 5H); 7.17 (dd, J=8.3, 4.5 Hz, 1H); 7.03 (dd, J=8.2, 4.4 Hz, 1H); 6.71 (dd, J=9.9, 3.7 Hz, 1H); 5.18 (d, J=4.5 Hz, 3H); 3.63-3.56 (m, 1H); 3.49 (dd, J=10.4, 4.8 Hz, 1H); 0.88 (t, J=4.4 Hz, 9H); 0.14 (d, J=4.4 Hz, 3H); −0.11 (d, J=4.4 Hz, 3H).

Step 4: (R)-5-(2-Azido-1-((tert-butyldimethylsilyl)oxy)ethyl)-8-(benzyloxy)quinolin-2(1H)-one

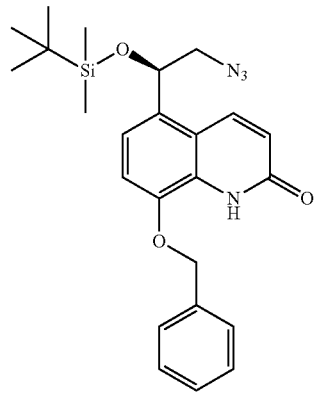 [SMILES: CC(C)(C)[Si](C)(C)O[C@@H](CN=[N+]=[N-])c1ccc(OCc2ccccc2)c2[nH]c(=O)ccc12]

(R)-8-(Benzyloxy)-5-(2-bromo-1-((tert-butyldimethylsilyl)oxy)ethyl)quinolin-2(1H)-one (10.0 g, 20.5 mmol) was dissolved in dimethyl formamide (180 mL) and water (20 mL). Sodium iodide (3.39 g, 22.6 mmol) and sodium azide (1.47 g, 22.6 mmol) were added sequentially. The reaction mixture was stirred at RT until all the solid was in solution. The solution was heated at 80° C. for 40 hours then cooled to RT and diluted with ethyl acetate (300 mL). The mixture was washed with water, brine (×2) and the organic extract was dried (magnesium sulfate), filtered and concentrated under reduced pressure. The crude residue was triturated with iso-hexane to afford the desired compound (8.16 g, 88%). The material was used without further purification in the next step.

$^1$H NMR (400 MHz, CDCl$_3$): δ 9.19 (s, 1H), 8.18 (d, J=9.9 Hz, 1H), 7.45-7.36 (m, 4H), 7.20 (d, J=8.3 Hz, 1H), 7.04 (d, J=8.3 Hz, 1H), 6.70 (dd, J=9.9, 2.2 Hz, 1H), 5.19-5.13 (m, 3H), 3.48 (dd, J=12.7, 8.1 Hz, 1H), 3.26 (dd, J=12.7, 3.8 Hz, 1H), 0.89 (s, 9H), 0.14 (s, 3H), −0.11 (s, 3H).

Step 5: (R)-5-(2-Amino-1-hydroxyethyl)-8-hydroxy-quinolin-2(1H)-one hydrochloride

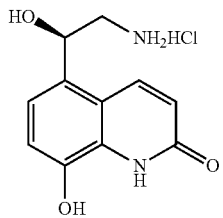

To a solution of (R)-5-(2-azido-1-((tert-butyldimethylsilyl)oxy)ethyl)-8-(benzyloxy)quinolin-2(1H)-one (4.50 g, 10.0 mmol) in ethanol (50 mL) was added 10% palladium on charcoal (4.50 g) followed by 1-methyl-1,4-cyclohexadiene (11.0 mL, 97.9 mmol). The reaction was warmed to 60° C. (CARE—POSSIBLE EXOTHERM) and then stirred at 60° C. for 2 hours. The reaction mixture was allowed to cool and filtered through a pad of celite. The filter cake was washed with further ethanol and the filtrate was evaporated at reduced pressure. The residue was evaporated from iso-propanol (×2) and dissolved in iso-propanol (30 mL). HCl-dioxane (4 M, 50 mL, 200 mmol) was added and the reaction mixture stirred at RT for 18 hours. The resultant suspension was filtered, the filter cake washed with ether and the solid dried under vacuum in the presence of P$_2$O$_5$ to afford the title compound (1.65 g, 62%).

$^1$H NMR (400 MHz, MeOD): δ 7.71 (d, J=9.8 Hz, 1H), 6.57 (d, J=8.2 Hz, 1H), 6.31 (d, J=8.2 Hz, 1H), 6.02 (dd, J=9.8, 6.5 Hz, 1H), 4.58 (dd, J=9.6, 3.5 Hz, 1H), 2.47-2.31 (m, 2H).

The synthesis of Compound 1 to 9 is shown below.

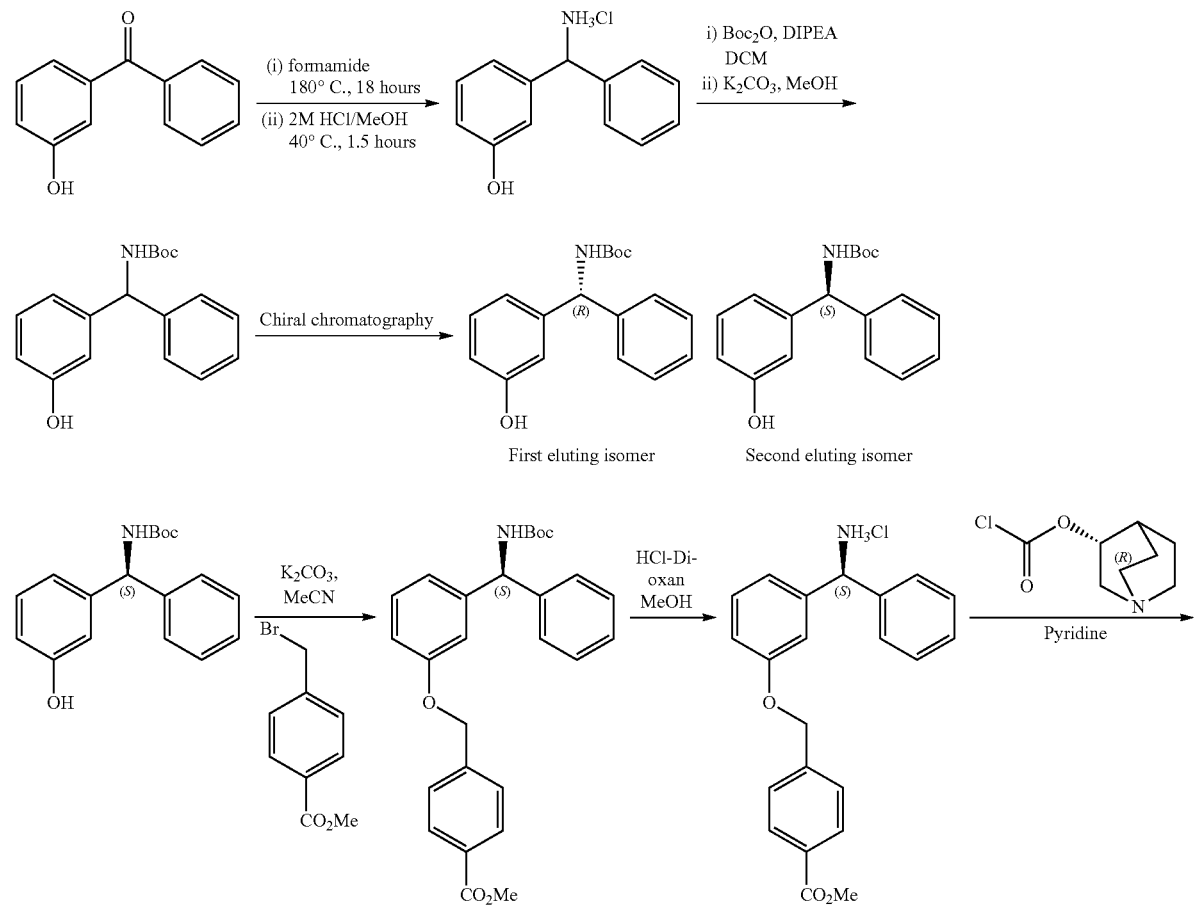

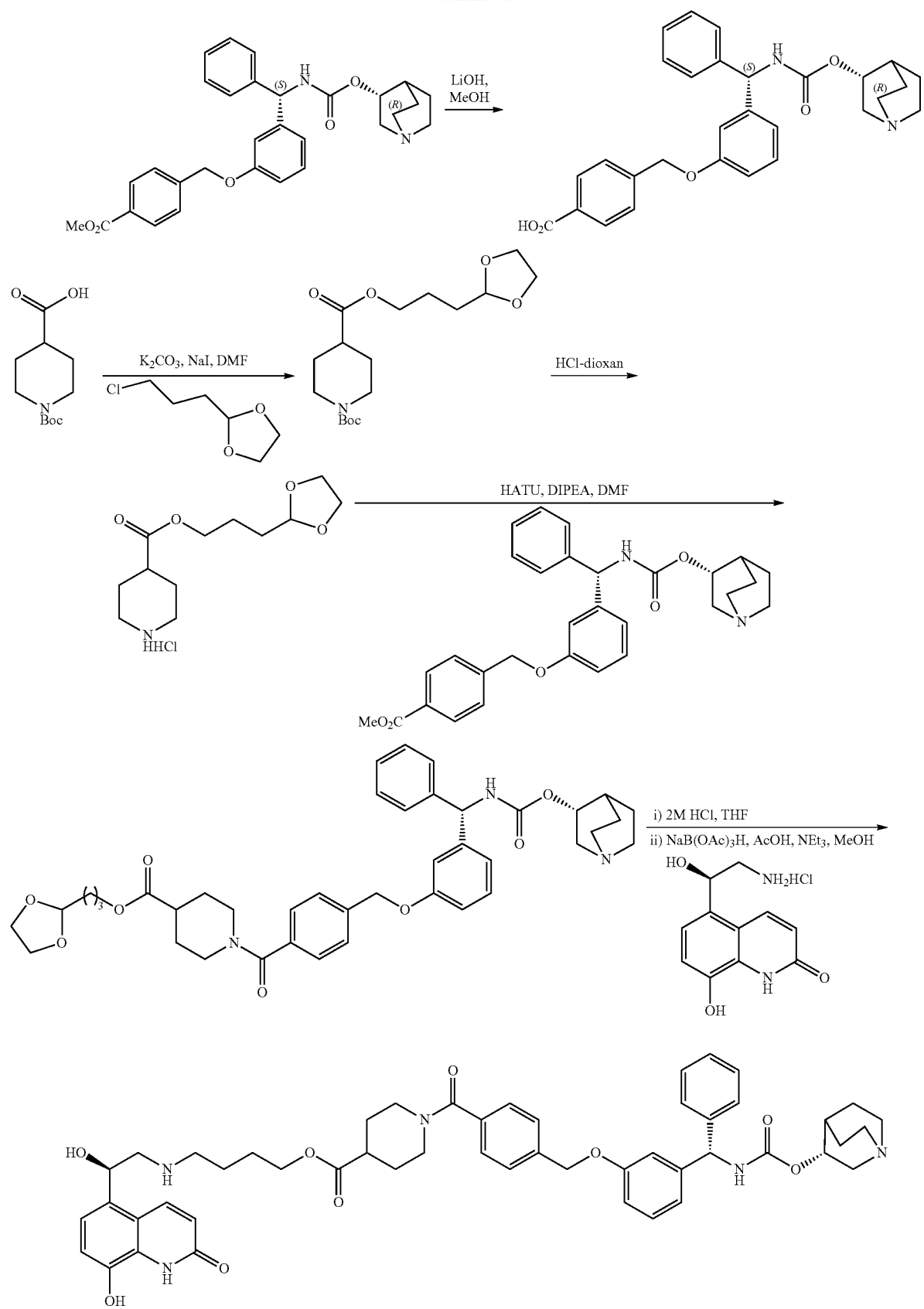

Example 1

4-(((R)-2-Hydroxy-2-(8-hydroxy-2-oxo-1,2-dihydro-quinolin-5-yl)ethyl)-amino)butyl 1-(4-((3-((S)-phenyl((((R)-quinuclidin-3-yloxy)carbonyl)amino)methyl)-phenoxy)methyl)benzoyl)piperidine-4-carboxylate (Compound 1)

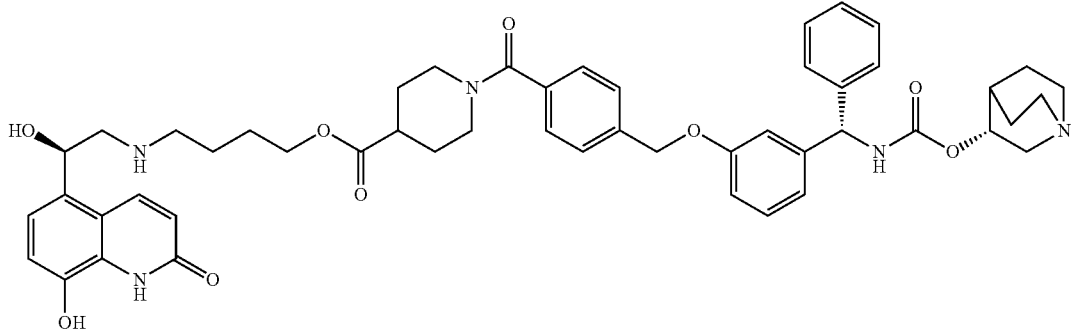 [SMILES: O=C(N[C@@H](c1ccccc1)c1cccc(OCc2ccc(C(=O)N3CCC(C(=O)OCCCCNC[C@H](O)c4ccc(O)c5[nH]c(=O)ccc45)CC3)cc2)c1)O[C@H]1CN2CCC1CC2]

Step 1
N-((3-Hydroxyphenyl)(phenyl)methyl)formamide

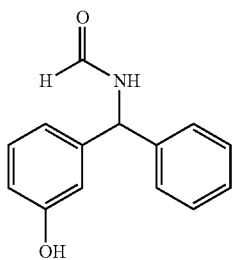 [SMILES: O=CNC(c1ccccc1)c1cccc(O)c1]

3-Hydroxybenzophenone (25 g, 126.1 mmol) in formamide (130 mL, 3.3 mmol) was heated to 180° C. for 18 hours. The reaction was allowed to cool slightly then poured into ice-cooled water, stirred for 30 minutes, filtered and washed with water. The solid was stirred in water (60 mL) and ethanol (60 mL) and heated to 50° C. for 1 hour, then allowed to cool. The solid was filtered and washed with water to give the title compound as a brown solid (33.94 g, 118%).

$^1$H NMR (400 MHz, CD$_3$OD): δ 7.39-7.28 (m, 5H); 7.21-7.13 (m, 1H); 6.79 (d, J=7.78 Hz, 1H); 6.73-6.68 (m, 2H); 5.45 (s, 1H).

Step 2: 3-(Amino(phenyl)methyl)phenol hydrochloride

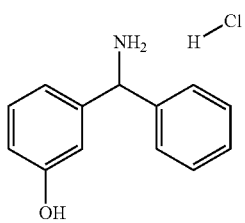

Methanol (125 mL), was cooled to 0° C. and acetyl chloride (17.8 mL) added dropwise to give a 2 M solution of methanolic hydrogen chloride. N-((3-hydroxyphenyl)(phenyl)methyl)formamide was stirred at 40° C. for 1.5 hours with the 2 M methanolic hydrogen chloride solution. The solvent was removed under reduced pressure and the residue re-dissolved in methanol and the solvent removed under reduced pressure. This process was repeated three times to give the title compound as a brown solid (29.09 g, 97.9%)

$^1$H NMR (400 MHz, DMSO-d$_6$): δ 9.76 (s, 1H); 9.07 (s, 3H); 7.59-7.53 (m, 2H); 7.51-7.37 (m, 3H); 7.26 (t, J=7.89 Hz, 1H); 6.99 (d, J=7.75 Hz, 1H); 6.90 (t, J=1.97 Hz, 1H); 6.81 (dd, J=8.10, 2.32 Hz, 1H); 5.58 (d, J=5.82 Hz, 1H).

Step 3: tert-Butyl ((3-hydroxyphenyl)(phenyl)methyl)carbamate

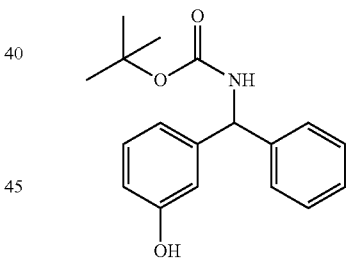

3-(Amino(phenyl)methyl)phenol hydrochloride (29.09 g, 123.4 mmol) in dichloromethane (450 mL) was cooled to 0° C. and diisopropylethylamine (65.9 mL, 370.2 mmol) and di-tert-butyl dicarbonate (59.2 g, 271.5 mmol) was added slowly. The reaction was stirred at 0° C. for 2 hours then warmed to RT over 16 hours. The solvent was removed and the residue purified through a silica plug, eluting with 0-20% ethyl acetate in iso-hexane to give a black oil. To this mixture in methanol (300 mL) was added potassium carbonate (51 g, 370.2 mmol) and stirred at RT for 16 hours. The suspension was filtered, the filtrate was evaporated at reduced pressure and the residue re-dissolved in ethyl acetate (370 mL). Silica (73 g) was added and the suspension was stirred for 30 minutes, filtered, and the filter cake washed with further ethyl acetate. The filtrate was evaporated to dryness. The dark solid residue was dissolved in ethyl acetate (200 mL), charcoal was added and the suspension was heated under refluxed for 1 hour. The suspension was filtered through celite and the solvent removed at reduced pressure. The dark solid was dissolved in dichloromethane, iso-hexane was added and the solvent evaporated (repeated 3 times) to give the title compound as a yellow solid (34.81 g, 92%).

$^1$H NMR (400 MHz, CDCl$_3$): δ 7.36-7.16 (m, 6H); 6.80 (d, J=7.79 Hz, 1H); 6.74-6.69 (m, 2H); 5.83 (s, 1H); 5.15 (s, 1H); 1.53-1.30 (s, 9H).

Step 4: (S)-tert-Butyl ((3-hydroxyphenyl)(phenyl)methyl)carbamate

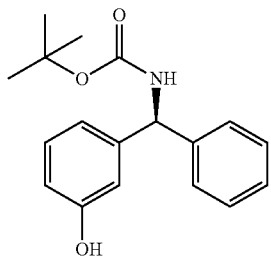 [SMILES: CC(C)(C)OC(=O)N[C@@H](c1ccccc1)c1cccc(O)c1]

The racemic mixture from step 3 was purified by SFC using a CHIRALPAK® AD 20 μM 250×110 mm column using n-heptane/2-propanol/diethylamine (60/40/0.1) as eluant with a flow rate of 570 ml/min at 25° C. From 54.1 g of crude material (S)-tert-butyl ((3-hydroxyphenyl)(phenyl)methyl)carbamate (R$_f$=8.5-8.6 min, 23.9 g, 99.2 e.e.) was obtained.

Step 5: (S)-Methyl 4-((3-(((tert-butoxycarbonyl)amino)(phenyl)methyl)-phenoxy)methyl)benzoate

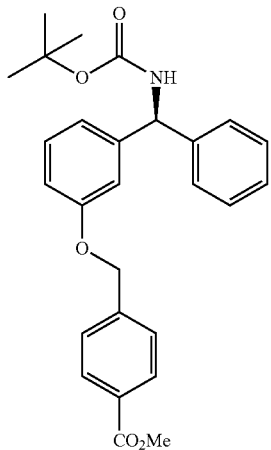

A mixture of (S)-tert-butyl ((3-hydroxyphenyl)(phenyl)methyl)carbamate (3.20 g, 10.7 mmol), methyl 4-(bromomethyl)benzoate (2.70 g, 11.8 mmol) and potassium carbonate (2.20 g, 16.1 mmol) in acetonitrile (54 mL) was stirred at RT for 16 hours. The reaction mixture was concentrated at reduced pressure and the residue partitioned between ethyl acetate and water. The aqueous phase was extracted with further ethyl acetate and the combined organic extracts combined, dried with anhydrous magnesium sulfate, filtered and the solvent evaporated at reduced pressure. The residue was recrystallised from ethyl acetate and iso-hexane to afford the title compound as a white solid (3.25 g, 68%).

$^1$H NMR (400 MHz, CDCl$_3$): δ 8.04 (d, J=8.2 Hz, 2H); 7.46 (d, J=8.2 Hz, 2H); 7.34-7.20 (m, 6H); 6.90-6.81 (m, 3H); 5.87 (s, 1H); 5.13 (s, 1H); 5.07 (s, 2H); 3.92 (s, 3H); 1.44 (s, 9H).

Step 6: (S)-Methyl 4-((3-(amino(phenyl)methyl)phenoxy)methyl)benzoate hydrochloride

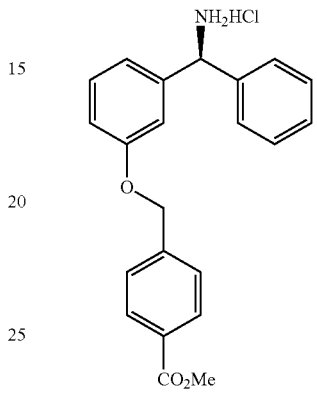

To a solution of (S)-methyl 4-((3-(((tert-butoxycarbonyl)amino)(phenyl)methyl)-phenoxy)methyl)benzoate (3.21 g, 7.20 mmol) in methanol (36 mL) was added hydrogen chloride in dioxane (4 M, 9.0 mL, 36 mmol). The reaction mixture was stirred at RT for 16 hours. The solvent was removed at reduced pressure to afford the title compound (2.65 g, >95%).

$^1$H NMR (400 MHz, CDCl$_3$): δ 9.21 (s, 2H); 8.03 (d, J=8.1 Hz, 2H); 7.64 (d, J=8.1 Hz, 2H); 7.59 (d, J=7.6 Hz, 2H); 7.49-7.34 (m, 5H); 7.17 (d, J=7.7 Hz, 1H); 7.06 (dd, J=8.3, 2.4 Hz, 1H); 5.64 (s, 1H); 5.28 (s, 2H); 3.91 (s, 3H).

Step 7

Methyl 4-((3-((S)-phenyl((((R)-quinuclidin-3-yloxy)carbonyl)amino)methyl)-phenoxy)methyl)benzoate

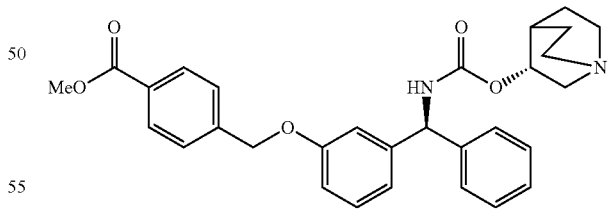

To a stirred solution of (S)-methyl 4-((3-(amino(phenyl)methyl)phenoxy)-methyl)benzoate hydrochloride (12.0 g, 31.3 mmol) in pyridine (100 mL) at 0° C. was added portion-wise (R)-quinuclidin-3-yl carbonochloridate (8.50 g, 37.5 mmol). The reaction was stirred at 0° C. for 1 hour and then allowed to warm to RT for 16 hours. Water was added to the reaction mixture and extracted with ethyl acetate (×3). The combined extracts were washed with brine, dried (sodium sulfate), filtered and the solvent evaporated at reduced pressure. The crude material was purified by chromatography on a KP-NH Biotage cartridge eluting with 0-20% methanol in ethyl acetate to afford the title compound (10.3 g, 66%).

Step 8; 4-((3-((S)-Phenyl((((R)-quinuclidin-3-yloxy)carbonyl)amino)methyl)-phenoxy)methyl)benzoic acid

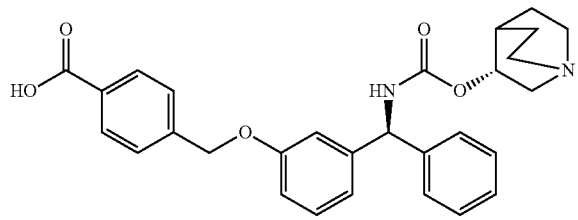 [SMILES: O=C(N[C@@H](c1ccccc1)c1cccc(OCc2ccc(C(=O)O)cc2)c1)O[C@H]1CN2CCC1CC2]

To a stirred solution of methyl 4-((3-((S)-phenyl((((R)-quinuclidin-3-yloxy)carbonyl)amino)methyl)phenoxy)methyl)benzoate (2.27 g, 4.50 mmol) in THF (23 mL) was added an aqueous solution of lithium hydroxide (2.0 M, 9.0 ml, 18.0 mmol). The mixture was stirred at RT for 16 hours. The pH of the reaction mixture was adjusted to 6 by the addition of 4M aqueous hydrochloric acid. The mixture was then extracted with 10% methanolic ethyl acetate (×2) and the combined organic extracts evaporated at reduced pressure. The residue was then dissolved in ethanol and re-evaporated at reduced pressure to afford the title compound as a pale yellow solid (1.85 g, 84%).

$^1$H NMR (400 MHz, DMSO-d$_6$): δ 8.41 (d, J=9.4 Hz, 1H); 7.99 (d, J=7.9 Hz, 2H); 7.58 (d, J=8.0 Hz, 2H); 7.42-7.26 (m, 6H); 7.09 (s, 1H); 7.02-6.91 (m, 2H); 5.87 (d, J=9 Hz, 1H); 5.21 (s, 2H); 4.76 (s, 1H); 3.98-2.72 (m, 6H); 2.12-1.54 (m, 5H).

Step 9: 4-(3-(1,3-Dioxolan-2-yl)propyl) 1-tert-butyl piperidine-1,4-dicarboxylate

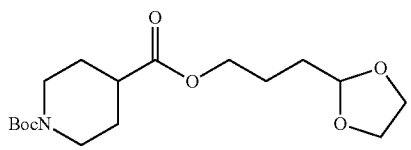 [SMILES: CC(C)(C)OC(=O)N1CCC(C(=O)OCCCC2OCCO2)CC1]

To a stirred solution of piperidine-4-carboxylic acid N-tert-butoxycarbonyl (1.86 g, 8.11 mmol) in DMF (20 mL) was added potassium carbonate (1.68 g, 12.2 mmol). The reaction mixture was stirred at RT for 20 minutes and then a solution of 2-(3-chloropropyl)-1,3-dioxolane (0.815 g, 5.41 mmol) in DMF (5 mL) and sodium iodide (0.973 g, 6.49 mmol) was added. The resultant mixture was heated at 80° C. for 18 hours. The reaction mixture was allowed to cool and diluted with ethyl acetate and water. The organic phase was removed, washed with brine (×2), dried (magnesium sulfate), filtered and the solvent evaporated at reduced pressure. The residue was purified by flash column chromatography eluting with 0 to 25% ethyl acetate/iso-hexane to afford the title compound (0.719 g, 39%).

$^1$H NMR (400 MHz, CDCl$_3$): δ 4.90-4.88 (m, 1H); 4.14-4.11 (m, 2H); 4.02-3.83 (m, 6H); 2.86-2.80 (m, 2H); 2.47-2.40 (m, 1H); 1.89-1.60 (m, 8H); 1.45 (s, 9H).

Step 10: 3-(1,3-Dioxolan-2-yl)propyl piperidine-4-carboxylate hydrochloride

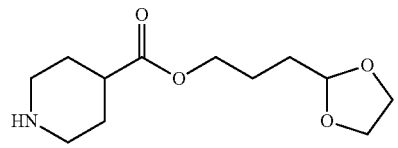 [SMILES: O=C(OCCCC1OCCO1)C1CCNCC1]

HCl-dioxane (4 M, 5 mL, 20 mmol) was added to 4-(3-(1,3-dioxolan-2-yl)propyl) 1-tert-butyl piperidine-1,4-dicarboxylate (0.71 g, 2.07 mmol) and the reaction mixture was stirred at RT for 1.5 hours. The solvent was evaporated at reduced pressure. The crude material was used directly without purification.

Step 11; 3-(1,3-Dioxolan-2-yl)propyl 1-(4-((3-((S)-phenyl((((R)-quinuclidin-3-yloxy)-carbonyl)amino)methyl)phenoxy)methyl)benzoyl)piperidine-4-carboxylate

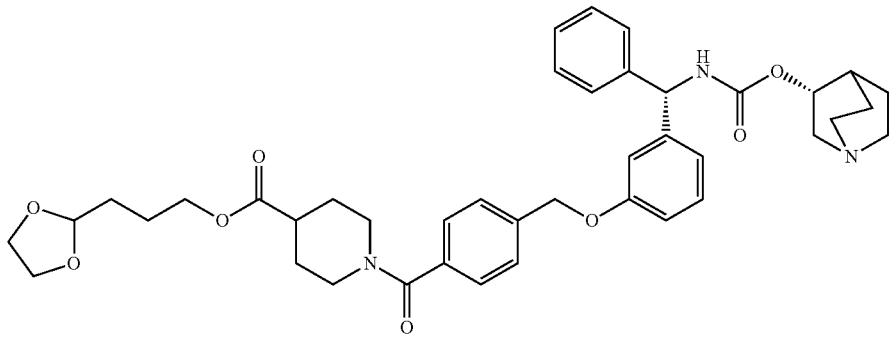 [SMILES: O=C(N[C@@H](c1ccccc1)c1cccc(OCc2ccc(C(=O)N3CCC(C(=O)OCCCC4OCCO4)CC3)cc2)c1)O[C@H]1CN2CCC1CC2]

To a stirred solution of 4-((3-((S)-phenyl((((R)-quinuclidin-3-yloxy)carbonyl)amino)methyl)phenoxy)methyl)benzoic acid (0.300 g, 0.57 mmol) in DMF (2.5 mL) was added di-iso-propylethylamine (0.40 mL, 2.29 mmol) and HATU (0.262 g, 0.69 mmol) and the mixture stirred at RT for 30 minutes. To the resultant solution was added a solution of 3-(1,3-dioxolan-2-yl)propyl piperidine-4-carboxylate hydrochloride (0.241 g, 0.86 mmol) in DMF (1.8 mL). The mixture was stirred at RT for 18 hours. The mixture was diluted with ethyl acetate, washed with 10% aqueous potassium carbonate, brine (×2), dried (magnesium sulfate), filtered and the solvent evaporated at reduced pressure. The residue was used directly in the next step with no further purification.

Step 12: 4-Oxobutyl 1-(4-((3-((S)-phenyl((((R)-quinuclidin-3-yloxy)carbonyl)amino)-methyl)phenoxy)methyl)benzoyl)piperidine-4-carboxylate

Step 13: 4-(((R)-2-Hydroxy-2-(8-hydroxy-2-oxo-1,2-dihydroquinolin-5-yl)ethyl)-amino)butyl 1-(4-((3-((S)-phenyl((((R)-quinuclidin-3-yloxy)carbonyl)amino)methyl)-phenoxy)methyl)benzoyl)piperidine-4-carboxylate (Compound 1)

To a suspension of (R)-5-(2-amino-1-hydroxyethyl)-8-hydroxyquinolin-2(1H)-one hydrochloride (0.136 g, 0.53 mmol) in methanol (3.5 mL) was added triethylamine (0.148 mL, 1.06 mmol). The mixture was stirred for 10 minutes and then a solution of 4-oxobutyl 1-(4-((3-((S)-phenyl((((R)-quinuclidin-3-yloxy)carbonyl)amino)methyl)-phenoxy)methyl)benzoyl)piperidine-4-carboxylate (0.337 g, 0.50 mmol) in methanol (3.4 mL) was added. The mixture was stirred at RT for 1 hour. Sodium triacetoxyborohydride (0.267 g, 1.26 mmol) followed by acetic acid (0.121 mL, 2.12 mmol) was added and the reaction continued for a further 18 hours. The reaction mixture was quenched with water and evaporated at reduced pressure. The residue dissolved in iso-butanol and washed with water. The organic phase was evaporated at reduced pressure and the crude

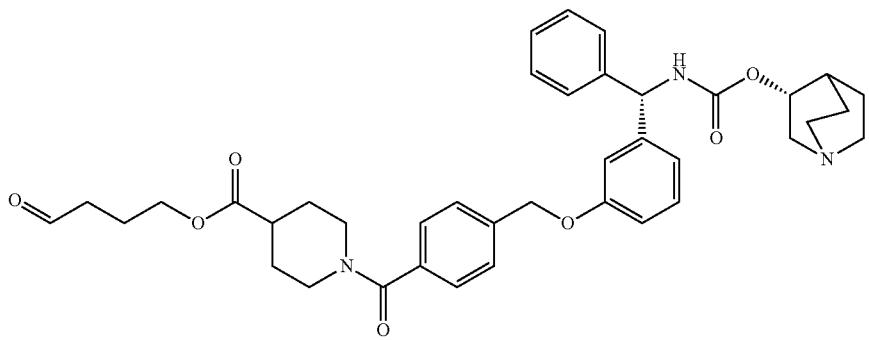 [SMILES: O=CCCCOC(=O)C1CCN(C(=O)c2ccc(COc3cccc([C@@H](NC(=O)O[C@H]4CN5CCC4CC5)c4ccccc4)c3)cc2)CC1]

To a solution of 3-(1,3-dioxolan-2-yl)propyl 1-(4-((3-((S)-phenyl((((R)-quinuclidin-3-yloxy)carbonyl)amino)methyl)phenoxy)methyl)benzoyl)piperidine-4-carboxylate in THF (4.7 mL) was added 2 M aqueous hydrochloric acid (4.7 mL). The reaction mixture was stirred at RT for 4 hours. The reaction mixture was partitioned between saturated sodium hydrogen carbonate and ethyl acetate. The organic phase removed and the aqueous phase was extracted with further ethyl acetate (×2). The combined organic phases were washed with brine, dried (magnesium sulfate), filtered and the solvent evaporated at reduced pressure. The residue was used directly in the next step with no further purification.

material was purified by reverse phase preparative HPLC to afford the title compound (0.072 g, 16%).

$^1$H NMR (400 MHz, DMSO-$d_6$ @85° C.): δ 8.23-8.17 (m, 3H); 7.78-7.70 (m, 1H); 7.48 (d, J=7.9 Hz, 2H); 7.41-7.20 (m, 8H); 7.08 (d, J=8.1 Hz, 1H); 7.05-7.01 (m, 1H); 6.97-6.88 (m, 3H); 6.49 (d, J=9.9 Hz, 1H); 5.83 (d, J=8.8 Hz, 1H); 5.12 (s, 2H); 5.04 (dd, J=7.7, 4.9 Hz, 1H); 4.63-4.57 (m, 1H); 4.06 (t, J=6.5 Hz, 2H); 3.98-3.86 (m, 1H); 3.13-3.03 (m, 3H); 2.83-2.52 (m, 9H); 1.94-1.83 (m, 3H); 1.80-1.70 (m, 1H); 1.67-1.37 (m, 9H); 1.36-1.25 (m, 1H). 1H obscured by water signal.

The following compounds were prepared as described in Example 1 using the appropriate tert-butoxycarbonyl amino-acid in Step 9 and the product in the subsequent steps.

| Cpd. | Appropriate tert-butoxycarbonyl amino-acid | Structure |
|---|---|---|
| 2 | (Boc-Ala-OH structure) | (Compound 2 structure) |
| 3 | (Boc-Val-OH structure) | (Compound 3 structure) |
| 4 | (Boc-Leu-OH structure) | (Compound 4 structure) |

-continued
| Cpd. | Appropriate tert-butoxycarbonyl amino-acid | Structure |
|---|---|---|
| 5 | 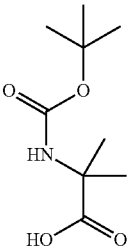 | 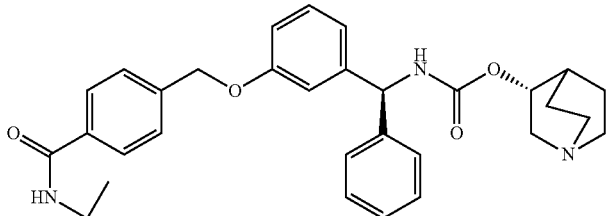 |
| 6 | 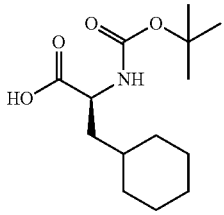 [SMILES: CC(C)(C)OC(=O)N[C@@H](CC1CCCCC1)C(=O)O] | 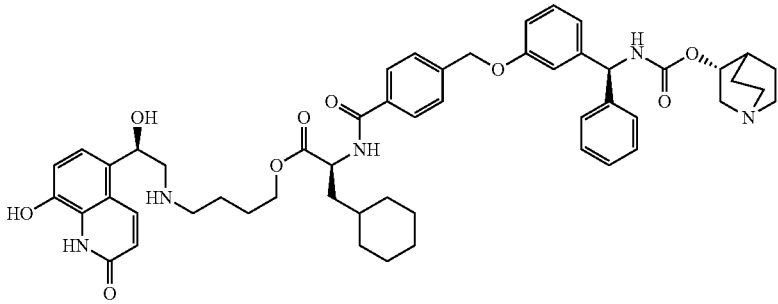 [SMILES: O=C(N[C@@H](c1ccccc1)c1cccc(OCc2ccc(C(=O)N[C@@H](CC3CCCCC3)C(=O)OCCCCNC[C@H](O)c3ccc(O)c4[nH]c(=O)ccc34)cc2)c1)O[C@H]1CN2CCC1CC2] |
| 7 | 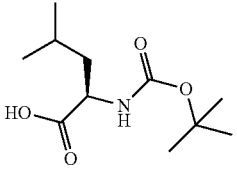 [SMILES: CC(C)C[C@@H](NC(=O)OC(C)(C)C)C(=O)O] | 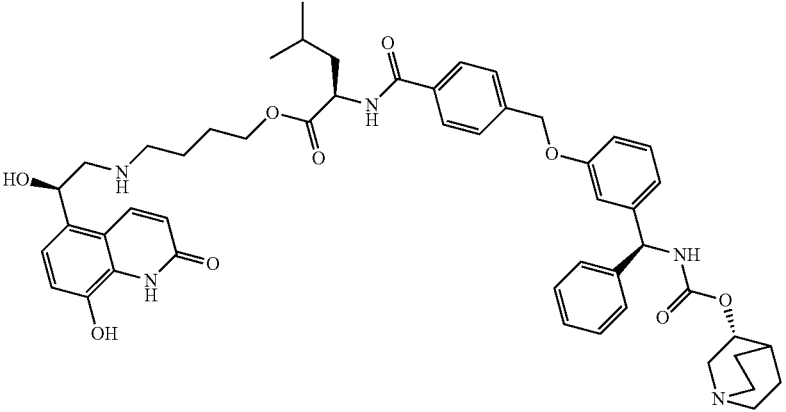 [SMILES: CC(C)C[C@@H](NC(=O)c1ccc(COc2cccc([C@@H](NC(=O)O[C@H]3CN4CCC3CC4)c3ccccc3)c2)cc1)C(=O)OCCCCNC[C@H](O)c1ccc(O)c2[nH]c(=O)ccc12] |

| Cpd. | Appropriate tert-butoxycarbonyl amino-acid | Structure |
|---|---|---|
| 8 | 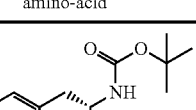 | 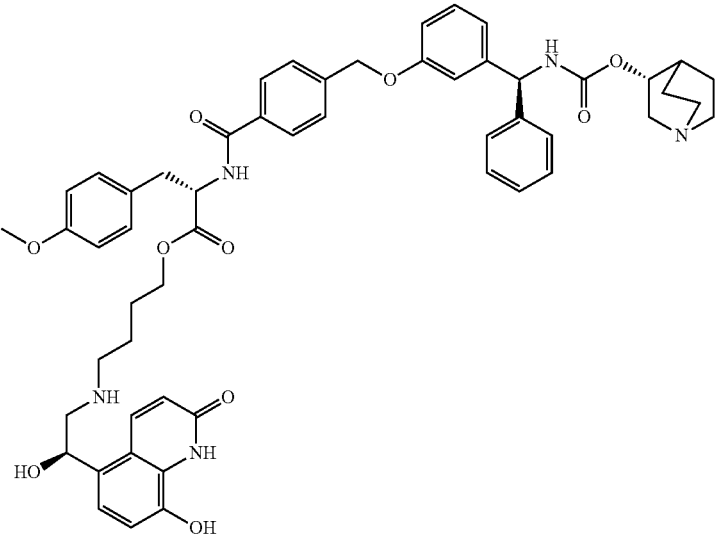 [SMILES: COc1ccc(C[C@H](NC(=O)c2ccc(COc3cccc([C@@H](NC(=O)O[C@H]4CN5CCC4CC5)c4ccccc4)c3)cc2)C(=O)OCCCCNC[C@H](O)c2ccc(O)c3[nH]c(=O)ccc23)cc1] |
| 9 | 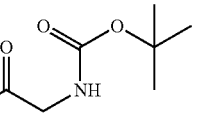 | 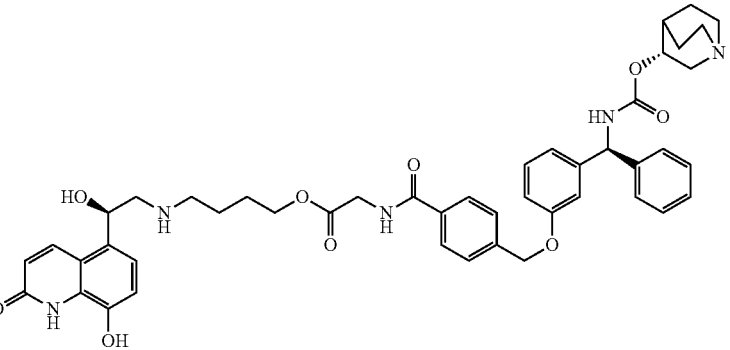 |

Example 1A (R)-Quinuclidin-3-yl ((S)-(3-((4-(4-(((R)-2-hydroxy-2-(8-hydroxy-2-oxo-1,2-dihydroquinolin-5-yl)ethyl)amino)piperidine-1-carbonyl)benzyl)oxy)phenyl)-(phenyl)methyl)carbamate (Compound 9A)

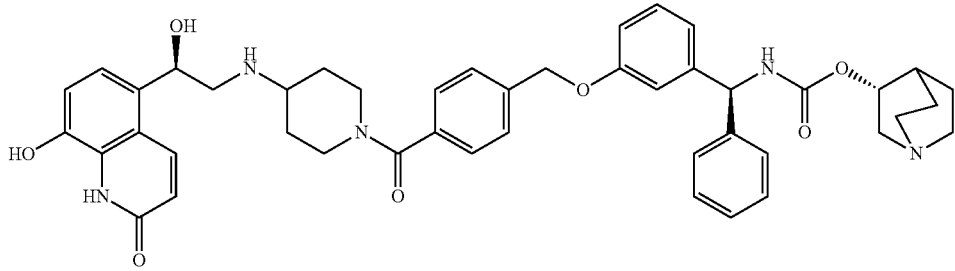 [SMILES: O=C(N[C@@H](c1ccccc1)c1cccc(OCc2ccc(C(=O)N3CCC(NC[C@H](O)c4ccc(O)c5[nH]c(=O)ccc45)CC3)cc2)c1)O[C@H]1CN2CCC1CC2]

The title compound was prepared as described in Example 1 with 1,4-dioxa-8-azaspiro[4.5]decane replacing of 3-(1,3-dioxolan-2-yl)propyl piperidine-4-carboxylate hydrochloride in Step 11 and the subsequent products used in Steps 12-13.

$^1$H NMR (400 MHz, DMSO-d$_6$, 105° C.): δ 8.25-8.17 (m, 3H); 7.57 (d, J=8.8 Hz, 1H); 7.47 (d, J=7.9 Hz, 2H); 7.37-7.27 (m, 6H); 7.28-7.20 (m, 2H); 7.09 (d, J=8.1 Hz, 1H); 7.03 (d, J=2.2 Hz, 1H); 6.98-6.88 (m, 3H); 6.49 (d, J=9.9 Hz, 1H); 5.83 (d, J=8.7 Hz, 1H); 5.12 (s, 2H); 5.04-4.97 (m, 1H); 4.64-4.58 (m, 1H); 3.87 (s, 2H); 3.12-3.00 (m, 3H); 2.83 (t, J=6.2 Hz, 2H); 2.79-2.56 (m, 6H); 1.93-1.89 (m, 1H); 1.79 (d, J=14.6 Hz, 3H); 1.64-1.56 (m, 1H); 1.52-1.45 (m, 1H); 1.34-1.22 (m, 3H).

Example 1B (R)-Quinuclidin-3-yl ((S)-(3-((4-(4-((((R)-2-hydroxy-2-(8-hydroxy-2-oxo-1,2-dihydroquinolin-5-yl)ethyl)amino)methyl)piperidine-1-carbonyl)benzyl)oxy)-phenyl)(phenyl)methyl)carbamate (Compound 9B)

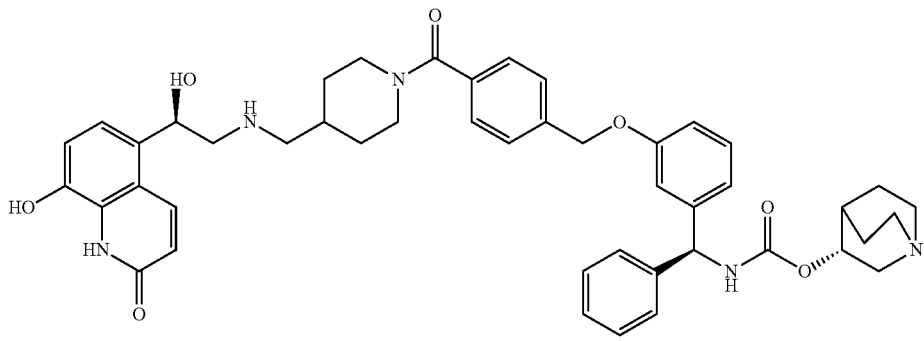 [SMILES: O=C(N[C@@H](c1ccccc1)c1cccc(OCc2ccc(C(=O)N3CCC(CNC[C@H](O)c4ccc(O)c5[nH]c(=O)ccc45)CC3)cc2)c1)O[C@H]1CN2CCC1CC2]

The title compound was prepared as in Example 1 with 4-(1,3-dioxolan-2-yl)piperidine replacing 3-(1,3-dioxolan-2-yl)propyl piperidine-4-carboxylate hydrochloride in Step 11 and the subsequent products used in Steps 12-13.

$^1$H NMR (400 MHz, DMSO-$d_6$, 110° C.): δ (d, J=9.9 Hz, 1H); 7.84 (d, J=8.6 Hz, 1H); 7.49 (d, J=7.9 Hz, 2H); 7.39-7.20 (m, 8H); 7.16 (d, J=8.2 Hz, 1H); 7.04-7.00 (m, 2H); 6.99-6.90 (m, 2H); 6.57 (d, J=9.9 Hz, 1H); 5.85 (d, J=8.7 Hz, 1H); 5.40 (dd, J=8.0, 5.0 Hz, 1H); 5.13 (s, 2H); 4.97-4.91 (m, 1H); 4.04 (d, J=13.5 Hz, 2H); 3.66 (ddd, J=14.0, 8.4, 2.6 Hz, 1H); 3.33-3.11 (m, 6H); 3.12-2.95 (m, 5H); 2.25 (d, J=4.4 Hz, 1H); 2.16-1.71 (m, 7H); 1.28 (dd, J=24.1, 12.0 Hz, 2H).

Example 1C 4-(((R)-2-hydroxy-2-(8-hydroxy-2-oxo-1,2-dihydroquinolin-5-yl)ethyl)amino)butyl 1-(3-((3-((S)-phenyl((((R)-quinuclidin-3-yloxy)carbonyl)amino)-methyl)phenoxy)methyl)benzoyl)piperidine-4-carboxylate (Compound 9C)

Step 1: 3-((3-((S)-Phenyl((((R)-quinuclidin-3-yloxy)carbonyl)amino)methyl)-phenoxy)methyl)benzoic acid

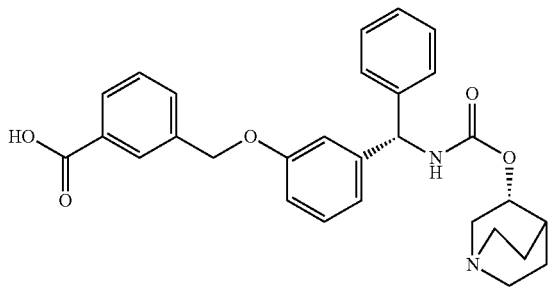

The title compound was prepared as described in Example 1 Step 5 to Step 8 with methyl 3-(bromomethyl)benzoate replacing methyl 4-(bromomethyl)benzoate in Step 5 and the products used in subsequent steps.

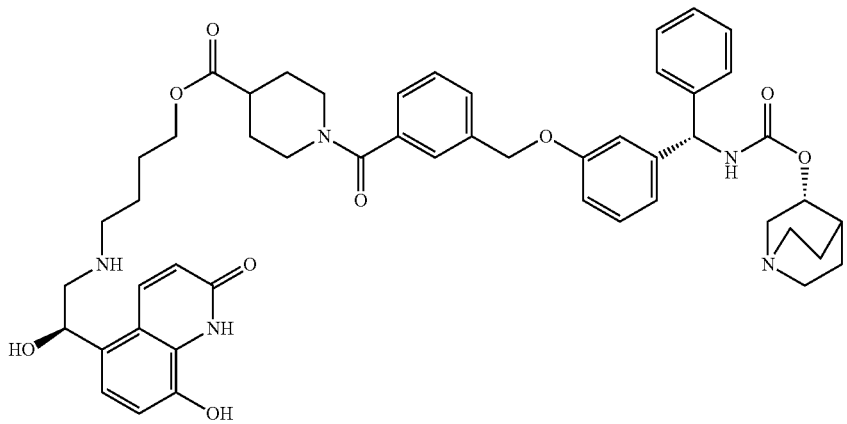 [SMILES: O=C(N[C@@H](c1ccccc1)c1cccc(OCc2cccc(C(=O)N3CCC(C(=O)OCCCCNC[C@H](O)c4ccc(O)c5[nH]c(=O)ccc45)CC3)c2)c1)O[C@H]1CN2CCC1CC2]

$^1$H NMR (400 MHz, DMSO-d$_6$/D$_2$O): δ 8.27 (s, 1H); 7.96 (s, 1H); 7.84 (d, J=7.7 Hz, 1H); 7.55 (d, J=7.7 Hz, 1H); 7.46-7.40 (m, 1H); 7.31-7.18 (m, 7H); 7.02 (s, 1H); 6.88 (t, J=9.5 Hz, 2H); 5.78 (s, 1H); 5.14 (s, 2H); 4.72 (s, 1H); 3.36 (m, 1H); 3.06-2.72 (m, 5H); 2.09-2.02 (m, 1H), 1.94 (s, 1H); 1.77 (s, 1H); 1.70-1.51 (m, 2H).

Step 2: 4-(((R)-2-hydroxy-2-(8-hydroxy-2-oxo-1,2-dihydroquinolin-5-yl)ethyl)amino)-butyl 1-(3-((3-((S)-phenyl((((R)-quinuclidin-3-yloxy)carbonyl)amino)methyl)phenoxy)-methyl)benzoyl)piperidine-4-carboxylate (Compound 9C)

The title compound was prepared as described in Example 1 Step 11 to Step 13 with 3-((3-((S)-phenyl((((R)-quinuclidin-3-yloxy)carbonyl)amino)methyl)phenoxy)-methyl)benzoic acid replacing 4-((3-((S)-phenyl((((R)-quinuclidin-3-yloxy)carbonyl)-amino)methyl)phenoxy)methyl)benzoic acid in Step 11 and the products used in subsequent steps.

$^1$H NMR (400 MHz, DMSO-d$_6$): δ 10.50 (s, 2H); 9.69 (s, 1H); 8.65 (s, 3H); 8.45 (d, J=9.2 Hz, 1H); 8.16 (d, J=10.0 Hz, 1H); 7.55-7.41 (m, 3H); 7.35-7.20 (m, 7H); 7.15 (d, J=8.2 Hz, 1H); 7.05-6.92 (m, 3H); 6.91 (dd, J=8.2, 2.4 Hz, 1H); 6.58 (d, J=9.9 Hz, 1H); 6.19 (s, 1H); 5.83 (d, J=9.1 Hz, 1H); 5.32 (d, J=9.7 Hz, 1H); 5.12 (s, 2H); 4.88-4.83 (m, 1H); 4.33 (s, 1H); 4.10-4.04 (m, 2H); 3.69-3.51 (m, 2H); 3.36-2.90 (m, 8H); 2.70-2.60 (m, 1H); 2.23 (s, 1H); 2.12-2.01 (m, 1H); 1.97-1.52 (m, 12H).

Example 1D 4-(((R)-2-Hydroxy-2-(8-hydroxy-2-oxo-1,2-dihydroquinolin-5-yl)ethyl)-amino)butyl 1-(5-((3-((S)-phenyl((((R)-quinuclidin-3-yloxy)carbonyl)amino)methyl)-phenoxy)methyl)furan-2-carbonyl)piperidine-4-carboxylate (Compound 9D)

Step 1: 5-((3-((S)-Phenyl((((R)-quinuclidin-3-yloxy)carbonyl)amino)methyl)-phenoxy)methyl)furan-2-carboxylic acid

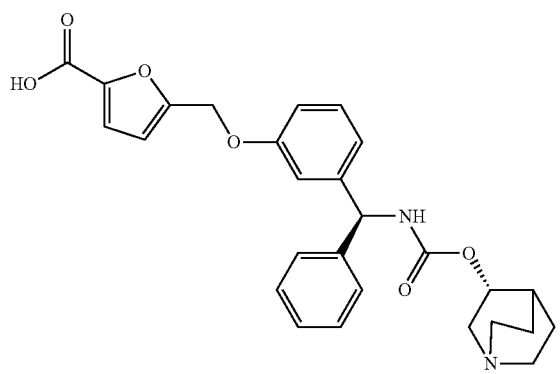

The title compound was prepared as described in Example 1 Step 5 to Step 8 with methyl 5-(chloromethyl)furan-2-carboxylate replacing methyl 4-(bromomethyl)benzoate in Step 5 and the products used in subsequent steps.

$^1$H NMR (400 MHz, DMSO-d$_6$): δ 8.32 (d, J=9.3 Hz, 1H); 7.36-7.28 (m, 4H); 7.28-7.20 (m, 2H); 7.08 (s, 1H); 6.91 (t, J=9.4 Hz, 2H); 6.83 (d, J=3.3 Hz, 1H); 6.58 (d, J=3.3 Hz, 1H); 5.82 (d, J=9.2 Hz, 1H); 5.06 (s, 2H); 4.73 (s, 1H); 2.98 (s, 2H); 2.88 (s, 2H); 2.76 (d, J=14.8 Hz, 1H); 2.07 (s, 1H); 1.94 (s, 1H); 1.73 (s, 1H); 1.65 (s, 2H); 1.55 (s, 1H).

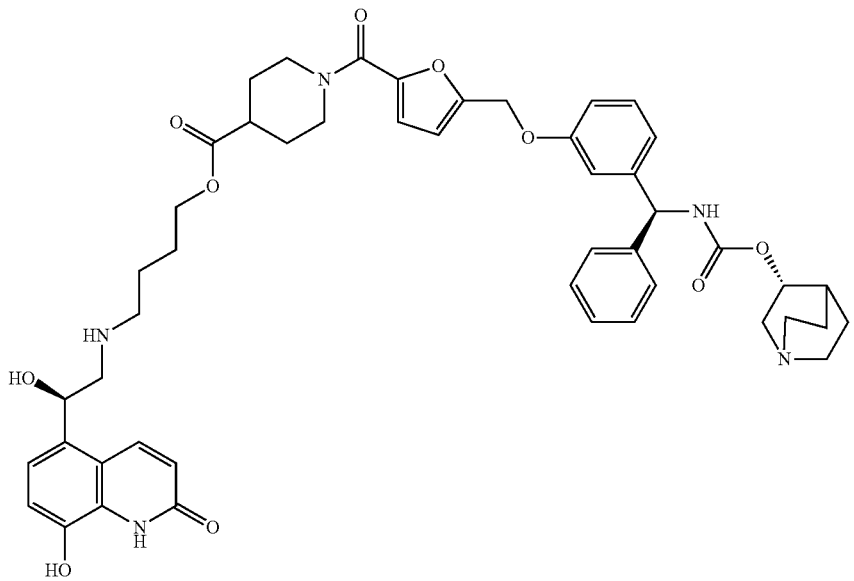 [SMILES: O=C(N[C@@H](c1ccccc1)c1cccc(OCc2ccc(C(=O)N3CCC(C(=O)OCCCCNC[C@H](O)c4ccc(O)c5[nH]c(=O)ccc45)CC3)o2)c1)O[C@H]1CN2CCC1CC2]

Step 2: 4-(((R)-2-Hydroxy-2-(8-hydroxy-2-oxo-1,2-dihydroquinolin-5-yl)ethyl)amino)-butyl 1-(5-((3-((S)-phenyl((((R)-quinuclidin-3-yloxy)carbonyl)amino)methyl)phenoxy)-methyl)furan-2-carbonyl)piperidine-4-carboxylate (Compound 9D)

The title compound was prepared as described in Example 1 Step 11 to Step 13 with 5-((3-((S)-phenyl((((R)-quinuclidin-3-yloxy)carbonyl)amino)methyl)phenoxy)-methyl)furan-2-carboxylic acid replacing 4-((3-((S)-phenyl((((R)-quinuclidin-3-yloxy)carbonyl)amino)methyl)phenoxy)methyl)benzoic acid in Step 11 and the products used in subsequent steps.

$^1$H NMR (400 MHz, DMSO-$d_6$): δ 8.36-8.08 (m, 4H); 7.33-7.19 (m, 6H); 7.11 (d, J=8.2 Hz, 1H); 7.03 (s, 1H); 6.97-6.90 (m, 4H); 6.68 (d, J=3.4 Hz, 1H); 6.53 (d, J=9.9 Hz, 1H); 5.82 (d, J=9.2 Hz, 1H); 5.20 (dd, J=8.0, 4.6 Hz, 1H); 5.10 (s, 2H); 4.60 (s, 1H); 4.16 (d, J=13.1 Hz, 2H); 4.05 (t, J=5.9 Hz, 2H); 3.18-3.07 (m, 1H); 2.90-2.55 (m, 9H); 1.88 (d, J=17.3 Hz, 4H); 1.67-1.31 (m, 12H).

Example 1E 4-(((R)-2-Hydroxy-2-(8-hydroxy-2-oxo-1,2-dihydroquinolin-5-yl)ethyl)-amino)butyl 1-(1-methyl-5-((3-((S)-phenyl((((R)-quinuclidin-3-yloxy)carbonyl)amino)-methyl)phenoxy)methyl)-1H-pyrazole-3-carbonyl)piperidine-4-carboxylate (Compound 9E)

Step 1: 1-Methyl-5-((3-((S)-phenyl((((R)-quinuclidin-3-yloxy)carbonyl)amino)-methyl)phenoxy)methyl)-1H-pyrazole-3-carboxylic acid

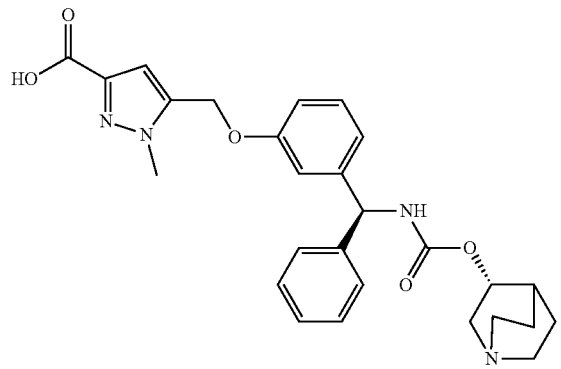

The title compound was prepared as described in Example 1 Step 5 to Step 8 with 5-bromomethyl-1-methyl-1H-pyrazole-3-carboxylic acid methyl ester replacing methyl 4-(bromomethyl)benzoate in Step 5 and the products used in subsequent steps.

$^1$H NMR (400 MHz, DMSO-$d_6$): δ 8.26 (d, J=9.3 Hz, 1H); 7.33-7.18 (m, 6H); 7.07 (s, 1H); 6.99-6.91 (m, 2H); 6.74 (s, 1H); 5.82 (d, J=9.2 Hz, 1H); 5.18 (s, 2H); 4.60 (s, 2H); 3.88 (s, 3H); 3.18-3.07 (m, 1H); 2.74 (m, 4H); 1.94 (s, 1H); 1.83 (s, 1H); 1.62 (s, 1H); 1.52 (s, 1H); 1.39 (s, 1H).

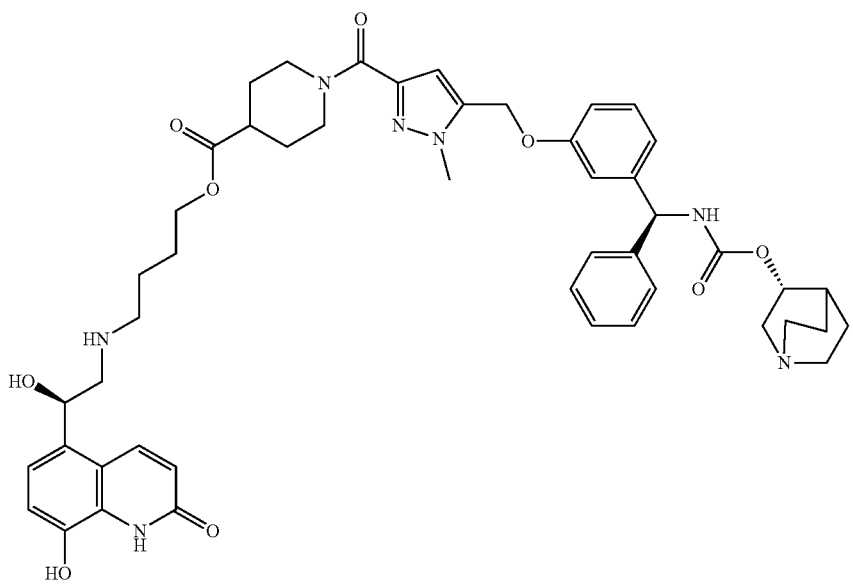 [SMILES: Cn1nc(C(=O)N2CCC(C(=O)OCCCCNC[C@H](O)c3ccc(O)c4[nH]c(=O)ccc34)CC2)cc1COc1cccc([C@@H](NC(=O)O[C@H]2CN3CCC2CC3)c2ccccc2)c1]

Step 2; 4-(((R)-2-Hydroxy-2-(8-hydroxy-2-oxo-1,2-dihydroquinolin-5-yl)ethyl)amino)-butyl 1-(1-methyl-5-((3-((S)-phenyl((((R)-quinuclidin-3-yloxy)carbonyl)amino)methyl)-phenoxy)methyl)-1H-pyrazole-3-carbonyl)piperidine-4-carboxylate (Compound 9E)

The title compound was prepared as described in Example 1 Step 11 to Step 13 with 1-methyl-5-((3-((S)-phenyl((((R)-quinuclidin-3-yloxy)carbonyl)amino)methyl)-phenoxy)methyl)-1H-pyrazole-3-carboxylic acid replacing 4-((3-((S)-phenyl((((R)-quinuclidin-3-yloxy)carbonyl)amino)methyl)phenoxy)methyl)benzoic acid in Step 11 and the products used in subsequent steps.

$^1$H NMR (400 MHz, DMSO-d$_6$): δ 8.34-8.18 (m, 3H); 8.18 (d, J=9.9 Hz, 1H); 7.34-7.18 (m, 6H); 7.13-7.04 (m, 2H); 6.99-6.90 (m, 3H); 6.67 (s, 1H); 6.53 (d, J=9.9 Hz, 1H); 5.83 (d, J=9.1 Hz, 1H); 5.20-5.11 (m, 3H); 4.59 (s, 1H); 4.50 (d, J=12.8 Hz, 1H); 4.34 (s, 1H); 4.08-4.01 (m, 2H); 3.87 (s, 3H); 3.34-3.02 (m, 2H); 2.89-2.55 (m, 10H); 1.95-1.79 (m, 4H); 1.69-1.36 (m, 10H).

Example 1F

Quinuclidin-3-yl((S)-(3-((3-(4-((((R)-2-hydroxy-2-(8-hydroxy-2-oxo-1,2-dihydroquinolin-5-yl)ethyl)amino)methyl)piperidine-1-carbonyl)-1-methyl-1H-pyrazol-5-yl)methoxy)phenyl)(phenyl)methyl)carbamate (Compound 9F)

Example 1G (R)-Quinuclidin-3-yl ((3-((3-(4-((((R)-2-hydroxy-2-(8-hydroxy-2-oxo-1,2-dihydroquinolin-5-yl)ethyl)amino)methyl)piperidine-1-carbonyl)benzyl)oxy)-phenyl)(phenyl)methyl)carbamate (Compound 9G)

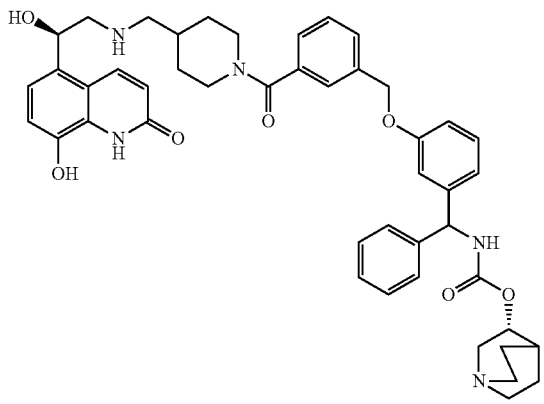

The title compound was prepared as described Example 1 with 4-(1,3-dioxolan-2-yl)piperidine replacing 3-(1,3-di-

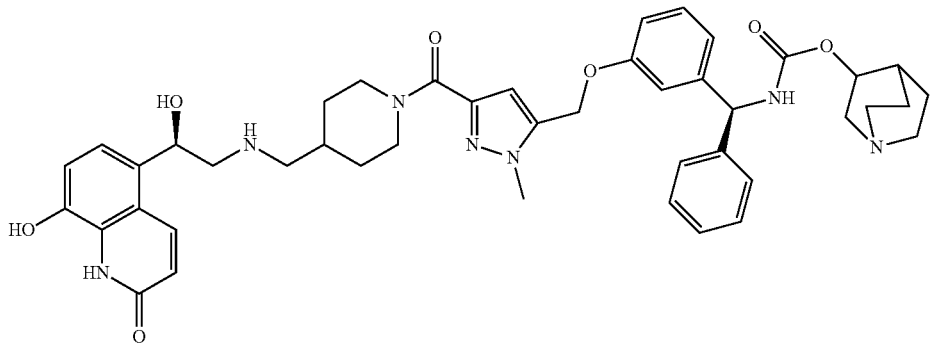 [SMILES: Cn1nc(C(=O)N2CCC(CNC[C@H](O)c3ccc(O)c4[nH]c(=O)ccc34)CC2)cc1COc1cccc([C@@H](NC(=O)OC2CN3CCC2CC3)c2ccccc2)c1]

The title compound was prepared as described Example 1 with 4-(1,3-dioxolan-2-yl)piperidine replacing 3-(1,3-dioxolan-2-yl)propyl piperidine-4-carboxylate hydrochloride and 1-methyl-5-((3-((S)-phenyl((((R)-quinuclidin-3-yloxy)carbonyl)amino)-methyl)phenoxy)methyl)-1H-pyrazole-3-carboxylic acid replacing 4-((3-((S)-phenyl((((R)-quinuclidin-3-yloxy)carbonyl)amino)methyl)phenoxy)-methyl)benzoic acid in Step 11 and the subsequent products used in Steps 12-13.

$^1$H NMR (400 MHz, DMSO, 110° C.): δ 8.20 (d, J=9.9 Hz, 1H); 7.84 (d, J=8.7 Hz, 1H); 7.34-7.21 (m, 6H); 7.16 (d, J=8.2 Hz, 1H); 7.04-6.92 (m, 4H); 6.61-6.55 (m, 2H); 5.86 (d, J=8.6 Hz, 1H); 5.39 (dd, J=8.0, 5.0 Hz, 1H); 5.18 (s, 2H); 4.96-4.91 (m, 1H); 4.52 (d, J=13.0 Hz, 2H); 3.88 (s, 3H); 3.65-2.94 (m, 10H); 2.26 (d, J=4.5 Hz, 1H); 2.18-1.76 (m, 9H); 1.27 (dd, J=12.2, 4.1 Hz, 2H).

oxolan-2-yl)propyl piperidine-4-carboxylate hydrochloride and 3-((3-((S)-phenyl((((R)-quinuclidin-3-yloxy)carbonyl)amino)-methyl)phenoxy)methyl)benzoic acid replacing 4-((3-((S)-phenyl((((R)-quinuclidin-3-yloxy)carbonyl)amino)methyl)phenoxy)methyl)benzoic acid in Step 11 and the subsequent products used in Steps 12-13.

$^1$H NMR (400 MHz, DMSO-d$_6$, @ 110° C.); 8.22 (d, J=9.9 Hz, 1H); 8.15 (s, 2H); 7.54 (d, J=8.3 Hz, 1H); 7.49-7.39 (m, 3H); 7.32-7.30 (m, 5H); 7.23 (t, J=8.2 Hz, 2H); 7.09 (d, J=8.2 Hz, 1H); 7.02 (dd, J=2.1, 2.1 Hz, 1H); 6.98-6.89 (m, 3H); 6.49 (d, J=9.8 Hz, 1H); 5.83 (d, J=8.7 Hz, 1H); 5.13 (s, 2H); 5.05 (dd, J=4.8, 7.6 Hz, 1H); 4.65-4.61 (m, 1H); 4.02-3.91 (m, 2H); 3.12 (dd, J=8.3, 14.4 Hz, 1H); 2.90-2.61 (m, 8H); 2.60-2.51 (m, 3H); 1.93 (dd, J=3.2, 6.3 Hz, 1H); 1.83-1.45 (m, 6H); 1.37-1.30 (m, 1H); 1.18-1.07 (m, 2H).

Synthesis of Compounds 10 to 15
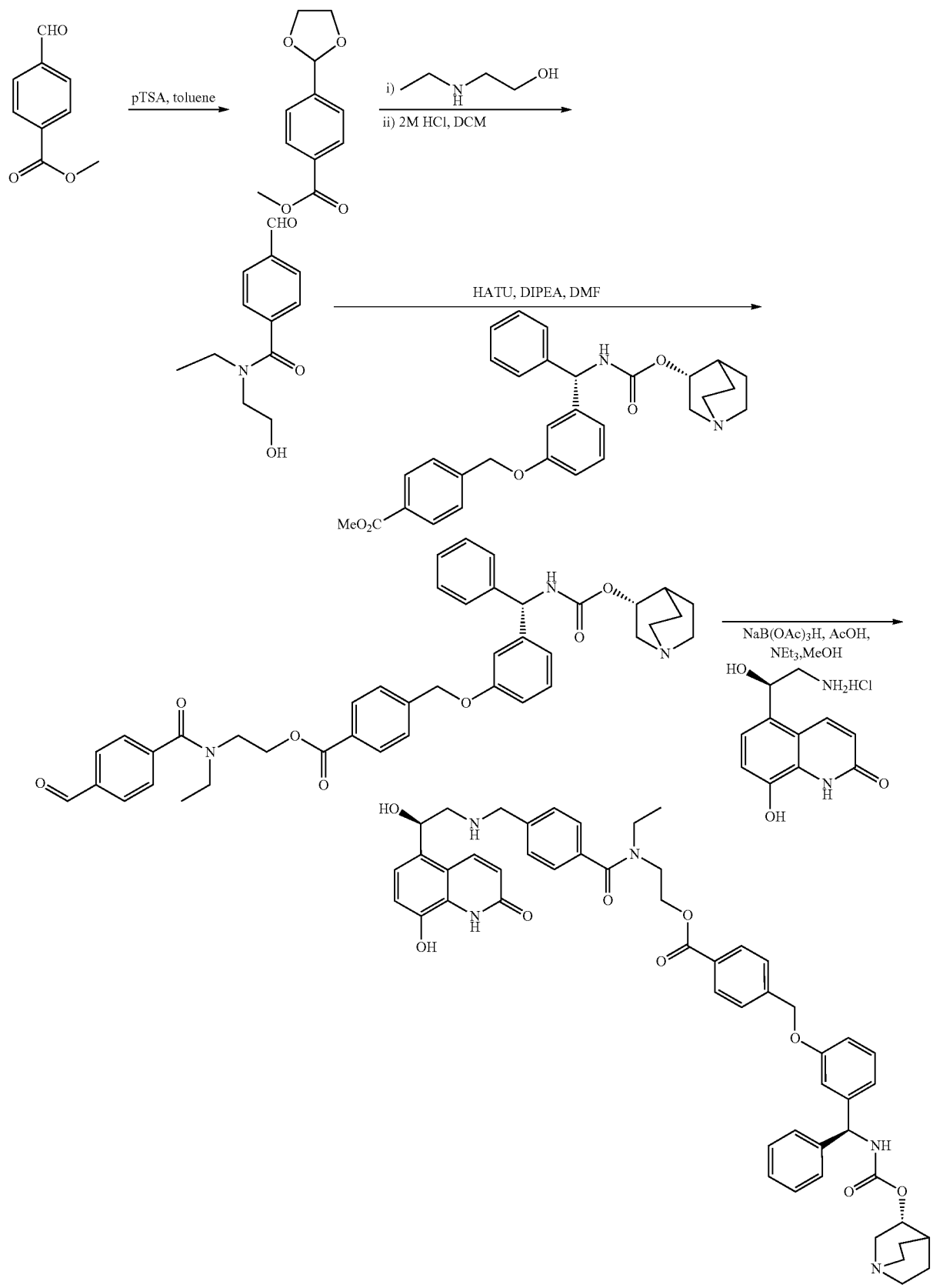

Example 2

2-(N-Ethyl-4-(((((R)-2-hydroxy-2-(8-hydroxy-2-oxo-1,2-dihydroquinolin-5-yl)ethyl)amino)methyl)benzamido)ethyl 4-((3-((S)-phenyl((((R)-quinuclidin-3-yloxy)carbonyl)amino)methyl)phenoxy)methyl)benzoate (Compound 10)

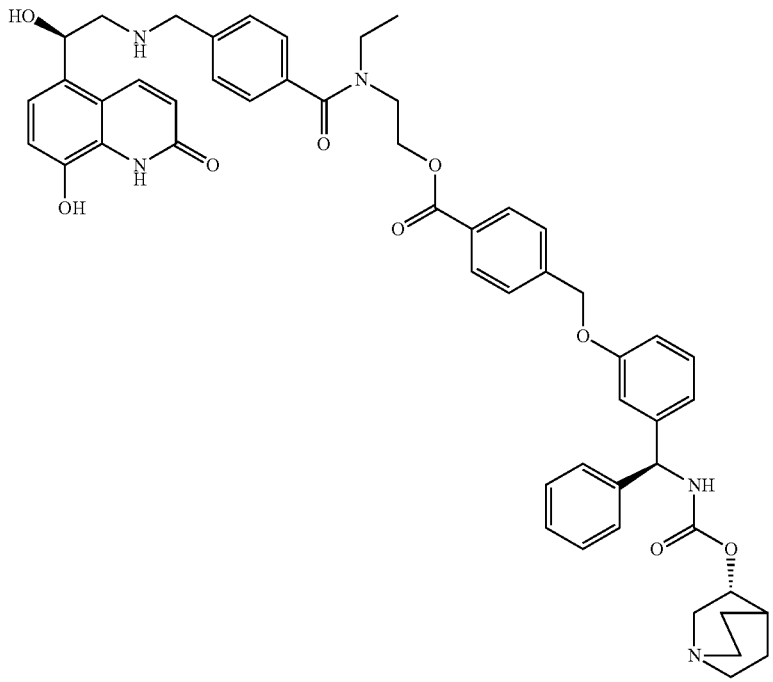

Step 1: Methyl 4-(1,3-dioxolan-2-yl)benzoate

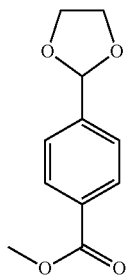

To stirred solution of methyl 4-formylbenzoate (5.0 g, 30.46 mmol) in toluene (196 mL) was added ethylene glycol (8.49 mL, 152.3 mmol) and para-toluenesulfonic acid monohydrate (0.58 g, 3.05 mmol). The reaction mixture was heated at reflux under Dean and Stark conditions for 1.5 hours. The solvent was evaporated at reduced pressure and the residue partitioned between ethyl acetate and saturated aqueous sodium hydrogen carbonate. The organic phase was removed and washed with further saturated aqueous sodium hydrogen carbonate, brine and dried (magnesium sulfate). The mixture was filtered and the solvent evaporated at reduced pressure to afford the title compound (6.29 g, 99%).

$^1$H NMR (400 MHz, CDCl$_3$): δ 8.09-8.02 (m, 2H); 7.58-7.51 (m, 2H); 5.86 (s, 1H); 4.16-4.01 (m, 4H); 3.92 (s, 3H).

Step 2: N-Ethyl-4-formyl-N-(2-hydroxyethyl)benzamide

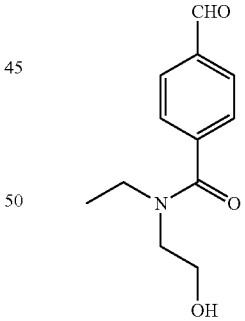

A solution of methyl 4-(1,3-dioxolan-2-yl)benzoate (0.63 g, 3.0 mmol) in 2-(ethylamino)ethanol (2.93 mL, 30.0 mmol) was heated in a microwave at 130° C. for 2 hours. The reaction mixture was partitioned between DCM and 1M aqueous hydrochloric acid and stirred vigorously for 1 hour. The organic phase was removed, washed with brine and passed through a hydrophobic frit. The solvent was evaporated at reduced pressure to afford the title compound (0.334 g, 50%).

$^1$H NMR (400 MHz, CDCl$_3$): δ 10.06 (s, 1H); 7.95 (d, J=7.8 Hz, 2H); 7.58 (d, J=7.9 Hz, 2H); 3.76 (t, J=57.5 Hz, 4H); 3.44-3.16 (m, 3H); 1.18-1.11 (m, 3H).

Step 3: 2-(N-Ethyl-4-formylbenzamido)ethyl 4-((3-((S)-phenyl((((R)-quinuclidin-3-yloxy)carbonyl)amino)methyl)phenoxy)methyl)benzoate

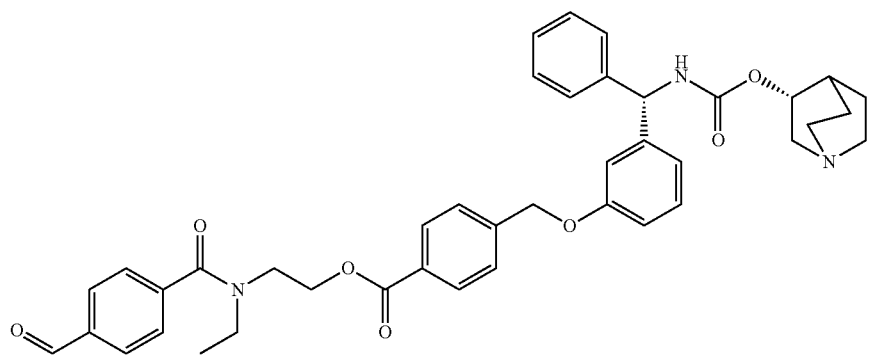 [SMILES: CCN(CCOC(=O)c1ccc(COc2cccc([C@@H](NC(=O)O[C@H]3CN4CCC3CC4)c3ccccc3)c2)cc1)C(=O)c1ccc(C=O)cc1]

The title compound was prepared as described in Example 1 Step 11 with N-ethyl-4-formyl-N-(2-hydroxyethyl)benzamide replacing 3-(1,3-dioxolan-2-yl)propyl piperidine-4-carboxylate hydrochloride. The product was used directly without further purification.

Step 4; 2-(N-Ethyl-4-(((((R)-2-hydroxy-2-(8-hydroxy-2-oxo-1,2-dihydroquinolin-5-yl)ethyl)amino)methyl)benzamido)ethyl 4-((3-((S)-phenyl((((R)-quinuclidin-3-yloxy)carbonyl)amino)methyl)phenoxy)methyl)benzoate (Compound 10)

The title compound was prepared as described in Example 1 Step 13 with 2-(N-ethyl-4-formylbenzamido)ethyl 4-((3-((S)-phenyl((((R)-quinuclidin-3-yloxy)carbonyl)amino)-methyl)phenoxy)methyl)benzoate replacing 4-oxobutyl 1-(4-((3-((S)-phenyl((((R)-quinuclidin-3-yloxy)carbonyl)amino)methyl)phenoxy)methyl)benzoyl)piperidine-4-carboxylate.

$^1$H NMR (400 MHz, DMSO-d$_6$): δ 10.30 (bs, 1H); 8.28-8.21 (m, 2H); 8.11 (d, J=9.9 Hz, 1H); 8.04-7.84 (m, 2H); 7.58 (d, J=8.0 Hz, 2H); 7.40-7.18 (m, 10H); 7.09-7.02 (m, 2H); 6.97-6.86 (m, 3H); 6.48 (d, J=9.9 Hz, 1H); 5.82 (d, J=9.1 Hz, 1H); 5.18 (s, 2H); 5.07 (dd, J=8.0, 4.3 Hz, 1H); 4.62-4.30 (m, 3H); 3.85-3.07 (m, 7H); 2.81-2.54 (m, 7H); 1.95-1.74 (m, 2H); 1.66-1.29 (m, 3H); 1.23-0.98 (m, 3H).

The following compounds were prepared as described in Example 2 using the appropriate amine in Step 2 and the product in the subsequent steps.

| Cpd. | Appropriate amine | Structure |
|---|---|---|
| 11 | 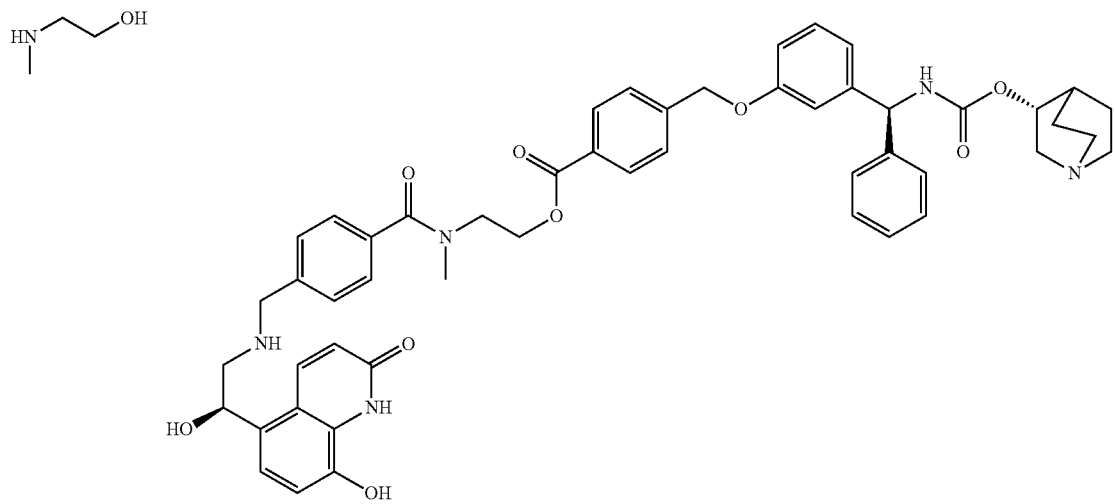 | 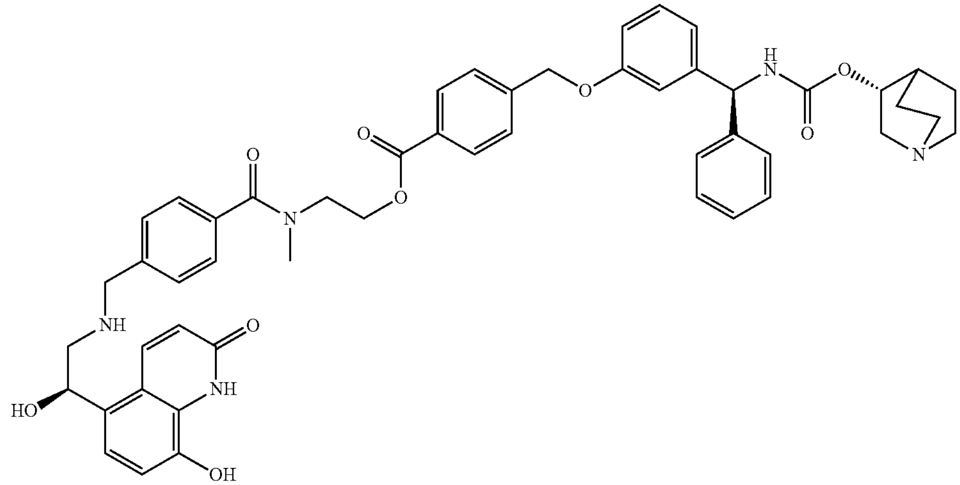 [SMILES: CN(CCOC(=O)c1ccc(COc2cccc([C@@H](NC(=O)O[C@H]3CN4CCC3CC4)c3ccccc3)c2)cc1)C(=O)c1ccc(CNC[C@H](O)c2ccc(O)c3[nH]c(=O)ccc23)cc1] |

| Cpd. | Appropriate amine | Structure |
|---|---|---|
| 12 | 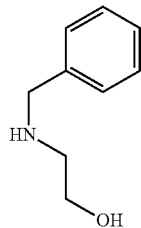 | 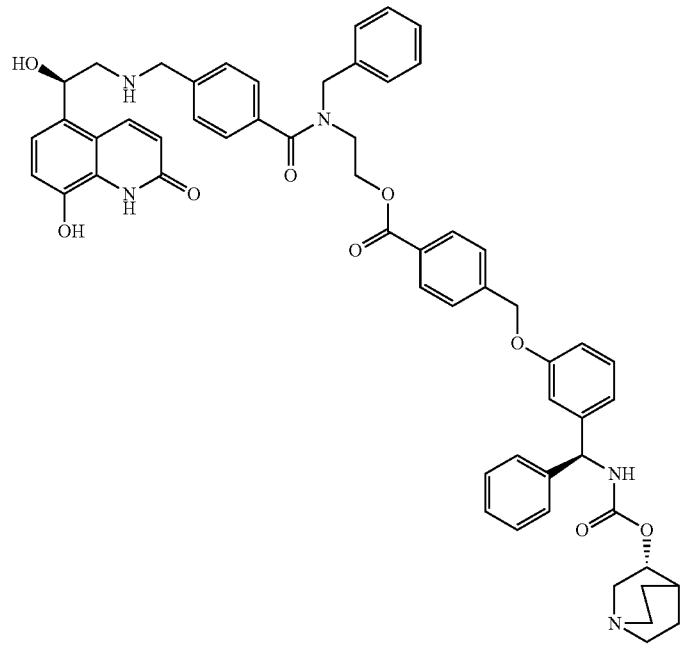 [SMILES: O=C(N[C@@H](c1ccccc1)c1cccc(OCc2ccc(C(=O)OCCN(Cc3ccccc3)C(=O)c3ccc(CNC[C@H](O)c4ccc(O)c5[nH]c(=O)ccc45)cc3)cc2)c1)O[C@H]1CN2CCC1CC2] |
| 13 | 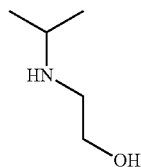 | 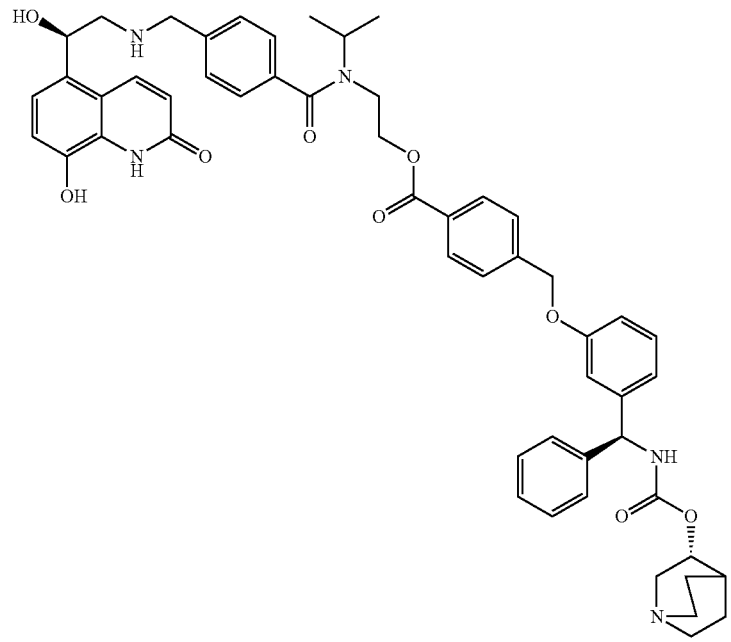 [SMILES: CC(C)N(CCOC(=O)c1ccc(COc2cccc([C@@H](NC(=O)O[C@H]3CN4CCC3CC4)c3ccccc3)c2)cc1)C(=O)c1ccc(CNC[C@H](O)c2ccc(O)c3[nH]c(=O)ccc23)cc1] |

-continued
| Cpd. | Appropriate amine | Structure |
|---|---|---|
| 14 | 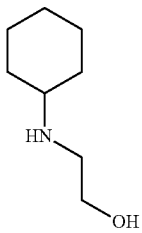 | 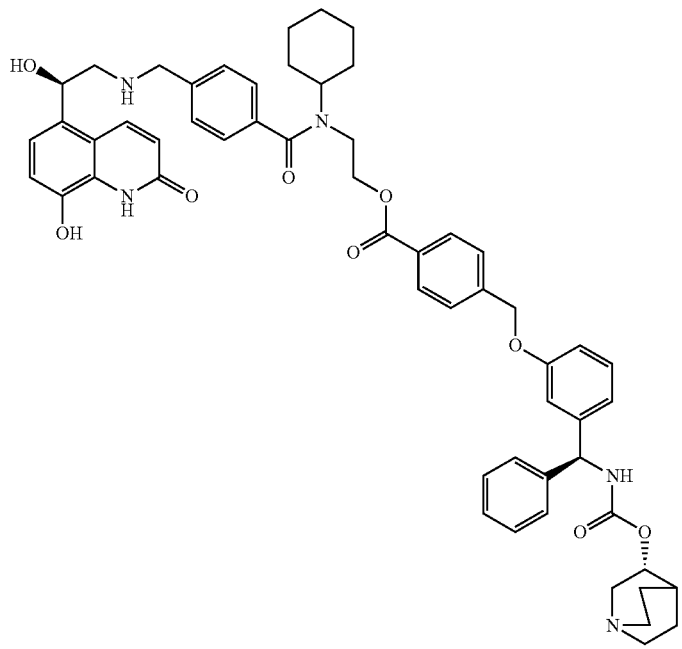 [SMILES: O=C(N[C@@H](c1ccccc1)c1cccc(OCc2ccc(C(=O)OCCN(C(=O)c3ccc(CNC[C@H](O)c4ccc(O)c5[nH]c(=O)ccc45)cc3)C3CCCCC3)cc2)c1)O[C@H]1CN2CCC1CC2] |
| 15 | 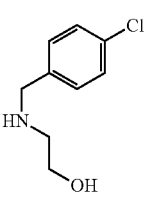 | 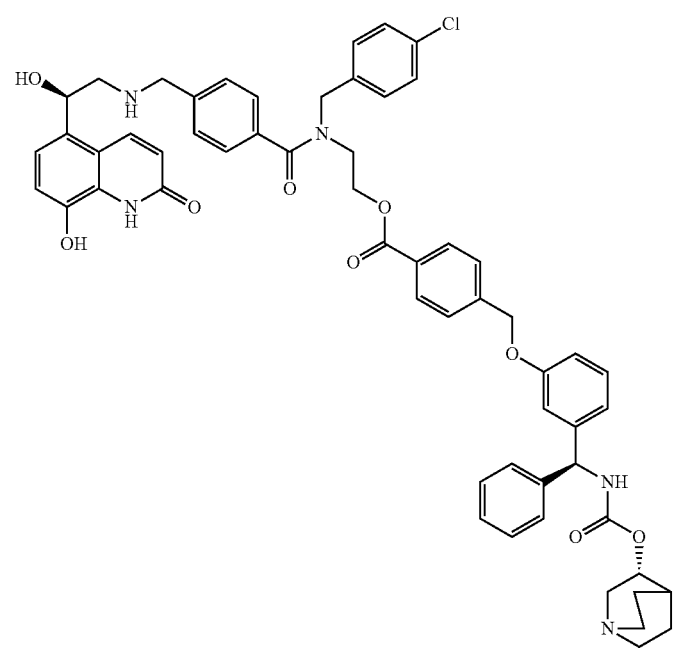 [SMILES: O=C(N[C@@H](c1ccccc1)c1cccc(OCc2ccc(C(=O)OCCN(Cc3ccc(Cl)cc3)C(=O)c3ccc(CNC[C@H](O)c4ccc(O)c5[nH]c(=O)ccc45)cc3)cc2)c1)O[C@H]1CN2CCC1CC2] |

Example 3

2-(3-((((R)-2-Hydroxy-2-(8-hydroxy-2-oxo-1,2-dihydroquinolin-5-yl)ethyl)-amino)methyl)-N-methylbenzamido)ethyl 4-((3-((S)-phenyl((((R)-quinuclidin-3-yloxy)carbonyl)amino)methyl)phenoxy)methyl)benzoate (Compound 16)

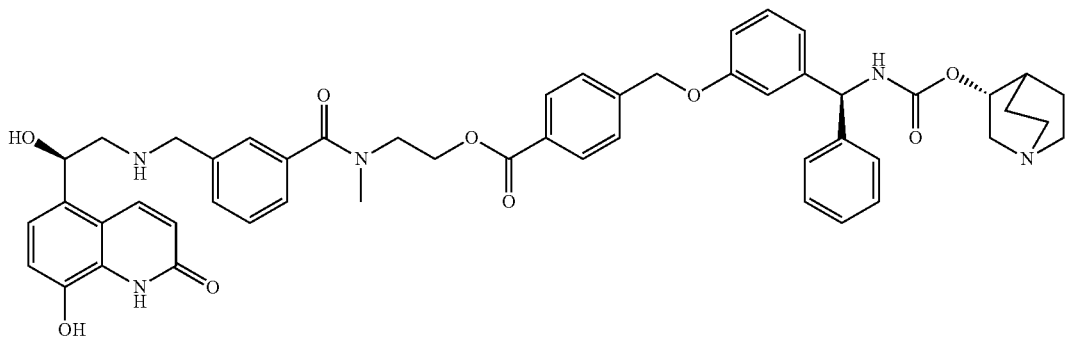 [SMILES: CN(CCOC(=O)c1ccc(COc2cccc([C@@H](NC(=O)O[C@H]3CN4CCC3CC4)c3ccccc3)c2)cc1)C(=O)c1cccc(CNC[C@H](O)c2ccc(O)c3[nH]c(=O)ccc23)c1]

Step 1: Methyl 3-(1,3-dioxolan-2-yl)benzoate

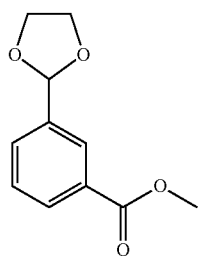

The title compound was prepared as described in Example 2 Step 1 with methyl 3-formylbenzoate replacing methyl 4-formylbenzoate.

Step 2: 3-Formyl-N-(2-hydroxyethyl)-N-methylbenzamide

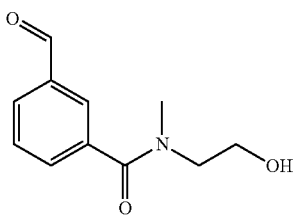

The title compound was prepared as described in Example 2 Step 2 with methyl 3-(1,3-dioxolan-2-yl)benzoate and N-methylethanolamine replacing methyl 4-(1,3-dioxolan-2-yl)benzoate and N-ethylethanolamine respectively.

Step 3: 2-(3-Formyl-N-methylbenzamido)ethyl 4-((3-((S)-phenyl((((R)-quinuclidin-3-yloxy)carbonyl)amino)methyl)phenoxy)methyl)benzoate

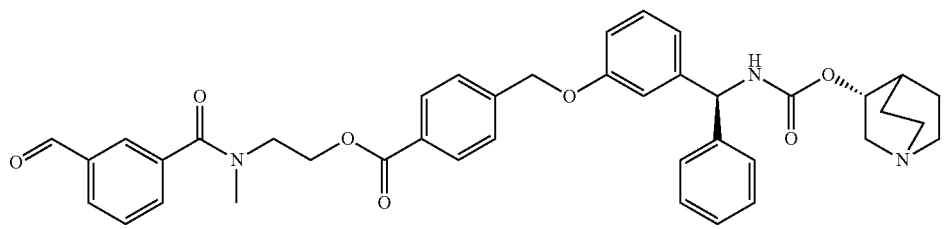 [SMILES: CN(CCOC(=O)c1ccc(COc2cccc([C@@H](NC(=O)O[C@H]3CN4CCC3CC4)c3ccccc3)c2)cc1)C(=O)c1cccc(C=O)c1]

The title compound was prepared as described in Example 1 Step 11 with 3-formyl-N-(2-hydroxyethyl)-N-methylbenzamide replacing 3-(1,3-dioxolan-2-yl)propyl piperidine-4-carboxylate hydrochloride. The product was used directly without further purification.

Step 4: 2-(3-(((((R)-2-Hydroxy-2-(8-hydroxy-2-oxo-1,2-dihydroquinolin-5-yl)ethyl)-amino)methyl)-N-methylbenzamido)ethyl 4-((3-((S)-phenyl((((R)-quinuclidin-3-yloxy)-carbonyl)amino)methyl)phenoxy)methyl)benzoate (Compound 16)

The title compound was prepared as described in Example 1 Step 13.

The following compounds were prepared as described in Example 2 with the appropriate aldehyde replacing methyl 4-formylbenzoate in Step 1 and ethanolamine replacing 2-(ethylamino)ethanol in Step 2. The subsequent steps are as described in Example 2.

| Cpd. | Appropriate aldehyde | Structure |
|---|---|---|
| 17 | | 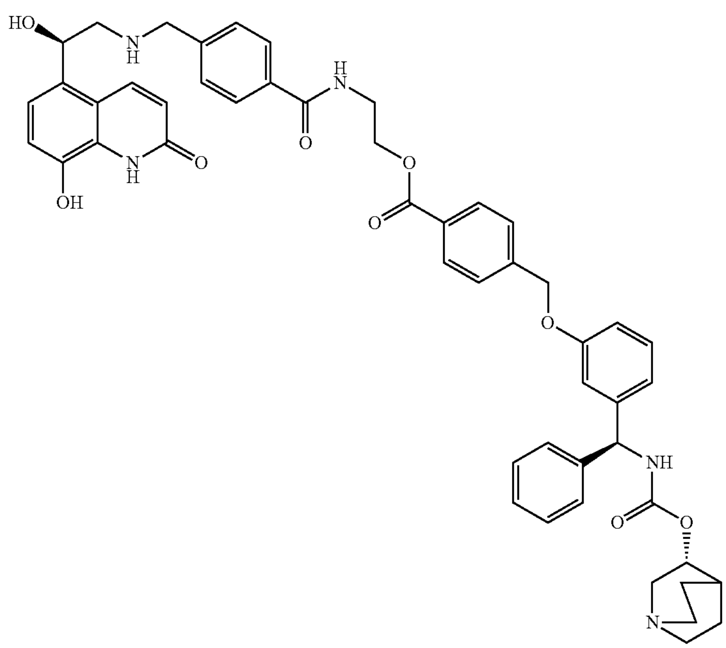 [SMILES: O=C(N[C@@H](c1ccccc1)c1cccc(OCc2ccc(C(=O)OCCNC(=O)c3ccc(CNC[C@H](O)c4ccc(O)c5[nH]c(=O)ccc45)cc3)cc2)c1)O[C@H]1CN2CCC1CC2] |
| 18 | | 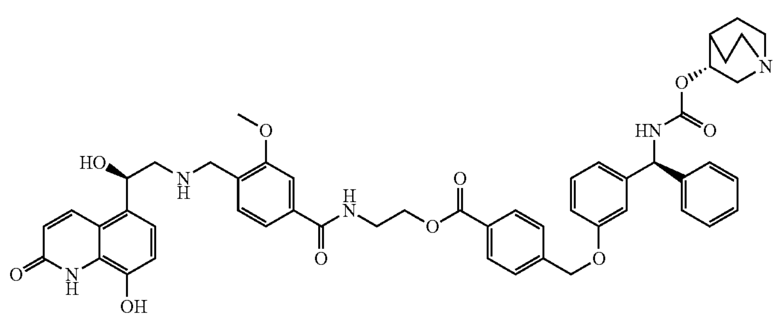 [SMILES: COc1cc(C(=O)NCCOC(=O)c2ccc(COc3cccc([C@@H](NC(=O)O[C@H]4CN5CCC4CC5)c4ccccc4)c3)cc2)ccc1CNC[C@H](O)c1ccc(O)c2[nH]c(=O)ccc12] |

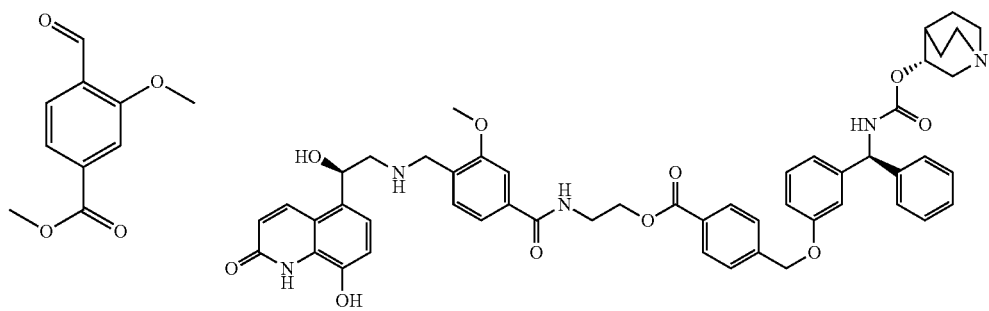

-continued

| Cpd. | Appropriate aldehyde | Structure |
|---|---|---|
| 19 | | 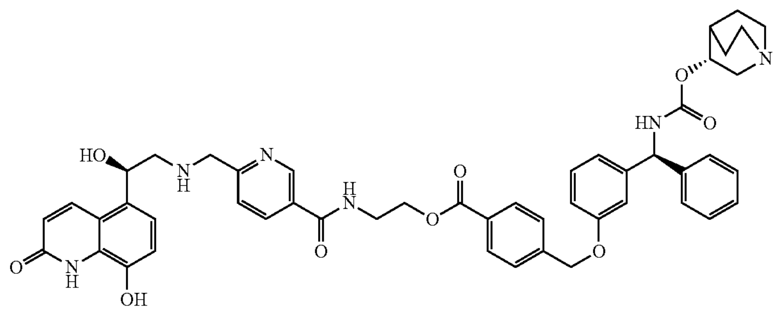 [SMILES: O=C(N[C@@H](c1ccccc1)c1cccc(OCc2ccc(C(=O)OCCNC(=O)c3ccc(CNC[C@H](O)c4ccc(O)c5[nH]c(=O)ccc45)nc3)cc2)c1)O[C@H]1CN2CCC1CC2] |
| 20 | | 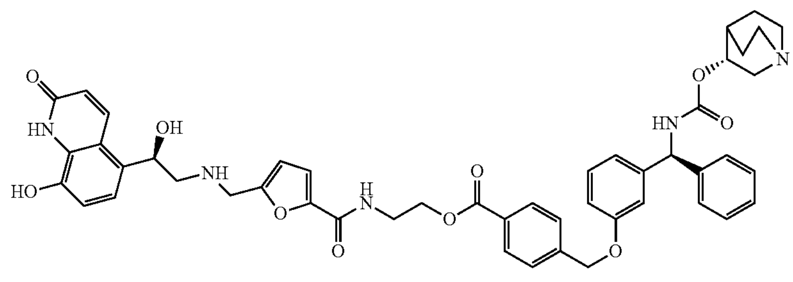 [SMILES: O=C(N[C@@H](c1ccccc1)c1cccc(OCc2ccc(C(=O)OCCNC(=O)c3ccc(CNC[C@H](O)c4ccc(O)c5[nH]c(=O)ccc45)o3)cc2)c1)O[C@H]1CN2CCC1CC2] |
| 21 | | 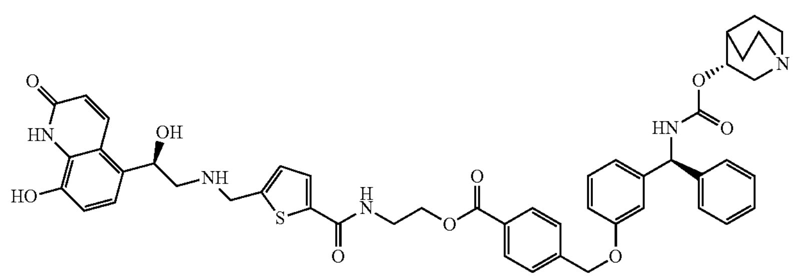 |

The following compounds were prepared as described in Example 2 with the appropriate aldehyde replacing methyl 4-formylbenzoate in Step 1 and propanolamine replacing 2-(ethylamino)ethanol in Step 2. The subsequent steps are as described in Example 2.

| Cpd. | Appropriate aldehyde | Structure |
|---|---|---|
| 21A | | 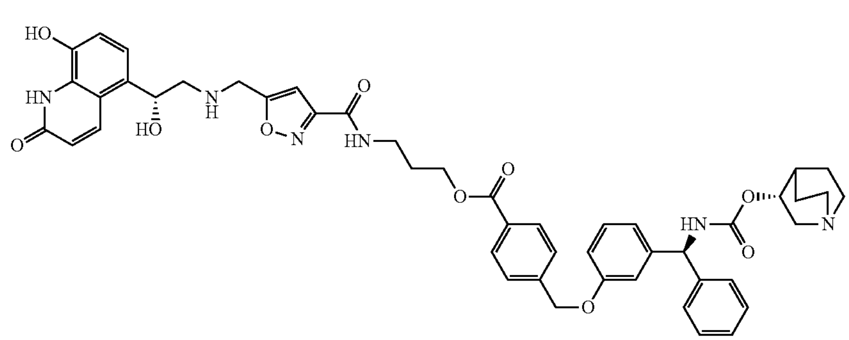 [SMILES: O=C(N[C@@H](c1ccccc1)c1cccc(OCc2ccc(C(=O)OCCCNC(=O)c3cc(CNC[C@H](O)c4ccc(O)c5[nH]c(=O)ccc45)on3)cc2)c1)O[C@H]1CN2CCC1CC2] |

| Cpd. | Appropriate aldehyde | Structure |
|---|---|---|
| 21B | | 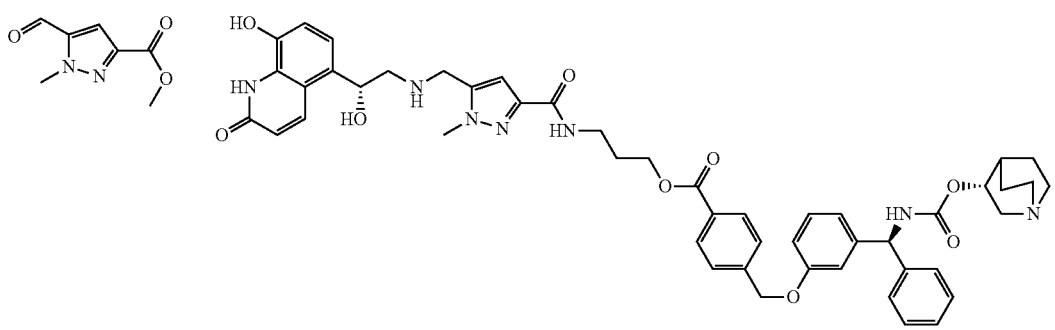 |

Example 4

4-(((R)-2-Hydroxy-2-(8-hydroxy-2-oxo-1,2-dihydroquinolin-5-yl)ethyl)amino)butyl 2-methoxy-4-((3-((S)-phenyl((((R)-quinuclidin-3-yloxy)carbonyl)amino)methyl)phenoxy)methyl)benzoate (Compound 22)

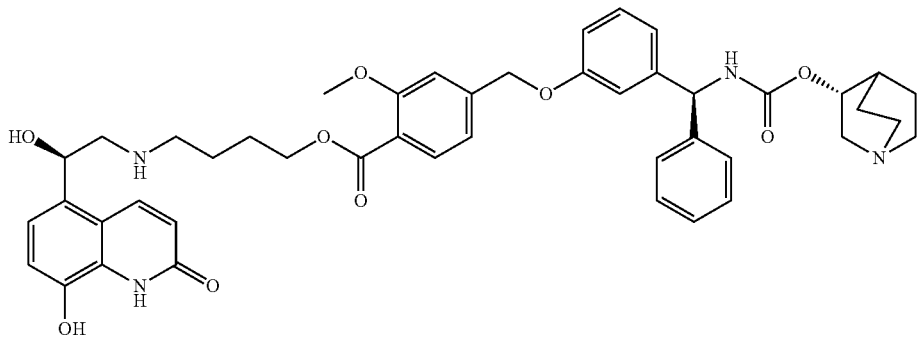 [SMILES: COc1cc(COc2cccc([C@@H](NC(=O)O[C@H]3CN4CCC3CC4)c3ccccc3)c2)ccc1C(=O)OCCCCNC[C@H](O)c1ccc(O)c2[nH]c(=O)ccc12]

Step 1: Methyl 4-(bromomethyl)-2-methoxybenzoate

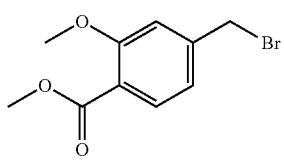

To a solution of methyl 2-methoxy-4-methylbenzoate (2.07 g, 11.5 mmol) in chloroform (30 mL) was added benzoyl peroxide (0.14 g, 0.57 mmol) and N-bromosuccinimide (2.04 g, 11.5 mmol). The reaction mixture was heated at reflux for 3 hours. The reaction mixture was washed with saturated sodium hydrogen carbonate and the organic phase was poured through a hydrophobic frit and the solvent evaporated at reduced pressure. The crude material was used in the next step without further purification.

Step 2: (S)-Methyl 4-((3-(((tert-butoxycarbonyl)amino)(phenyl)methyl)phenoxy)methyl)-2-methoxybenzoate

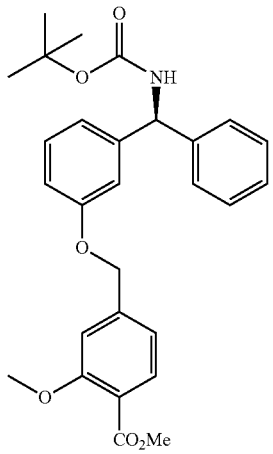 [SMILES: COC(=O)c1ccc(COc2cccc([C@@H](NC(=O)OC(C)(C)C)c3ccccc3)c2)cc1OC]

The title compound was prepared as described in Example 1 Step 5 with methyl 4-(bromomethyl)-2-methoxybenzoate replacing methyl 4-(bromomethyl)benzoate.

¹H NMR (400 MHz, CDCl₃): δ 7.84-7.76 (m, 1H); 7.36-7.18 (m, 6H); 7.09-6.77 (m, 5H); 5.87 (s, 1H); 5.17 (s, 1H); 5.03 (s, 2H); 3.92-3.87 (m, 6H); 1.49 (s, 9H).

Step 3: (S)-4-((3-(((tert-Butoxycarbonyl)amino)(phenyl)methyl)phenoxy)methyl)-2-methoxybenzoic acid

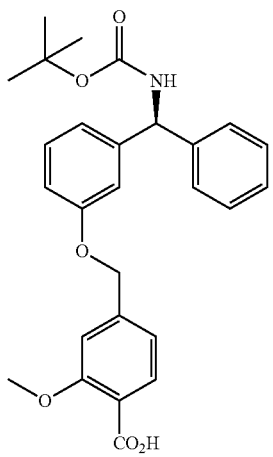 [SMILES: COc1cc(COc2cccc([C@@H](NC(=O)OC(C)(C)C)c3ccccc3)c2)ccc1C(=O)O]

To a solution of (S)-methyl 4-((3-(((tert-butoxycarbonyl)amino)(phenyl)-methyl)phenoxy)methyl)-2-methoxybenzoate (0.90 g, 1.89 mmol) in a mixture of THF (9 mL) and methanol (9 mL) was added aqueous 2 M sodium hydroxide (9 mL). The reaction mixture was stirred at RT for 18 hours. 10% aqueous citric acid was added to the reaction mixture to pH 3. The mixture was extracted with ethyl acetate (×2). The combined organic phases were washed with brine, dried (magnesium sulfate), filtered and the solvent evaporated at reduced pressure to afford the title compound (0.82 g, 87%).

¹H NMR (400 MHz, CDCl₃): δ 8.20-8.16 (m, 1H); 7.37-7.19 (m, 6H); 7.13 (d, J=6.7 Hz, 2H); 6.93-6.83 (m, 3H); 5.87 (s, 1H); 5.16-5.03 (m, 3H); 4.12-4.03 (m, 3H); 1.43 (s, 9H).

Step 4: (S)-3-(1,3-Dioxolan-2-yl)propyl 4-((3-(((tert-butoxycarbonyl)amino)(phenyl)-methyl)phenoxy)methyl)-2-methoxybenzoate

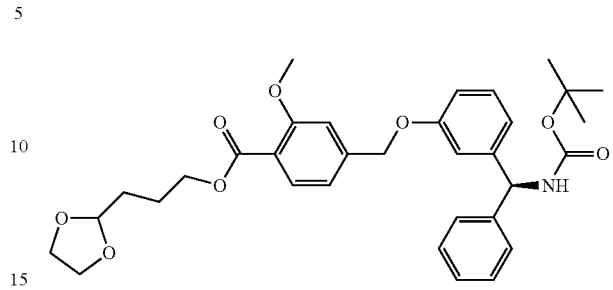

The title compound was prepared as described in Example 1 Step 9 with (S)-4-((3-(((tert-butoxycarbonyl)amino)(phenyl)methyl)phenoxy)methyl)-2-methoxybenzoic acid replacing piperidine-4-carboxylic acid N-tert-butoxycarbonyl.

Step 5: 3-(1,3-Dioxolan-2-yl)propyl 2-methoxy-4-((3-((S)-phenyl((((R)-quinuclidin-3-yloxy)carbonyl)amino)methyl)phenoxy)methyl)benzoate

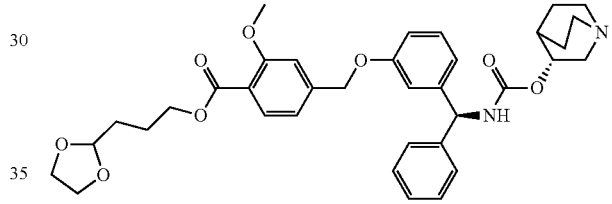

The title compound was prepared as described in Example 1 Step 6 and Step 7 with (S)-3-(1,3-dioxolan-2-yl)propyl 4-((3-(((tert-butoxycarbonyl)amino)(phenyl)-methyl)phenoxy)methyl)-2-methoxybenzoate replacing (S)-methyl 4-((3-(((tert-butoxycarbonyl)amino)(phenyl)methyl)phenoxy)methyl)benzoate in Step 6 and the subsequent product used in Step 7.

Step 6: 4-(((R)-2-Hydroxy-2-(8-hydroxy-2-oxo-1,2-dihydroquinolin-5-yl)ethyl)-amino)butyl 2-methoxy-4-((3-((S)-phenyl((((R)-quinuclidin-3-yloxy)carbonyl)amino)-methyl)phenoxy)methyl)benzoate (Compound 22)

The title compound was prepared as described in Example 1 Step 12 and Step 13 with 3-(1,3-dioxolan-2-yl)propyl 2-methoxy-4-((3-((S)-phenyl((((R)-quinuclidin-3-yloxy)carbonyl)amino)methyl)phenoxy)methyl)benzoate replacing 3-(1,3-dioxolan-2-yl)propyl 1-(4-((3-((S)-phenyl((((R)-quinuclidin-3-yloxy)carbonyl)amino)methyl)-phenoxy)methyl)benzoyl)piperidine-4-carboxylate in Step 12 and the subsequent product used in Step 13.

¹H NMR (400 MHz, DMSO-d₆): δ 8.29 (s, 1H); 8.24 (d, J=9.6 Hz, 1H); 8.17 (d, J=9.9 Hz, 1H); 7.64 (d, J=7.9 Hz, 1H); 7.34-7.18 (m, 8H); 7.12-7.02 (m, 2H); 6.97-6.87 (m, 3H); 6.51 (d, J=9.9 Hz, 1H); 5.82 (d, J=9.0 Hz, 1H); 5.13 (s, 2H); 4.57 (s, 1H); 4.21 (t, J=6.2 Hz, 2H); 3.80 (s, 3H); 3.10 (s, 1H); 2.81 (d, J=6.3 Hz, 2H); 2.74 (d, J=7.7 Hz, 4H); 2.67 (s, 1H); 2.62 (s, 2H); 1.97-1.72 (m, 3H); 1.74-1.66 (m, 2H); 1.64-1.56 (m, 2H); 1.48 (s, 2H); 1.34 (s, 1H).

The following compounds were prepared as described in Example 4 with the appropriate toluene replacing methyl 2-methoxy-4-methylbenzoate in Step 1.
| Cpd. | Appropriate toluene | Structure |
|---|---|---|
| 23 | | 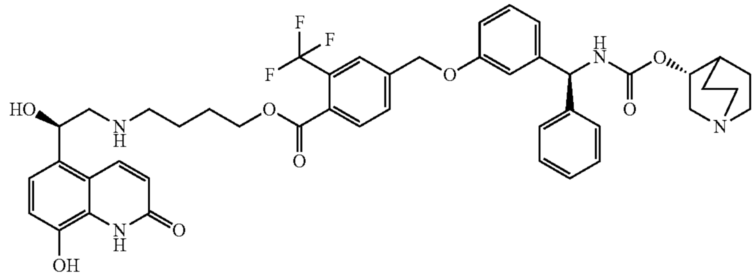 [SMILES: O=C(N[C@@H](c1ccccc1)c1cccc(OCc2ccc(C(=O)OCCCCNC[C@H](O)c3ccc(O)c4[nH]c(=O)ccc34)c(C(F)(F)F)c2)c1)O[C@H]1CN2CCC1CC2] |
| 24 | | 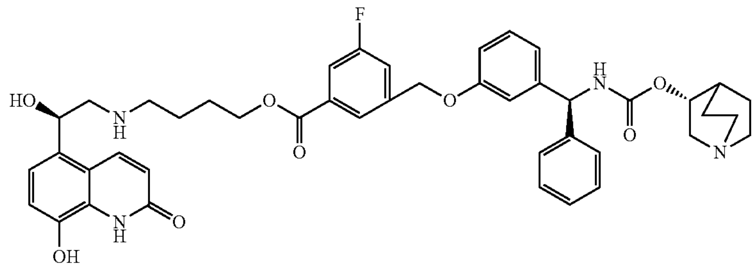 |
| 25 | | 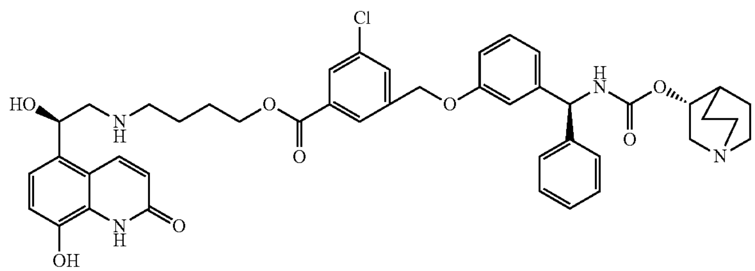 [SMILES: O=C(N[C@@H](c1ccccc1)c1cccc(OCc2cc(Cl)cc(C(=O)OCCCCNC[C@H](O)c3ccc(O)c4[nH]c(=O)ccc34)c2)c1)O[C@H]1CN2CCC1CC2] |
Example 5
2-(N-(3-(((R)-2-hydroxy-2-(8-hydroxy-2-oxo-1,2-dihydroquinolin-5-yl)ethyl)amino)propyl)acetamido)ethyl 4-((3-((S)-phenyl((((R)-quinuclidin-3-yloxy)carbonyl)amino)methyl)phenoxy)methyl)benzoate (Compound 26)
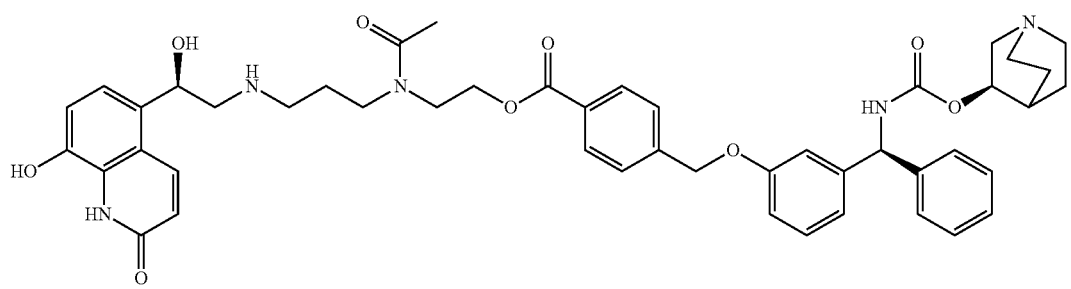 [SMILES: CC(=O)N(CCCNC[C@H](O)c1ccc(O)c2[nH]c(=O)ccc12)CCOC(=O)c1ccc(COc2cccc([C@@H](NC(=O)O[C@H]3CN4CCC3CC4)c3ccccc3)c2)cc1]

Step 1: 2-((2-(1,3-Dioxolan-2-yl)ethyl)(benzyl)amino)ethanol

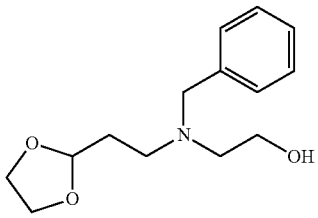 [SMILES: OCCN(CCC1OCCO1)Cc1ccccc1]

A solution of 2-benzylethanolamine (4.00 g, 26.5 mmol), 2-bromoethyl-1,3-dioxalane (5.27 g, 29.1 mmol) and di-iso-propylethylamine (6.12 mL, 34.45 mmol) in acetonitrile (100 mL) were heated at reflux for 18 hours. The reaction mixture was diluted with DCM, washed with water and the organic phase poured through a hydrophobic frit. The solvent was evaporated at reduced pressure and the residue loaded onto an SCX-2 cartridge. The column was eluted with ethanol (5 column volumes) followed by 10% triethylamine in ethanol (5 column volumes). Product containing fractions were combined and the solvent evaporated at reduced pressure to afford the title compound (3.15 g, 47%).

$^1$H NMR (400 MHz, CDCl$_3$): δ 7.34-7.21 (m, 5H); 4.93-4.82 (m, 1H); 3.99-3.77 (m, 4H); 3.66-3.50 (m, 4H); 2.69-2.55 (m, 4H); 1.93-1.79 (m, 2H); 1.27-1.17 (m, 1H).

Step 2: N-(2-(1,3-Dioxolan-2-yl)ethyl)-N-benzyl-2-((tert-butyldimethylsilyl)oxy)-ethanamine

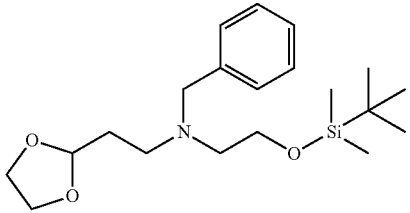 [SMILES: CC(C)(C)[Si](C)(C)OCCN(CCC1OCCO1)Cc1ccccc1]

To a stirred solution of 2-((2-(1,3-dioxolan-2-yl)ethyl)(benzyl)amino)ethanol (2.81 g, 11.2 mmol) in DMF (10 mL) was added imidazole (1.67 g, 24.61 mmol) and tert-butyldimethylsilyl chloride (3.35 g, 22.39 mmol). The reaction mixture was stirred at RT for 18 hours. The reaction mixture was diluted with ethyl acetate and washed with water and brine. The organic phase was dried (magnesium sulfate), filtered and the solvent evaporated art reduced pressure (3.87 g, 95%).

$^1$H NMR (400 MHz, CDCl$_3$): δ 7.32-7.17 (m, 5H); 4.90-4.85 (m, 1H); 3.98-3.75 (m, 4H); 3.69-3.61 (m, 4H); 2.72-2.52 (m, 4H); 1.88-1.76 (m, 2H); 0.96-0.77 (m, 9H); 0.05-0.01 (m, 6H).

Step 3: N-(2-(1,3-Dioxolan-2-yl)ethyl)-2-((tert-butyldimethylsilyl)oxy)ethanamine

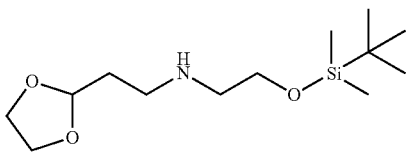 [SMILES: CC(C)(C)[Si](C)(C)OCCNCCC1OCCO1]

To a stirred solution of N-(2-(1,3-dioxolan-2-yl)ethyl)-N-benzyl-2-((tert-butyldimethylsilyl)oxy)ethanamine (3.87 g, 10.6 mmol) in ethanol (100 mL) was added 10% palladium on carbon (1.93 g) and 1-methyl-1,4-cyclohexadiene (5.93 mL, 53.0 mmol). The suspension was heated at reflux for 30 minutes and allowed to cool. The suspension was filtered through celite and the filter cake washed with further ethanol. The solvent was evaporated at reduced pressure to afford the title compound (2.64 g, 91%).

$^1$H NMR (400 MHz, CDCl$_3$): δ 4.91-4.81 (m, 1H); 3.96-3.71 (m, 4H); 3.67-3.56 (m, 2H); 2.74-2.61 (m, 4H); 1.86-1.72 (m, 2H); 1.68 (s, 2H); 0.83-0.78 (m, 9H); 0.09-0.13 (m, 6H).

Step 4: N-(2-(1,3-Dioxolan-2-yl)ethyl)-N-(2-((tert-butyldimethylsilyl)oxy)ethyl)-acetamide

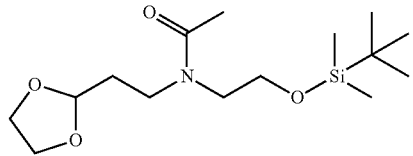 [SMILES: CC(=O)N(CCO[Si](C)(C)C(C)(C)C)CCC1OCCO1]

To an ice-cooled solution of N-(2-(1,3-dioxolan-2-yl)ethyl)-2-((tert-butyldimethylsilyl)oxy)ethanamine (0.85 g, 3.09 mmol) and di-iso-propylethylamine (0.82 mL, 4.63 mmol) was added acetyl chloride (0.26 mL, 3.71 mmol). The reaction mixture was stirred with ice-cooling for 1 hour, then the coolant was removed and stirring continued at RT for 18 hours. The reaction mixture was washed with saturated aqueous sodium hydrogen carbonate and the organic phase poured through a hydrophobic fit. The solvent was evaporated at reduced pressure to afford the title compound (0.64 g, 65%).

$^1$H NMR (400 MHz, CDCl$_3$): δ 4.84 (dt, J=6.3, 4.5 Hz, 1H); 3.97-3.76 (m, 4H); 3.75-3.63 (m, 2H); 3.55-3.29 (m, 4H); 2.10-2.04 (m, 3H); 1.97-1.84 (m, 2H); 0.84 (s, 9H); 0.00 (s, 6H)

Step 5: N-(2-(1,3-Dioxolan-2-yl)ethyl)-N-(2-hydroxyethyl)acetamide

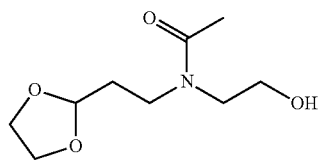

To a stirred solution of N-(2-(1,3-dioxolan-2-yl)ethyl)-N-(2-((tert-butyldimethylsilyl)oxy)ethyl)acetamide (0.65 g, 2.04 mmol) in THF (5 mL) was added a solution of tetrabutylammonium fluoride (1.0 M in THF, 2.24 mL). The reaction mixture was stirred at RT for 18 hours. The reaction mixture was diluted with water and extracted with ethyl acetate (×3). The combined organic extracts were dried (magnesium sulfate), filtered and the solvent evaporated at reduced pressure. The residue was purified by flash column chromatography eluting with 0 to 100% ethyl acetate/isohexane to afford the title compound (0.287 g, 69%) which was used directly in the next step.

Step 6: 2-(N-(2-(1,3-dioxolan-2-yl)ethyl)acetamido)ethyl 4-((3-((S)-phenyl((((R)-quinuclidin-3-yloxy)carbonyl)amino)methyl)phenoxy)methyl)benzoate

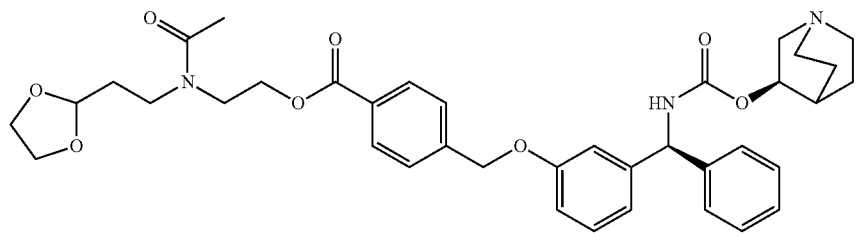 [SMILES: CC(=O)N(CCOC(=O)c1ccc(COc2cccc([C@@H](NC(=O)O[C@H]3CN4CCC3CC4)c3ccccc3)c2)cc1)CCC1OCCO1]

The title compound was prepared as described in Example 1 Step 11 with N-(2-(1,3-dioxolan-2-yl)ethyl)-N-(2-hydroxyethyl)acetamide replacing 3-(1,3-dioxolan-2-yl)propyl piperidine-4-carboxylate hydrochloride.

Step 7: 2-(N-(3-(((R)-2-hydroxy-2-(8-hydroxy-2-oxo-1,2-dihydroquinolin-5-yl)ethyl)-amino)propyl)acetamido)ethyl 4-((3-((S)-phenyl((((R)-quinuclidin-3-yloxy)carbonyl)-amino)methyl)phenoxy)methyl) benzoate (Compound 26)

The title compound was prepared as described in Example 1 Step 12 and Step 13 with 2-(N-(2-(1,3-dioxolan-2-yl)ethyl)acetamido)ethyl 4-((3-((S)-phenyl((((R)-quinuclidin-3-yloxy)carbonyl)amino)methyl)phenoxy)methyl)benzoate replacing 3-(1,3-dioxolan-2-yl)propyl 1-(4-((3-((S)-phenyl((((R)-quinuclidin-3-yloxy)carbonyl)amino)-methyl)phenoxy)methyl)benzoyl)piperidine-4-carboxylate in Step 12 and the subsequent product used in Step 13.

$^1$H NMR (400 MHz, DMSO-$d_6$): δ 8.27 (s, 2H); 8.20 (d, J=9.9 Hz, 1H); 7.94 (d, J=7.9 Hz, 2H); 7.61-7.50 (m, 3H); 7.32-7.29 (m, 4H); 7.28-7.19 (m, 2H); 7.08 (d, J=8.1 Hz, 1H); 7.04-6.99 (m, 1H); 6.98-6.88 (m, 3H); 6.47 (d, J=9.9 Hz, 1H); 5.85-5.79 (m, 1H); 5.17 (s, 2H); 5.04-4.99 (m, 1H); 4.63-4.56 (m, 1H); 4.46-4.34 (m, 2H); 3.70-3.61 (m, 2H); 3.43-3.35 (m, 2H); 3.08-3.03 (m, 1H); 2.82-2.55 (m, 9H); 2.01 (s, 3H); 1.93-1.84 (m, 1H); 1.75-1.58 (m, 4H); 1.52-1.42 (m, 1H); 1.36-1.23 (m, 1H).

The following compounds were prepared as described in Example 5 with the appropriate alcohol in Step 1 and acylating agent in Step 4.

-continued
| 32 | 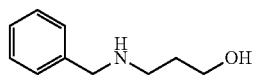 [SMILES: OCCCNCc1ccccc1] | 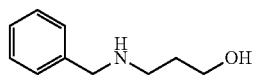 [SMILES: OCCCNCc1ccccc1] |
| Cpd. | Structure |
|---|---|
| 27 | 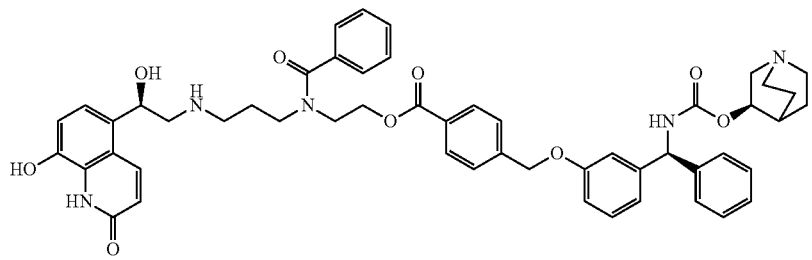 [SMILES: O=C(N[C@@H](c1ccccc1)c1cccc(OCc2ccc(C(=O)OCCN(CCCNC[C@H](O)c3ccc(O)c4[nH]c(=O)ccc34)C(=O)c3ccccc3)cc2)c1)O[C@H]1CN2CCC1CC2] |
| 28 | 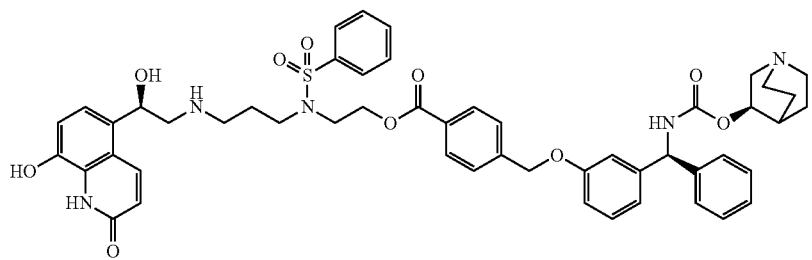 [SMILES: O=C(N[C@@H](c1ccccc1)c1cccc(OCc2ccc(C(=O)OCCN(CCCNC[C@H](O)c3ccc(O)c4[nH]c(=O)ccc34)S(=O)(=O)c3ccccc3)cc2)c1)O[C@H]1CN2CCC1CC2] |
| 29 | 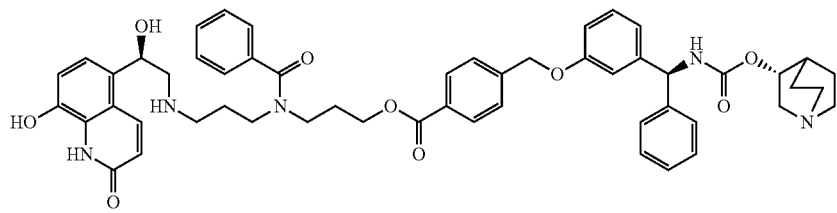 [SMILES: O=C(N[C@@H](c1ccccc1)c1cccc(OCc2ccc(C(=O)OCCCN(CCCNC[C@H](O)c3ccc(O)c4[nH]c(=O)ccc34)C(=O)c3ccccc3)cc2)c1)O[C@H]1CN2CCC1CC2] |
| 30 | 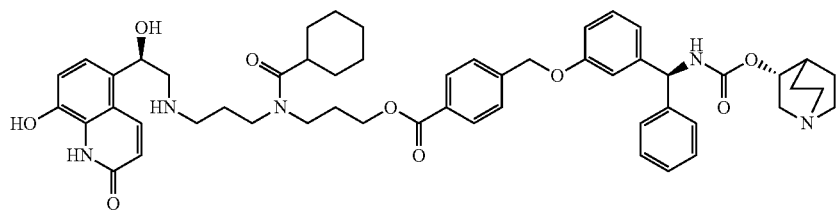 [SMILES: O=C(N[C@@H](c1ccccc1)c1cccc(OCc2ccc(C(=O)OCCCN(CCCNC[C@H](O)c3ccc(O)c4[nH]c(=O)ccc34)C(=O)C3CCCCC3)cc2)c1)O[C@H]1CN2CCC1CC2] |
| 31 | 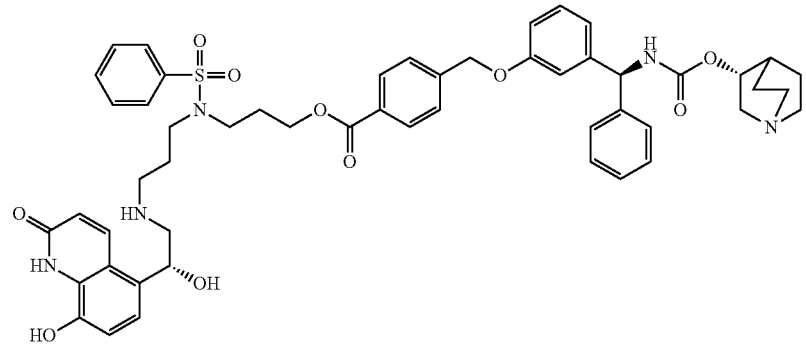 [SMILES: O=C(N[C@@H](c1ccccc1)c1cccc(OCc2ccc(C(=O)OCCCN(CCCNC[C@H](O)c3ccc(O)c4[nH]c(=O)ccc34)S(=O)(=O)c3ccccc3)cc2)c1)O[C@H]1CN2CCC1CC2] |

32

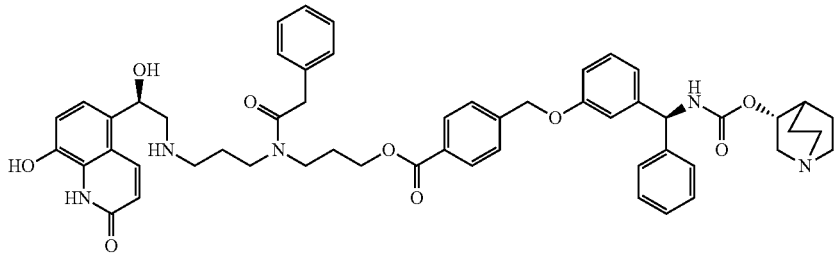 [SMILES: O=C(N[C@@H](c1ccccc1)c1cccc(OCc2ccc(C(=O)OCCCN(CCCNC[C@H](O)c3ccc(O)c4[nH]c(=O)ccc34)C(=O)Cc3ccccc3)cc2)c1)O[C@H]1CN2CCC1CC2]

Example 6

Trans-4-(((R)-2-hydroxy-2-(8-hydroxy-2-oxo-1,2-dihydroquinolin-5-yl)ethyl-amino)butyl 4-((3-((S)-phenyl((((R)-quinuclidin-3-yloxy)carbonyl)amino)methyl)-phenoxy)methyl)cyclohexanecarboxylate (Compound 33)

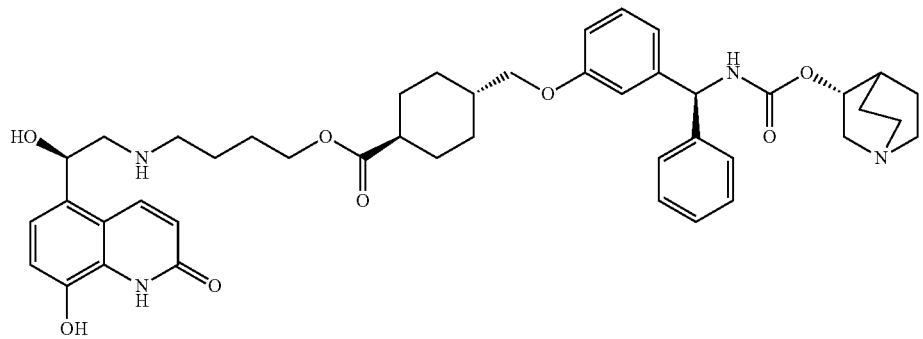 [SMILES: O=C(N[C@@H](c1ccccc1)c1cccc(OC[C@H]2CC[C@H](C(=O)OCCCCNC[C@H](O)c3ccc(O)c4[nH]c(=O)ccc34)CC2)c1)O[C@H]1CN2CCC1CC2]

Step 1: Trans-4-(((tert-butyldimethylsilyl)oxy)methyl)cyclohexanecarboxylic acid

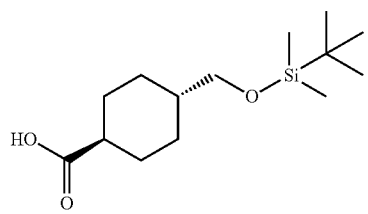 [SMILES: CC(C)(C)[Si](C)(C)OC[C@H]1CC[C@H](C(=O)O)CC1]

To a stirred solution of trans-4-(1-hydroxymethyl)-cyclohexanecarboxylic acid (1.00 g, 6.32 mmol) and 2,6-lutidine (2.95 mL, 25.29 mmol) in DCM (61 mL) was added drop wise tert-butyldimethylsilyl triflate (4.36 mL, 18.96 mmol). The reaction mixture was stirred at RT for 1.5 hours. The reaction mixture was quenched with water and the organic phase removed. The aqueous phase was extracted with further DCM (×2). The combined organic extracts were combined and washed with brine, dried (magnesium sulfate), filtered and the solvent evaporated at reduced pressure. The residue was dissolved in THF (30 mL) and methanol (90 mL) and 10% aqueous potassium carbonate (30 mL) added. The reaction mixture was stirred at RT for 2 hours. The solvent was evaporated at reduced pressure and the residue partitioned between water and ether. The organic phase was discarded. The aqueous phase was washed with further ether (×2). The pH of the aqueous extract was adjusted to 5 and extracted with ethyl acetate (×3). The combined ethyl acetate extracts were washed with brine, dried (magnesium sulfate), filtered and the solvent evaporated at reduced pressure to afford the title compound (1.59 g, 93%).

$^1$H NMR (400 MHz, CDCl$_3$): δ 3.37 (d, J=6.2 Hz, 2H); 2.27-2.17 (m, 1H); 2.00 (d, J=11.3 Hz, 2H); 1.81 (dd, J=13.2, 3.7 Hz, 2H); 1.50-1.33 (m, 3H); 1.04-0.72 (m, 11H); −0.00 (t, J=3.1 Hz, 6H).

Step 2: Trans-3-(1,3-Dioxolan-2-yl)propyl 4-(((tert-butyldimethylsilyl)oxy)-methyl)cyclohexanecarboxylate

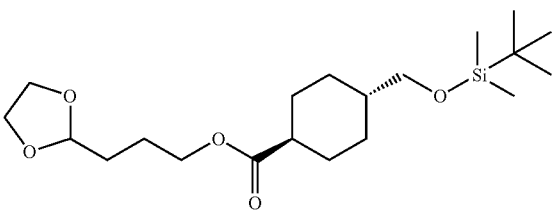 [SMILES: CC(C)(C)[Si](C)(C)OC[C@H]1CC[C@H](C(=O)OCCCC2OCCO2)CC1]

The title compound was prepared as described in Example 1 Step 9 with trans-4-(((tert-butyldimethylsilyl)oxy)methyl)cyclohexanecarboxylic acid replacing piperidine-4-carboxylic acid N-tert-butoxycarbonyl.

¹H NMR (400 MHz, CDCl₃): δ 4.91-4.87 (m, 1H); 4.15-4.07 (m, 2H); 3.99-3.82 (m, 4H); 3.40 (d, J=6.2 Hz, 2H); 2.26-2.16 (m, 1H); 1.99 (d, J=13.1 Hz, 2H); 1.84-1.67 (m, 6H); 1.49-1.34 (m, 3H); 1.06-0.80 (m, 11H); 0.00 (s, 6H).

Step 3: Trans-3-(1,3-Dioxolan-2-yl)propyl 4-(hydroxymethyl)cyclohexanecarboxylate

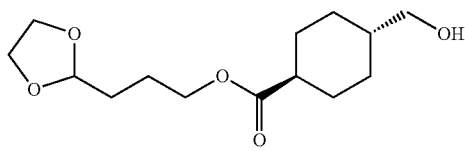 [SMILES: O=C(OCCCC1OCCO1)[C@H]1CC[C@H](CO)CC1]

The title compound was prepared as described in Example 5 Step 5 with trans-3-(1,3-dioxolan-2-yl)propyl 4-(((tert-butyldimethylsilyl)oxy)methyl)-cyclohexanecarboxylate replacing N-(2-(1,3-dioxolan-2-yl)ethyl)-N-(2-((tert-butyldimethylsilyl)oxy)ethyl)acetamide.

¹H NMR (400 MHz, CDCl₃): δ 4.91-4.87 (m, 1H); 4.14-4.07 (m, 2H); 4.01-3.81 (m, 4H); 3.50-3.43 (m, 2H); 2.29-2.19 (m, 1H); 2.06-1.98 (m, 2H); 1.87 (dd, J=13.1, 3.7 Hz, 2H); 1.80-1.69 (m, 3H); 1.53-1.39 (m, 3H); 1.29-1.21 (m, 2H); 1.06-0.90 (m, 2H).

Step 4: Trans-3-(1,3-Dioxolan-2-yl)propyl 4-((tosyloxy)methyl)cyclohexanecarboxylate

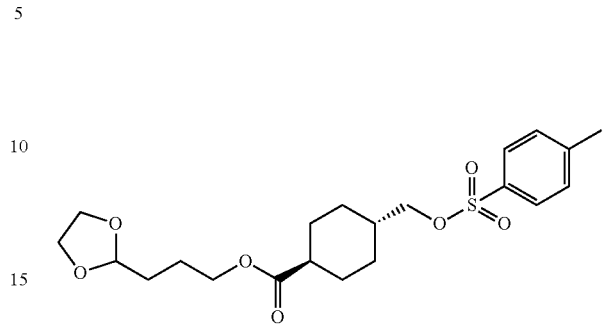

To an ice-cooled solution of trans-3-(1,3-dioxolan-2-yl)propyl 4-(hydroxymethyl)cyclohexanecarboxylate (0.306 g, 1.13 mmol) in pyridine (0.9 mL) was added para-toluenesulfonyl chloride (0.236 g, 1.24 mmol). The reaction mixture was stirred at this temperature for 1 hour and the coolant removed. The reaction mixture was stirred at RT for 18 hours. The reaction mixture was diluted with ethyl acetate and washed with water, brine, dried (magnesium sulfate), filtered and the solvent evaporated at reduced pressure. The residue was used directly without purification.

Step 5: Trans-3-(1,3-Dioxolan-2-yl)propyl 4-((3-((S)-phenyl((((R)-quinuclidin-3-yloxy)carbonyl)amino)methyl)phenoxy)methyl)cyclohexanecarboxylate

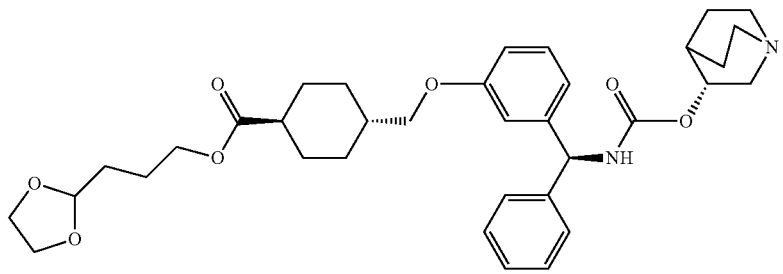 [SMILES: O=C(N[C@@H](c1ccccc1)c1cccc(OC[C@H]2CC[C@H](C(=O)OCCCC3OCCO3)CC2)c1)O[C@H]1CN2CCC1CC2]

The title compound was prepared as described in Example 1 Step 5, Step 6 and Step 7 with trans-3-(1,3-dioxolan-2-yl)propyl 4-((tosyloxy)methyl)-cyclohexanecarboxylate replacing methyl 4-(bromomethyl)benzoate in Step 6 and the subsequent products used in Step 6 and Step 7.

Step 6: Trans-4-(((R)-2-Hydroxy-2-(8-hydroxy-2-oxo-1,2-dihydroquinolin-5-yl)ethyl)-amino)butyl 4-((3-((S)-phenyl((((R)-quinuclidin-3-yloxy)carbonyl)amino)methyl)-phenoxy)methyl)cyclohexanecarboxylate (Compound 33)

The title compound was prepared as described in Example 1 Step 12 and Step 13 with trans-3-(1,3-dioxolan-2-yl)propyl 4-((3-((S)-phenyl((((R)-quinuclidin-3-yloxy-carbonyl)amino)methyl)phenoxy)methyl)cyclohexanecarboxylate replacing 3-(1,3-dioxolan-2-yl)propyl 1-(4-((3-((S)-phenyl(((((R)-quinuclidin-3-yloxy)carbonyl)-amino)methyl)phenoxy)methyl)benzoyl)piperidine-4-carboxylate in Step 12 and the subsequent product used in Step 13.

$^1$H NMR (400 MHz, DMSO-d$_6$): δ 8.28-8.16 (m, 4H); 7.36-7.28 (m, 4H); 7.25-7.18 (m, 2H); 7.09 (d, J=8.2 Hz, 1H); 6.96-6.87 (m, 3H); 6.81-6.77 (m, 1H); 6.53 (d, J=9.9 Hz, 1H); 5.81 (d, J=9.0 Hz, 1H); 5.13 (t, J=6.3 Hz, 1H); 4.61-4.55 (m, 1H); 4.02 (t, J=6.1 Hz, 2H); 3.74 (d, J=6.3 Hz, 2H); 3.16-3.06 (m, 1H); 2.84-2.54 (m, 9H); 2.30-2.21 (m, 1H); 1.97-1.27 (m, 16H); 1.14-1.02 (m, 2H).

The following compounds were prepared as described in Example 6 except that trans-4-(((tert-butyldimethylsilyl)oxy)methyl)cyclohexanecarboxylic acid was coupled to the required amine using the method of Example 1 Step 11.

| Cpd. | Appropriate amine | Structure |
|---|---|---|
| 33A | 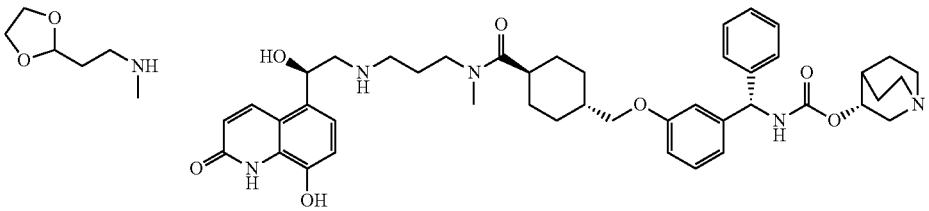 | 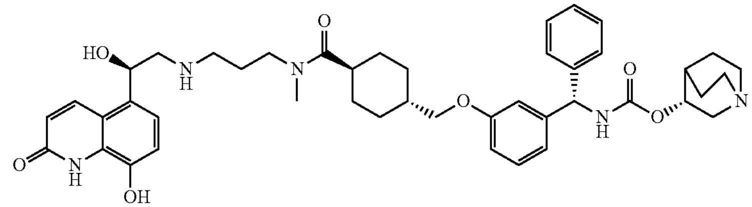 [SMILES: CN(CCCNC[C@H](O)c1ccc(O)c2[nH]c(=O)ccc12)C(=O)[C@H]1CC[C@H](COc2cccc([C@@H](NC(=O)O[C@H]3CN4CCC3CC4)c3ccccc3)c2)CC1] |
| 33B | 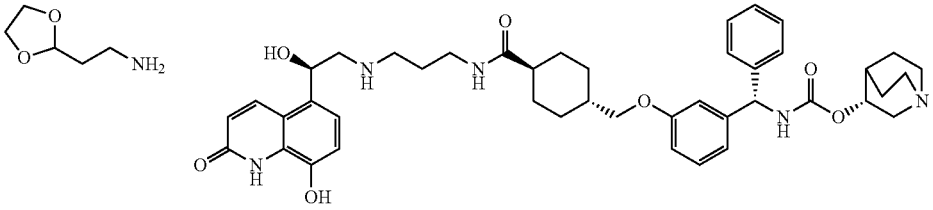 | 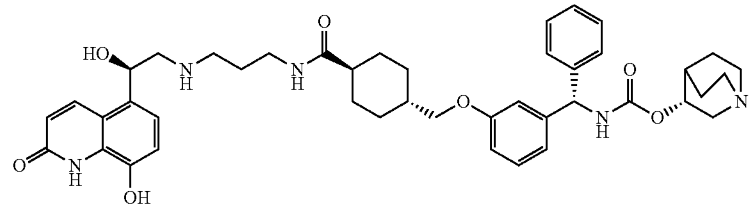 [SMILES: O=C(N[C@@H](c1ccccc1)c1cccc(OC[C@H]2CC[C@H](C(=O)NCCCNC[C@H](O)c3ccc(O)c4[nH]c(=O)ccc34)CC2)c1)O[C@H]1CN2CCC1CC2] |

Example 7

2-(3-(4-((((R)-2-Hydroxy-2-(8-hydroxy-2-oxo-1,2-dihydroquinolin-5-yl)ethyl)amino)methyl)phenyl)-1-methylureido)ethyl 4-((3-((S)-phenyl((((R)-quinuclidin-3-yloxy)carbonyl)amino)methyl)phenoxy)methyl)benzoate (Compound 34)

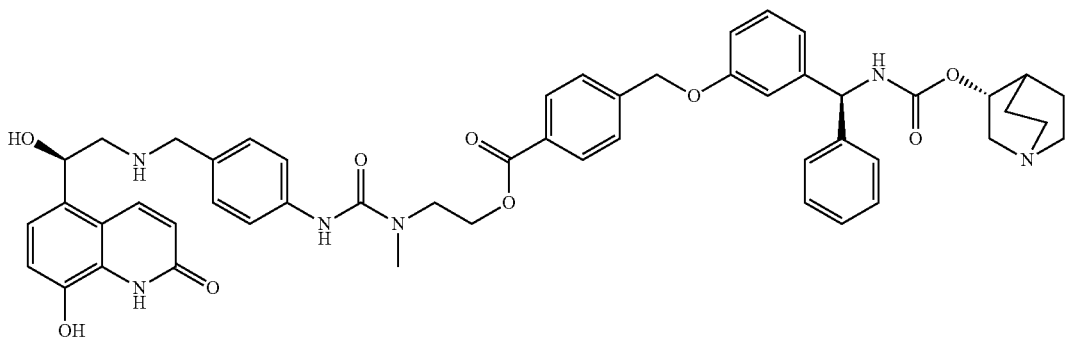 [SMILES: CN(CCOC(=O)c1ccc(COc2cccc([C@@H](NC(=O)O[C@H]3CN4CCC3CC4)c3ccccc3)c2)cc1)C(=O)Nc1ccc(CNC[C@H](O)c2ccc(O)c3[nH]c(=O)ccc23)cc1]

Step 1: Methyl 4-(3-(2-hydroxyethyl)-3-methylureido)benzoate

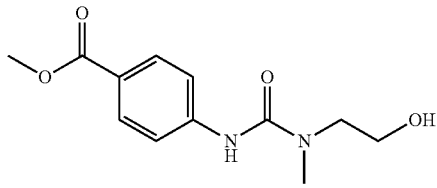 [SMILES: COC(=O)c1ccc(NC(=O)N(C)CCO)cc1]

To an ice-cooled solution of N-methylethanolamine (0.600 g, 7.99 mmol) in DCM (80 mL) was added methyl 4-isocyanatobenzoate (1.56 g, 8.79 mmol). After 20 minutes the coolant was removed and the reaction mixture was stirred for 2 hours. The solvent was evaporated at reduced pressure and the residue was purified by flash column chromatography eluting with 0 to 100% ethyl acetate/iso-hexane to afford the title compound (2.26 g, 112%).

$^1$H NMR (400 MHz, CDCl$_3$): δ 8.74 (s, 1H); 7.89 (m, 2H): 7.50 (m, 2H); 5.02 (m, 1H); 3.80 (s, 3H); 3.59 (m, 2H); 3.44 (m, 2H); 3.00 (s, 3H).

Step 2: 1-(2-Hydroxyethyl)-3-(4-(hydroxymethyl)phenyl)-1-methylurea

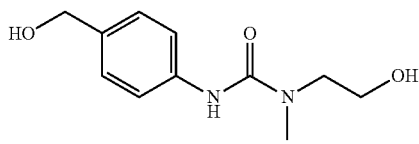 [SMILES: CN(CCO)C(=O)Nc1ccc(CO)cc1]

To a cooled (−78° C.) solution of methyl 4-(3-(2-hydroxyethyl)-3-methylureido)benzoate (2.02 g, 8.00 mmol) in THF (80 mL) was added a solution of lithium aluminium hydride (2.0 M solution in THF, 6.0 mL, 12.0 mmol). After 20 minutes the coolant was removed and the reaction mixture stirred at RT for 18 h. The reaction mixture was quenched with water (0.46 mL), 2 M aqueous sodium hydroxide (0.46 mL) and water (3×0.46 mL). The mixture was diluted with ethyl acetate and magnesium sulfate added. The mixture stirred for 1 hour and then filtered. The filtrate was evaporated at reduced pressure and the residue was purified by flash column chromatography eluting with 0 to 100% ethyl acetate/iso-hexane to afford the title compound (1.09 g, 60%).

$^1$H NMR (400 MHz, DMSO-d$_6$): δ 8.30 (s, 1H); 7.36 (d, J=8.3 Hz, 2H); 7.16 (d, J=8.2 Hz, 2H); 5.05-4.94 (m, 2H); 4.40 (d, J=5.6 Hz, 2H); 3.56 (dd, J=10.5, 5.3 Hz, 2H); 2.95 (s, 3H).

Step 3: 3-(4-Formylphenyl)-1-(2-hydroxyethyl)-1-methylurea

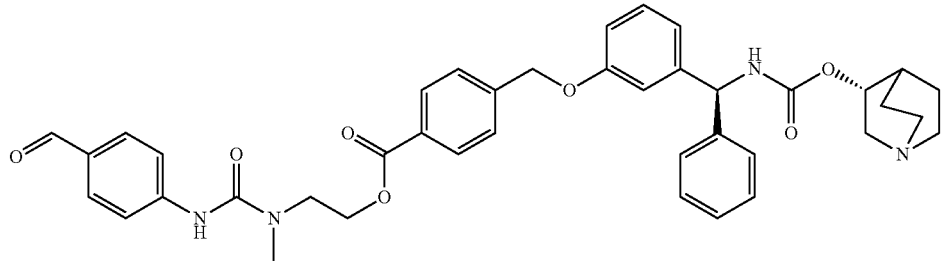 [SMILES: CN(CCOC(=O)c1ccc(COc2cccc([C@@H](NC(=O)O[C@H]3CN4CCC3CC4)c3ccccc3)c2)cc1)C(=O)Nc1ccc(C=O)cc1]

To a solution of 1-(2-hydroxyethyl)-3-(4-(hydroxymethyl)phenyl)-1-methylurea (0.50 g, 2.23 mmol) in DCM (30 mL) was added manganese (IV) oxide (0.78 g, 8.92 mmol). The reaction mixture was stirred at RT for 3 hours. The suspension was filtered through celite and the filter pad washed with further DCM. The filtrate was evaporated at reduced pressure to afford the title compound (0.23 g, 49%).

$^1$H NMR (400 MHz, DMSO-d$_6$): δ 9.82 (s, 1H); 8.86 (s, 1H); 7.82-7.75 (m, 2H); 7.66 (d, J=8.5 Hz, 2H); 5.03 (d, J=5.8 Hz, 1H); 3.61-3.55 (m, 2H); 3.45-3.37 (m, 2H); 2.99 (s, 3H).

Step 4: 2-(3-(4-Formylphenyl)-1-methylureido)ethyl 4-((3-((S)-phenyl((((R)-quinuclidin-3-yloxy)carbonyl)amino)methyl)phenoxy)methyl)benzoate The title compound was prepared as described in Example 1 Step 11 with 3-(4-formylphenyl)-1-(2-hydroxyethyl)-1-methylurea replacing 3-(1,3-dioxolan-2-yl)propyl piperidine-4-carboxylate hydrochloride.

Step 5: 2-(3-(4-((((R)-2-Hydroxy-2-(8-hydroxy-2-oxo-1,2-dihydroquinolin-5-yl)ethyl)-amino)methyl)phenyl)-1-methylureido)ethyl 4-((3-((S)-phenyl((((R)-quinuclidin-3-yloxy)carbonyl)amino)methyl)phenoxy)methyl)benzoate (Compound 34)

The title compound was prepared as described in Example 1 Step 13 with 2-(3-(4-formylphenyl)-1-methylureido)ethyl 4-((3-((S)-phenyl((((R)-quinuclidin-3-yloxy)-carbonyl)amino)methyl)phenoxy)methyl)benzoate replacing 4-oxobutyl 1-(4-((3-((S)-phenyl((((R)-quinuclidin-3-yloxy)carbonyl)amino)methyl)phenoxy)methyl)-benzoyl)piperidine-4-carboxylate.

$^1$H NMR (400 MHz, DMSO-d$_6$): δ 10.28 (br s, 1H); 8.28 (s, 1H); 8.23 (s, 2H); 8.09 (d, J=9.95 Hz, 1H); 7.96 (d, J=8.04 Hz, 2H); 7.52 (d, J=7.99 Hz, 2H); 7.39-7.13 (m, 10H); 7.09-7.00 (m, 2H); 6.97-6.83 (m, 3H); 6.47 (d, J=9.88 Hz, 1H); 5.82 (d, J=8.82 Hz, 1H); 5.15 (s, 2H); 5.07 (dd, J=7.96, 4.45 Hz, 1H); 4.57 (s, 1H); 4.45-4.39 (m, 2H); 3.76-3.69 (m, 4H); 3.16-3.05 (m, 1H); 3.04 (s, 3H); 2.77-2.61 (m, 6H); 2.36-2.32 (m, 1H); 1.94-1.75 (m, 2H); 1.62-1.31 (m, 4H).

The following compounds were prepared as described in Example 7 with the appropriate amine in Step 1.

-continued
| Cpd. | Appropriate amine | Structure |
|---|---|---|
| 41 |  | 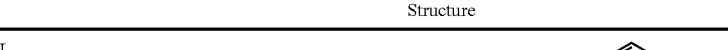 |
The following compounds were prepared as described in Example 2 Step 3 and Step 4 with the commercially available alcohol replacing N-ethyl-4-formyl-N-(2-hydroxyethyl)benzamide in Step 2.
| Cpd. | Commercially available alcohol | Structure |
|---|---|---|
| 42 | 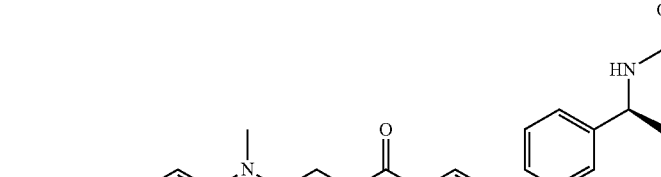 | 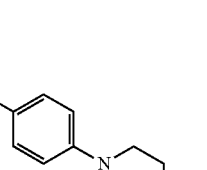 |
| 43 | 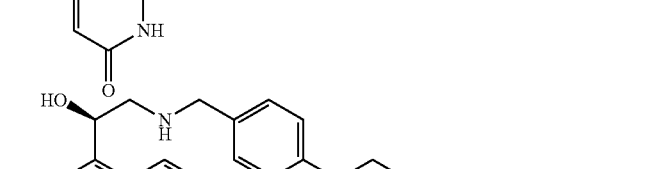 | 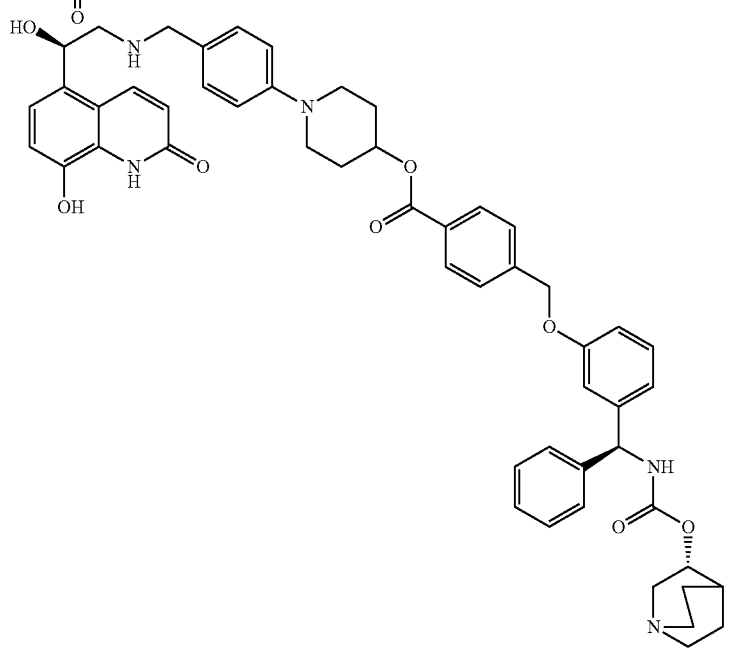 |

| Cpd. | Commercially available alcohol | Structure |
|---|---|---|
| 44 | | 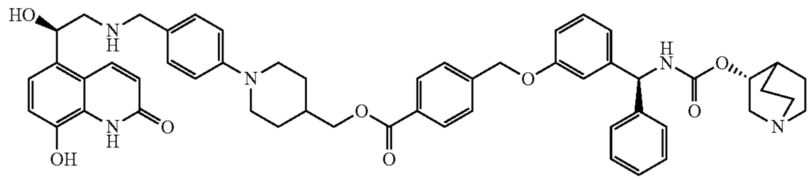 [SMILES: O=C(N[C@@H](c1ccccc1)c1cccc(OCc2ccc(C(=O)OCC3CCN(c4ccc(CNC[C@H](O)c5ccc(O)c6[nH]c(=O)ccc56)cc4)CC3)cc2)c1)O[C@H]1CN2CCC1CC2] |

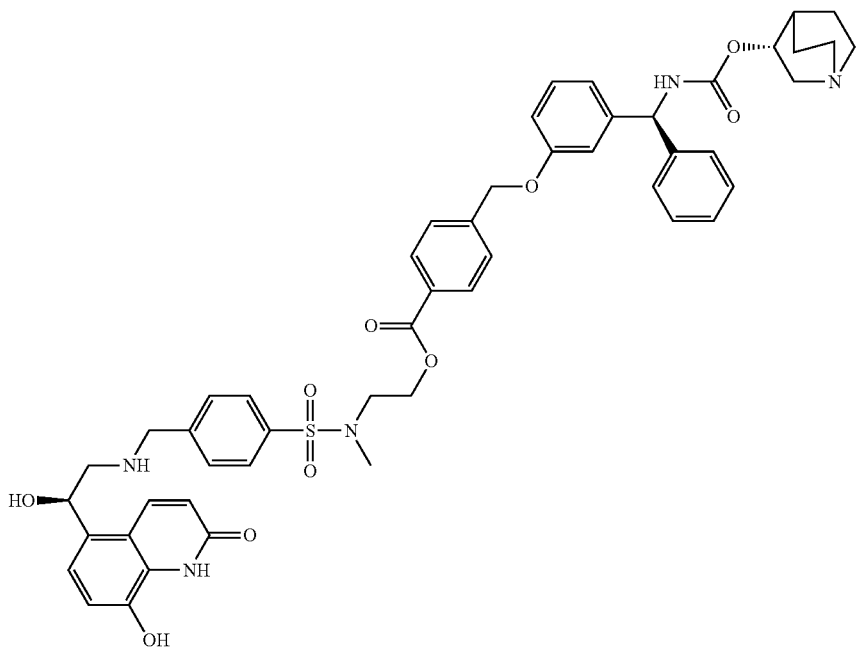 [SMILES: CN(CCOC(=O)c1ccc(COc2cccc([C@@H](NC(=O)O[C@H]3CN4CCC3CC4)c3ccccc3)c2)cc1)S(=O)(=O)c1ccc(CNC[C@H](O)c2ccc(O)c3[nH]c(=O)ccc23)cc1]

Example 8

2-(4-((((R)-2-Hydroxy-2-(8-hydroxy-2-oxo-1,2-dihydroquinolin-5-yl)ethyl)-amino)methyl)-N-methylphenylsulfonamido)ethyl 4-((3-((S)-phenyl((((R)-quinuclidin-3-yloxy)carbonyl)amino)methyl)phenoxy)methyl)benzoate (Compound 45)

Step 1: 4-Formyl-N-(2-hydroxyethyl)-N-methylbenzenesulfonamide

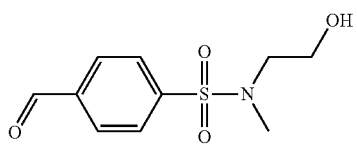 [SMILES: CN(CCO)S(=O)(=O)c1ccc(C=O)cc1]

To an ice-cooled solution of 2-(methylamino)ethanol (0.196 mL, 2.44 mmol) and triethylamine (0.407 mL, 2.93 mmol) in DCM (10 mL) was added 4-formylbenzenesulfonyl chloride (0.500 g, 2.44 mmol). The reaction mixture was warmed slowly to RT and stirred at RT for 80 hours. The reaction mixture was diluted with DCM and was washed with 10% aqueous potassium hydrogen sulfate and dried (magnesium sulfate). The mixture filtered and the solvent evaporated at reduced pressure to afford the title compound (0.548 g, 92%).

$^1$H NMR (400 MHz, CDCl$_3$): δ 10.12 (s, 1H); 8.09-8.04 (m, 2H); 8.00-7.97 (m, 2H); 3.82-3.78 (m, 2H); 3.24 (t, J=5.2 Hz, 2H); 2.90 (s, 3H); 1.93 (t, J=5.2 Hz, 1H).

Step 2: 2-(4-((((R)-2-hydroxy-2-(8-hydroxy-2-oxo-1,2-dihydroquinolin-5-yl)ethyl)-amino)methyl)-N-methylphenylsulfonamido)ethyl 4-((3-((S)-phenyl((((R)-quinuclidin-3-yloxy)carbonyl)amino)methyl)phenoxy)methyl)benzoate (Compound 45)

The title compound was prepared as described in Example 2 Step 3 and Step 4 with 4-formyl-N-(2-hydroxyethyl)-N-methylbenzenesulfonamide replacing N-ethyl-4-formyl-N-(2-hydroxyethyl)benzamide in Step 3 and the subsequent product used in Step 4.

Example 9

2-(4-(4-((((R)-2-Hydroxy-2-(8-hydroxy-2-oxo-1,2-dihydroquinolin-5-yl)ethyl)amino)methyl)benzyl)piperazin-1-yl)ethyl 4-((3-((S)-phenyl((((R)-quinuclidin-3-yloxy)carbonyl)amino)methyl)phenoxy)methyl)benzoate (Compound 46)

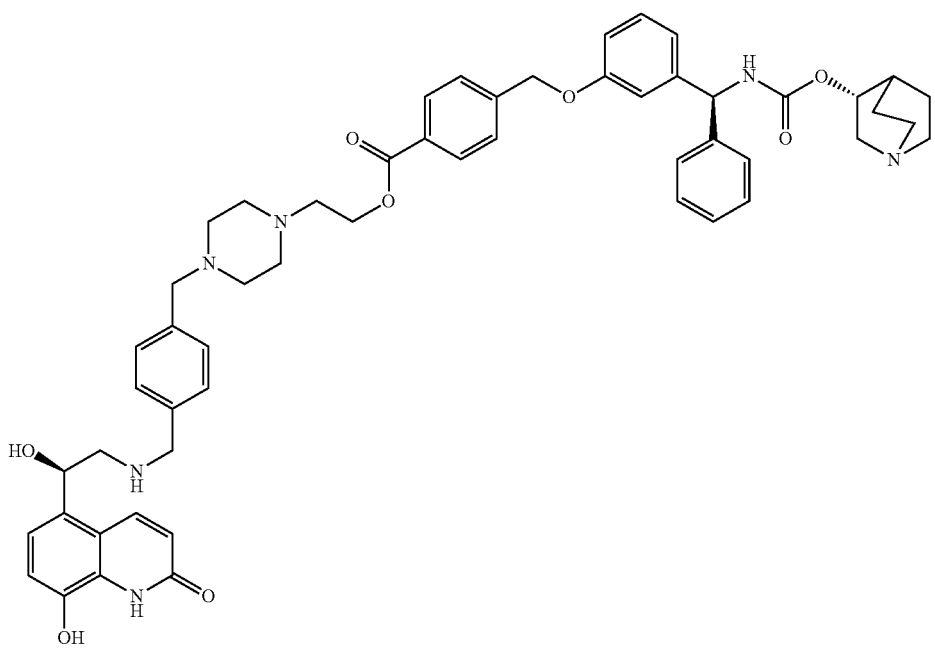 [SMILES: O=C(N[C@@H](c1ccccc1)c1cccc(OCc2ccc(C(=O)OCCN3CCN(Cc4ccc(CNC[C@H](O)c5ccc(O)c6[nH]c(=O)ccc56)cc4)CC3)cc2)c1)O[C@H]1CN2CCC1CC2]

Step 1: 4-((4-(2-Hydroxyethyl)piperazin-1-yl)methyl)benzaldehyde

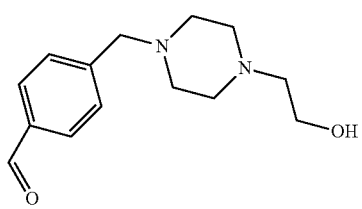 [SMILES: O=Cc1ccc(CN2CCN(CCO)CC2)cc1]

To a solution of 4-(dimethoxymethyl)benzaldehyde (2.08 g, 10.0 mmol) in methanol (30 mL) was added 1-(2-hydroxyethyl)piperidine (1.02 mL, 8.31 mmol). The reaction mixture was stirred at RT for 30 minutes and then sodium triacetoxyborohydride (2.97 g, 14.0 mmol) added. The reaction mixture was stirred at RT for 16 hours. The reaction mixture was diluted with ethyl acetate and washed with 10% aqueous potassium carbonate, water and brine. The organic phase was dried (magnesium sulfate), filtered and the solvent evaporated at reduced pressure. The residue was loaded onto an SCX-2 cartridge and the column was eluted with ethanol (5 column volumes) followed by 10% triethylamine in ethanol (5 column volumes). Product containing fractions were combined and the solvent evaporated at reduced pressure. The resultant residue was dissolved in THF (20 mL) and 2 M aqueous hydrochloric acid (20 mL) added. The reaction mixture was stirred at RT for 18 hours. To the reaction mixture was added 10% aqueous potassium carbonate and the mixture extracted with DCM. The organic phase was passed through a hydrophobic frit and the solvent evaporated to afford the title compound (1.28 g, 48%).

$^1$H NMR (400 MHz, CDCl$_3$): δ 10.0 (s, 1H); 7.85-7.83 (m, 2H); 7.52 (d, J=8.8 Hz, 2H); 3.62-3.56 (m, 4H); 2.75-2.50 (m, 10H); 1.43 (br s, 1H).

Step 2: 2-(4-(4-((((R)-2-Hydroxy-2-(8-hydroxy-2-oxo-1,2-dihydroquinolin-5-yl)ethyl)-amino)methyl)benzyl)piperazin-1-yl)ethyl 4-((3-((S)-phenyl((((R)-quinuclidin-3-yloxy)carbonyl)amino)methyl)phenoxy)methyl)benzoate (Compound 46)

The title compound was prepared as described in Example 2 Step 3 and Step 4 with 4-((4-(2-hydroxyethyl)piperazin-1-yl)methyl)benzaldehyde replacing N-ethyl-4-formyl-N-(2-hydroxyethyl)benzamide in Step 3 and the subsequent product used in Step 4.

The following compound was prepared as described in Example 9 Step 1 and Step 2 with the appropriate aminoalcohol replacing 1-(2-hydroxyethyl)piperidine in Step 1.

| Cpd. | Commercially available alcohol | Structure |
|---|---|---|
| 47 | HN(Me)CH₂CH₂OH | 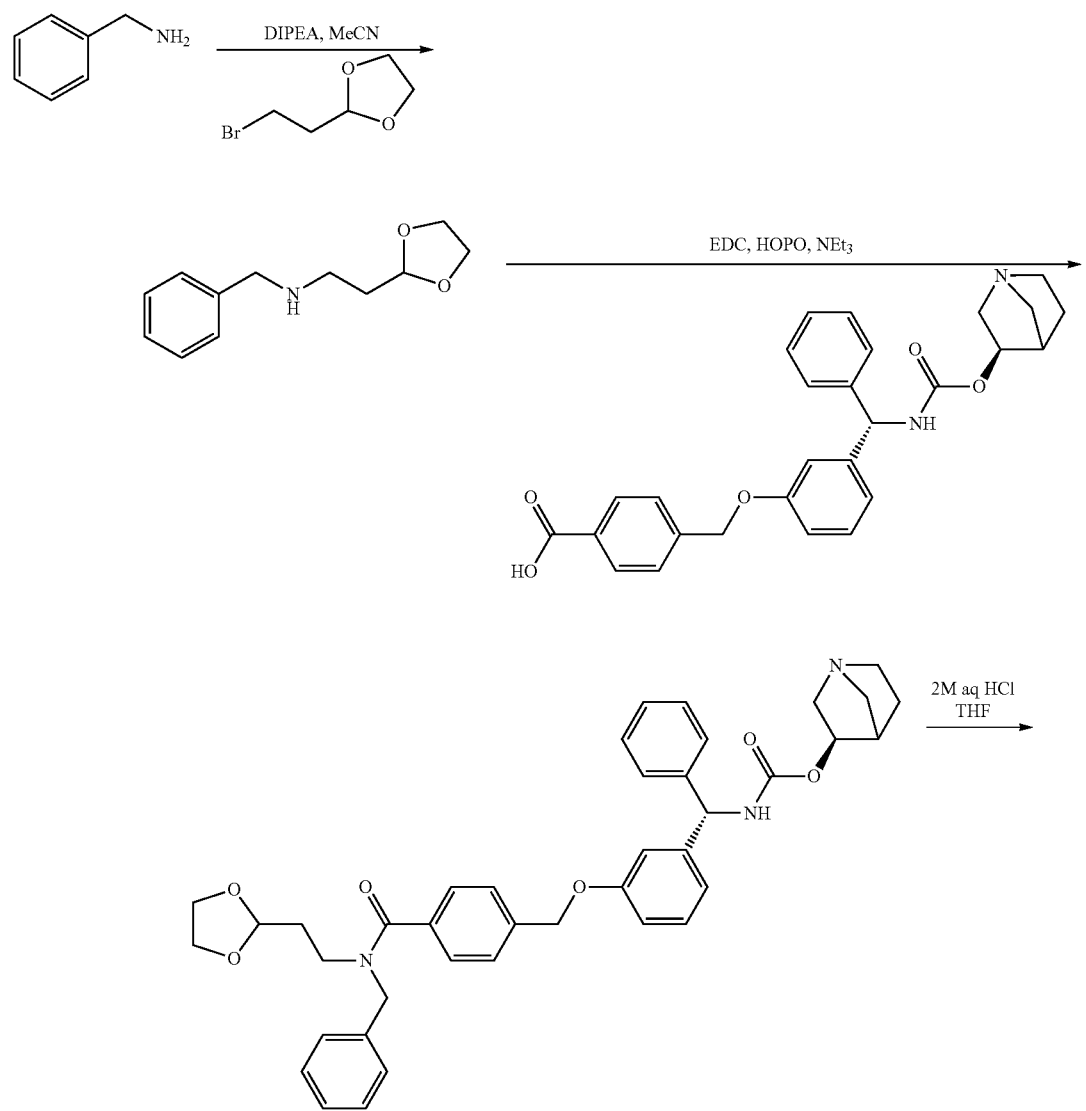 |
Synthesis of Compounds 48 to 51

-continued
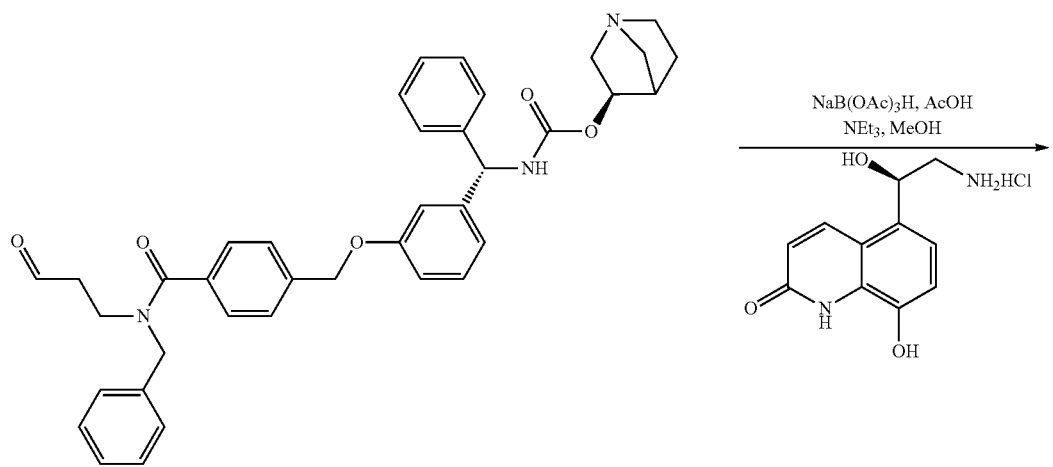
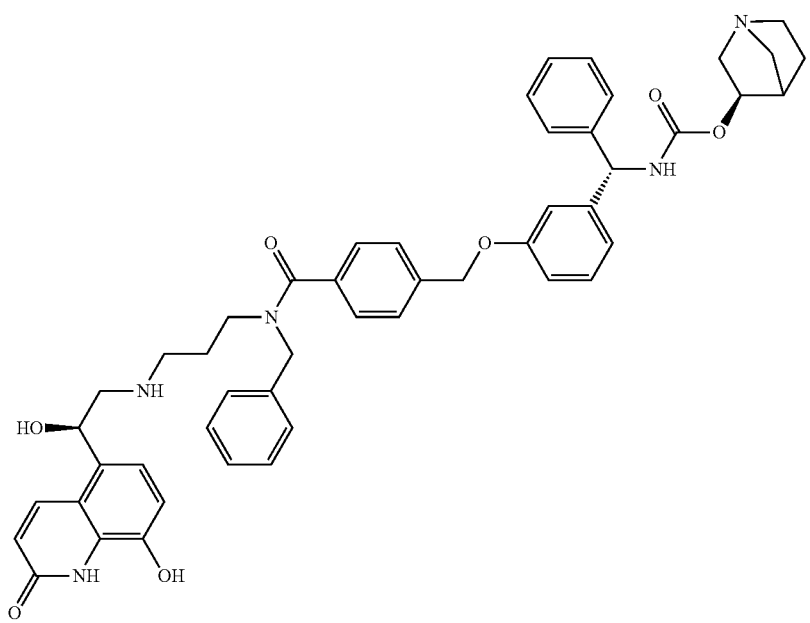

Example 10

(R)-Quinuclidin-3-yl ((S)-(3-((4-(benzyl(3-(((R)-2-hydroxy-2-(8-hydroxy-2-oxo-1,2-dihydroquinolin-5-yl)ethyl)amino)propyl)carbamoyl)benzyl)oxy)phenyl)-(phenyl)methyl)carbamate (Compound 48)

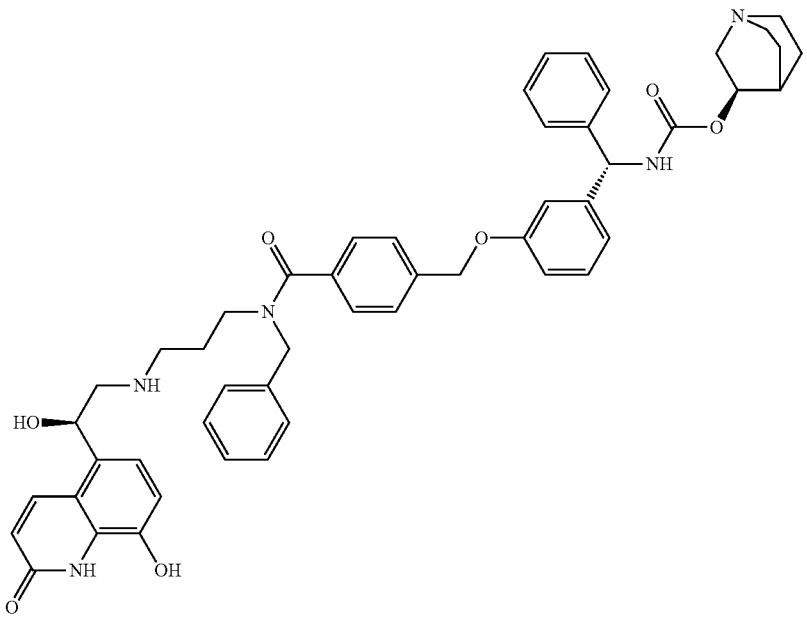 [SMILES: O=C(N[C@@H](c1ccccc1)c1cccc(OCc2ccc(C(=O)N(CCCNC[C@H](O)c3ccc(O)c4[nH]c(=O)ccc34)Cc3ccccc3)cc2)c1)O[C@H]1CN2CCC1CC2]

Step 1: N-Benzyl-2-(1,3-dioxolan-2-yl)ethanamine

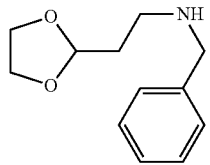 [SMILES: c1ccc(CNCCC2OCCO2)cc1]

To a mixture of benzylamine (2.18 mL, 20.0 mmol) and di-iso-propylethylamine (2.61 mL, 15.0 mmol) in acetonitrile (30 mL) was added 2-(2-bromoethyl)-1,3-dioxolane (1.17 mL, 10.0 mmol). The reaction mixture was stirred at room temperature for 72 hours. The reaction mixture was diluted with ethyl acetate and washed with water and brine. The organic phase was dried (magnesium sulfate), filtered and the solvent evaporated at reduced pressure. The residue was purified by flash column chromatography eluting with 0 to 4% methanol/dichloromethane to afford the title compound (0.836 g, 40%).

$^1$H NMR (400 MHz, CDCl$_3$): δ 7.52-7.22 (m, 5H); 4.95-4.88 (m, 1H); 3.96-3.79 (m, 7H); 2.80-2.76 (m, 2H); 1.93-1.88 (m, 2H).

Step 2: (R)-Quinuclidin-3-yl ((S)-(3-((4-((2-(1,3-dioxolan-2-yl)ethyl)(benzyl)-carbamoyl)benzyl)oxy)phenyl)(phenyl)methyl)carbamate Triethylamine (0.278 mL, 2.00 mmol) was added to a solution of 4-((3-((S)-phenyl((((R)-quinuclidin-3-yloxy)carbonyl)amino)methyl)phenoxy)methyl)benzoic acid (0.418 g, 0.80 mmol) in DMF (2 mL). This mixture was stirred at room temperature for 5 minutes and then 2-hydroxypyridine-N-oxide (0.107 g, 0.96 mmol) and EDC (0.184 g, 0.96 mmol) and the mixture stirred for a further 10 minutes. A solution of N-benzyl-2-(1,3-dioxolan-2-yl)ethanamine (0.331 g, 1.6 mmol) in DMF (2 mL) was added. The reaction mixture was heated at 40° C. for 4 hours followed by stirring at room temperature for 48 hours. The reaction mixture was diluted with ethyl acetate and washed with 10% aqueous potassium carbonate and twice with brine. The organic phase was dried (magnesium sulfate), filtered and the solvent evaporated at reduced pressure. The residue was purified by flash column chromatography eluting with 100% ethyl acetate to 8% methanolic ammonia/ethyl acetate to afford the title compound (0.471 g, 87%). The material was used in the next step with no further characterisation.

Step 3: (R)-Quinuclidin-3-yl ((S)-(3-((4-(benzyl(3-(((R)-2-hydroxy-2-(8-hydroxy-2-oxo-1,2-dihydroquinolin-5-yl)ethyl)amino)propyl)carbamoyl)benzyl)oxy)phenyl)-(phenyl)methyl)carbamate

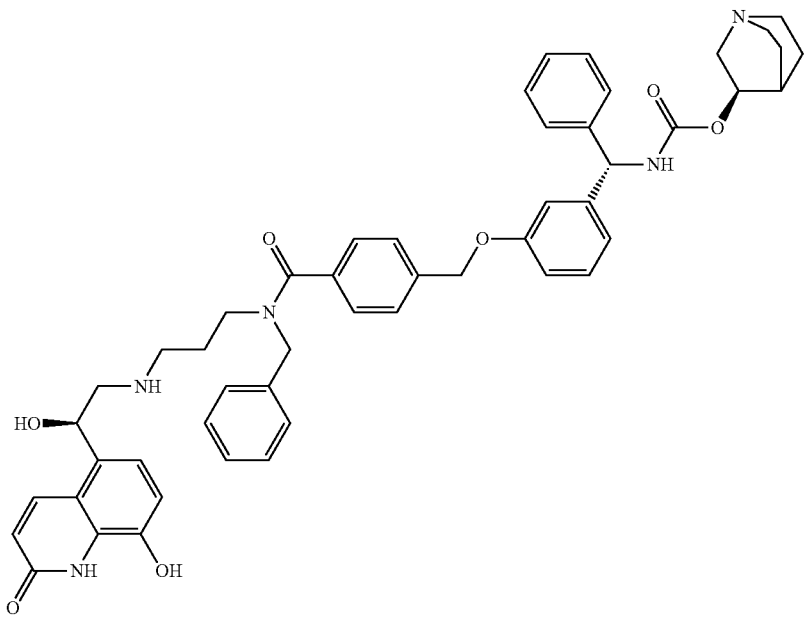 [SMILES: O=C(N[C@@H](c1ccccc1)c1cccc(OCc2ccc(C(=O)N(CCCNC[C@H](O)c3ccc(O)c4[nH]c(=O)ccc34)Cc3ccccc3)cc2)c1)O[C@H]1CN2CCC1CC2]

The title compound was prepared as described in Example 1 Step 12 and Step 13 with (R)-quinuclidin-3-yl ((S)-(3-((4-((2-(1,3-dioxolan-2-yl)ethyl)(benzyl)carbamoyl)-benzyl)oxy)phenyl)(phenyl)methyl)carbamate replacing 3-(1,3-dioxolan-2-yl)propyl 1-(4-((3-((S)-phenyl((((R)-quinuclidin-3-yloxy)carbonyl)amino)methyl)phenoxy)methyl)-benzoyl)piperidine-4-carboxylate in Step 12 and the subsequent product used in Step 13.

$^1$H NMR (400 MHz, DMSO-d$_6$, 105° C.): δ 8.21-8.15 (m, 3H); 7.58 (s, 1H); 7.46 (d, J=7.9 Hz, 2H); 7.41-7.29 (m, 7H); 7.29-7.20 (m, 6H); 7.07-7.00 (m, 2H); 6.97-6.85 (m, 3H); 6.47 (d, J=9.9 Hz, 1H); 5.83 (d, J=7.2 Hz, 1H); 5.11 (s, 2H); 4.98 (dd, J=7.7, 4.9 Hz, 1H); 4.66-4.58 (m, 3H); 3.40-3.25 (m, 2H); 3.08 (dd, J=14.4, 8.3 Hz, 1H); 2.78-2.56 (m, 9H); 1.93-1.89 (m, 1H); 1.81-1.70 (m, 1H); 1.70-1.56 (m, 3H); 1.53-1.44 (m, 1H); 1.36-1.27 (m, 1H).

The following compounds were prepared as described in Example 10 with the appropriate amine replacing benzylamine in Step 1 and the subsequent products used in Step 2 and Step 3.

| Cpd. | Appropriate amine | Structure |
|---|---|---|
| 49 | | 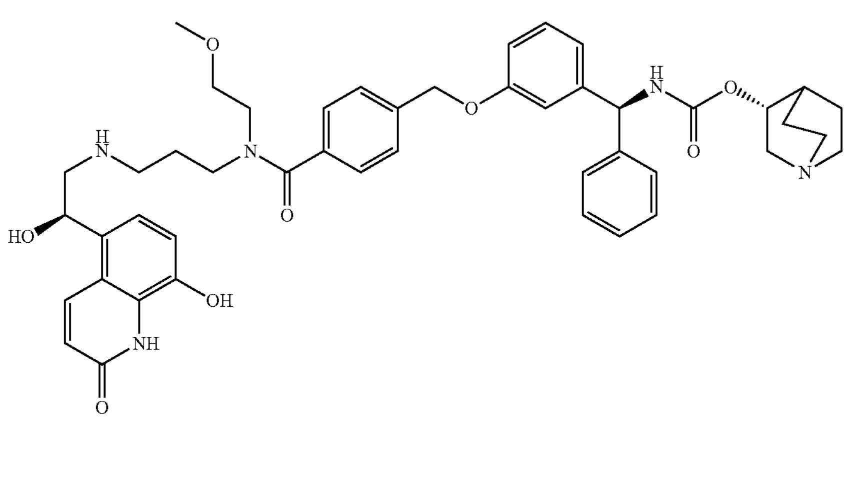 [SMILES: COCCN(CCCNC[C@H](O)c1ccc(O)c2[nH]c(=O)ccc12)C(=O)c1ccc(COc2cccc([C@@H](NC(=O)O[C@H]3CN4CCC3CC4)c3ccccc3)c2)cc1] |

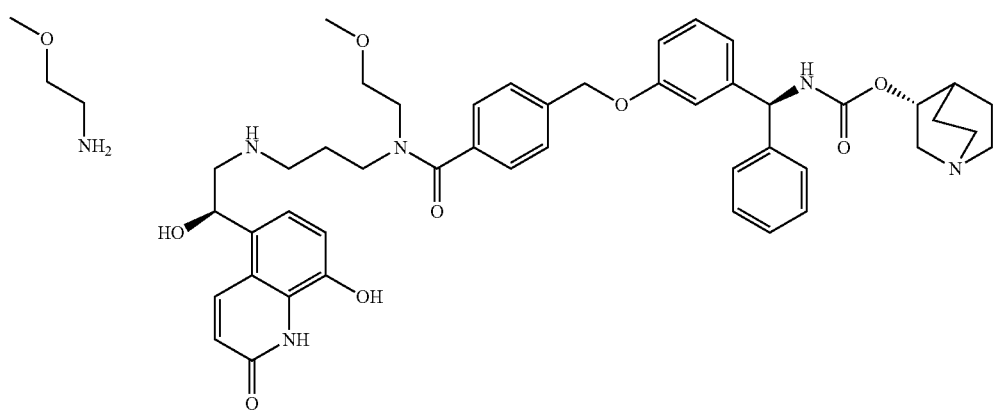

| Cpd. | Appropriate amine | Structure |
|---|---|---|
| 50 | | 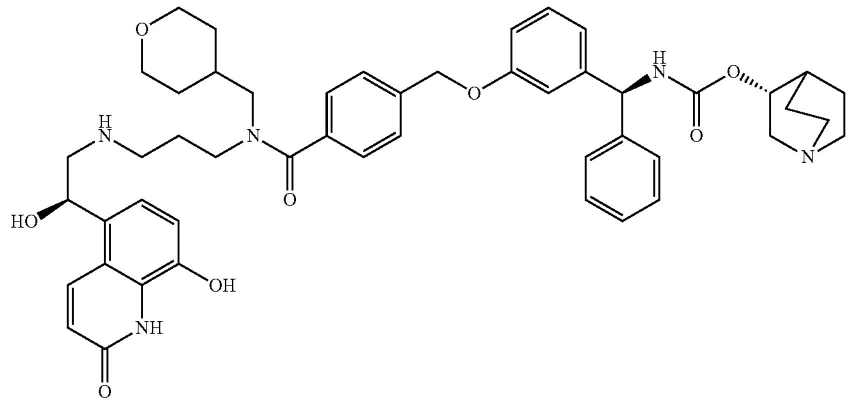 [SMILES: O=C(N[C@@H](c1ccccc1)c1cccc(OCc2ccc(C(=O)N(CCCNC[C@H](O)c3ccc(O)c4[nH]c(=O)ccc34)CC3CCOCC3)cc2)c1)O[C@H]1CN2CCC1CC2] |
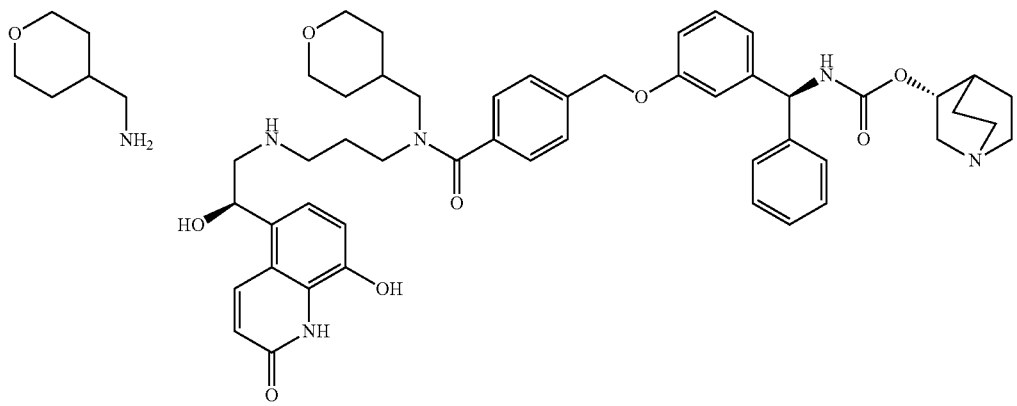
| 51 | | |
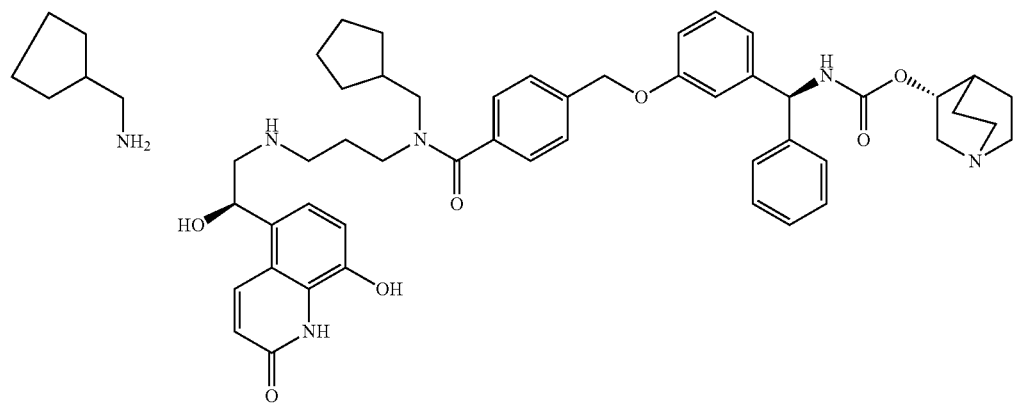
The following compounds were prepared as described in Example 10 with the appropriate acid replacing 4-((3-((S)-phenyl((((R)-quinuclidin-3-yloxy)carbonyl)amino)methyl)phenoxy)methyl)benzoic acid in Step 2 and the subsequent products used in Step 3.
| Cpd. | Structure | Appropriate acid |
|---|---|---|
| 48A | 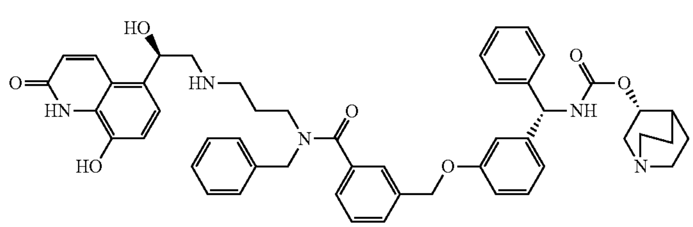 [SMILES: O=C(N[C@@H](c1ccccc1)c1cccc(OCc2cccc(C(=O)N(CCCNC[C@H](O)c3ccc(O)c4[nH]c(=O)ccc34)Cc3ccccc3)c2)c1)O[C@H]1CN2CCC1CC2] | |
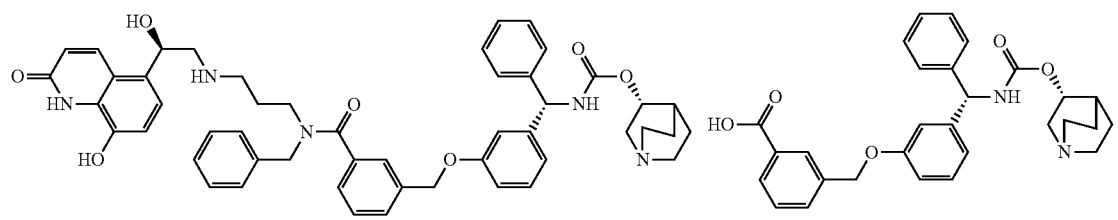

-continued
| Cpd. | Structure | Appropriate acid |
|---|---|---|
| 48B | 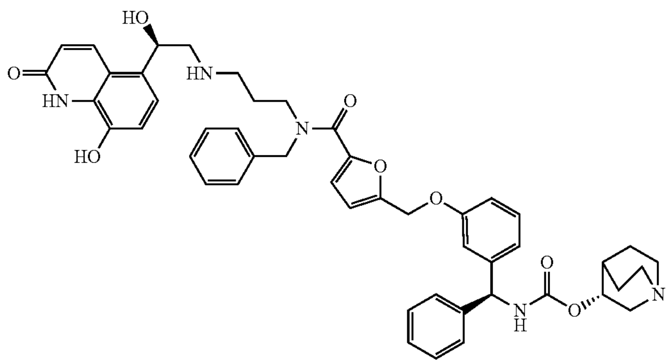 [SMILES: O=C(N[C@@H](c1ccccc1)c1cccc(OCc2ccc(C(=O)N(CCCNC[C@H](O)c3ccc(O)c4[nH]c(=O)ccc34)Cc3ccccc3)o2)c1)O[C@H]1CN2CCC1CC2] | |
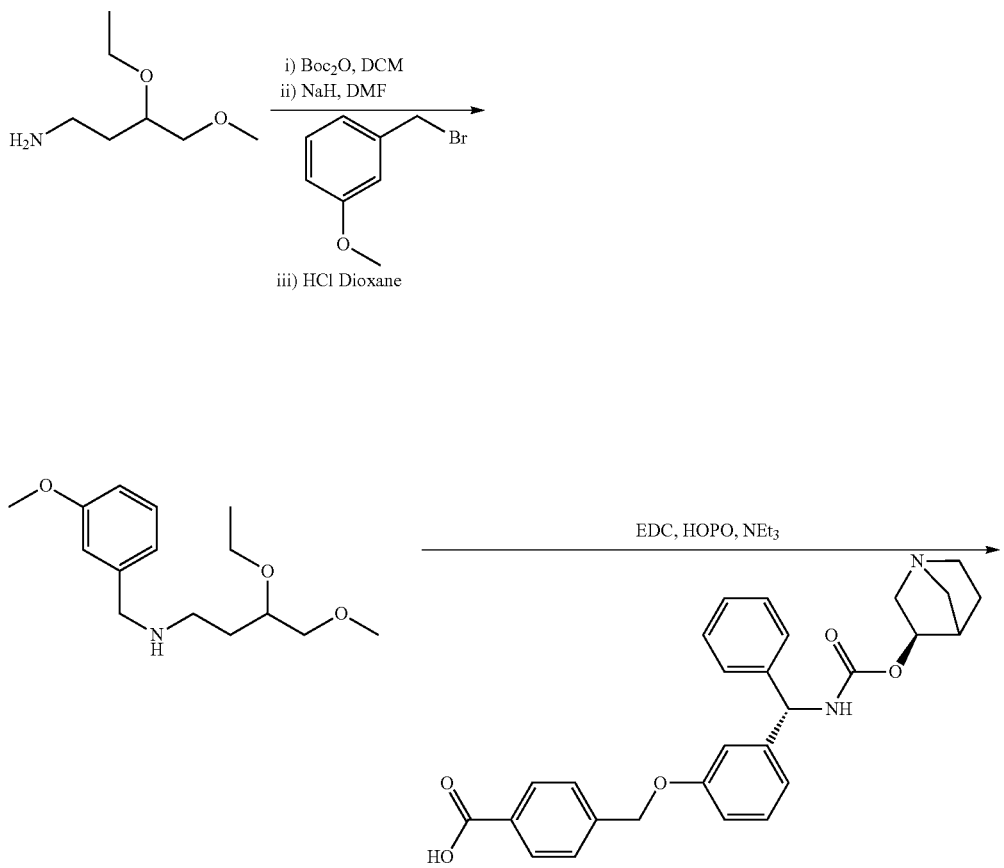
Synthesis of Compounds 52 to 68
25

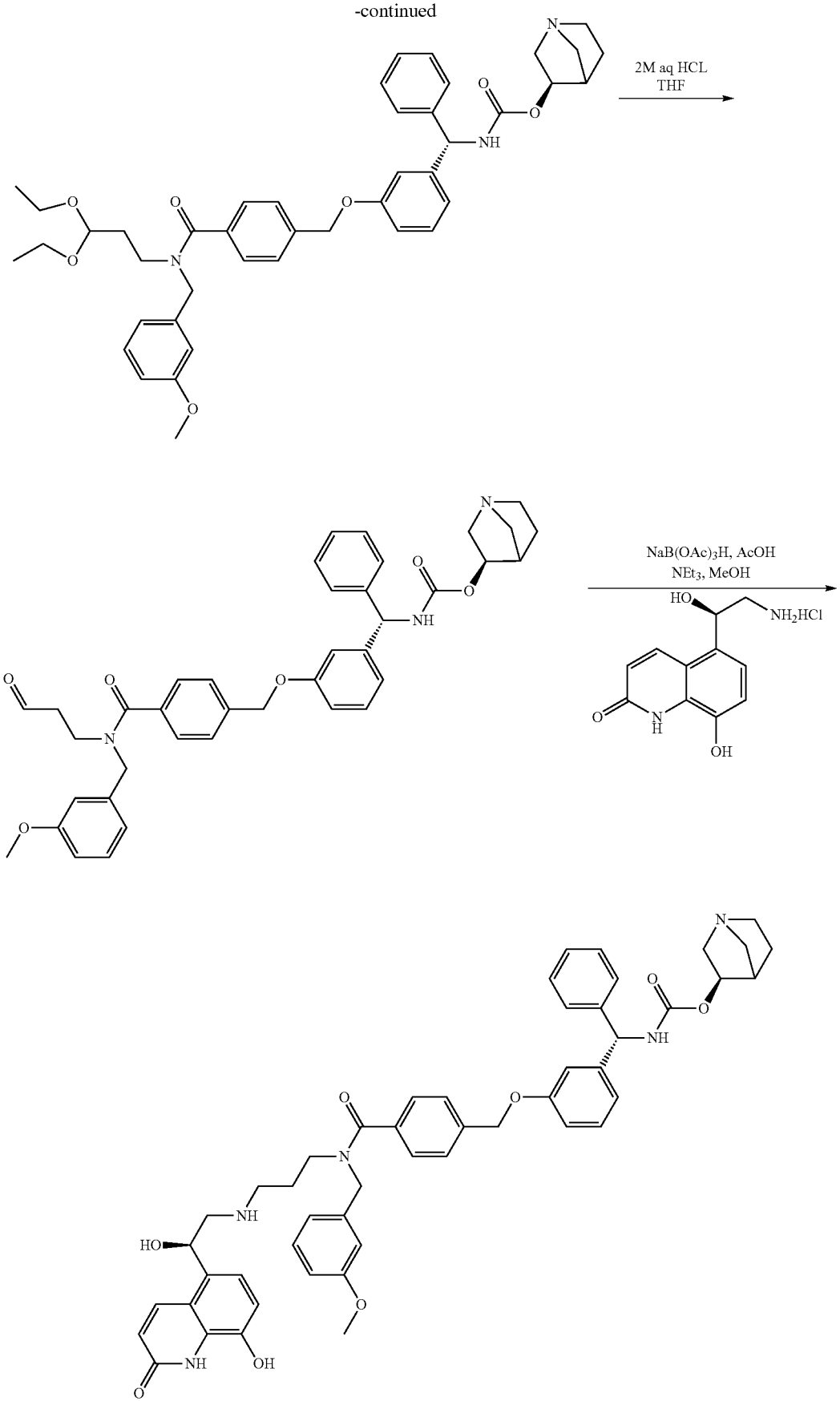

Example 11

(R)-Quinuclidin-3-yl((S)-(3-((4-((3-(((R)-2-hydroxy-2-(8-hydroxy-2-oxo-1,2-dihydroquinolin-5-yl)ethyl)amino)propyl)(3-methoxybenzyl)carbamoyl)benzyl)oxy)phenyl)(phenyl)methyl)carbamate (Compound 52)

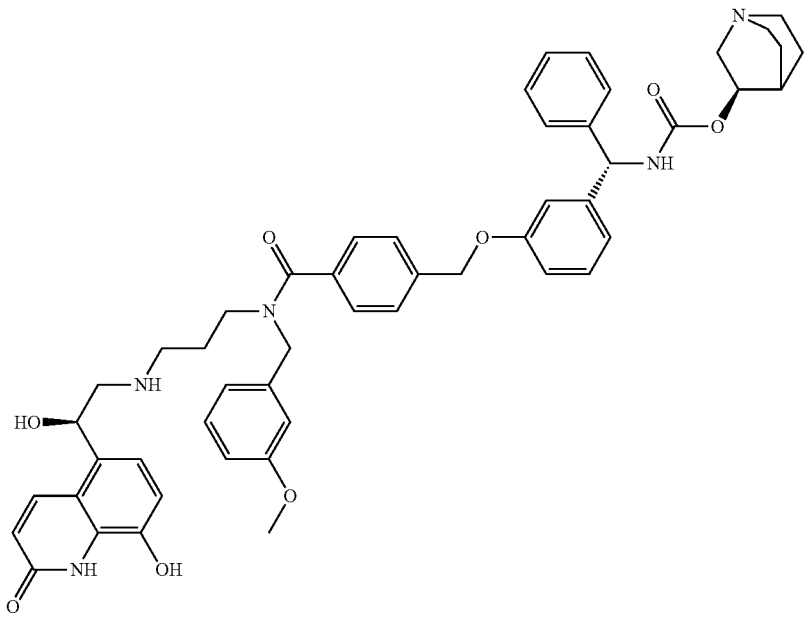 [SMILES: COc1cccc(CN(CCCNC[C@H](O)c2ccc(O)c3[nH]c(=O)ccc23)C(=O)c2ccc(COc3cccc([C@@H](NC(=O)O[C@H]4CN5CCC4CC5)c4ccccc4)c3)cc2)c1]

Step 1: tert-Butyl (3,3-diethoxypropyl)carbamate

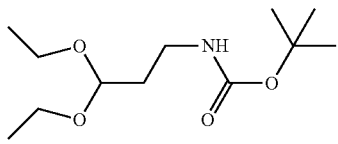 [SMILES: CCOC(CCNC(=O)OC(C)(C)C)OCC]

A solution of di-tert-butyl dicarbonate (6.74 g, 31.0 mmol) in DCM (50 mL) was added to a solution of 1-amino-3,3-diethoxypropane (5.0 g, 34.0 mmol) in DCM (50 mL). The reaction mixture was stirred at room temperature for 2 hours. The reaction mixture was washed with 10% aqueous potassium hydrogen sulfate and the organic phase dried (magnesium sulfate), filtered and the solvent evaporated at reduced pressure to afford the title product (8.13 g, 100%).

$^1$H NMR (400 MHz, CDCl$_3$): δ 5.00 (s, 1H), 4.56-4.53 (m, 1H); 3.69-3.62 (m, 2H); 3.54-3.46 (m, 2H); 3.24-3.20 (m, 2H); 1.84-1.80 (m, 2H); 1.49 (s, 9H); 1.23-1.19 (m, 6H).

Step 2: 2-(1,3-Dioxolan-2-yl)-N-(3-methoxybenzyl)ethanamine

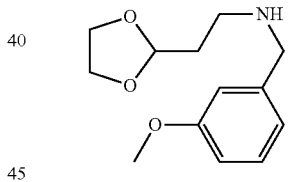

To a stirred solution of tert-butyl (3,3-diethoxypropyl)carbamate (1.0 g, 4.05 mmol) in DMF (15 mL) was added sodium hydride (0.25 g, 6.25 mmol). The reaction mixture was stirred at room temperature for 30 minutes and 3-methoxybenzyl bromide (0.875 mL, 6.25 mmol) added. The reaction mixture was stirred at room temperature for 72 hours. The reaction mixture was diluted with ethyl acetate and washed with water and twice with brine. The organic phase was dried (magnesium sulfate), filtered and the solvent evaporated at reduced pressure. The residue was dissolved in ethanol (10 mL) and 4M hydrogen chloride in dioxane (10 mL) added. The reaction mixture was stirred at room temperature for 2 hours and the solvent evaporated at reduced pressure. The residue was loaded onto an SCX-2 cartridge and eluted with ethanol (4 column volumes) and then 10% triethylamine/ethanol (4 column volumes). The product containing fractions were combined and the solvent evaporated at reduced pressure to afford the title compound (0.543 g, 50%).

$^1$H NMR (400 MHz, CDCl$_3$): δ 7.25-7.21 (m, 1H); 6.90-6.80 (m, 2H); 6.78-6.77 (m, 1H); 4.60 (t, J=5.6 Hz, 1H); 3.81 (s, 3H); 3.76 (s, 2H); 3.55-3.43 (m 2H); 2.72 (t, J=6.8 Hz, 2H); 1.87-1.79 (m, 2H); 1.50 (s, 1H); 1.29-1.09 (m, 6H).

Step 3: (R)-Quinuclidin-3-yl ((S)-(3-((4-((2-(1,3-dioxolan-2-yl)ethyl)(3-methoxybenzyl)carbamoyl)benzyl)oxy)phenyl)(phenyl)methyl)carbamate

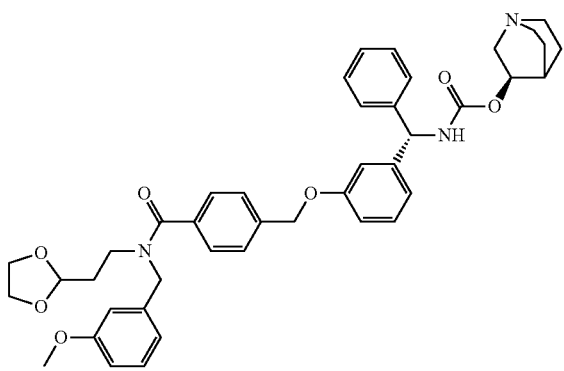 [SMILES: COc1cccc(CN(CCC2OCCO2)C(=O)c2ccc(COc3cccc([C@@H](NC(=O)O[C@H]4CN5CCC4CC5)c4ccccc4)c3)cc2)c1]

The title compound was prepared as described in Example 10 Step 2 with 2-(1,3-dioxolan-2-yl)-N-(3-methoxybenzyl)ethanamine replacing N-benzyl-2-(1,3-dioxolan-2-yl)ethanamine.

Step 4: (R)-Quinuclidin-3-yl ((S)-(3-((4-((3-(((R)-2-hydroxy-2-(8-hydroxy-2-oxo-1,2-dihydroquinolin-5-yl)ethyl)amino)propyl)(3-methoxybenzyl)carbamoyl)benzyl)-oxy)phenyl)(phenyl)methyl)carbamate The title compound was prepared as described in Example 1 Step 12 and Step 13 with (R)-quinuclidin-3-yl ((S)-(3-((4-((2-(1,3-dioxolan-2-yl)ethyl)(3-methoxybenzyl)-carbamoyl)benzyl)oxy)phenyl)(phenyl)methyl)carbamate replacing 3-(1,3-dioxolan-2-yl)propyl 1-(4-((3-((S)-phenyl((((R)-quinuclidin-3-yloxy)carbonyl)amino)methyl)-phenoxy)methyl)benzoyl)piperidine-4-carboxylate in Step 12 and the subsequent product used in Step 13.

$^1$H NMR (400 MHz, DMSO-d$_6$, 85° C.): δ 8.23-8.13 (m, 3H); 7.72 (s, 1H); 7.47 (d, J=7.9 Hz, 2H); 7.39 (d, J=7.9 Hz, 2H); 7.33-7.18 (m, 7H); 7.07-7.01 (m, 2H); 6.96-6.80 (m, 6H); 6.47 (d, J=9.9 Hz, 1H); 5.82 (d, J=8.1 Hz, 1H); 5.10 (s, 2H); 5.00-4.94 (m, 1H); 4.63-4.55 (m, 3H); 3.76 (s, 3H); 3.38-3.28 (m, 2H); 3.08 (m, 1H); 2.74-2.47 (m, 9H); 1.90 (s, 1H); 1.73-1.54 (m, 4H); 1.52-1.43 (m, 1H); 1.31 (t, J=10.8 Hz, 1H).

The following compounds were prepared as described in Example 11 with the appropriate benzyl halide replacing 3-methoxybenzyl bromide in Step 2 and the subsequent products used in Steps 3-4.

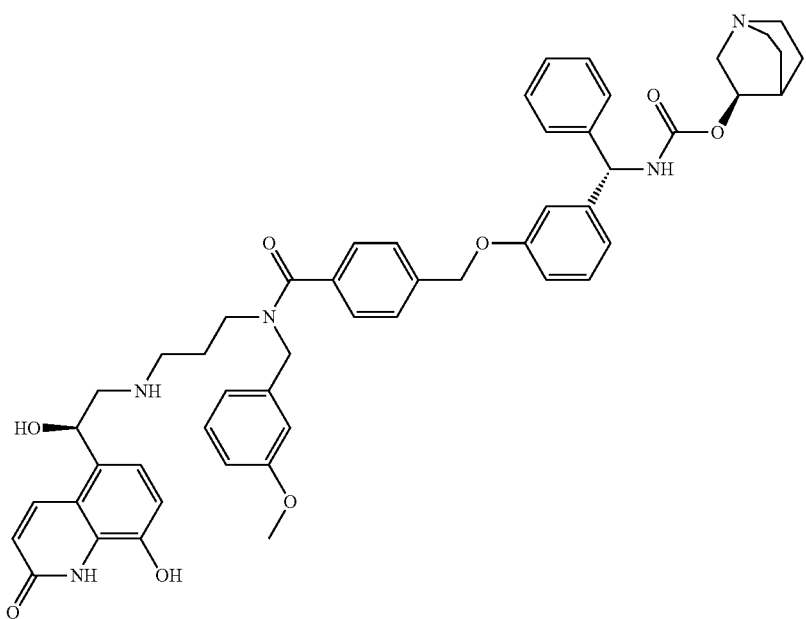 [SMILES: COc1cccc(CN(CCCNC[C@H](O)c2ccc(O)c3[nH]c(=O)ccc23)C(=O)c2ccc(COc3cccc([C@@H](NC(=O)O[C@H]4CN5CCC4CC5)c4ccccc4)c3)cc2)c1]

| Cpd. | Appropriate benzyl halide | Structure |
|---|---|---|
| 53 | 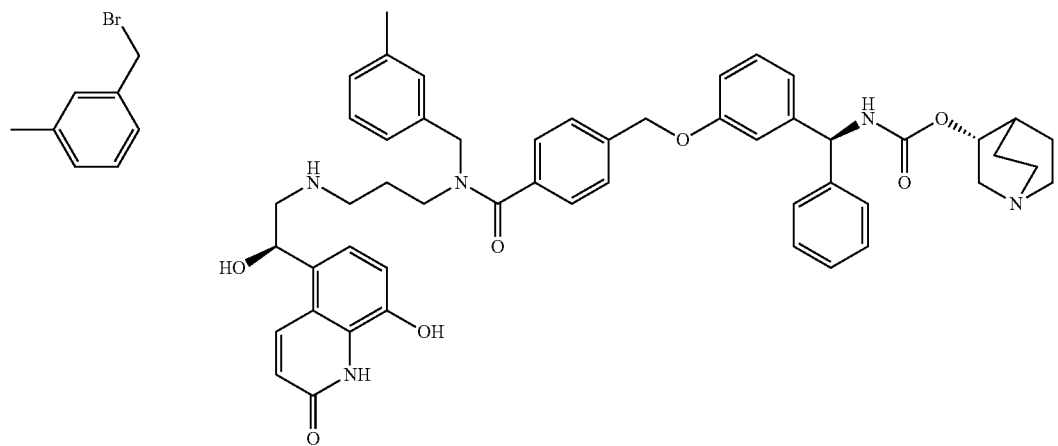 | 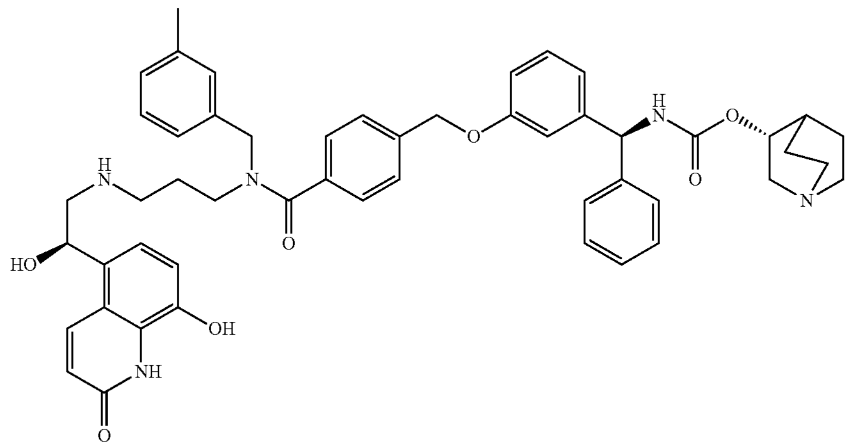 [SMILES: Cc1cccc(CN(CCCNC[C@H](O)c2ccc(O)c3[nH]c(=O)ccc23)C(=O)c2ccc(COc3cccc([C@@H](NC(=O)O[C@H]4CN5CCC4CC5)c4ccccc4)c3)cc2)c1] |
| 54 | 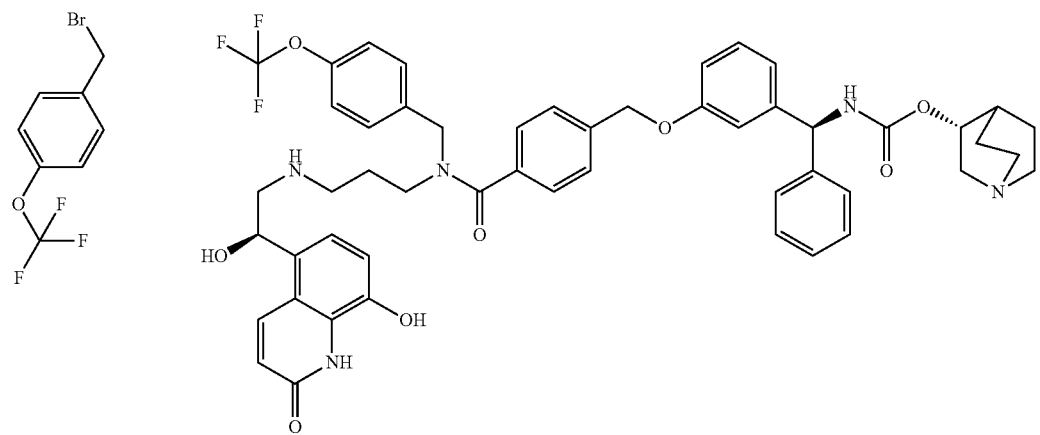 | 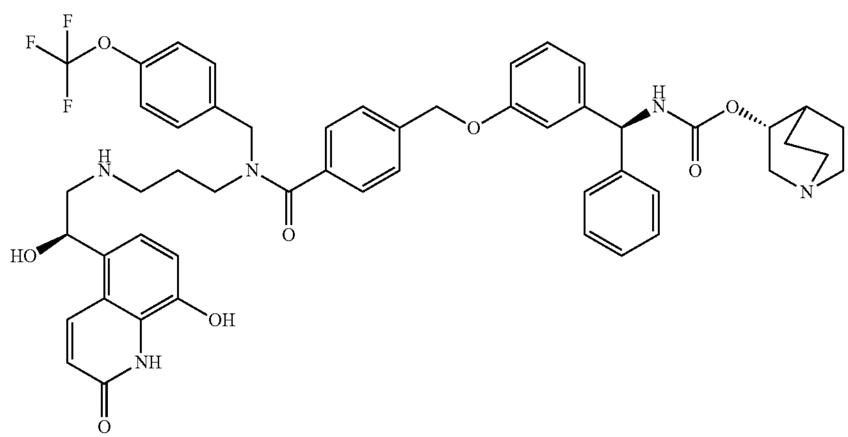 [SMILES: O=C(N[C@@H](c1ccccc1)c1cccc(OCc2ccc(C(=O)N(CCCNC[C@H](O)c3ccc(O)c4[nH]c(=O)ccc34)Cc3ccc(OC(F)(F)F)cc3)cc2)c1)O[C@H]1CN2CCC1CC2] |
| 55 | 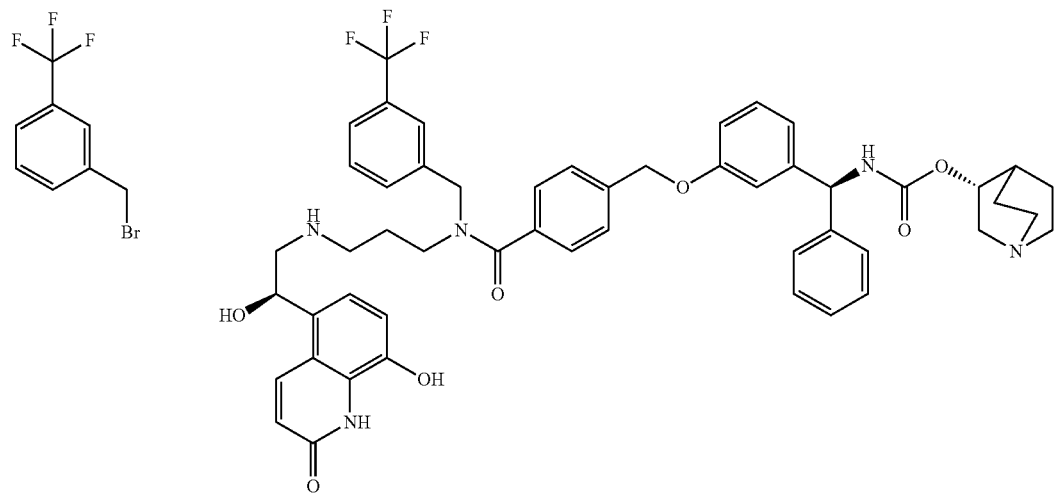 | 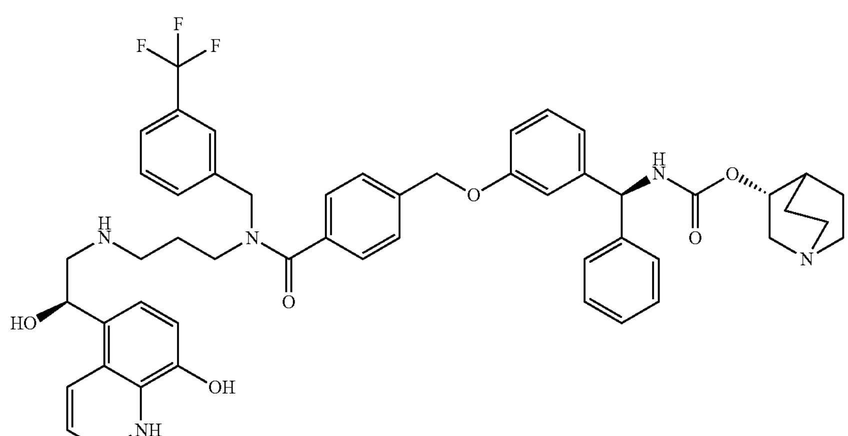 |

-continued
| Cpd. | Appropriate benzyl halide | Structure |
|------|---------------------------|-----------|
| 56 | 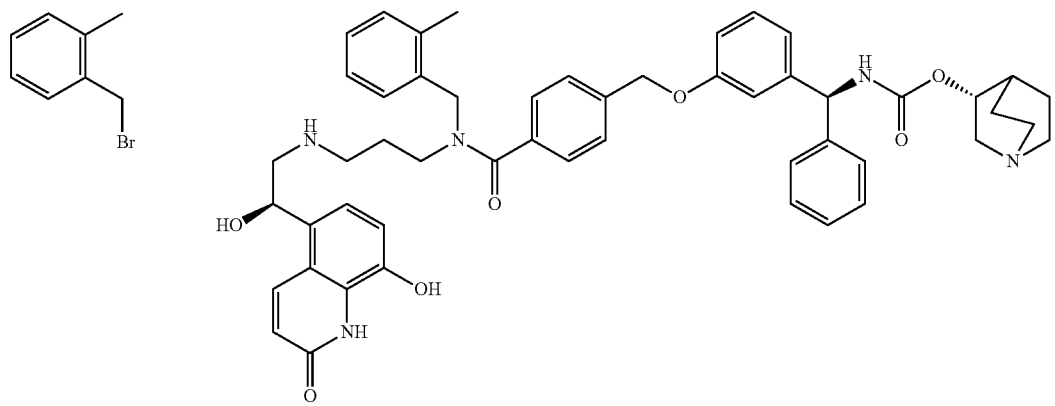 | 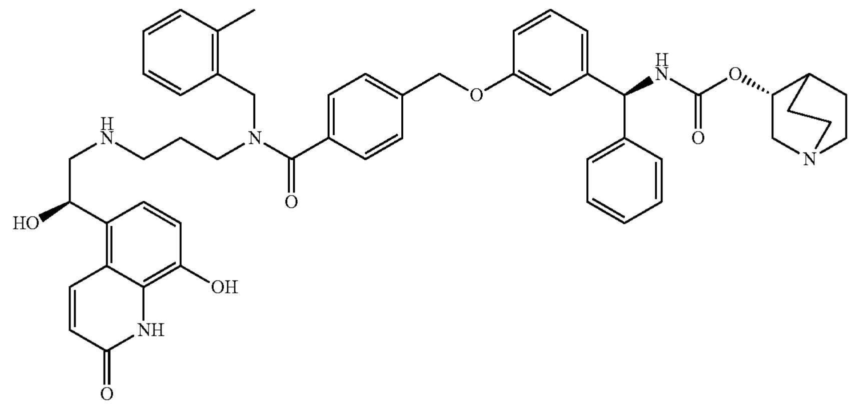 [SMILES: Cc1ccccc1CN(CCCNC[C@H](O)c1ccc(O)c2[nH]c(=O)ccc12)C(=O)c1ccc(COc2cccc([C@@H](NC(=O)O[C@H]3CN4CCC3CC4)c3ccccc3)c2)cc1] |
| 57 | 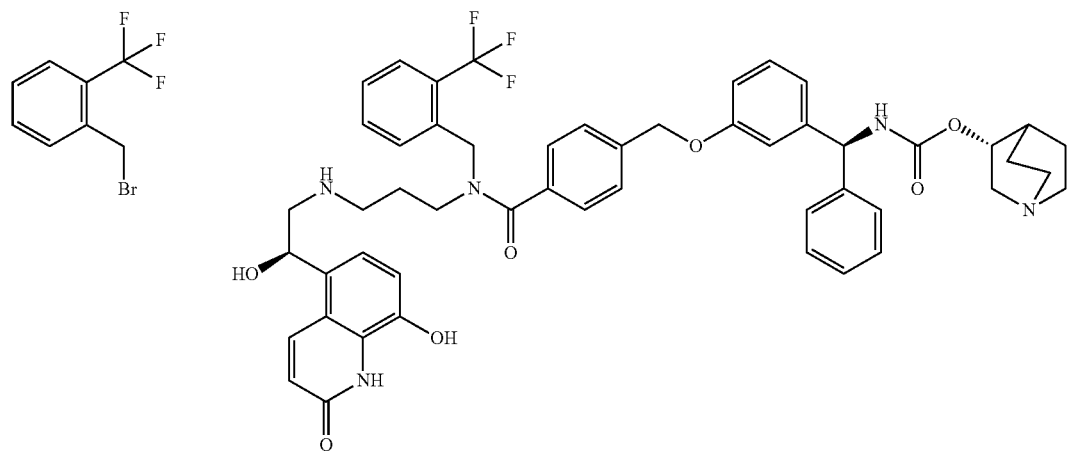 | 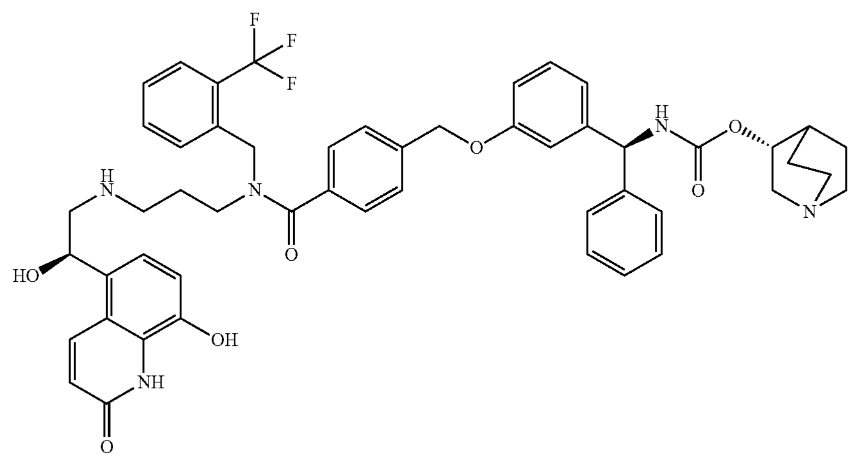 [SMILES: O=C(N[C@@H](c1ccccc1)c1cccc(OCc2ccc(C(=O)N(CCCNC[C@H](O)c3ccc(O)c4[nH]c(=O)ccc34)Cc3ccccc3C(F)(F)F)cc2)c1)O[C@H]1CN2CCC1CC2] |
| 58 | 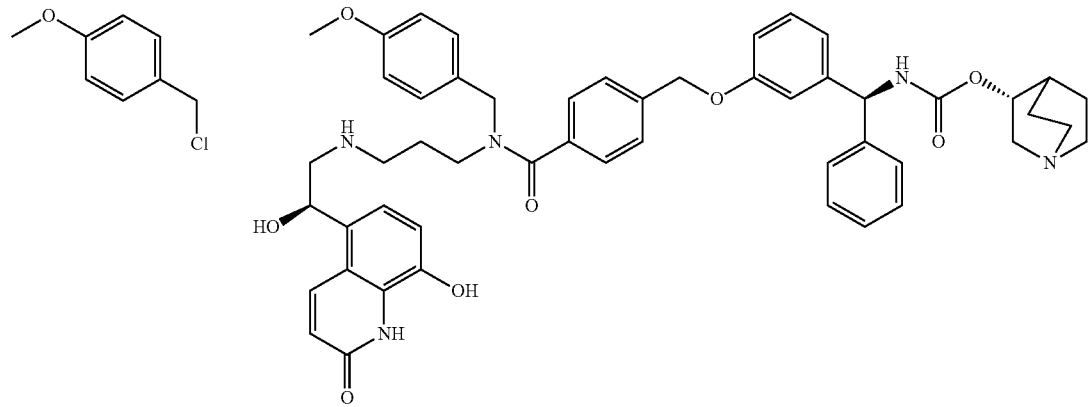 | 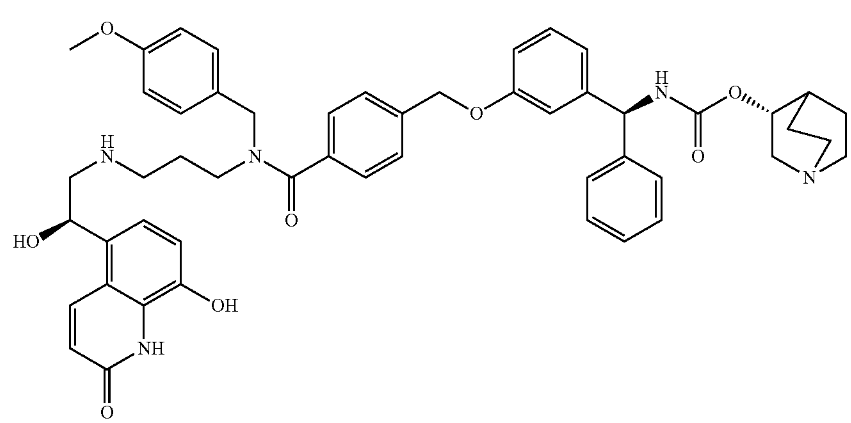 [SMILES: COc1ccc(CN(CCCNC[C@H](O)c2ccc(O)c3[nH]c(=O)ccc23)C(=O)c2ccc(COc3cccc([C@@H](NC(=O)O[C@H]4CN5CCC4CC5)c4ccccc4)c3)cc2)cc1] |

| Cpd. | Appropriate benzyl halide | Structure |
|---|---|---|
| 59 | 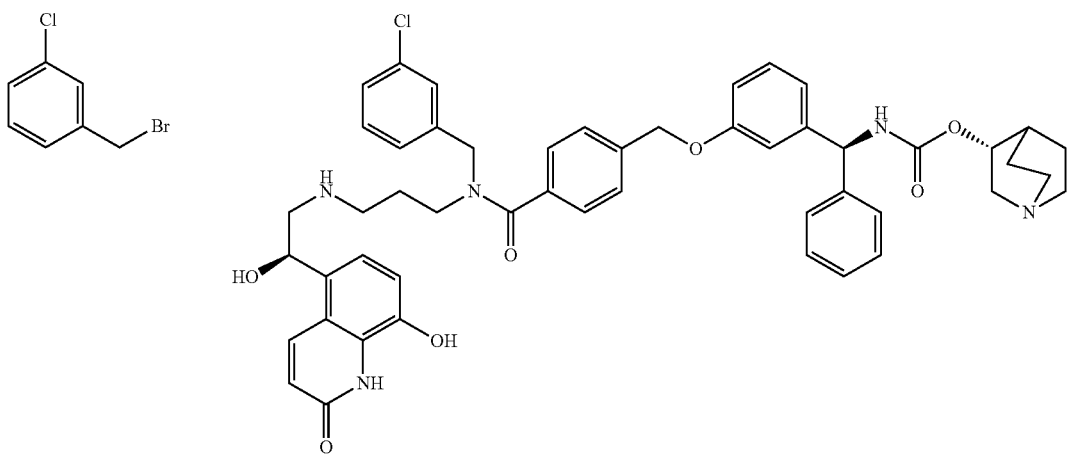 | 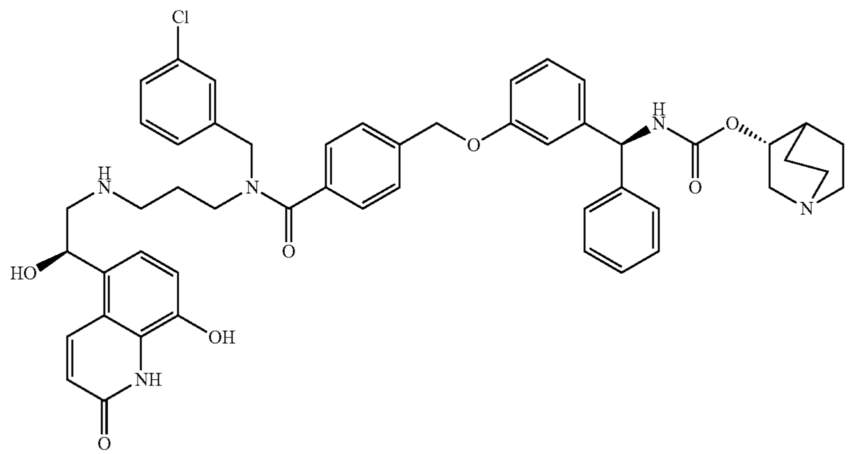 [SMILES: O=C(N[C@@H](c1ccccc1)c1cccc(OCc2ccc(C(=O)N(CCCNC[C@H](O)c3ccc(O)c4[nH]c(=O)ccc34)Cc3cccc(Cl)c3)cc2)c1)O[C@H]1CN2CCC1CC2] |
| 60 | 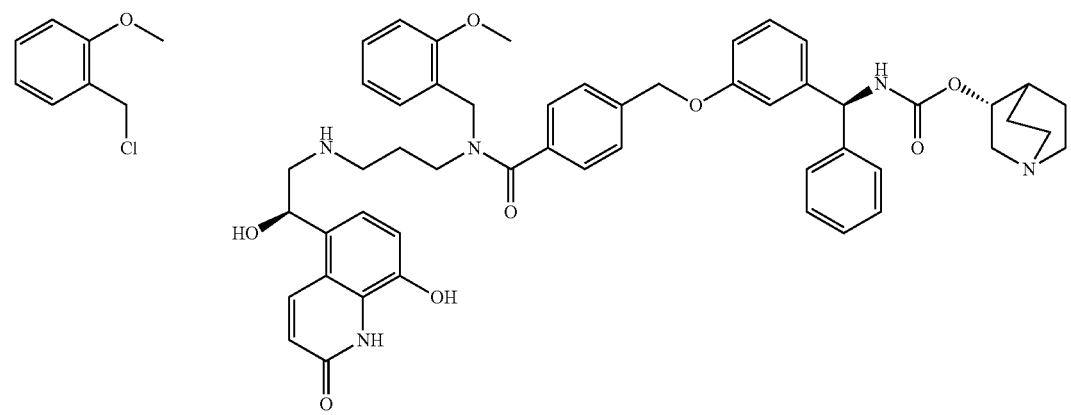 | 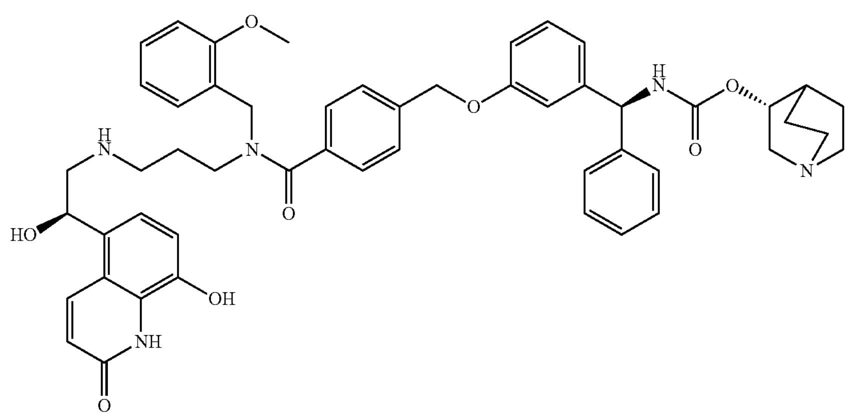 [SMILES: COc1ccccc1CN(CCCNC[C@H](O)c1ccc(O)c2[nH]c(=O)ccc12)C(=O)c1ccc(COc2cccc([C@@H](NC(=O)O[C@H]3CN4CCC3CC4)c3ccccc3)c2)cc1] |
| 61 | 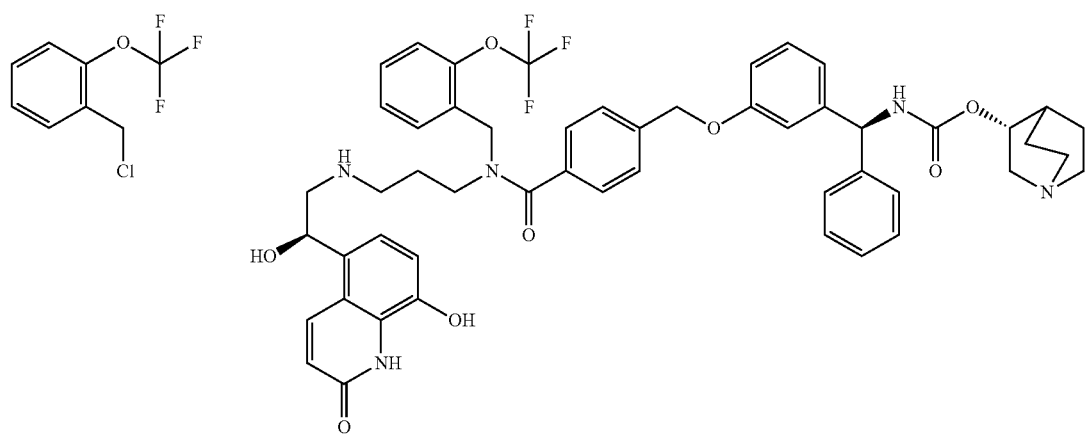 | 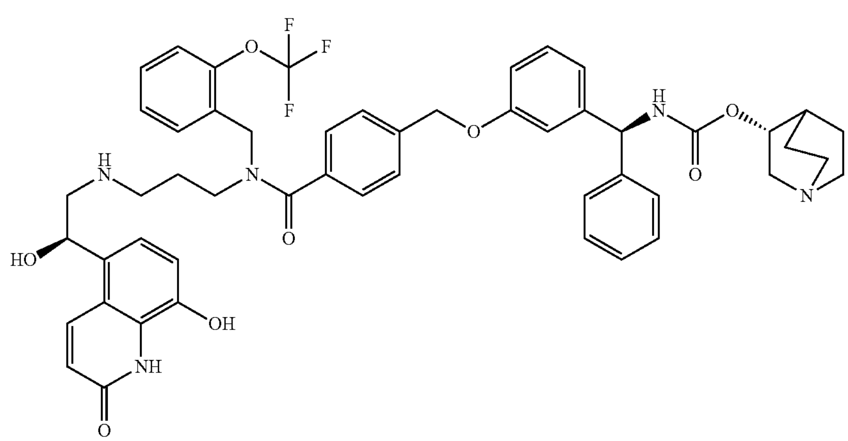 [SMILES: O=C(N[C@@H](c1ccccc1)c1cccc(OCc2ccc(C(=O)N(CCCNC[C@H](O)c3ccc(O)c4[nH]c(=O)ccc34)Cc3ccccc3OC(F)(F)F)cc2)c1)O[C@H]1CN2CCC1CC2] |

-continued
| Cpd. | Appropriate benzyl halide | Structure |
|---|---|---|
| 62 | 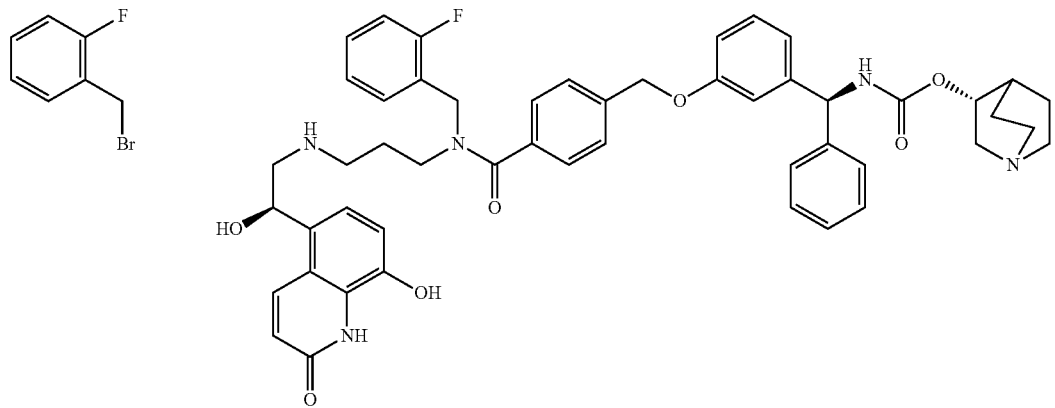 | 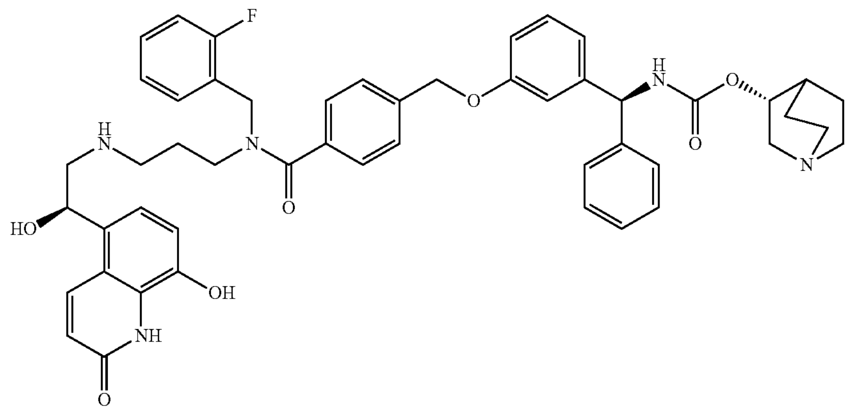 [SMILES: O=C(N[C@@H](c1ccccc1)c1cccc(OCc2ccc(C(=O)N(CCCNC[C@H](O)c3ccc(O)c4[nH]c(=O)ccc34)Cc3ccccc3F)cc2)c1)O[C@H]1CN2CCC1CC2] |
| 63 | 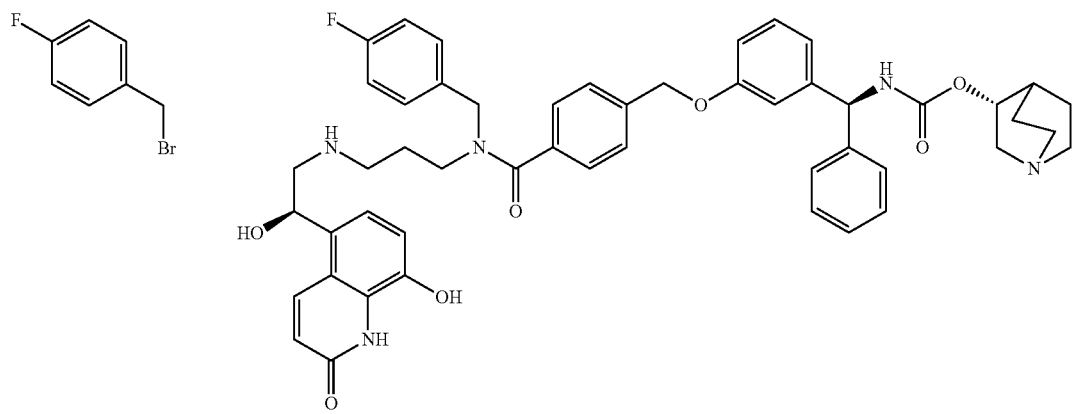 | 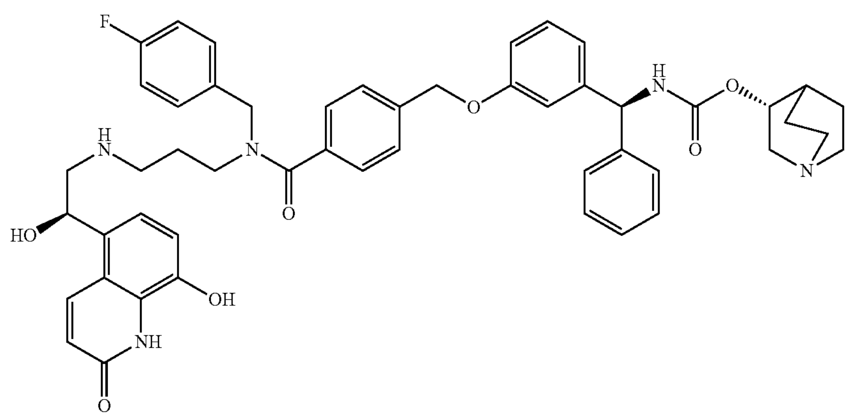 |
| 64 | 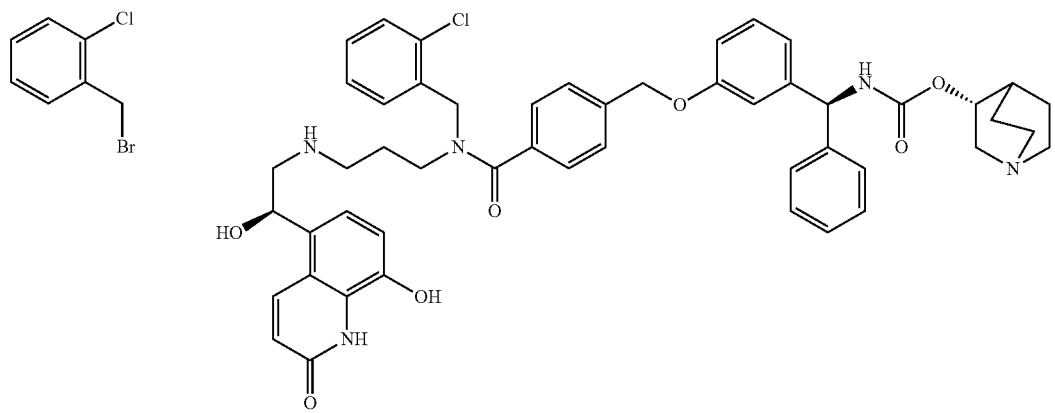 | 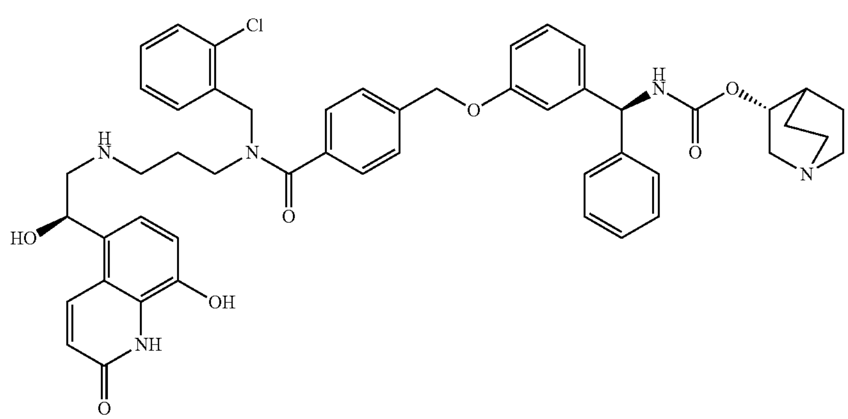 [SMILES: O=C(N[C@@H](c1ccccc1)c1cccc(OCc2ccc(C(=O)N(CCCNC[C@H](O)c3ccc(O)c4[nH]c(=O)ccc34)Cc3ccccc3Cl)cc2)c1)O[C@H]1CN2CCC1CC2] |

| Cpd. | Appropriate benzyl halide | Structure |
|---|---|---|
| 65 | 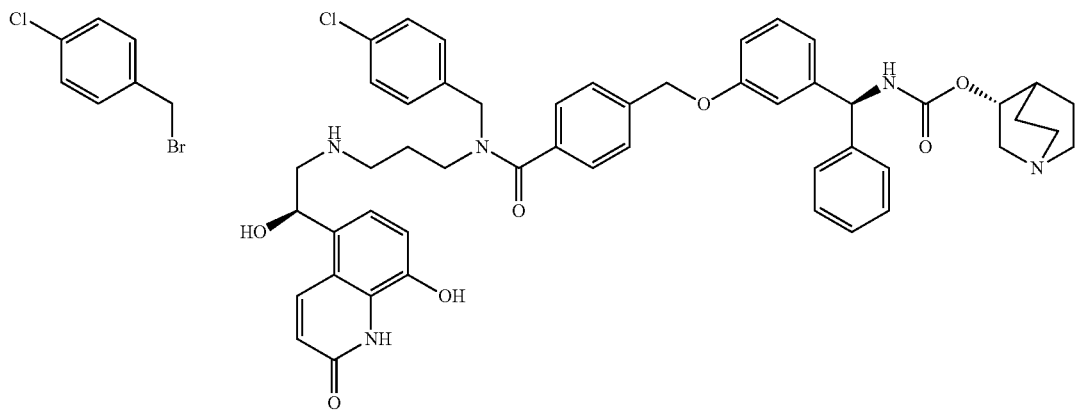 | 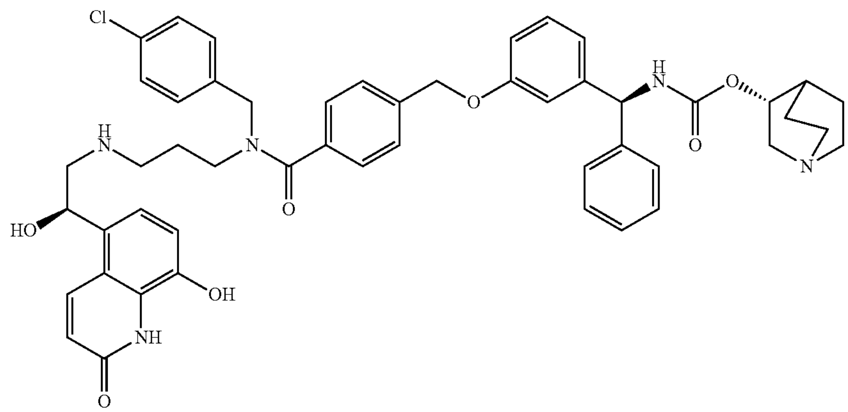 [SMILES: O=C(N[C@@H](c1ccccc1)c1cccc(OCc2ccc(C(=O)N(CCCNC[C@H](O)c3ccc(O)c4[nH]c(=O)ccc34)Cc3ccc(Cl)cc3)cc2)c1)O[C@H]1CN2CCC1CC2] |
| 66 | 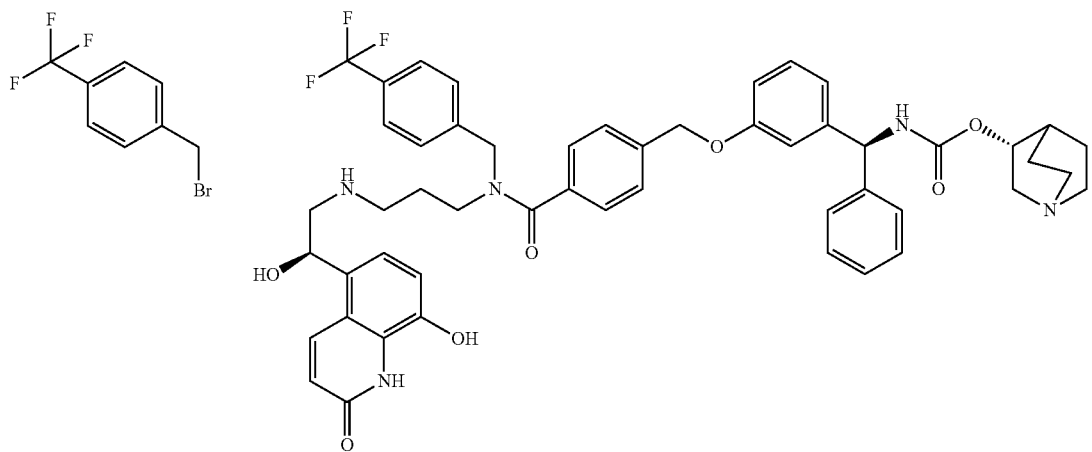 | 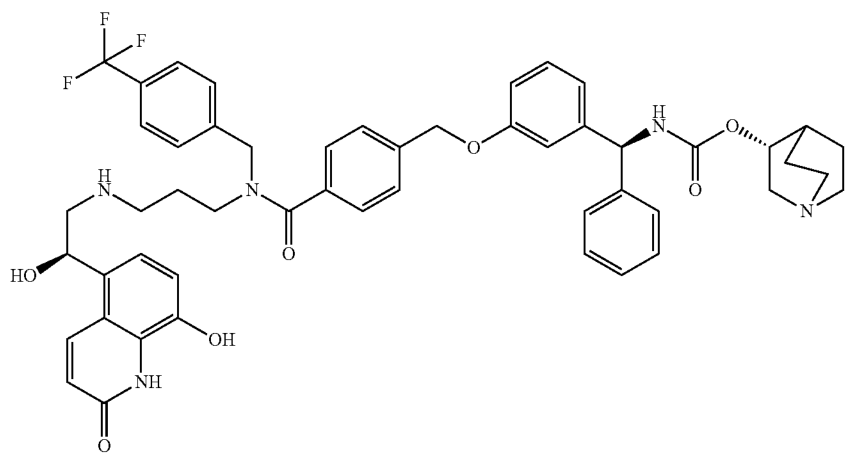 [SMILES: O=C(N[C@@H](c1ccccc1)c1cccc(OCc2ccc(C(=O)N(CCCNC[C@H](O)c3ccc(O)c4[nH]c(=O)ccc34)Cc3ccc(C(F)(F)F)cc3)cc2)c1)O[C@H]1CN2CCC1CC2] |
| 67 | 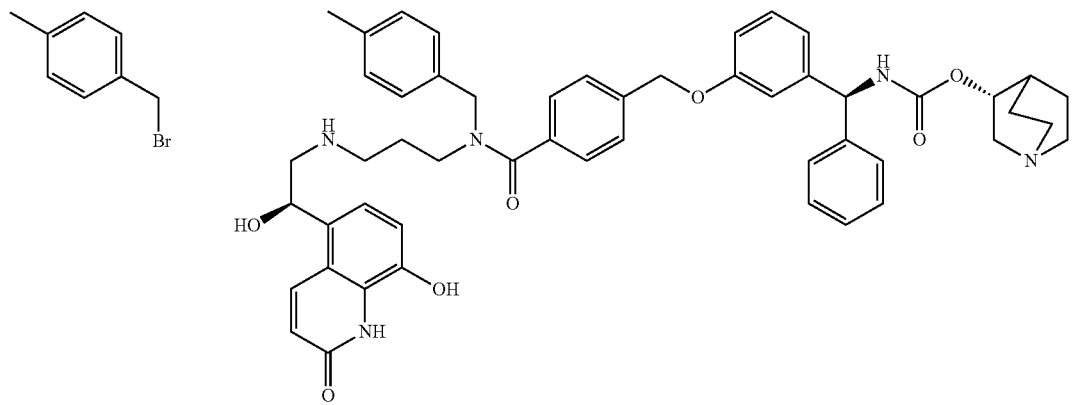 | 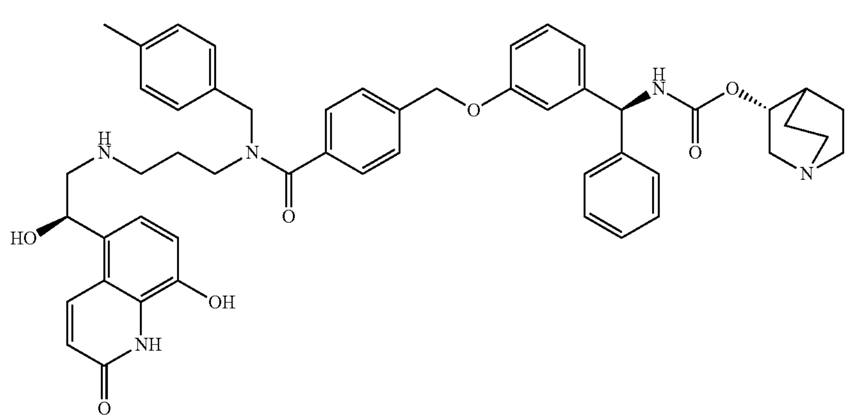 [SMILES: Cc1ccc(CN(CCCNC[C@H](O)c2ccc(O)c3[nH]c(=O)ccc23)C(=O)c2ccc(COc3cccc([C@@H](NC(=O)O[C@H]4CN5CCC4CC5)c4ccccc4)c3)cc2)cc1] |

| Cpd. | Appropriate benzyl halide | Structure |
|---|---|---|
| 68 | | 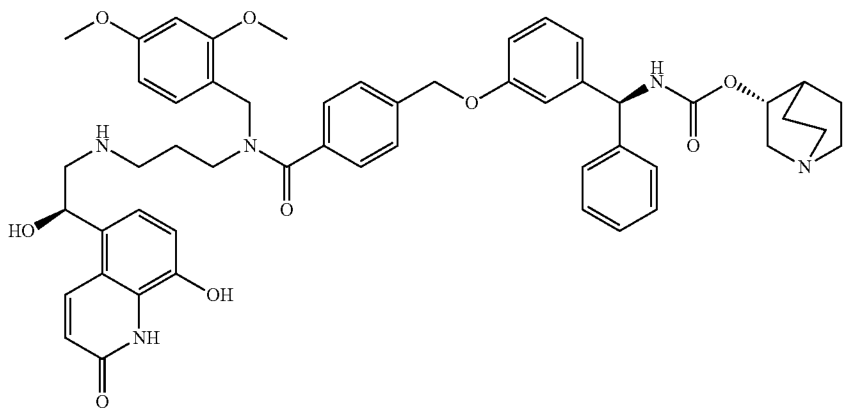 [SMILES: COc1ccc(CN(CCCNC[C@H](O)c2ccc(O)c3[nH]c(=O)ccc23)C(=O)c2ccc(COc3cccc([C@@H](NC(=O)O[C@H]4CN5CCC4CC5)c4ccccc4)c3)cc2)c(OC)c1] |
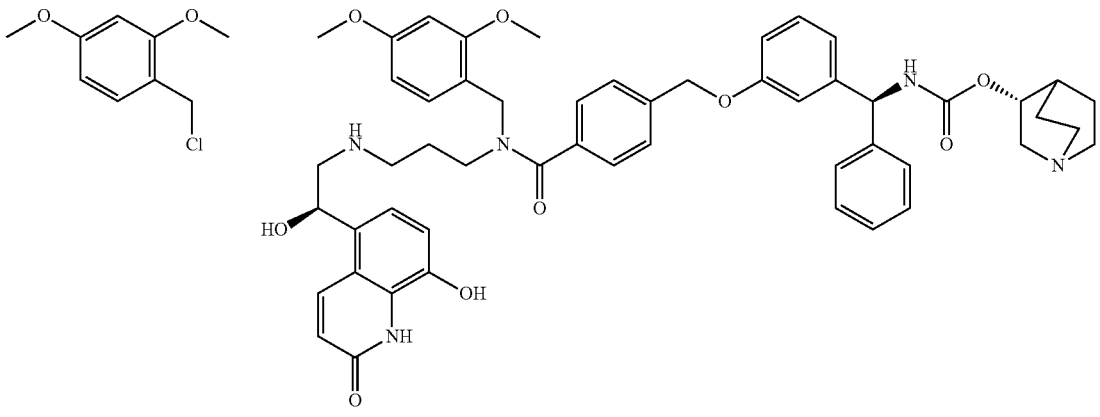
Example 12
(R)-Quinuclidin-3-yl ((S)-(3-((4-(cyclopentyl(3-(((R)-2-hydroxy-2-(8-hydroxy-2-oxo-1,2-dihydro-quinolin-5-yl)ethyl)amino)propyl)carbamoyl)benzyl)-oxy)phenyl)(phenyl)methyl)carbamate (Compound 69)
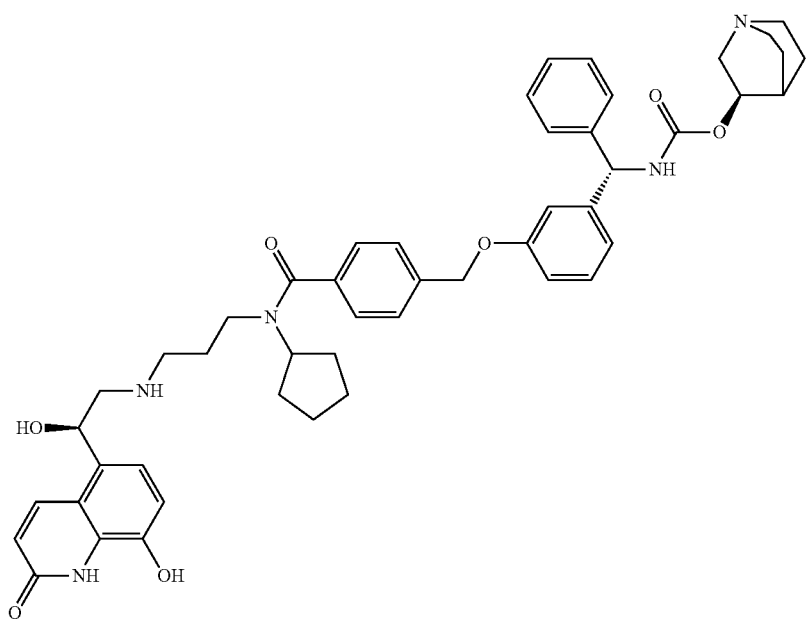 [SMILES: O=C(N[C@@H](c1ccccc1)c1cccc(OCc2ccc(C(=O)N(CCCNC[C@H](O)c3ccc(O)c4[nH]c(=O)ccc34)C3CCCC3)cc2)c1)O[C@H]1CN2CCC1CC2]

Step 1: N-(2-(1,3-dioxolan-2-yl)ethyl)cyclopentanamine

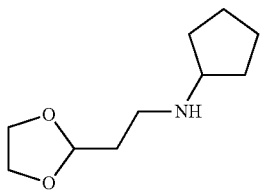 [SMILES: C1CCC(NCCC2OCCO2)C1]

To a suspension of N-benzylcyclopentanamine hydrochloride (0.986 g, 4.66 mmol) in acetonitrile (10 mL) was added di-iso-propylethylamine (2.0 mL, 11.5 mmol) and the mixture stirred at room temperature for 10 minutes. A solution of 2-(2-bromoethyl)-1,3-dioxolane (1.01 g, 5.58 mmol) in acetonitrile (5 mL) was added and the mixture heated at 80° C. for 48 hours. The reaction mixture was diluted with DCM and was washed with water, dried (magnesium sulfate), filtered and the solvent evaporated at reduced pressure. The residue was loaded onto an SCX-2 cartridge and eluted with acetonitrile (4 column volumes) and then 10% triethylamine/acetonitrile (4 column volumes). The product containing fractions were combined and the solvent evaporated at reduced pressure. The residue was dissolved in ethanol (10 mL) and 10% palladium on charcoal (0.90 g) added. The mixture was stirred at room temperature for 5 minutes and then 1-methyl-1,4-cyclohexadiene (1.9 mL, 16.9 mmol) added. The reaction mixture heated to reflux and then the reaction mixture stirred under reflux for 1 hour. The reaction mixture allowed to cool and the suspension filtered. The filtrate was evaporated at reduced pressure to afford the title compound (0.249 g, 40%).

$^1$H NMR (400 MHz, CDCl$_3$): δ 4.96-4.90 (m, 1H); 4.01-3.92 (m, 2H); 3.89-3.80 (m, 2H); 3.12-3.01 (m, 1H); 2.81-2.72 (m, 2H); 1.99-1.81 (m, 5H); 1.75-1.47 (m, 4H); 1.39-1.26 (m, 2H).

Step 2: (R)-Quinuclidin-3-yl ((S)-(3-((4-((2-(1,3-dioxolan-2-yl)ethyl)(cyclopentyl)-carbamoyl)benzyl)oxy)phenyl)(phenyl)methyl)carbamate

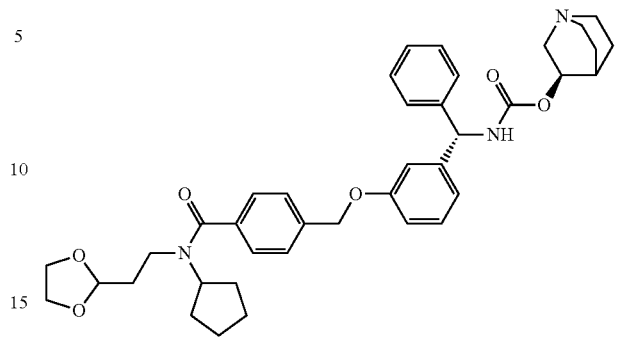

The title compound was prepared as described in Example 10 Step 2 with 2-(1,3-dioxolan-2-yl)-N-(3-methoxybenzyl)ethanamine replacing N-(2-(1,3-dioxolan-2-yl)ethyl)cyclopentanamine.

Step 3: (R)-Quinuclidin-3-yl ((S)-(3-((4-(cyclopentyl(3-(((R)-2-hydroxy-2-(8-hydroxy-2-oxo-1,2-dihydroquinolin-5-yl)ethyl)amino)propyl)carbamoyl)benzyl)oxy)-phenyl)(phenyl)methyl)carbamate
(Compound 69)

The title compound was prepared as described in Example 1 Step 12 and Step 13 with (R)-quinuclidin-3-yl ((S)-(3-((4-((2-(1,3-dioxolan-2-yl)ethyl)(cyclopentyl)-carbamoyl)benzyl)oxy)phenyl)(phenyl)methyl)carbamate replacing 3-(1,3-dioxolan-2-yl)propyl 1-(4-((3-((S)-phenyl((((R)-quinuclidin-3-yloxy)carbonyl)amino)methyl)-phenoxy)methyl)benzoyl)piperidine-4-carboxylate in Step 12 and the subsequent product used in Step 13.

$^1$H NMR (400 MHz, DMSO-d$_6$, @ 110° C.): δ 8.25-8.12 (m, 3H); 7.53 (s, 1H); 7.46 (d, J=7.9 Hz, 2H); 7.32 (d, J=5.8 Hz, 6H); 7.28-7.20 (m, 2H); 7.09 (d, J=8.1 Hz, 1H); 7.04 (s, 1H); 6.98-6.86 (m, 3H); 6.48 (d, J=9.9 Hz, 1H); 5.84 (d, J=7.8 Hz, 1H); 5.11 (s, 2H); 5.06-4.99 (m, 1H); 4.65-4.60 (m, 1H); 4.05 (d, J=8.6 Hz, 1H); 3.32-3.21 (2H); 3.10 (dd, J=14.4, 8.4 Hz, 1H); 2.82-2.53 (m, 9H); 1.91 (s, 1H); 1.78-1.56 (m, 11H); 1.49-1.43 (m, 2H); 1.32 (m, 1H).

The following compounds were prepared as described in Example 12 with the appropriate amine replacing N-benzylcyclopentanamine hydrochloride in Step 1 and the subsequent products used in Steps 2-3.

| Cpd. | Appropriate amine | Structure |
|---|---|---|
| 70 | | 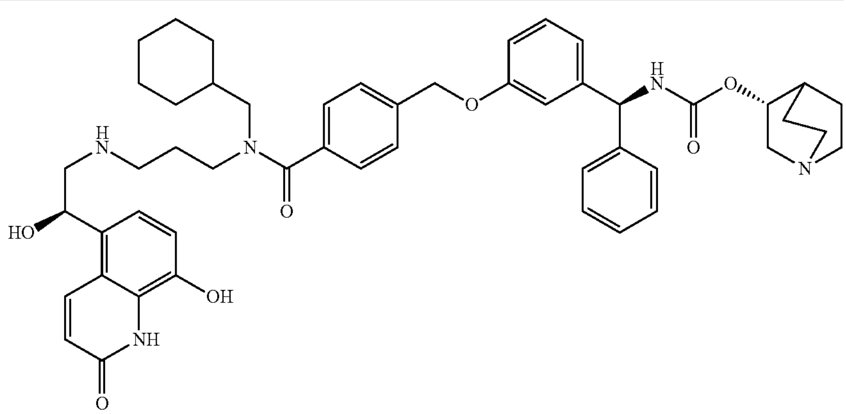 [SMILES: O=C(N[C@@H](c1ccccc1)c1cccc(OCc2ccc(C(=O)N(CCCNC[C@H](O)c3ccc(O)c4[nH]c(=O)ccc34)CC3CCCCC3)cc2)c1)O[C@H]1CN2CCC1CC2] |

-continued
| Cpd. | Appropriate amine | Structure |
|---|---|---|
| 71 | | 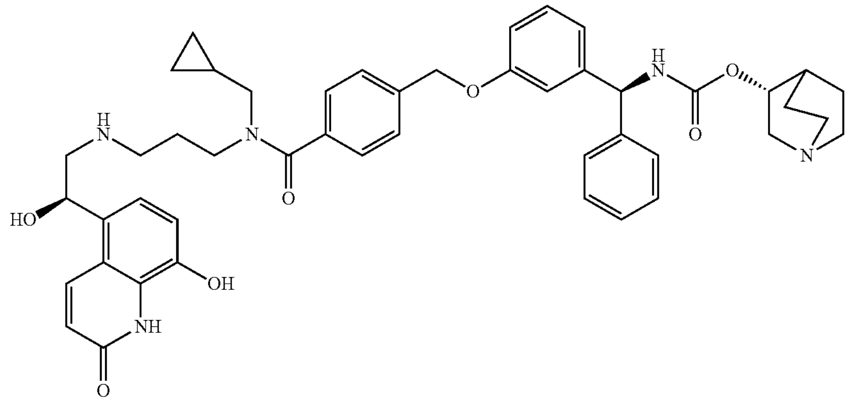 [SMILES: O=C(N[C@@H](c1ccccc1)c1cccc(OCc2ccc(C(=O)N(CCCNC[C@H](O)c3ccc(O)c4[nH]c(=O)ccc34)CC3CC3)cc2)c1)O[C@H]1CN2CCC1CC2] |
| 72 | | 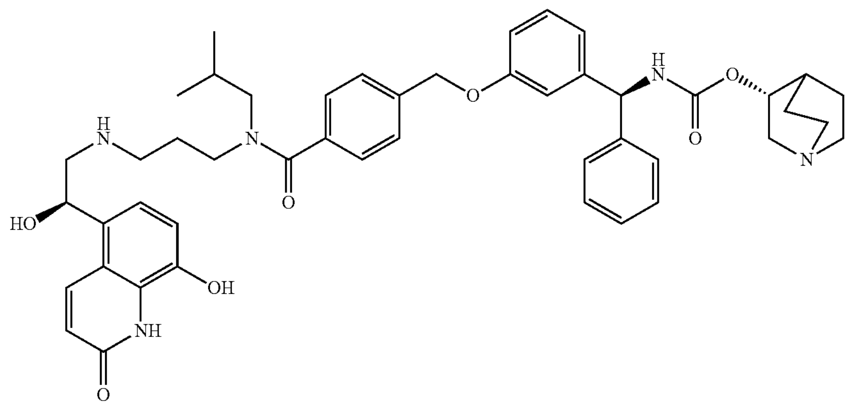 [SMILES: CC(C)CN(CCCNC[C@H](O)c1ccc(O)c2[nH]c(=O)ccc12)C(=O)c1ccc(COc2cccc([C@@H](NC(=O)O[C@H]3CN4CCC3CC4)c3ccccc3)c2)cc1] |
General Synthesis for Compounds 73-77
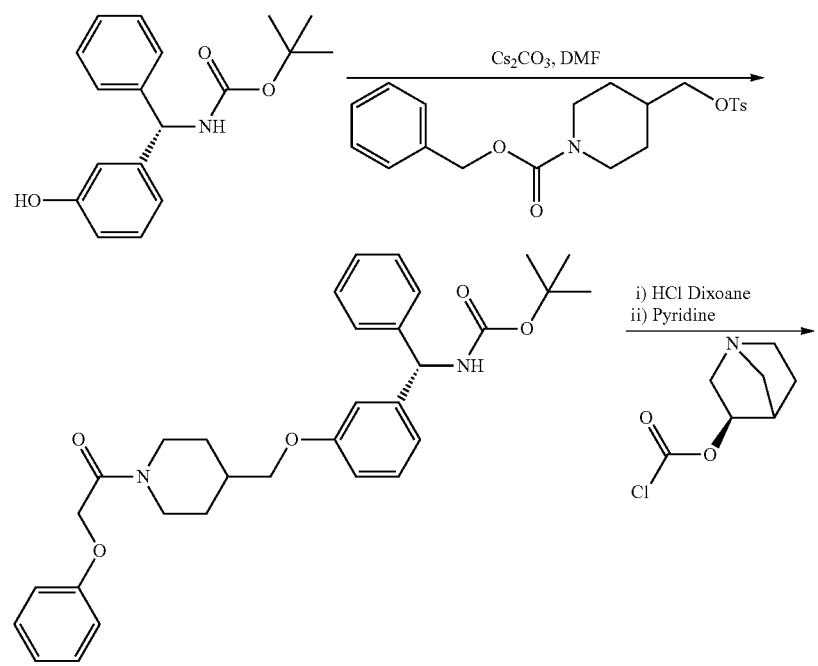

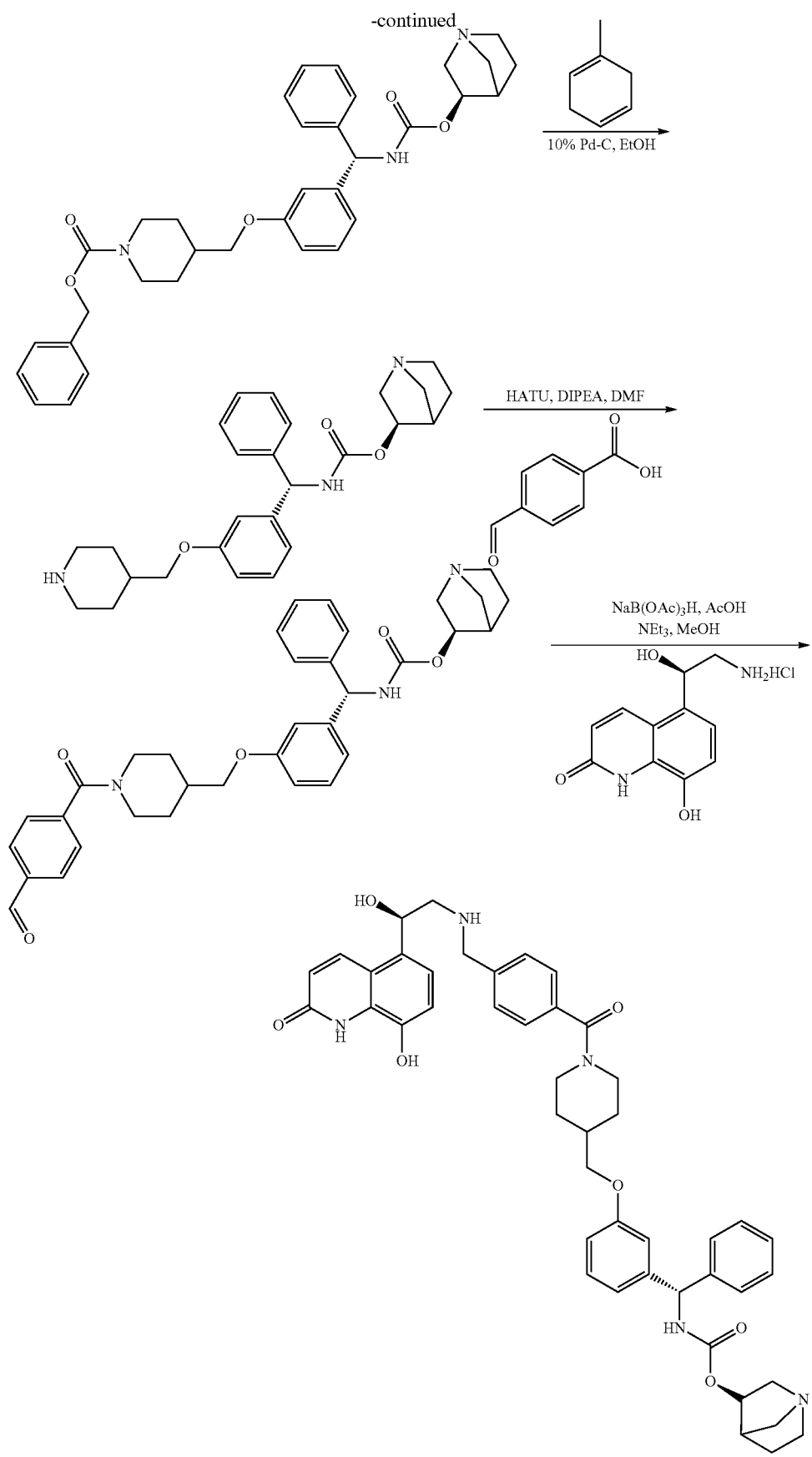

Example 13

(R)-Quinuclidin-3-yl ((S)-(3-((1-(4-((((R)-2-hydroxy-2-(8-hydroxy-2-oxo-1,2-dihydroquinolin-5-yl)ethyl)amino)methyl)benzoyl)piperidin-4-yl)methoxy)phenyl)-(phenyl)methyl)carbamate (Compound 73)

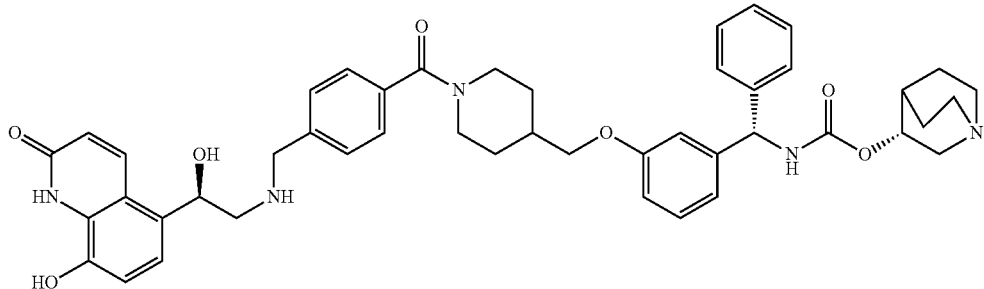 [SMILES: O=C(N[C@@H](c1ccccc1)c1cccc(OCC2CCN(C(=O)c3ccc(CNC[C@H](O)c4ccc(O)c5[nH]c(=O)ccc45)cc3)CC2)c1)O[C@H]1CN2CCC1CC2]

Step 1: (S)-Benzyl 4-((3-(((tert-butoxycarbonyl)amino)(phenyl)methyl)-phenoxy)methyl)piperidine-1-carboxylate

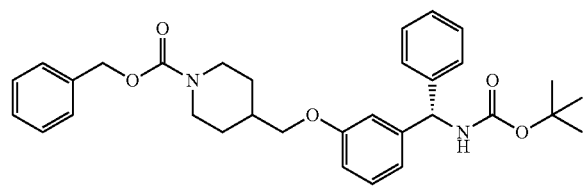 [SMILES: CC(C)(C)OC(=O)N[C@@H](c1ccccc1)c1cccc(OCC2CCN(C(=O)OCc3ccccc3)CC2)c1]

To a mixture of (S)-tert-butyl ((3-hydroxyphenyl)(phenyl)methyl)carbamate (8.0 g, 26.7 mmol) and cesium carbonate (13.1 g, 37.4 mmol) in DMF (130 ml) was added 4-(toluene-4-sulfonyloxymethyl)-piperidine-1-carboxylic acid benzyl ester (12.94 g, 32.1 mmol). The resulting reaction mixture was stirred at 50° C. for 17 hours. The reaction mixture was diluted with water and extracted with ethyl acetate (×3). The combined organic extracts were washed with brine (×3), dried (magnesium sulfate), filtered and the solvent evaporated at reduced pressure. The residue was purified by flash column chromatography eluting with 0 to 50% ethyl acetate/iso-hexane to afford the title compound (13.7 g, 93%).

$^1$H NMR (400 MHz, CDCl$_3$): δ 7.38-7.18 (m, 11H); 6.84-6.72 (m, 3H); 5.86 (s, 1H); 5.13 (s, 3H); 4.23 (s, 2H); 3.76 (d, J=6.3 Hz, 2H); 2.82 (s, 2 µl); 1.99-1.88 (m, 1H); 1.82 (d, J=13.2 Hz, 2H); 1.44 (s, 9H); 1.26 (t, J=7.1 Hz, 2H).

Step 2: Benzyl 4-((3-((S)-phenyl((((R)-quinuclidin-3-yloxy)carbonyl)amino)-methyl)phenoxy)methyl)piperidine-1-carboxylate

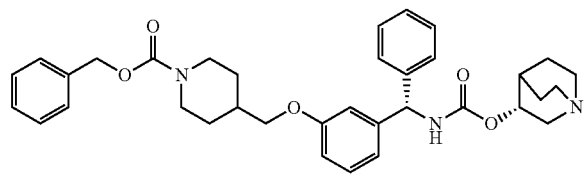 [SMILES: O=C(N[C@@H](c1ccccc1)c1cccc(OCC2CCN(C(=O)OCc3ccccc3)CC2)c1)O[C@H]1CN2CCC1CC2]

The title compound was prepared as described in Example 1 Step 6 and Step 7 with (S)-benzyl 4-((3-(((tert-butoxycarbonyl)amino)(phenyl)methyl)phenoxy)-methyl)piperidine-1-carboxylate replacing (S)-methyl 4-((3-(((tert-butoxycarbonyl)-amino)(phenyl)methyl)phenoxy)methyl)benzoate in Step 6 and the subsequent product used in Step 7.

Step 3: (R)-Quinuclidin-3-yl ((S)-phenyl(3-(piperidin-4-ylmethoxy)phenyl)methyl)-carbamate

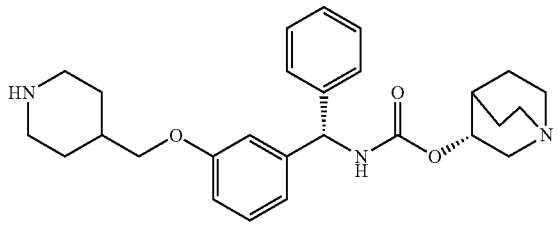 [SMILES: O=C(N[C@@H](c1ccccc1)c1cccc(OCC2CCNCC2)c1)O[C@H]1CN2CCC1CC2]

To a solution of benzyl 4-((3-((5)-phenyl((((R)-quinuclidin-3-yloxy)carbonyl)-amino)methyl)phenoxy)methyl)piperidine-1-carboxylate (1.32 g, 2.26 mmol) in ethanol (100 mL) was added palladium on charcoal (0.66 g) and stirred at room temperature for 10 minutes. 1-Methyl-1,4-cyclohexadiene (1.27 mL, 11.3 mmol) was added and the reaction mixture heated to reflux. The reaction mixture was stirred under reflux for 1 hour. The reaction mixture was allowed to cool and the suspension filtered. The filtrate was evaporated at reduced pressure to afford the title compound (1.05 g, 100%).

$^1$H NMR (400 MHz, DMSO-d$_6$): δ 9.78 (s, 1H); 8.44 (d, J=9.4 Hz, 1H); 7.33 (d, J=4.5 Hz, 4H); 7.28-7.21 (m, 2H); 6.97 (d, J=7.8 Hz, 1H); 6.90 (s, 1H); 6.83 (dd, J=8.2, 2.4 Hz, 1H); 5.83 (d, J=9.1 Hz, 1H); 4.88-4.83 (m, 1H); 3.82 (d, J=6.5 Hz, 3H); 3.35-3.06 (m, 6H); 2.90 (m, 2H); 2.23 (s, 1H); 2.12-1.64 (m, 5H); 1.52-1.37 (m, 2H).

Step 4: (R)-Quinuclidin-3-yl((S)-(3-((1-(4-formyl-benzoyl)piperidin-4-yl)methoxy)phenyl)(phenyl)methyl)carbamate

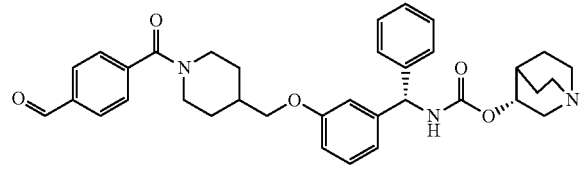 [SMILES: O=Cc1ccc(C(=O)N2CCC(COc3cccc([C@@H](NC(=O)O[C@H]4CN5CCC4CC5)c4ccccc4)c3)CC2)cc1]

The title compound was prepared as described in Example 1 Step 11 with (R)-quinuclidin-3-yl ((S)-phenyl(3-(piperidin-4-ylmethoxy)phenyl)methyl)carbamate and 4-formyl benzoic acid 3-(1,3-dioxolan-2-yl)propyl piperidine-4-carboxylate hydrochloride and 4-((3-((S)-phenyl((((R)-quinuclidin-3-yloxy)carbonyl)amino)methyl)phenoxy)methyl) benzoic acid respectively.

$^1$H NMR (400 MHz, CDCl$_3$): δ 10.08-10.03 (m, 1H); 7.97-7.90 (m, 2H); 7.56 (d, J=8.0 Hz, 2H); 7.35-7.20 (m, 7H); 6.84 (d, J=7.7 Hz, 1H); 6.79-6.72 (m, 2H); 5.86 (d, J=7.7 Hz, 1H); 5.14 (s, 1H); 4.79 (d, J=12.9 Hz, 1H); 3.80 (s, 2H); 3.69 (d, J=13.3 Hz, 1H); 3.07 (s, 1H); 2.84 (s, 1H); 2.15-1.02 (m, 16H).

Step 5: 13 (R)-Quinuclidin-3-yl ((S)-(3-((1-(4-((((R)-2-hydroxy-2-(8-hydroxy-2-oxo-1,2-dihydro-quinolin-5-yl)ethyl)amino)methyl)benzoyl)piperidin-4-yl)methoxy)phenyl)-(phenyl)methyl)carbamate (Compound 73)

The title compound was prepared as described in Example 1 Step 13 with (R)-quinuclidin-3-yl ((S)-(3-((1-(4-formyl-benzoyl)piperidin-4-yl)methoxy)phenyl)-(phenyl)methyl) carbamate replacing 1-(4-((3-((S)-phenyl(((((R)-quinuclidin-3-yloxy)carbonyl)amino)methyl)phenoxy)methyl)benzoyl) piperidine-4-carboxylate $^1$H NMR (400 MHz, DMSO-d$_6$, 110° C.): δ 8.21-8.13 (m, 2H); 7.55 (d, J=9.0 Hz, 1H); 7.38-7.28 (m, 8H); 7.28-7.20 (m, 2H); 7.09 (d, J=8.1 Hz, 1H); 6.99-6.89 (m, 3H); 6.85-6.80 (m, 1H); 6.46 (d, J=9.9 Hz, 1H); 5.83 (d, J=8.5 Hz, 1H); 5.08 (dd, J=7.6, 4.7 Hz, 1H); 4.67-4.61 (m, 1H); 4.05 (d, J=13.2 Hz, 3H); 3.91-3.85 (m, 2H); 3.82 (s, 2H); 3.12 (dd, J=14.4, 8.3 Hz, 1H); 3.01-2.92 (m, 2H); 2.91-2.52 (m, 5H); 2.09-2.01 (m, 1H); 1.95-1.91 (m, 1H); 1.83-1.75 (m, 3H); 1.69-1.59 (m, 1H); 1.56-1.46 (m, 1H); 1.38-1.24 (m, 4H).

The following compound was prepared as described in Example 13 with the appropriate acid replacing 4-formyl benzoic acid in Step 4 and the subsequent products used in Step 5.

| Cpd. | Structure | Appropriate acid |
|---|---|---|
| 74 | ![structure] | ![acid] |

Example 14

(R)-Quinuclidin-3-yl ((S)-(3-((1-(4-(2-(((R)-2-hydroxy-2-(8-hydroxy-2-oxo-1,2-dihydroquinolin-5-yl)ethyl)amino)ethyl)benzoyl)piperidin-4-yl)methoxy)phenyl)(phenyl)methyl)carbamate (Compound 75)

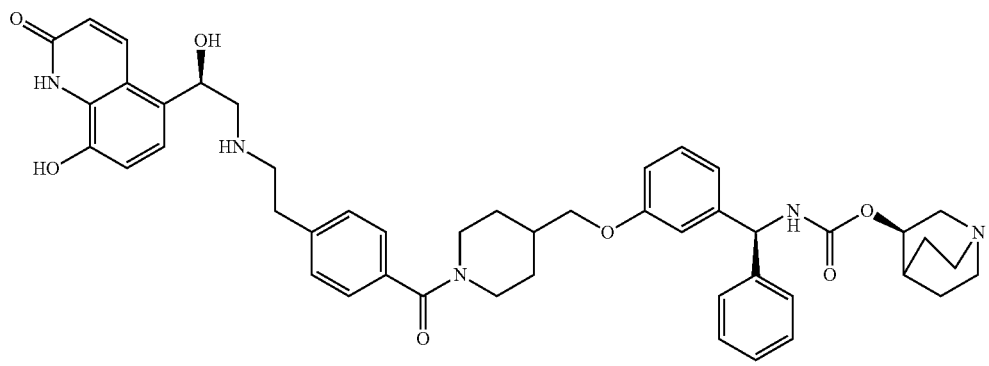 [SMILES: O=C(N[C@@H](c1ccccc1)c1cccc(OCC2CCN(C(=O)c3ccc(CCNC[C@H](O)c4ccc(O)c5[nH]c(=O)ccc45)cc3)CC2)c1)O[C@H]1CN2CCC1CC2]

Step 1: (R)-Quinuclidin-3-yl((S)-(3-((1-(4-((1,3-dioxolan-2-yl)methyl)benzoyl)piperidin-4-yl)methoxy)phenyl)(phenyl)methyl)carbamate

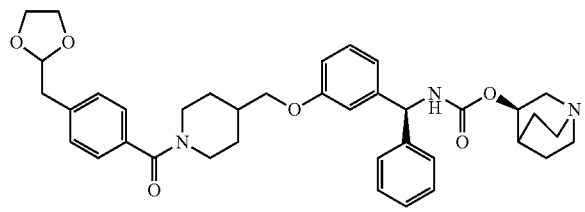 [SMILES: O=C(N[C@@H](c1ccccc1)c1cccc(OCC2CCN(C(=O)c3ccc(CC4OCCO4)cc3)CC2)c1)O[C@H]1CN2CCC1CC2]

The title compound was prepared as described in Example 1 Step 11 with (R)-quinuclidin-3-yl ((S)-phenyl(3-(piperidin-4-ylmethoxy)phenyl)methyl)carbamate and 4-(1,3-dioxolan-2-ylmethyl)benzoic acid replacing 3-(1,3-dioxolan-2-yl)propyl piperidine-4-carboxylate hydrochloride and 4-((3-((S)-phenyl((((R)-quinuclidin-3-yloxy)carbonyl)amino)methyl)phenoxy)methyl)benzoic acid respectively.

Step 2: (R)-Quinuclidin-3-yl ((S)-(3-((1-(4-(2-(((R)-2-hydroxy-2-(8-hydroxy-2-oxo-1,2-dihydroquinolin-5-yl)ethyl)amino)ethyl)benzoyl)piperidin-4-yl)methoxy)-phenyl)(phenyl)methyl)carbamate (Compound 75)

The title compound was prepared as described in Example 1 Step 12 and Step 13 with (R)-quinuclidin-3-yl((S)-(3-((1-(4-((1,3-dioxolan-2-yl)methyl)benzoyl)piperidin-4-yl)methoxy)phenyl)(phenyl)methyl)carbamate replacing 3-(1,3-dioxolan-2-yl)propyl 1-(4-((3-((S)-phenyl((((R)-quinuclidin-3-yloxy)carbonyl)amino)methyl)phenoxy)-methyl)benzoyl)piperidine-4-carboxylate in Step 12 and the product used in subsequent steps.

$^1$H NMR (400 MHz, DMSO-d$_6$, 110° C.): δ 8.19 (d, J=9.9 Hz, 1H); 7.83 (d, J=8.7 Hz, 1H); 7.38-7.29 (m, 7H); 7.30-7.22 (m, 3H); 7.16 (d, J=8.2 Hz, 1H); 7.02 (d, J=8.1 Hz, 1H); 6.96-6.89 (m, 2H); 6.84 (dd, J=8.2, 2.5 Hz, 1H); 6.57 (d, J=9.9 Hz, 1H); 5.84 (d, J=8.7 Hz, 1H); 5.37 (dd, J=7.9, 5.0 Hz, 1H); 4.96-4.91 (m, 1H); 4.05 (d, J=12.3 Hz, 2H); 3.88 (d, J=6.2 Hz, 2H); 3.66 (ddd, J=13.9, 8.4, 2.6 Hz, 1H); 3.36-2.90 (m, 11H); 2.28-2.24 (m, 1H); 2.08-1.77 (m, 8H); 1.37-1.27 (m, 3H).

The following compounds were prepared as described in Example 14 with the appropriate acid replacing 4-(1,3-dioxolan-2-ylmethyl)benzoic acid in Step 2 and the subsequent products used in Step 2.

| Cpd. | Structure | Appropriate acid |
| --- | --- | --- |
| 76 | 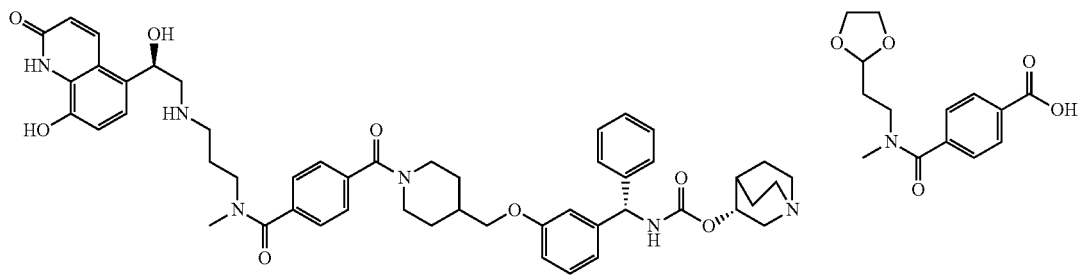 | |
| 77 | 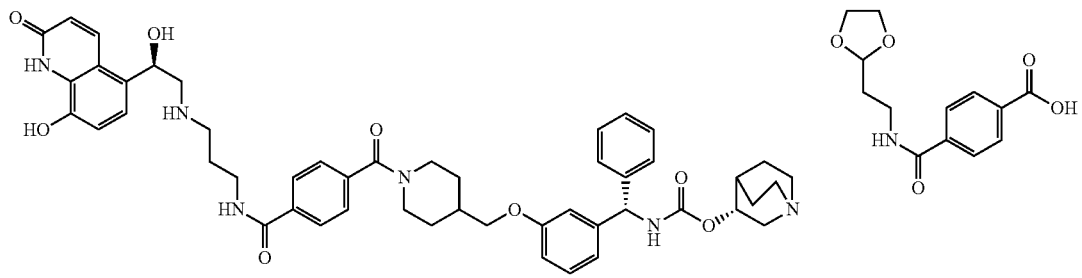 | |

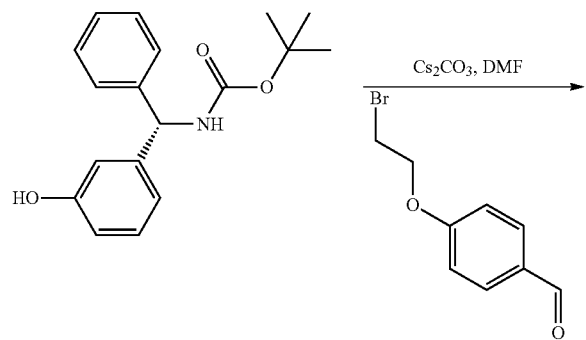
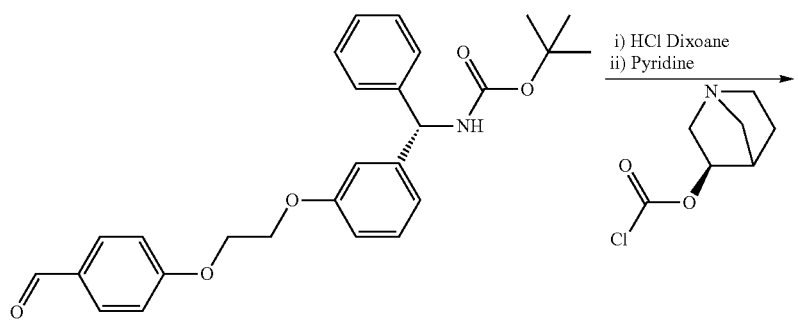
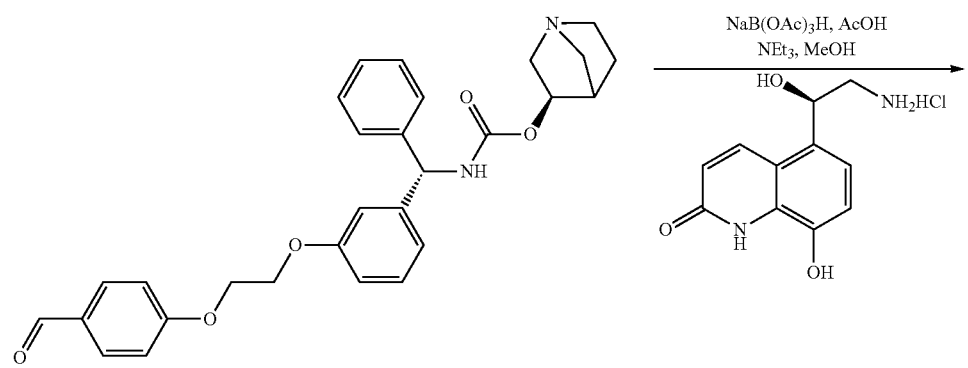
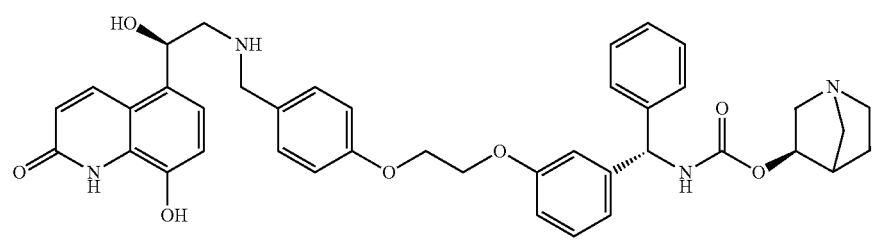

Example 15

(R)-Quinuclidin-3-yl ((S)-(3-(2-(4-(((((R)-2-hydroxy-2-(8-hydroxy-2-oxo-1,2-dihydroquinolin-5-yl)ethyl)amino)methyl)phenoxy)ethoxy)phenyl)-(phenyl)methyl)carbamate (Compound 78)

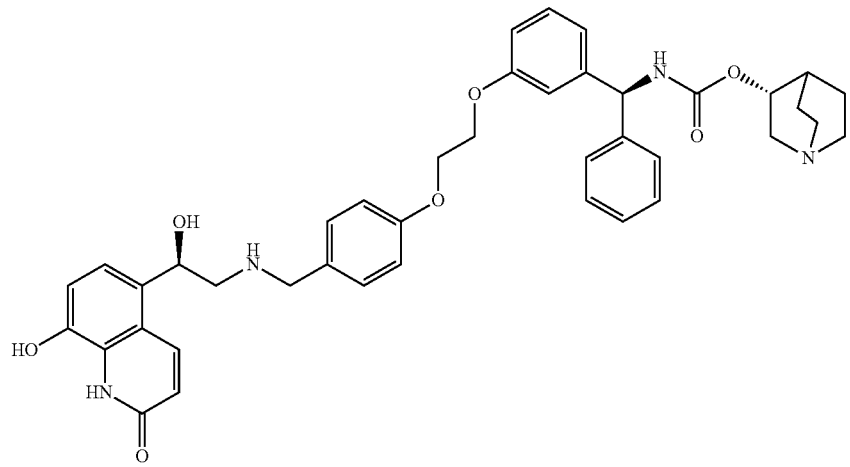 [SMILES: O=C(N[C@@H](c1ccccc1)c1cccc(OCCOc2ccc(CNC[C@H](O)c3ccc(O)c4[nH]c(=O)ccc34)cc2)c1)O[C@H]1CN2CCC1CC2]

Step 1: (S)-tert-Butyl ((3-(2-(4-formylphenoxy)ethoxy)phenyl)(phenyl)methyl)carbamate

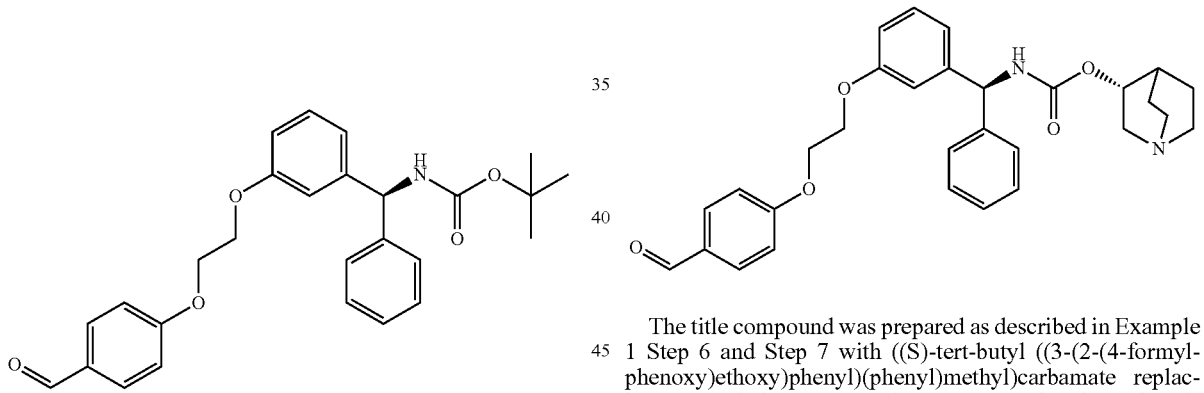

To a stirred solution of (S)-tert-butyl ((3-hydroxyphenyl)(phenyl)methyl)-carbamate (1.76 g, 5.9 mmol) in DMF (10 mL) was added cesium carbonate (4.0 g, 12.0 mmol). The reaction mixture was then stirred at room temperature for 20 minutes. 4-(2-Bromoethoxy)benzenecarboxaldehyde (1.35 g, 5.9 mmol) was added and the reaction mixture was stirred at room temperature for 5 hours. The reaction mixture was diluted with water and extracted with ethyl acetate (×3). The combined organic extracts were washed with brine (×3), dried (magnesium sulfate), filtered and the solvent evaporated at reduced pressure. The residue was purified by flash column chromatography eluting with 0 to 50% ethyl acetate/iso-hexane to afford the title compound (1.6 g, 61%).

$^1$H NMR (400 MHz, DMSO): δ 9.89 (s, 1H); 7.97-7.83 (m, 3H); 7.36-7.13 (m, 8H); 7.01-6.89 (m, 2H); 6.85 (dd, J=8.2, 2.5 Hz, 1H); 5.80 (d, J=9.5 Hz, 1H); 4.44 (t, J=4.1 Hz, 2H); 4.35-4.28 (m, 2H); 1.40 (s, 9H).

Step 2: (R)-Quinuclidin-3-yl ((S)-(3-(2-(4-formylphenoxy)ethoxy)phenyl)-(phenyl)methyl)carbamate The title compound was prepared as described in Example 1 Step 6 and Step 7 with ((S)-tert-butyl ((3-(2-(4-formylphenoxy)ethoxy)phenyl)(phenyl)methyl)carbamate replacing (S)-methyl 4-((3-(((tert-butoxycarbonyl)amino)(phenyl)methyl)phenoxy)-methyl)benzoate in Step 6 and the subsequent product used in Step 7.

Step 3: (R)-Quinuclidin-3-yl((S)-(3-(2-(4-(((((R)-2-hydroxy-2-(8-hydroxy-2-oxo-1,2-dihydroquinolin-5-yl)ethyl)amino)methyl)phenoxy)ethoxy)phenyl)-(phenyl)methyl)carbamate (Compound 78)

The title compound was prepared as described in Example 1 Step 13 with (R)-quinuclidin-3-yl ((S)-(3-(2-(4-formylphenoxy)ethoxy)phenyl)(phenyl)methyl)carbamate replacing 4-oxobutyl 1-(4-((3-((5)-phenyl((((R)-quinuclidin-3-yloxy)carbonyl)amino)-methyl)phenoxy)methyl)benzoyl)piperidine-4-carboxylate.

$^1$H NMR (400 MHz, DMSO-d$_6$, 110° C.): δ 8.10 (d, J=9.9 Hz, 1H); 7.83 (d, J=8.6 Hz, 1H); 7.45 (d, J=8.2 Hz, 2H); 7.35-7.22 (m, 6H); 7.12 (d, J=8.2 Hz, 1H); 7.03-6.96 (m, 5H); 6.88 (d, J=8.3 Hz, 1H); 6.53 (d, J=9.9 Hz, 1H); 5.85 (d, J=8.6 Hz, 1H); 5.39-5.32 (m, 1H); 4.94 (d, J=7.6 Hz, 1H); 4.38-4.27 (m, 4H); 4.20 (s, 2H); 3.70-3.61 (m, 1H); 3.30-3.07 (m, 7H); 2.25 (s, 1H); 2.03 (s, 1H); 1.97-1.90 (m, 1H); 1.86 (s, 1H); 1.76 (s, 1H).

The following compound was prepared as described in Example 15 with 3-(2-bromoethoxy)benzenecarboxaldehyde replacing 4-(2-bromoethoxy)-benzenecarboxaldehyde in Step 2 and the subsequent products used in Step 2.

The title compound was prepared as described in Example 1 Step 5 to Step 8 with methyl bromoacetate replacing methyl 4-(bromomethyl)benzoate in Step 5 and the products used in subsequent steps.

| Cpd. | Structure |
|---|---|
| 79 | 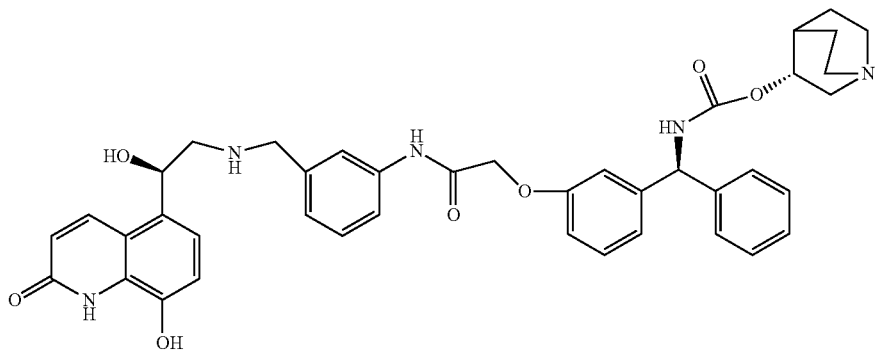 [SMILES: O=C(COc1cccc([C@@H](NC(=O)O[C@H]2CN3CCC2CC3)c2ccccc2)c1)Nc1cccc(CNC[C@H](O)c2ccc(O)c3[nH]c(=O)ccc23)c1] |

Example 16

(R)-Quinuclidin-3-yl ((S)-(3-(2-((3-((((R)-2-hydroxy-2-(8-hydroxy-2-oxo-1,2-dihydroquinolin-5-yl)ethyl)amino)methyl)phenyl)amino)-2-oxoethoxy)phenyl)-(phenyl)methyl)carbamate (Compound 80)

$^1$H NMR (400 MHz, DMSO-d$_6$): δ 8.32-8.24 (m, 1H); 7.34-7.12 (m, 6H); 6.89 (s, 1H); 6.84 (d, J=7.6 Hz, 1H); 6.69 (dd, J=8.2, 2.5 Hz, 1H); 5.79 (d, J=9.2 Hz, 1H); 4.72-4.70 (m, 1H); 4.37 (s, 2H); 3.30-3.29 (m, 1H); 2.93 (s, 2H); 2.89-2.69 (m, 4H); 2.05-2.03 (m, 1H); 1.92-1.88 (m, 1H); 1.70-1.50 (m, 3H).

Step 1: 2-(3-((S)-Phenyl((((R)-quinuclidin-3-yloxy)carbonyl)amino)methyl)-phenoxy)acetic acid Step 2: (R)-Quinuclidin-3-yl ((S)-(3-(2-((3-(hydroxymethyl)phenyl)amino)-2-oxoethoxy)phenyl)(phenyl)methyl)carbamate

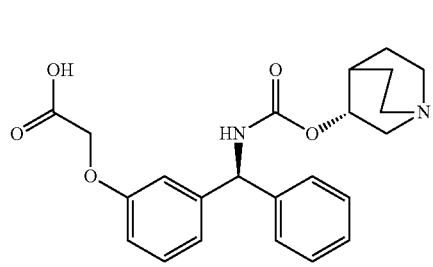 [SMILES: O=C(O)COc1cccc([C@@H](NC(=O)O[C@H]2CN3CCC2CC3)c2ccccc2)c1]

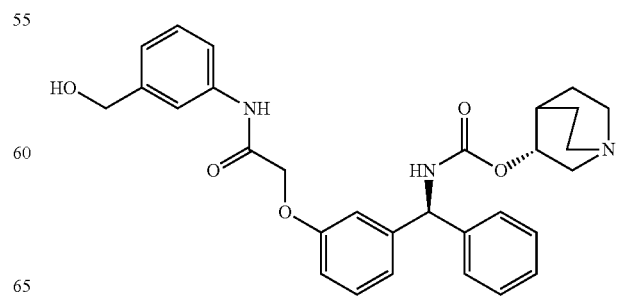

The title compound was prepared as described in Example 1 Step 11 with 3-aminobenzyl alcohol and 2-(3-((S)-phenyl ((((R)-quinuclidin-3-yloxy)carbonyl)amino)-methyl)phenoxy)acetic acid replacing 3-(1,3-dioxolan-2-yl)propyl piperidine-4-carboxylate hydrochloride and 4-((3-((S)-phenyl ((((R)-quinuclidin-3-yloxy)carbonyl)-amino)methyl) phenoxy)methyl)benzoic acid respectively. Crude material used directly in the next step without further purification.

Step 3: (R)-Quinuclidin-3-yl ((S)-(3-(2-((3-formylphenyl)amino)-2-oxoethoxy)phenyl)-(phenyl)methyl)carbamate

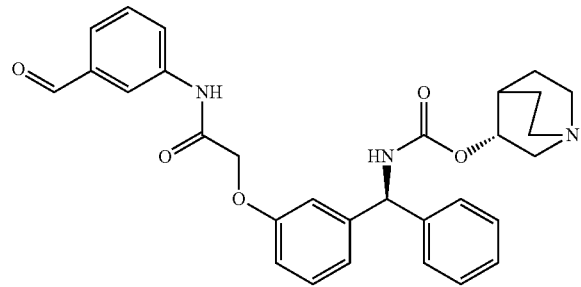 [SMILES: O=Cc1cccc(NC(=O)COc2cccc([C@@H](NC(=O)O[C@H]3CN4CCC3CC4)c3ccccc3)c2)c1]

To a solution of (R)-quinuclidin-3-yl ((S)-(3-(2-((3-(hydroxymethyl)-phenyl)amino)-2-oxoethoxy)phenyl)(phenyl) methyl)carbamate (0.35 g, 0.68 mmol) in 1,4-dioxane (25 mL) was added manganese (IV) oxide (0.58 g, 6.8 mmol) and the reaction mixture stirred at room temperature for 2 hours and then at 50° C. for 15 hours. The suspension was filtered through a pad of celite. The solvent was evaporated at reduced pressure to afford the crude material. This material was used in the next step without further purification.

Step 4: (R)-Quinuclidin-3-yl((S)-(3-(2-((3-((((R)-2-hydroxy-2-(8-hydroxy-2-oxo-1,2-dihydroquinolin-5-yl)ethyl)amino)methyl)phenyl)amino)-2-oxoethoxy) phenyl)-(phenyl)methyl)carbamate (Compound 80)

The title compound was prepared as described in Example 1 Step 13 with (R)-quinuclidin-3-yl ((S)-(3-(2-((3-(hydroxymethyl)phenyl)amino)-2-oxoethoxy)-phenyl)(phenyl) methyl)carbamate replacing 4-oxobutyl 1-(4-((3-((S)-phenyl((((R)-quinuclidin-3-yloxy)carbonyl)amino)methyl) phenoxy)methyl)benzoyl)piperidine-4-carboxylate.

$^1$H NMR (400 MHz, DMSO-d$_6$): δ 10.02 (s, 1H); 8.25 (d, J=9.3 Hz, 1H); 8.11 (d, J=9.9 Hz, 1H); 7.61 (s, 1H); 7.49 (d, J=8.2 Hz, 1H); 7.35-7.17 (m, 7H); 7.08-7.01 (m, 3H); 6.99-6.81 (m, 3H); 6.46 (d, J=9.9 Hz, 1H); 5.83 (d, J=8.3 Hz, 1H); 5.06 (dd, J=8.0, 4.2 Hz, 1H); 4.66 (s, 2H); 4.56 (s, 1H); 3.73 (s, 2H); 3.07 (t, J=10.6 Hz, 1H); 2.73-2.59 (m, 6H); 1.89 (s, 1H); 1.78 (s, 1H); 1.57 (s, 1H); 1.45 (s, 2H); 1.31 (s, 1H).

Large Scale Synthesis of (S)-3-(amino(phenyl)methyl)phenol hydrochloride

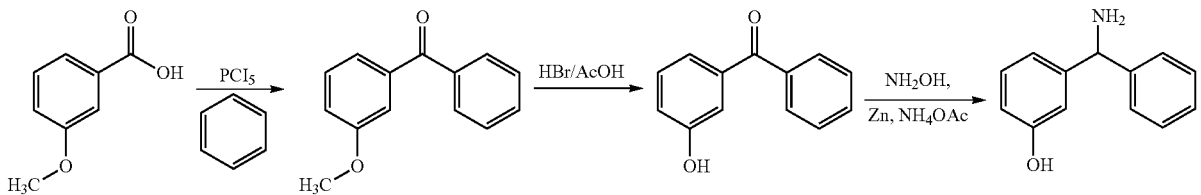

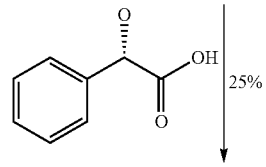

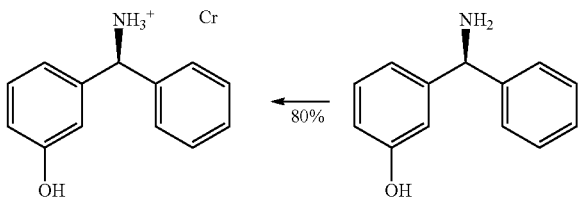

Step 1: (3-Methoxyphenyl)(phenyl)methanone

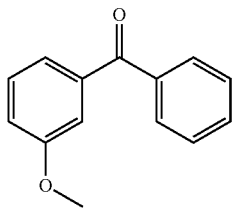 [SMILES: COc1cccc(C(=O)c2ccccc2)c1]

To a mixture of phosphorus pentachloride (3763 g, 18.1 mol) in 7500 mL of benzene, 3-methoxy benzoic acid (2500 g, 16.4 mol) was added in portions. The mixture was stirred for 50 minutes until it became homogenous. The formation of the acid chloride was controlled by TLC. After completion, the mixture was cooled down to 10° C., the reactor was covered with aluminum foil and aluminium trichloride (4820 g, 36.1 mol) was added in portions (internal temperature was held up to 30° C. maximum). Stirring was continued for 18 hours at RT. The reaction was monitored by TLC (AcOEt:hex 1:9). After completion, the reaction mixture was poured into ice and was diluted with AcOEt (7 L). The organic layer was then separated and the aqueous layer was extracted with AcOEt (2×10 L, 1×6 L). The combined organic layers were washed with water (5×3 L) to pH~6-7, saturated aqueous sodium hydrogen carbonate solution (15 L), dried (sodium sulfate), filtered and the solvent evaporated at reduced pressure to give a crude oil. The product was purified by vacuum distillation (130-139° C., 2 mbar) to obtain the title compound as a (2637 g, 76%) pale yellow oil.

$^1$H NMR (600 MHz, CDCl$_3$); δ 7.80 (m, 2H); 7.57 (m, 1H); 7.46 (m, 2H); 7.32-7.37 (m, 3H); 7.12 (m, 1H); 3.83 (s, 3H).

Step 2: (3-Hydroxyphenyl)(phenyl)methanone

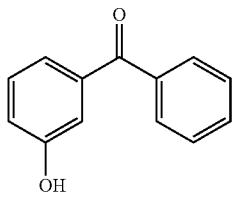 [SMILES: O=C(c1ccccc1)c1cccc(O)c1]

1458 g (6.9 mol) of (3-methoxyphenyl)(phenyl)methanone was dissolved in 2090 mL of AcOH. To this solution, 2320 ml (20.6 mol) of 48% HBr was added and the mixture was stirred at 90° C. for 18 hours. The reaction was monitored by TLC (AcOEt:hex 1:9). After the reaction was completed the mixture was cooled down to RT and poured into ice with stirring. The precipitated solid was filtered, washed with water and dried yielding the title compound as a white solid (1234 g, 91%). $^1$H NMR (600 MHz, CDCl$_3$); δ 7.80 (m, 2H); 7.58 (m, 1H); 7.47 (m, 2H); 7.39 (m, 1H); 7.28-7.34 (m, 2H); 7.11 (m, 1H); 5.59 (brs, 1H).

Step 3: 3-(Amino(phenyl)methyl)phenol

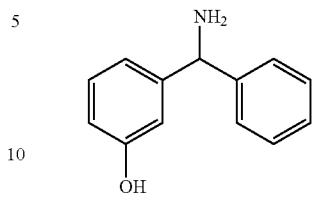

(3-Hydroxyphenyl)(phenyl)methanone (400 g, 2 mol) was dissolved in methanol (4 L). Hydroxylamine hydrochloride (168 g, 2.4 mol) and sodium acetate (331 g, 4 mol) were added to the resulting solution. The mixture was heated at reflux for 18 hours. After cooling to RT the solvent was evaporated at reduced pressure, then water (3 L) was added to the residue. The product was extracted with ethyl acetate (3×3 L). The combined organic extracts were washed with saturated aqueous sodium hydrogen carbonate, brine, dried (sodium sulfate), filtered and the solvent evaporated at reduced pressure. The crude residue (1085 g) was used in the next step without purification. The crude oxime, 362 g, (287 g, 1.3 mol of pure oxime based on analysis) was dissolved in ethanol (860 mL) and 25% aqueous ammonia (3000 mL). To this mixture ammonium acetate (52 g, 0.7 mol) was added followed by portion wise addition of zinc powder (440 g, 6.7 mol) to maintain an internal temperature not exceeding 40° C. The mixture was stirred without heating for 18 hours then filtered through a pad of celite. The filter cake was washed with ethyl acetate. The filtrate was collected and the formed layers were separated. The aqueous layer was extracted with ethyl acetate (5×5 L). The combined organic extracts layers were washed with brine (×2) and the solvent was evaporated at reduced pressure. The product was dried in vacuo (35° C., 18 hours).

$^1$H NMR (600 MHz, DMSO-d$_6$); δ 9.25 (brs, 1H); 7.36 (m, 2H); 7.25 (m, 2H); 7.15 (m, 1H); 7.03 (m, 1H); 6.79 (m, 2H); 6.54 (m, 1H); 4.98 (s, 1H); 2.17 (brs, 2H).

Step 4: Crystallization of (S)-3-(amino(phenyl)methyl)phenol (S)-mandelate

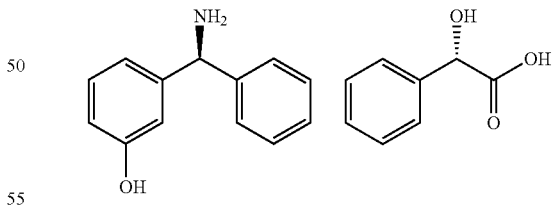

Salt formation: 3-(Amino(phenyl)methyl)phenol (1081 g, 5.4 mol) was dissolved in iso-propanol (21.62 L) and heated to reflux. To the mixture a solution of S-mandelic acid (908 g, 6 mol) in iso-propanol (2160 mL) was added dropwise. The mixture was heated at reflux for 1 hour and then allowed to cool to 10° C. (over 18 hours). The precipitate formed was filtered, washed with cold iso-propanol and dried in vacuo at 35° C.

The obtained salt was refluxed in 95% iso-propanol for 1 hour. The mixture was allowed to cool down to 10° C. over 18 hours. The solid was filtered, washed with cold iso-propanol and dried in the vacuum oven at 35° C. The crystallization process was repeated two or more times until the ee was >98% by chiral HPLC analysis.

Step 5: (S)-3-(Amino(phenyl)methyl)phenol hydrochloride

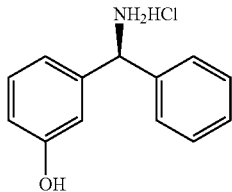

(S)-3-(Amino(phenyl)methyl)phenol (S)-mandelate (1027 g, 2.9 mol) was suspended in ethyl acetate. A solution of sodium hydrogen carbonate (737 g, 8.8 mol) in water (11.05 L) was added drop wise and the mixture was stirred at RT for 18 hours. The mixture was separated and the aqueous layer was extracted with ethyl acetate (5×10 L). The combined organic extracts were combined and the solvent evaporated at reduced pressure to give 464 g (85%) of amine as pale yellow crystals.

The amine (464 g, 2.3 mol) was suspended in methanol and 4 M HCl in AcOEt (3500 mL, 14 mol) was added drop wise. The mixture was stirred for 18 hours and the solvent evaporated at reduced pressure. The residue was triturated with ether (2740 mL) for 18 hours. The suspension was filtered, the filter cake washed with ether and dried.

$^1$H NMR (600 MHz, DMSO-$d_6$): δ 9.74 (s, 1H); 9.19 (s, 3H); 7.54 (m, 2H); 7.40 (m, 2H); 7.33 (m, 1H); 7.19 (m, 1H); 7.00 (m, 1H); 6.89 (m, 1H); 6.78 (m, 1H); 5.49 (s, 1H).

| Cpd. | LCMS/HPLC Method | NMR data (400 MHz) | Salt |
|---|---|---|---|
| 1 | A | (DMSO-$d_6$ @85° C.): δ 8.23-8.17 (m, 3 H); 7.78-7.70 (m, 1 H); 7.48 (d, J = 7.9 Hz, 2 H); 7.41-7.20 (m, 8 H); 7.08 (d, J = 8.1 Hz, 1 H); 7.05-7.01 (m, 1 H); 6.97-6.88 (m, 3 H); 6.49 (d, J = 9.9 Hz, 1 H); 5.83 (d, J = 8.8 Hz, 1 H); 5.12 (s, 2 H); 5.04 (dd, J = 7.7, 4.9 Hz, 1 H); 4.63-4.57 (m, 1 H); 4.06 (t, J = 6.5 Hz, 2 H); 3.98-3.86 (m, 1 H); 3.13-3.03 (m, 3 H); 2.83-2.52 (m, 9 H); 1.94-1.83 (m, 3 H); 1.80-1.70 (m, 1 H); 1.67-1.37 (m, 9 H); 1.36-1.25 (m, 1 H). 1 H obscured by water signal | Diformate |
| 2 | C | (DMSO-$d_6$): δ 10.4 (br s, 1 H); 8.79 (d, J = 6.86 Hz, 1 H); 8.26 (s, 3 H); 8.19 (d, J = 9.93 Hz, 1 H); 7.87 (d, J = 8.03 Hz, 2 H); 7.50 (d, J = 7.95 Hz, 2 H); 7.33-7.18 (m, 6 H); 7.11 (d, J = 8.16 Hz, 1 H); 7.04 (s, 1 H); 6.99-6.85 (m, 3 H); 6.53 (d, J = 9.86 Hz, 1 H); 5.82 (d, J = 9.17 Hz, 1 H); 5.22 (dd, J = 8.14, 4.39 Hz, 1 H); 5.13 (s, 2 H); 4.60 (s, 1 H); 4.45 (q, J = 7.13 Hz, 1 H); 4.08 (d, J = 6.13 Hz, 2 H); 3.20-3.09 (m, 1 H); 2.94-2.57 (m, 8 H); 1.88 (d, J = 48.44 Hz, 2 H); 1.71-1.40 (m, 8 H); 1.41 (d, J = 7.25 Hz, 3 H). | Diformate |
| 3 | C | (DMSO-$d_6$): δ 10.3 (br s, 1 H); 8.58 (d, J = 7.75 Hz, 1 H); 8.29 (s, 2 H); 8.24 (d, J = 9.05 Hz, 1 H); 8.18 (d, J = 9.92 Hz, 1 H); 7.87 (d, J = 8.00 Hz, 2 H); 7.50 (d, J = 7.95 Hz, 2 H); 7.31 (d, J = 5.12 Hz, 4 H); 7.26-7.19 (m, 2 H); 7.10 (d, J = 8.17 Hz, 1 H); 7.04 (s, 1 H); 6.94 (dd, J = 8.05, 4.12 Hz, 2 H); 6.88 (dd, J = 8.24, 2.49 Hz, 1 H); 6.52 (d, J = 9.86 Hz, 1 H); 5.82 (d, J = 9.15 Hz, 1 H); 5.22-5.08 (m, 3 H); 4.58 (s, 1 H); 4.28 (t, J = 7.54 Hz, 1 H); 4.12-4.03 (m, 2 H); 3.12 (t, J = 10.35 Hz, 1 H); 2.84-2.59 (m, 8 H); 2.25-2.13 (m, 1 H); 1.92 (s, 1 H); 1.80 (s, 1 H); 1.77-1.31 (m, 8 H); 0.97 (dd, J = 15.78, 6.72 Hz, 6 H). | Diformate |
| 4 | A | (DMSO-$d_6$): δ 10.4 (br s, 1 H); 8.72 (d, J = 7.61 Hz, 1 H); 8.30 (s, 2 H); 8.26 (d, J = 8.55 Hz, 1 H); 8.19 (d, J = 9.93 Hz, 1 H); 7.87 (d, J = 8.02 Hz, 2 H); 7.50 (d, J = 7.96 Hz, 2 H); 7.31 (d, J = 5.01 Hz, 4 H); 7.27-7.16 (m, 2 H); 7.11 (d, J = 8.16 Hz, 1 H); 7.04 (s, 1 H); 6.99-6.91 (m, 2 H); 6.88 (dd, J = 8.28, 2.48 Hz, 1 H); 6.53 (d, J = 9.86 Hz, 1 H); 5.82 (d, J = 8.98 Hz, 1 H); 5.22-5.16 (m, 1 H); 5.14 (s, 2 H); 4.60 (s, 1 H); 4.48 (m, 1 H); 4.08 (t, J = 5.96 Hz, 2 H); 3.19-3.08 (m, 1 H); 2.85-2.57 (m, 8 H); 1.93 (s, 1 H); 1.99-1.37 (m, 12 H); 0.90 (dd, J = 17.43, 6.43 Hz, 6 H). | Diformate |
| 5 | C | (DMSO-$d_6$): δ 10.4 (br s, 1 H); 8.59 (s, 1 H); 8.30 (s, 2 H); 8.26 (d, J = 8.71 Hz, 1 H); 8.17 (d, J = 9.93 Hz, 1 H); 7.83 (d, J = 8.01 Hz, 2 H); 7.47 (d, J = 7.97 Hz, 2 H); 7.31 (d, J = 4.97 Hz, 4 H); 7.26-7.19 (m, 2 H); 7.10 (d, J = 8.16 Hz, | Diformate |

| Cpd. | LCMS/HPLC Method | NMR data (400 MHz) | Salt |
|---|---|---|---|
| | | 1 H); 7.04 (s, 1 H); 6.99-6.91 (m, 2 H); 6.88 (dd, J = 8.26, 2.53 Hz, 1 H); 6.52 (d, J = 9.86 Hz, 1 H); 5.82 (d, J = 9.08 Hz, 1 H); 5.18 (dd, J = 8.17, 4.54 Hz, 1 H); 5.12 (s, 2 H); 4.60 (s, 1 H); 4.02 (d, J = 6.12 Hz, 2 H); 3.19-3.09 (m, 1 H); 2.86-2.57 (m, 8 H); 1.93 (s, 1 H); 1.81 (s, 1 H); 1.46 (t, J = 40.03 Hz, 14 H). | |
| 6 | A | (DMSO-$d_6$): δ 10.3 (br s, 1 H); 8.70 (d, J = 7.52 Hz, 1 H); 8.28 (s, 1 H); 8.24 (d, J = 8.92 Hz, 1 H); 8.18 (d, J = 9.93 Hz, 1 H); 7.87 (d, J = 8.02 Hz, 2 H); 7.51 (d, J = 7.98 Hz, 2 H); 7.33-7.19 (m, 6 H); 7.09 (d, J = 8.15 Hz, 1 H); 7.04 (s, 1 H); 6.94 (d, J = 8.01 Hz, 2 H); 6.88 (d, J = 8.35 Hz, 1 H); 6.52 (d, J = 9.87 Hz, 1 H); 5.82 (d, J = 8.95 Hz, 1 H); 5.15-5.08 (m, 3 H); 4.58 (s, 1 H); 4.54-4.46 (m, 1 H); 4.09-4.04 (m, 2 H); 3.11 (m, 1 H); 2.82-2.57 (m, 7 H); 1.91 (s, 1 H); 1.93-1.34 (m, 17 H); 1.26-1.04 (m, 4 H); 1.00-0.82 (m, 2 H). | Formate |
| 7 | C | (DMSO-$d_6$): δ 10.4 (br s, 1 H); 8.71 (d, J = 7.63 Hz, 1 H); 8.27 (s, 2 H); 8.24 (s, 1 H); 8.18 (d, J = 9.93 Hz, 1 H); 7.87 (d, J = 8.02 Hz, 2 H); 7.51 (d, J = 7.95 Hz, 2 H); 7.32-7.18 (m, 6 H); 7.10 (d, J = 8.15 Hz, 1 H); 7.04 (s, 1 H); 6.97-6.93 (m, 2 H); 6.91-6.85 (m, 1 H); 6.52 (d, J = 9.86 Hz, 1 H); 5.82 (d, J = 8.87 Hz, 1 H); 5.22-5.08 (m, 3 H); 4.59 (s, 1 H); 4.48 (m, 1 H); 4.11-4.04 (m, 2 H); 3.12 m, 1 H); 2.85-2.60 (m, 8 H); 1.92 (s, 1 H); 1.95-1.36 (m, 12 H); 0.90 (dd, J = 17.10, 6.42 Hz, 6 H). | Diformate |
| 8 | B | (DMSO-$d_6$): δ 10.50 (d, J = 19.21 Hz, 2 H); 9.52 (s, 1 H); 8.81 (d, J = 7.63 Hz, 1 H); 8.59 (s, 2 H); 8.45 (d, J = 9.21 Hz, 1 H); 8.16 (d, J = 9.93 Hz, 1 H); 7.80 (d, J = 8.02 Hz, 2 H); 7.49 (d, J = 8.03 Hz, 2 H); 7.34-7.14 (m, 9 H); 7.03-6.94 (m, 3 H); 6.90 (d, J = 8.30 Hz, 1 H); 6.84 (d, J = 8.35 Hz, 2 H); 6.59 (d, J = 9.89 Hz, 1 H); 6.17 (s, 1 H); 5.83 (d, J = 9.05 Hz, 1 H); 5.31 (d, J = 9.26 Hz, 1 H); 5.12 (s, 2 H); 4.88-4.83 (m, 1 H); 4.62-4.55 (m, 1 H); 4.11-4.06 (m, 2 H); 3.72-3.60 (m, 4 H); 3.28-2.92 (m, 8 H); 2.23 (s, 1 H); 2.05 (s, 1 H); 1.89-1.55 (m, 7 H). | Ditrifluoro-acetate |
| 9 | A | (DMSO-d6): δ 8.99-8.92 (m, 1 H); 8.30 (s, 1 H); 8.23 (d, J = 9.4 Hz, 1 H); 8.18 (d, J = 9.9 Hz, 1 H); 7.86 (d, J = 7.9 Hz, 2 H); 7.52 (d, J = 7.9 Hz, 2 H); 7.31 (d, J = 5.0 Hz, 4 H); 7.28-7.19 (m, 2 H); 7.09 (d, J = 8.1 Hz, 1 H); 7.04 (s, 1 H); 6.96-6.85 (m, 3 H); 6.54-6.48 (m, 1 H); 5.82 (d, J = 9.2 Hz, 1 H); 5.14 (s, 2 H); 5.11-5.04 (m, 1 H); 4.57 (s, 1 H); 4.12-4.04 (m, 2 H); 4.01 (d, J = 5.8 Hz, 2 H); 3.09 (s, 1 H); 2.76-2.58 (m, 7 H); 1.91-1.25 (m, 11 H). | Formate |
| 9A | C | (DMSO-$d_6$, 105° C.): δ 8.25-8.17 (m, 3 H); 7.57 (d, J = 8.8 Hz, 1 H); 7.47 (d, J = 7.9 Hz, 2 H); 7.37-7.27 (m, 6 H); 7.28-7.20 (m, 2 H); 7.09 (d, J = 8.1 Hz, 1 H); 7.03 (d, J = 2.2 Hz, 1 H); 6.98-6.88 (m, 3 H); 6.49 (d, J = 9.9 Hz, 1 H); 5.83 (d, J = 8.7 Hz, 1 H); 5.12 (s, 2 H); 5.04-4.97 (m, 1 H); 4.64-4.58 (m, 1 H); 3.87 (s, 2 H); 3.12-3.00 (m, 3 H); 2.83 (t, J = 6.2 Hz, 2 H); 2.79-2.56 (m, 6 H); 1.93-1.89 (m, 1 H); 1.79 (d, J = 14.6 Hz, 3 H); 1.64-1.56 (m, 1 H); 1.52-1.45 (m, 1 H); 1.34-1.22 (m, 3 H). | Formate |
| 9B | C | (DMSO-$d_6$, 110° C.): δ (d, J = 9.9 Hz, 1 H); 7.84 (d, J = 8.6 Hz, 1 H); 7.49 (d, J = 7.9 Hz, 2 H); 7.39-7.20 (m, 8 H); 7.16 (d, J = 8.2 Hz, 1 H); 7.04-7.00 (m, 2 H); 6.99-6.90 (m, 2 H); 6.57 (d, J = 9.9 Hz, 1 H); 5.85 (d, J = 8.7 Hz, 1 H); 5.40 (dd, J = 8.0, 5.0 Hz, 1 H); 5.13 (s, 2 H); 4.97-4.91 (m, 1 H); 4.04 (d, J = 13.5 Hz, 2 H); 3.66 (ddd, J = 14.0, 8.4, 2.6 Hz, 1 H); 3.33-3.11 (m, 6 H); 3.12-2.95 (m, 5 H); 2.25 (d, J = 4.4 Hz, 1 H); 2.16-1.71 (m, 7 H); 1.28 (dd, J = 24.1, 12.0 Hz, 2 H). | Trifluoro-acetate |

| Cpd. | LCMS/HPLC Method | NMR data (400 MHz) | Salt |
|---|---|---|---|
| 9C | C | (DMSO-d$_6$): δ 10.50 (s, 2 H); 9.69 (s, 1 H); 8.65 (s, 3 H); 8.45 (d, J = 9.2 Hz, 1 H); 8.16 (d, J = 10.0 Hz, 1 H); 7.55-7.41 (m, 3 H); 7.35-7.20 (m, 7 H); 7.15 (d, J = 8.2 Hz, 1 H); 7.05-6.92 (m, 3 H); 6.91 (dd, J = 8.2, 2.4 Hz, 1 H); 6.58 (d, J = 9.9 Hz, 1 H); 6.19 (s, 1 H); 5.83 (d, J = 9.1 Hz, 1 H); 5.32 (d, J = 9.7 Hz, 1 H); 5.12 (s, 2 H); 4.88-4.83 (m, 1 H); 4.33 (s, 1 H); 4.10-4.04 (m, 2 H); 3.69-3.51 (m, 2 H); 3.36-2.90 (m, 8 H); 2.70-2.60 (m, 1 H); 2.23 (s, 1 H); 2.12-2.01 (m, 1 H); 1.97-1.52 (m, 12 H). | Diformate |
| 9D | C | (DMSO-d$_6$): δ 8.36-8.08 (m, 4 H); 7.33-7.19 (m, 6 H); 7.11 (d, J = 8.2 Hz, 1 H); 7.03 (s, 1 H); 6.97-6.90 (m, 4 H); 6.68 (d, J = 3.4 Hz, 1 H); 6.53 (d, J = 9.9 Hz, 1 H); 5.82 (d, J = 9.2 Hz, 1 H); 5.20 (dd, J = 8.0, 4.6 Hz, 1 H); 5.10 (s, 2 H); 4.60 (s, 1 H); 4.16 (d, J = 13.1 Hz, 2 H); 4.05 (t, J = 5.9 Hz, 2 H); 3.18-3.07 (m, 1 H); 2.90-2.55 (m, 9 H); 1.88 (d, J = 17.3 Hz, 4 H); 1.67-1.31 (m, 12 H). | Diformate |
| 9E | C | (DMSO-d$_6$): δ 8.34-8.18 (m, 3 H); 8.18 (d, J = 9.9 Hz, 1 H); 7.34-7.18 (m, 6 H); 7.13-7.04 (m, 2 H); 6.99-6.90 (m, 3 H); 6.67 (s, 1 H); 6.53 (d, J = 9.9 Hz, 1 H); 5.83 (d, J = 9.1 Hz, 1 H); 5.20-5.11 (m, 3 H); 4.59 (s, 1 H); 4.50 (d, J = 12.8 Hz, 1 H); 4.34 (s, 1 H); 4.08-4.01 (m, 2 H); 3.87 (s, 3 H); 3.34-3.02 (m, 2 H); 2.89-2.55 (m, 10 H); 1.95-1.79 (m, 4 H); 1.69-1.36 (m, 10 H). | Diformate |
| 9F | C | (DMSO, 110° C.): δ 8.20 (d, J = 9.9 Hz, 1 H); 7.84 (d, J = 8.7 Hz, 1 H); 7.34-7.21 (m, 6 H); 7.16 (d, J = 8.2 Hz, 1 H); 7.04-6.92 (m, 4 H); 6.61-6.55 (m, 2 H); 5.86 (d, J = 8.6 Hz, 1 H); 5.39 (dd, J = 8.0, 5.0 Hz, 1 H); 5.18 (s, 2 H); 4.96-4.91 (m, 1 H); 4.52 (d, J = 13.0 Hz, 2 H); 3.88 (s, 3 H); 3.65-2.94 (m, 10 H); 2.26 (d, J = 4.5 Hz, 1 H); 2.18-1.76 (m, 9 H); 1.27 (dd, J = 12.2, 4.1 Hz, 2 H). | Trifluoro-acetate |
| 9G | C | (DMSO-d$_6$, @ 110° C.); 8.22 (d, J = 9.9 Hz, 1H); 8.15 (s, 2H); 7.54 (d, J = 8.3 Hz, 1H); 7.49-7.39 (m, 3H); 7.32-7.30 (m, 5H); 7.23 (t, J = 8.2 Hz, 2H); 7.09 (d, J = 8.2 Hz, 1H); 7.02 (dd, J = 2.1, 2.1 Hz, 1H); 6.98-6.89 (m, 3H); 6.49 (d, J = 9.8 Hz, 1H); 5.83 (d, J = 8.7 Hz, 1H); 5.13 (s, 2H); 5.05 (dd, J = 4.8, 7.6 Hz, 1H); 4.65-4.61 (m, 1H); 4.02-3.91 (m, 2H); 3.12 (dd, J = 8.3, 14.4 Hz, 1H); 2.90-2.61 (m, 8H); 2.60-2.51 (m, 3H); 1.93 (dd, J = 3.2, 6.3 Hz, 1H); 1.83-1.45 (m, 6H); 1.37-1.30 (m, 1H); 1.18-1.07 (m, 2H). | Diformate |
| 10 | A | (DMSO-d6): δ 10.30 (bs, 1 H); 8.28-8.21 (m, 2 H); 8.11 (d, J = 9.9 Hz, 1 H); 8.04-7.84 (m, 2 H); 7.58 (d, J = 8.0 Hz, 2 H); 7.40-7.18 (m, 10 H); 7.09-7.02 (m, 2 H); 6.97-6.86 (m, 3 H); 6.48 (d, J = 9.9 Hz, 1 H); 5.82 (d, J = 9.1 Hz, 1 H); 5.18 (s, 2 H); 5.07 (dd, J = 8.0, 4.3 Hz, 1 H); 4.62-4.30 (m, 3 H); 3.85-3.07 (m, 7 H); 2.81-2.54 (m, 7 H); 1.95-1.74 (m, 2 H); 1.66-1.29 (m, 3 H); 1.23-0.98 (m, 3 H). | Formate |
| 11 | C | (DMSO-d$_6$): δ 10.29 (s, 1 H); 8.24 (s, 2 H); 8.11 (d, J = 9.93 Hz, 1 H); 7.93 (d, J = 46.05 Hz, 2 H); 7.57 (d, J = 7.99 Hz, 2 H); 7.32-7.18 (m, 11 H); 7.09-7.02 (m, 2 H); 6.98-6.86 (m, 3 H); 6.47 (d, J = 9.87 Hz, 1 H); 5.82 (d, J = 8.99 Hz, 1 H); 5.18 (s, 2 H); 5.07 (dd, J = 8.01, 4.33 Hz, 1 H); 4.66-4.34 (m, 3 H); 3.99-3.57 (m, 4 H); 3.25-2.86 (m, 4 H); 2.73-2.61 (m, 6 H); 1.99-1.72 (m, 2 H); 1.67-1.23 (m, 4 H) | Diformate |
| 12 | A | (DMSO-d6): δ 10.28 (bs, 1 H); 8.28-8.21 (m, 3 H); 8.11 (d, J = 9.9 Hz, 1 H); 8.02-7.76 (m, 2 H); 7.57 (d, J = 7.9 Hz, 2 H); 7.41-7.14 (m, 15 H); 7.08-7.01 (m, 2 H); 6.97-6.86 (m, 3 H); 6.46 (d, J = 9.9 Hz, 1 H); 5.82 (d, J = 9.0 Hz, 1 H); 5.18 (s, 2 H); 5.10-5.02 (m, 1 H); | Diformate |

| Cpd. | LCMS/HPLC Method | NMR data (400 MHz) | Salt |
|---|---|---|---|
| | | 4.85-4.26 (m, 5 H); 3.80-3.08 (m, 5 H); 2.82-2.54 (m, 7 H); 1.95-1.74 (m, 2 H); 1.66-1.29 (m, 3 H). | |
| 13 | C | (DMSO-d6 @85° C.): δ 8.19-8.12 (m, 3 H); 7.98 (d, J = 7.9 Hz, 2 H); 7.72 (bs, 1 H); 7.56 (d, J = 7.8 Hz, 2 H); 7.38-7.19 (m, 10 H); 7.08 (d, J = 8.1 Hz, 1 H); 7.03 (s, 1 H); 6.96-6.88 (m, 3 H); 6.46 (d, J = 9.8 Hz, 1 H); 5.83 (d, J = 8.5 Hz, 1 H); 5.18 (s, 2 H); 5.07 (dd, J = 7.7, 4.7 Hz, 1 H); 4.63-4.57 (m, 1 H); 4.48 (t, J = 6.2 Hz, 2 H); 4.05-3.94 (m, 1 H); 3.80 (s, 2 H); 3.67 (t, J = 17.6 Hz, 2 H); 3.09 (dd, J = 14.4, 8.2 Hz, 1 H); 2.85-2.53 (m, 7 H); 1.93-1.87 (m, 1 H); 1.80-1.68 (m, 1 H); 1.66-1.54 (m, 1 H); 1.53-1.43 (m, 1 H); 1.38-1.25 (m, 1 H); 1.17 (d, J = 6.7 Hz, 6 H). | Diformate |
| 14 | C | (DMSO-d6 @85° C.): δ 8.17-8.12 (m, 3 H); 7.97 (d, J = 7.9 Hz, 2 H); 7.75 (bs, 1 H); 7.56 (d, J = 8.0 Hz, 2 H); 7.39-7.19 (m, 10 H); 7.10-7.01 (m, 2 H); 6.96-6.88 (m, 3 H); 6.47 (d, J = 9.9 Hz, 1 H); 5.83 (d, J = 8.7 Hz, 1 H); 5.18 (s, 2 H); 5.08 (dd, J = 7.7, 4.5 Hz, 1 H); 4.65-4.58 (m, 1 H); 4.45 (t, J = 6.1 Hz, 2 H); 3.82 (s, 2 H); 3.70 (t, J = 6.5 Hz, 2 H); 3.61-3.50 (m, 1 H); 3.11 (dd, J = 14.7, 8.4 Hz, 1 H); 2.84-2.58 (m, 7 H); 1.94-1.89 (m, 1 H); 1.81-1.44 (m, 10 H); 1.38-1.28 (m, 1 H); 1.13-0.93 (m, 3 H). | Diformate |
| 15 | C | (DMSO-d6): δ 8.28-8.18 (m, 2 H); 8.11 (d, J = 9.9 Hz, 1 H); 7.89 (m, 2 H); 7.57 (d, J = 7.9 Hz, 2 H); 7.38-7.18 (m, 14 H); 7.09-7.02 (m, 2 H); 6.98-6.87 (m, 3 H); 6.46 (d, J = 9.8 Hz, 1 H); 5.82 (d, J = 9.0 Hz, 1 H); 5.18 (s, 2 H); 5.06 (s, 1 H); 4.80-4.27 (m, 5 H); 3.71 (m, 4 H); 3.14 (m, 1 H); 2.77-2.62 (m, 7 H); 1.92 (s, 1 H); 1.80 (s, 1 H); 1.48 (m, 3 H). | Formate |
| 16 | C | (DMSO-d$_6$, @ 85° C.): δ 9.79 (br s, 1 H); 8.18 (d, J = 9.98 Hz, 1 H); 8.13 (s, 2 H); 7.96 (d, J = 8.07 Hz, 3 H); 7.59-7.47 (m, 4 H); 7.44-7.36 (t, J = 7.39 Hz, 1 H); 7.33-7.22 (m, 7 H); 7.11 (d, J = 8.16 Hz, 1 H); 7.03 (s, 1 H); 7.01-6.87 (m, 3 H); 6.50 (d, J = 9.87 Hz, 1 H); 5.84 (d, J = 8.63 Hz, 1 H); 5.35-5.28 (m, 1 H); 5.18 (s, 2 H); 4.88-4.83 (m, 1 H); 4.49 (s, 2 H); 4.06 (s, 2 H); 3.80 (s, 2 H); 3.59-3.49 (m, 1 H); 3.2-2.8 (m, 10 H); 2.18 (s, 1 H); 2.05-1.67 (m, 4 H). | Diformate |
| 17 | C | (DMSO-d$_6$): δ 10.31 (s, 1 H); 8.65 (t, J = 5.67 Hz, 1 H); 8.30-8.18 (m, 2 H); 8.13 (d, J = 9.93 Hz, 1 H); 7.99 (d, J = 8.06 Hz, 2 H); 7.78 (d, J = 7.99 Hz, 2 H); 7.56 (d, J = 8.01 Hz, 2 H); 7.40 (d, J = 8.01 Hz, 2 H); 7.32-7.18 (m, 6 H); 7.05 (t, J = 6.86 Hz, 2 H); 6.96-6.85 (m, 3 H); 6.47 (d, J = 9.87 Hz, 1 H); 5.82 (d, J = 9.15 Hz, 1 H); 5.17 (s, 2 H); 5.07 (dd, J = 8.03, 4.34 Hz, 1 H); 4.59 (s, 1 H); 4.40 (t, J = 5.55 Hz, 2 H); 3.81 (s, 2 H); 3.65 (d, J = 6.59 Hz, 2 H); 3.14 (t, J = 11.74 Hz, 1 H); 2.72-2.64 (m, 7 H); 1.92 (s, 1 H); 1.81 (s, 1 H); 1.69-1.27 (m, 3 H). | Formate |
| 18 | A | (DMSO-d6): δ 8.70-8.63 (m, 1 H); 8.29-8.18 (m, 2 H); 8.13 (d, J = 9.9 Hz, 1 H); 7.99 (d, J = 8.1 Hz, 2 H); 7.56 (d, J = 8.0 Hz, 2 H); 7.40-7.15 (m, 9 H); 7.08-7.01 (m, 2 H); 6.97-6.85 (m, 3 H); 6.48 (d, J = 9.9 Hz, 1 H); 5.82 (d, J = 9.1 Hz, 1 H); 5.17 (s, 2 H); 5.05 (dd, J = 7.8, 4.5 Hz, 1 H); 4.58 (s, 1 H); 4.44-4.37 (m, 2 H); 3.79 (s, 2 H); 3.79-3.66 (m, 3 H); 3.67-3.59 (m, 5 H); 3.14 (m, 1 H); 2.77-2.61 (m, 4 H); 1.92 (s, 1 H); 1.80 (s, 1 H); 1.67-1.29 (m, 3 H). | Formate |
| 19 | C | (DMSO-d6): δ 8.91 (d, J = 2.2 Hz, 1 H); 8.89-8.83 (m, 1 H); 8.24 (s, 2 H); 8.19-8.08 (m, 2 H); 7.99 (d, J = 8.0 Hz, 2 H); 7.56 (d, J = 8.0 Hz, 2 H); 7.49 (d, J = 8.1 Hz, 1 H); 7.31-7.17 (m, 6 H); 7.10-7.01 (m, 2 H); 6.96-6.85 (m, 3 | Formate |

| Cpd. | LCMS/HPLC Method | NMR data (400 MHz) | Salt |
|---|---|---|---|
| | | H); 6.48 (d, J = 9.9 Hz, 1 H); 5.81 (d, J = 9.3 Hz, 1 H); 5.17 (s, 2 H); 5.09 (dd, J = 7.8, 4.4 Hz, 1 H); 4.58 (s, 1 H); 4.45-4.38 (m, 2 H); 3.94-3.81 (m, 2 H); 3.68-3.61 (m, 4 H); 3.11 (m, 1 H); 2.79-2.59 (m, 5 H); 1.91 (s, 1 H); 1.79 (s, 1 H); 1.68-1.25 (m, 3 H). | |
| 20 | C | (DMSO-d6): δ 8.52-8.45 (m, 1 H); 8.27-8.18 (m, 2 H); 8.14 (d, J = 9.9 Hz, 1 H); 7.98 (d, J = 8.0 Hz, 2 H); 7.55 (d, J = 7.9 Hz, 2 H); 7.31-7.18 (m, 6 H); 7.08-6.99 (m, 3 H); 6.96-6.85 (m, 3 H); 6.48 (d, J = 9.9 Hz, 1 H); 6.37 (d, J = 3.4 Hz, 1 H); 5.82 (d, J = 9.2 Hz, 1 H); 5.17 (s, 2 H); 5.03 (dd, J = 7.9, 4.3 Hz, 1 H); 4.57 (s, 1 H); 4.39-4.32 (m, 2 H); 3.80-3.72 (m, 2 H); 3.58 (d, J = 14.8 Hz, 2 H); 3.11 (m, 1 H); 2.77-2.60 (m, 8 H); 1.90 (s, 1 H); 1.79 (s, 1 H); 1.46 (m, 3 H). | Formate |
| 21 | C | (DMSO-d6): δ 8.58-8.51 (m, 1 H); 8.30 (s, 1 H); 8.17 (d, J = 9.5 Hz, 1 H); 8.08 (d, J = 9.9 Hz, 1 H); 7.93 (d, J = 8.0 Hz, 2 H); 7.52-7.48 (m, 3 H); 7.26-7.11 (m, 6 H); 7.03-6.97 (m, 2 H); 6.91-6.81 (m, 4 H); 6.41 (d, J = 9.9 Hz, 1 H); 5.76 (d, J = 9.1 Hz, 1 H); 5.11 (s, 2 H); 5.00 (dd, J = 7.9, 4.3 Hz, 1 H); 4.50 (s, 1 H); 4.35-4.28 (m, 2 H); 3.87 (s, 2 H); 3.55 (d, J = 7.1 Hz, 4 H); 3.03 (m, 1 H); 2.75-2.50 (m, 5 H); 1.83 (d, J = 5.3 Hz, 1 H); 1.72 (s, 1 H); 1.58-1.19 (m, 3 H). | Formate |
| 21A | C | (DMSO-d$_6$): δ 8.90-8.86 (m, 1 H); 8.39 (s, 1 H); 8.21 (d, J = 9.9 Hz, 1 H); 8.02 (d, J = 8.1 Hz, 2 H); 7.60 (d, J = 8.0 Hz, 2 H); 7.38-7.32 (m, 4 H); 7.32-7.25 (m, 2 H); 7.13-7.07 (m, 2 H); 7.00-6.91 (m, 3 H); 6.67 (s, 1 H); 6.53 (d, J = 9.9 Hz, 1 H); 5.88 (, 1 H); 5.22 (s, 2 H); 5.10-5.07 (m, 1 H); 4.66-4.55 (m, 1 H); 4.39-4.32 (m, 2 H); 3.97 (s, 2 H); 3.50-3.41 (m, 6 H); 3.18-3.06 (m, 1 H); 2.78-2.69 (m, 4 H); 2.06-2.00 (m, 2 H); 1.94 (s, 1 H); 1.83 (s, 1 H); 1.61 (s, 1 H); 1.51 (s, 1 H); 1.37 (s, 1 H). | Formate |
| 21B | C | (DMSO-d$_6$): δ 8.33-8.15 (m, 2 H); 8.18-8.11 (m, 2 H); 7.97 (d, J = 8.1 Hz, 2 H); 7.55 (d, J = 8.0 Hz, 2 H); 7.33-7.19 (m, 6 H); 7.10-7.01 (m, 2 H); 6.96-6.85 (m, 3 H); 6.54-6.44 (m, 2 H); 5.82 (d, J = 9.3 Hz, 1 H); 5.17 (s, 2 H); 5.04 (dd, J = 7.9, 4.4 Hz, 1 H); 4.58 (s, 1 H); 4.32-4.25 (m, 2 H); 3.80-3.75 (m, 5 H); 3.12 (t, J = 10.8 Hz, 1 H); 2.79-2.56 (m, 7 H); 1.94 (m, 3 H); 1.80 (s, 1 H); 1.59 (s, 1 H); 1.48 (s, 2 H); 1.35 (s, 1 H). | Formate |
| 22 | C | (DMSO-d6): δ 8.29 (s, 1 H); 8.24 (d, J = 9.6 Hz, 1 H); 8.17 (d, J = 9.9 Hz, 1 H); 7.64 (d, J = 7.9 Hz, 1 H); 7.34-7.18 (m, 8 H); 7.12-7.02 (m, 2 H); 6.97-6.87 (m, 3 H); 6.51 (d, J = 9.9 Hz, 1 H); 5.82 (d, J = 9.0 Hz, 1 H); 5.13 (s, 2 H); 4.57 (s, 1 H); 4.21 (t, J = 6.2 Hz, 2 H); 3.80 (s, 3 H); 3.10 (s, 1 H); 2.81 (d, J = 6.3 Hz, 2 H); 2.74 (d, J = 7.7 Hz, 4 H); 2.67 (s, 1 H); 2.62 (s, 2 H); 1.97-1.72 (m, 3 H); 1.74-1.66 (m, 2 H); 1.64-1.56 (m, 2 H); 1.48 (s, 2 H); 1.34 (s, 1 H). | Formate |
| 23 | C | (MeOD): δ 8.47 (s, 2 H); 8.37 (d, J = 9.9 Hz, 1 H); 7.89-7.80 (m, 2 H); 7.76 (d, J = 8.0 Hz, 1 H); 7.34-7.24 (m, 7 H); 7.04 (d, J = 8.2 Hz, 1 H); 6.99-6.88 (m, 3 H); 6.69 (d, J = 9.8 Hz, 1 H); 5.90 (s, 1 H); 5.44-5.36 (m, 1 H); 5.22 (s, 2 H); 4.99 (s, 2 H); 4.45-4.38 (m, 2 H); 3.68 (t, J = 10.8 Hz, 1 H); 3.31-3.08 (m, 8 H); 2.33-1.79 (m, 9 H). | Diformate |
| 24 | A | (DMSO-d$_6$): δ 8.26 (s, 2 H); 8.17 (d, J = 9.91 Hz, 1 H); 7.88 (s, 1 H); 7.65 (d, J = 9.04 Hz, 1 H); 7.59 (d, J = 9.28 Hz, 1 H); 7.32-7.17 (m, 7 H); 7.09 (d, J = 8.14 Hz, 1 H); 7.04 (s, 1 H); 6.98-6.86 (m, 3 H); 6.51 (d, J = 9.87 Hz, 1 H); 5.82 (d, J = 8.90 Hz, 1 H); 5.21-5.11 (m, 3 H); 4.58 (s, 1 H); 4.31 (t, J = 6.27 Hz, 2 H); 3.12 (t, J = 11.01 Hz, 2 H); 2.84 (d, J = 6.41 Hz, 2 | Diformate |

-continued

| Cpd. | LCMS/HPLC Method | NMR data (400 MHz) | Salt |
|---|---|---|---|
| | | H); 2.80-2.74 (m, 5 H); 2.69-2.56 (m, 3 H); 1.91 (s, 1 H); 1.81-1.71 (m, 3 H); 1.68-1.58 (m, 4 H); 1.48 (s, 2 H); 1.35 (s, 1 H). | |
| 25 | A | (DMSO-d6): δ 8.31-8.13 (m, 4 H); 7.97 (s, 1 H); 7.88-7.86 (m, 1 H); 7.80 (s, 1 H); 7.32-7.17 (m, 6 H); 7.11-7.02 (m, 2 H); 6.98-6.86 (m, 3 H); 6.50 (d, J = 9.9 Hz, 1 H); 5.82 (d, J = 9.0 Hz, 1 H); 5.19 (s, 2 H); 5.15-5.08 (m, 1 H); 4.57 (s, 1 H); 4.34-4.26 (m, 2 H); 3.10 (m, 1 H); 2.86-2.56 (m, 7 H); 1.90 (s, 1 H); 1.80-1.70 (m, 4 H); 1.64-1.55 (m, 4 H); 1.40 (m, 2 H). | Diformate |
| 26 | A | (DMSO-d$_6$): δ 8.27 (s, 2 H); 8.20 (d, J = 9.9 Hz, 1 H); 7.94 (d, J = 7.9 Hz, 2 H); 7.61-7.50 (m, 3 H); 7.32-7.29 (m, 4 H); 7.28-7.19 (m, 2 H); 7.08 (d, J = 8.1 Hz, 1 H); 7.04-6.99 (m, 1 H); 6.98-6.88 (m, 3 H); 6.47 (d, J = 9.9 Hz, 1 H); 5.85-5.79 (m, 1 H); 5.17 (s, 2 H); 5.04-4.99 (m, 1 H); 4.63-4.56 (m, 1 H); 4.46-4.34 (m, 2 H); 3.70-3.61 (m, 2 H); 3.43-3.35 (m, 2 H); 3.08-3.03 (m, 1 H); 2.82-2.55 (m, 9 H); 2.01 (s, 3 H); 1.93-1.84 (m, 1 H); 1.75-1.58 (m, 4 H); 1.52-1.42 (m, 1 H); 1.36-1.23 (m, 1 H). | Formate |
| 27 | B | (DMSO-d$_6$): δ 8.20-8.14 (m, 3 H); 7.96-7.91 (m, 2 H); 7.58-7.50 (m, 3 H); 7.43-7.27 (m, 9 H); 7.26-7.19 (m, 2 H); 7.08-7.02 (m, 2 H); 6.96-6.88 (m, 3 H); 6.47 (d, J = 9.9 Hz, 1 H); 5.83 (d, J = 7.0 Hz, 1 H); 5.18 (s, 2 H); 4.98 (dd, J = 7.5, 4.8 Hz, 1 H); 4.64-4.58 (m, 1 H); 4.49-4.42 (m, 2 H); 3.79-3.72 (m, 2 H); 3.48-3.39 (m, 2 H); 3.08 (dd, J = 14.3, 8.3 Hz, 1 H); 2.77-2.47 (m, 8 H); 1.92-1.89 (m, 1 H); 1.76-1.67 (m, 4 H); 1.62-1.58 (m, 1 H); 1.51-1.47 (m, 1 H); 1.33-1.28 (m, 1 H). | Diformate |
| 28 | C | (DMSO-d6): δ 8.35-8.18 (m, 3 H); 8.16 (d, J = 9.9 Hz, 1 H); 7.92 (d, J = 8.0 Hz, 2 H); 7.84-7.79 (m, 2 H); 7.67-7.51 (m, 5 H); 7.32-7.19 (m, 6 H); 7.12-7.02 (m, 2 H); 6.95 (d, J = 8.0 Hz, 2 H); 6.91-6.86 (m, 1 H); 6.50 (d, J = 9.9 Hz, 1 H); 5.83 (d, J = 8.5 Hz, 1 H); 5.19-5.06 (m, 3 H); 4.60 (s, 2 H); 4.42-4.35 (m, 2 H); 3.55-3.48 (m, 2 H); 2.81-2.56 (m, 9 H); 1.94 (s, 1 H); 1.83-1.70 (m, 3 H); 1.74-1.26 (m, 5 H). | Diformate |
| 29 | B | (DMSO-d$_6$, @ 85° C.): δ 8.14 (d, J = 15.87 Hz, 2 H); 7.81 (s, 2 H); 7.51 (d, J = 12.80 Hz, 2 H); 7.37-7.16 (m, 10 H); 7.08-6.86 (m, 5 H); 6.52-6.4 (m, 1 H); 5.86-5.75 (m, 1 H); 5.20-5.13 (m, 2 H); 5.07-4.95 (m, 1 H); 4.59 (s, 1 H); 4.24 (s, 2 H); 3.54-3.07 (m, 7 H); 2.81-2.55 (m, 7 H); 2.06-1.86 (m, 4 H); 1.81-1.4 (m, 4 H); 1.31 (s, 1 H). | Formate |
| 30 | C | (DMSO-d$_6$ @ 85° C.): δ 8.18 (s, 3 H); 7.97 (d, J = 8.00 Hz, 2 H); 7.55 (d, J = 7.99 Hz, 3 H); 7.32-7.21 (m, 7 H); 7.07 (d, J = 1.60 Hz, 1 H); 7.02 (s, 1 H); 6.94 (s, 3 H); 6.48 (d, J = 9.90 Hz, 1 H); 5.84-5.8 (m, 1 H); 5.18 (s, 2 H); 5.05-5.0 (m. 1 H); 4.63-4.56 (m, 1 H); 4.30 (s, 2 H); 3.43 (t, J = 6.93 Hz, 2 H); 3.34 (t, J = 7.26 Hz, 2 H); 2.80-2.58 (m, 7 H); 2.01-1.85 (m, 3 H); 1.78-1.1 (m, 18 H). | Diformate |
| 31 | A | (DMSO-d$_6$, D2O): δ 8.18 (d, J = 9.93 Hz, 1 H); 7.90 (d, J = 7.54 Hz, 2 H); 7.75 (d, J = 7.26 Hz, 2 H); 7.62 (d, J = 7.29 Hz, 1 H); 7.58-7.50 (m, 4 H); 7.31-7.19 (m, 6 H); 7.16 (d, J = 8.32 Hz, 1 H); 7.01 (d, J = 8.23 Hz, 1 H); 6.96-6.85 (m, 3 H); 6.60 (d, J = 9.86 Hz, 1 H); 5.76 (s, 1 H); 5.30-5.24 (m, 1 H); 5.13 (s, 2 H); 4.84 (s, 1 H); 4.24 (s, 2 H); 3.57 (s, 1 H); 3.27-2.93 (m, 13 H); 2.22 (s, 1 H); 2.1-1.6 (m, 8 H). | Ditrifluoro-acetate |
| 32 | C | (DMSO-d$_6$, D2O): δ 8.17 (d, J = 9.91 Hz, 1 H); 7.94 (d, J = 8.01 Hz, 2 H); 7.53 (d, J = 7.92 Hz, 2 H); 7.29-7.10 (m, 11 H); 7.07 (d, J = 8.19 Hz, 1 H); 6.98 (s, 1 H); 6.94-6.83 (m, 3 H); 6.50 (dd, J = 9.87, 6.02 Hz, 1 H); 5.77 (s, 1 H); | Parent |

| Cpd. | LCMS/HPLC Method | NMR data (400 MHz) | Salt |
|---|---|---|---|
| | | 5.14 (d, J = 4.00 Hz, 2 H); 5.03-4.98 (m, 1 H); 4.54 (s, 1 H); 4.28-4.17 (m, 2 H); 3.68-3.62 (m, 2 H); 3.43-3.26 (m, 4 H); 3.04 (s, 1 H); 2.72-2.56 (m, 5 H); 2.52-2.50 (m, 4 H); 1.93-1.84 (m, 3 H); 1.75 (s, 1 H); 1.62-1.54 (m, 3 H); 1.44 (s, 1 H); 1.31 (d, J = 12.68 Hz, 1 H). | |
| 33 | C | (DMSO-d6): δ 8.28-8.16 (m, 4 H); 7.36-7.28 (m, 4 H); 7.25-7.18 (m, 2 H); 7.09 (d, J = 8.2 Hz, 1 H); 6.96-6.87 (m, 3 H); 6.81-6.77 (m, 1 H); 6.53 (d, J = 9.9 Hz, 1 H); 5.81 (d, J = 9.0 Hz, 1 H); 5.13 (t, J = 6.3 Hz, 1 H); 4.61-4.55 (m, 1 H); 4.02 (t, J = 6.1 Hz, 2 H); 3.74 (d, J = 6.3 Hz, 2 H); 3.16-3.06 (m, 1 H); 2.84-2.54 (m, 9 H); 2.30-2.21 (m, 1 H); 1.97-1.27 (m, 16 H); 1.14-1.02 (m, 2 H). | Diformate |
| 33A | C | (DMSO-$d_6$, 110° C.): δ 8.22 (d, J = 9.9 Hz, 1 H); 7.80-7.71 (m, 1 H); 7.38-7.34 (m, 4 H); 7.32-7.22 (m, 2 H); 7.19 (d, J = 8.3 Hz, 1 H); 7.05 (d, J = 8.2 Hz, 1 H); 6.99-6.91 (m, 2 H); 6.88-6.81 (m, 1 H); 6.58 (d, J = 9.8 Hz, 1 H); 5.87 (d, J = 8.1 Hz, 1 H); 5.41-5.34 (m, 1 H); 4.99-4.94 (m, 1 H); 3.86-3.80 (m, 2 H); 3.75-3.63 (m, 1 H); 3.48-3.40 (m, 2 H); 3.37-2.95 (m, 13 H); 2.38-2.18 (m, 1 H); 2.13-1.75 (m, 11 H); 1.53-1.42 (m, 2 H); 1.29-1.17 (m, 2 H). | Trifluoro-acetate |
| 33B | C | (DMSO-$d_6$): δ 8.31 (s, 2 H); 8.29-8.21 (m, 1 H); 8.19 (d, J = 9.9 Hz, 1 H); 7.88-7.81 (m, 1 H); 7.34-7.27 (m, 4 H); 7.26-7.17 (m, 2 H); 7.11 (d, J = 8.2 Hz, 1 H); 6.97 (d, J = 8.1 Hz, 1 H); 6.95-6.85 (m, 2 H); 6.81-6.75 (m, 1 H); 6.54 (d, J = 9.9 Hz, 1 H); 5.90-5.71 (m, 1 H); 5.21 (dd, J = 8.5, 4.2 Hz, 1 H); 4.68-4.56 (m, 1 H); 3.74 (d, J = 6.2 Hz, 2 H); 3.20-3.04 (m, 3 H); 2.96-2.54 (m, 9 H); 2.12-1.99 (m, 1 H); 2.05-1.83 (m, 1 H); 1.95-1.74 (m, 3 H); 1.80-1.59 (m, 6 H); 1.64-1.38 (m, 1 H); 1.44-1.29 (m, 3 H); 1.11-0.96 (m, 2 H). | Diformate |
| 34 | C | (DMSO-$d_6$): δ 10.28 (br s, 1 H); 8.28 (s, 1 H); 8.23 (s, 2 H); 8.09 (d, J = 9.95 Hz, 1 H); 7.96 (d, J = 8.04 Hz, 1 H); 7.52 (d, J = 7.99 Hz, 2 H); 7.39-7.13 (m, 10 H); 7.09-7.00 (m, 2 H); 6.97-6.83 (m, 3 H); 6.47 (d, J = 9.88 Hz, 1 H); 5.82 (d, J = 8.82 Hz, 1 H); 5.15 (s, 2 H); 5.07 (dd, J = 7.96, 4.45 Hz, 1 H); 4.57 (s, 1 H); 4.45-4.39 (m, 2 H); 3.76-3.69 (m, 4 H); 3.16-3.05 (m, 1 H); 3.04 (s, 3 H); 2.77-2.61 (m, 6 H); 2.36-2.32 (m, 1 H); 1.94-1.75 (m, 2 H); 1.62-1.31 (m, 4 H). | Diformate |
| 35 | A | (DMSO-$d_6$): δ 10.32 (s, 1 H); 8.65 (s, 1 H); 8.24 (s, 3 H); 8.09 (d, J = 9.93 Hz, 1 H); 8.02 (d, J = 8.05 Hz, 2 H); 7.57 (d, J = 8.00 Hz, 2 H); 7.37-7.16 (m, 10 H); 7.10-7.02 (m, 2 H); 6.97-6.85 (m, 3 H); 6.48 (d, J = 9.86 Hz, 2 H); 5.82 (d, J = 9.15 Hz, 1 H); 5.18 (s, 2 H); 5.10 (t, J = 6.12 Hz, 1 H); 4.59 (s, 1 H); 4.31 (t, J = 5.35 Hz, 2 H); 3.79-3.67 (m, 2 H); 3.52-3.46 (m, 2 H); 3.20-3.08 (m, 1 H); 2.79-2.60 (m, 7 H); 1.93 (s, 1 H); 1.81 (s, 1 H); 1.72-1.26 (m, 3 H). | Diformate |
| 36 | C | (DMSO-$d_6$): δ 10.29 (s, 1 H); 8.29-8.21 (m, 2 H); 8.08 (d, J = 9.92 Hz, 1 H); 7.95 (s, 1 H); 7.78 (d, J = 8.03 Hz, 2 H); 7.49 (d, J = 7.98 Hz, 2 H); 7.42-7.17 (m, 13 H); 7.16 (d, J = 8.27 Hz, 2 H); 7.09-7.01 (m, 2 H); 6.97-6.85 (m, 3 H); 6.47 (d, J = 9.86 Hz, 1 H); 5.82 (d, J = 9.03 Hz, 1 H); 5.15 (s, 2 H); 5.10-5.04 (m, 1 H); 4.58 (s, 1 H); 4.40 (t, J = 5.23 Hz, 2 H); 4.08 (t, J = 5.20 Hz, 2 H); 3.70 (s, 2 H); 3.18-3.04 (m, 1 H); 2.79-2.58 (m, 6 H); 1.91 (s, 1 H); 1.79 (s, 1 H); 1.68-1.26 (m, 4 H). | Formate |
| 37 | C | (DMSO-$d_6$): δ 10.28 (br s, 1 H); 8.26 (s, 1 H); 8.23 (s, 2 H); 8.10 (d, J = 9.93 Hz, 1 H); 7.97 (d, J = 8.02 Hz, 2 H); 7.54 (d, J = 7.93 Hz, 2 H); 7.40 (d, J = 8.26 Hz, 2 H); 7.34-7.16 (m, 8 H); 7.09-7.00 (m, 2 H); 6.97-6.83 (m, 3 H); 6.48 (d, J = 9.87 Hz, 1 H); 5.82 (d, J = 8.95 Hz, | Formate |

| Cpd. | LCMS/HPLC Method | NMR data (400 MHz) | Salt |
|---|---|---|---|
| | | 1 H); 5.15 (s, 2 H); 5.08 (dd, J = 7.91, 4.50 Hz, 1 H); 4.58 (s, 1 H); 4.44-4.37 (m, 2 H); 3.72 (s, 4 H); 3.45-3.40 (m, 2 H); 3.12 (m, 1 H); 2.77-2.57 (m, 7 H); 1.91 (s, 1 H); 1.80 (s, 1 H); 1.67-1.27 (m, 3 H); 1.11 (t, J = 6.94 Hz, 3 H). | |
| 38 | C | (DMSO-$d_6$): δ 10.3 (br s, 1 H); 8.34 (s, 1 H); 8.25 (s, 3 H); 8.10 (d, J = 9.93 Hz, 1 H); 7.98 (d, J = 8.03 Hz, 2 H); 7.54 (d, J = 7.96 Hz, 2 H); 7.41 (d, J = 8.22 Hz, 2 H); 7.33-7.16 (m, 8 H); 7.10-7.02 (m, 2 H); 6.97-6.84 (m, 3 H); 6.48 (d, J = 9.85 Hz, 1 H); 5.82 (d, J = 8.99 Hz, 1 H); 5.16 (s, 2 H); 5.09 (dd, J = 7.88, 4.50 Hz, 1 H); 4.58 (s, 1 H); 4.42-4.30 (m, 3 H); 3.73 (s, 2 H); 3.60 (t, J = 6.30 Hz, 2 H); 3.22-3.04 (m, 1 H); 2.79-2.59 (m, 7 H); 1.91 (s, 1 H); 1.80 (s, 1 H); 1.66-1.30 (m, 3 H); 1.16 (d, J = 6.57 Hz, 6 H). | Diformate |
| 39 | C | (DMSO-$d_6$): δ 10.29 (1, br s,); 8.36 (s, 1 H); 8.27 (s, 3 H); 8.10 (d, J = 9.92 Hz, 1 H); 7.98 (d, J = 8.03 Hz, 2 H); 7.54 (d, J = 7.99 Hz, 2 H); 7.42 (d, J = 8.17 Hz, 2 H); 7.31-7.20 (m, 8 H); 7.11-7.00 (m, 2 H); 6.94 (t, J = 7.56 Hz, 2 H); 6.88 (dd, J = 8.26, 2.55 Hz, 1 H); 6.49 (d, J = 9.84 Hz, 1 H); 5.82 (d, J = 8.96 Hz, 1 H); 5.16 (s, 3 H); 4.62 (s, 1 H); 4.39-4.32 (m, 2 H); 3.99-3.85 (m, 1 H); 3.82 (s, 2 H); 3.72-3.54 (m, 2 H); 3.18 (s, 1 H); 2.85-2.56 (m, 6 H); 1.96 (s, 1 H); 1.83 (s, 1 H); 1.81-1.29 (m, 13 H); 1.18-1.04 (m, 1 H). | Diformate |
| 40 | C | (DMSO-$d_6$): δ 10.44 (s, 1 H); 8.65 (s, 1 H); 8.38 (d, J = 9.16 Hz, 1 H); 8.17-8.11 (m, 2 H); 7.92 (d, J = 8.03 Hz, 2 H); 7.50 (dd, J = 8.33, 2.60 Hz, 4 H); 7.38-7.19 (m, 13 H); 7.10 (d, J = 8.18 Hz, 1 H); 7.03 (s, 1 H); 6.97 (d, J = 8.01 Hz, 2 H); 6.89 (dd, J = 8.23, 2.57 Hz, 1 H); 6.53 (d, J = 9.86 Hz, 1 H); 5.83 (d, J = 8.85 Hz, 1 H); 5.35 (d, J = 9.34 Hz, 1 H); 5.14 (s, 2 H); 4.81-4.68 (m, 3 H); 4.44-4.37 (m, 2 H); 4.05 (s, 2 H); 3.76 (s, 2 H); 3.51-2.81 (m, 8 H); 2.12 (s, 1 H); 1.96 (s, 1 H); 1.88-1.52 (m, 3 H). | Formate |
| 41 | C | (DMSO-$d_6$): δ 10.32 (br s, 1 H); 8.52 (s, 1 H); 8.31-8.19 (m, 3 H); 8.08 (d, J = 9.93 Hz, 1 H); 7.91 (d, J = 8.04 Hz, 2 H); 7.49 (d, J = 8.05 Hz, 2 H); 7.43-7.10 (m, 14 H); 7.10-6.99 (m, 2 H); 6.97-6.82 (m, 3 H); 6.48 (d, J = 9.86 Hz, 1 H); 5.82 (d, J = 8.96 Hz, 1 H); 5.16-5.06 (m, 3 H); 4.67 (s, 2 H); 4.59 (s, 1 H); 4.42-4.35 (m, 2 H); 3.75 (s, 4 H); 3.14 (d, J = 12.33 Hz, 1 H); 2.82-2.54 (m, 7 H); 1.93 (s, 1 H); 1.81 (s, 1 H); 1.71-1.27 (m, 3 H). | Diformate |
| 42 | A | (DMSO-d6): δ 8.27-8.18 (m, 2 H); 8.09 (d, J = 9.9 Hz, 1 H); 7.88 (d, J = 8.1 Hz, 2 H); 7.52 (d, J = 8.0 Hz, 2 H); 7.32-7.18 (m, 6 H); 7.14 (d, J = 8.3 Hz, 2 H); 7.08-6.99 (m, 2 H); 6.96-6.84 (m, 3 H); 6.74 (d, J = 8.3 Hz, 2 H); 6.46 (d, J = 9.9 Hz, 1 H); 5.81 (d, J = 9.4 Hz, 1 H); 5.14 (s, 2 H); 5.07 (dd, J = 7.8, 4.6 Hz, 1 H); 4.56 (s, 1 H); 4.45-4.38 (m, 2 H); 3.77-3.69 (m, 2 H); 3.67 (s, 2 H); 3.09 (d, J = 15.6 Hz, 1 H); 2.95 (s, 3 H); 2.74-2.64 (m, 6 H); 1.97-1.34 (m, 6 H). | Formate |
| 43 | C | (DMSO-d6): δ 8.31-8.21 (m, 3 H); 8.10 (d, J = 9.9 Hz, 1 H); 7.99 (d, J = 8.1 Hz, 2 H); 7.57 (d, J = 8.0 Hz, 2 H); 7.37-7.17 (m, 8 H); 7.10-7.01 (m, 2 H); 6.99-6.85 (m, 5 H); 6.49 (d, J = 9.9 Hz, 1 H); 5.81 (d, J = 9.3 Hz, 1 H); 5.23-5.08 (m, 4 H); 4.62-4.55 (m, 1 H); 3.76 (s, 2 H); 3.53-3.42 (m, 2 H); 3.22-3.08 (m, 3 H); 2.83-2.52 (m, 7 H); 2.09-1.99 (m, 2 H); 1.96-1.74 (m, 4 H); 1.66-1.29 (m, 3 H). | Diformate |
| 44 | A | (DMSO-d6): δ 8.28-8.20 (m, 3 H); 8.09 (d, J = 9.9 Hz, 1 H); 7.98 (d, J = 8.1 Hz, 2 H); 7.57 (d, J = 8.0 Hz, 2 H); 7.35-7.15 (m, 8 H); 7.08-7.01 (m, 2 H); 6.97-6.85 (m, 5 H); 6.48 (d, J = 9.9 Hz, | Diformate |

| Cpd. | LCMS/HPLC Method | NMR data (400 MHz) | Salt |
|---|---|---|---|
| | | 1 H); 5.82 (d, J = 9.1 Hz, 1 H); 5.18 (s, 2 H); 5.11 (t, J = 6.2 Hz, 1 H); 4.62-4.54 (m, 1 H); 4.20 (d, J = 6.3 Hz, 2 H); 3.77-3.66 (m, 4 H); 3.18-3.08 (m, 1 H); 2.82-2.42 (m, 9 H); 1.96-1.75 (m, 5 H); 1.67-1.29 (m, 5 H). | |
| 45 | C | (DMSO-$d_6$): δ 10.30 (s, 1 H); 8.29-8.18 (m, 3 H); 8.13 (d, J = 9.93 Hz, 1 H); 7.97 (d, J = 8.07 Hz, 2 H); 7.72 (d, J = 8.07 Hz, 2 H); 7.60-7.48 (m, 4 H); 7.33-7.19 (m, 6 H); 7.05 (d, J = 5.55 Hz, 2 H); 6.96-6.85 (m, 3 H); 6.47 (d, J = 9.87 Hz, 1 H); 5.82 (d, J = 9.13 Hz, 1 H); 5.18 (s, 2 H); 5.07 (dd, J = 7.94, 4.33 Hz, 1 H); 4.59 (s, 1 H); 4.40 (t, J = 5.11 Hz, 2 H); 3.83 (s, 2 H); 3.38 (t, J = 5.30 Hz, 2 H); 3.13 (t, J = 10.60 Hz, 1 H); 2.78 (s, 3 H); 2.73-2.61 (m, 6 H); 1.99-1.72 (m, 2 H); 1.70-1.26 (m, 4 H). | Diformate |
| 46 | C | (DMSO-$d_6$): δ 10.27 (br s, 1 H); 8.31 (s, 1 H); 8.22 (d, J = 9.80 Hz, 1 H); 8.10 (d, J = 9.93 Hz, 1 H); 7.95 (d, J = 8.05 Hz, 2 H); 7.56 (d, J = 8.01 Hz, 2 H); 7.33-7.17 (m, 9 H); 7.08-7.00 (m, 2 H); 6.97-6.85 (m, 4 H); 6.45 (d, J = 9.86 Hz, 1 H); 5.81 (d, J = 9.39 Hz, 1 H); 5.17 (s, 2 H); 5.05 (dd, J = 8.05, 4.38 Hz, 1 H); 4.56 (s, 1 H); 4.40-4.33 (m, 2 H); 3.72 (s, 2 H); 3.4 (s, 2 H); 3.17-3.01 (m, 2 H); 2.71-2.63 (m, 6 H); 2.37-2.33 (m, 9 H); 1.94-1.69 (m, 2H); 1.64-1.24 (m, 4H). | Formate |
| 47 | C | (DMSO-$d_6$): δ 10.31 (br s, 1 H); 8.25 (d, J = 9.26 Hz, 1 H); 8.20 (s, 1 H); 8.10 (d, J = 9.93 Hz, 1 H); 7.95 (d, J = 8.05 Hz, 2 H); 7.57 (d, J = 8.00 Hz, 2 H); 7.37-7.15 (m, 10 H); 7.07-7.02 (m, 2 H); 6.96-6.86 (m, 3 H); 6.46 (d, J = 9.87 Hz, 1 H); 5.82 (d, J = 8.61 Hz, 1 H); 5.18 (s, 2 H); 5.08 (dd, J = 7.98, 4.35 Hz, 1 H); 4.59 (s, 1 H); 4.39 (t, J = 5.53 Hz, 2 H); 3.76 (s, 2 H); 3.54 (s, 2 H); 3.15 (m, 1 H); 2.80-2.61 (m, 7 H); 2.23 (s, 3 H); 1.97-1.73 (m, 2 H); 1.67-1.30 (m, 5 H). | Formate |
| 48 | C | (DMSO-$d_6$, 105° C.): δ 8.21-8.15 (m, 3 H); 7.58 (s, 1 H); 7.46 (d, J = 7.9 Hz, 2 H); 7.41-7.29 (m, 7 H); 7.29-7.20 (m, 6 H); 7.07-7.00 (m, 2 H); 6.97-6.85 (m, 3 H); 6.47 (d, J = 9.9 Hz, 1 H); 5.83 (d, J = 7.2 Hz, 1 H); 5.11 (s, 2 H); 4.98 (dd, J = 7.7, 4.9 Hz, 1 H); 4.66-4.58 (m, 3 H); 3.40-3.25 (m, 2 H); 3.08 (dd, J = 14.4, 8.3 Hz, 1 H); 2.78-2.56 (m, 9 H); 1.93-1.89 (m, 1 H); 1.81-1.70 (m, 1 H); 1.70-1.56 (m, 3 H); 1.53-1.44 (m, 1 H); 1.36-1.27 (m, 1 H). | Diformate |
| 48A | C | (DMSO-$d_6$, 105° C.): δ 8.18-8.13 (m, 3 H); 7.57 (d, J = 9.1 Hz, 1 H); 7.48-7.37 (m, 3 H); 7.37-7.19 (m, 12 H); 7.07-6.99 (m, 2 H); 6.96-6.89 (m, 2 H); 6.87 (dd, J = 8.1, 2.6 Hz, 1 H); 6.46 (d, J = 9.9 Hz, 1 H); 5.83 (d, J = 8.1 Hz, 1 H); 5.10 (s, 2 H); 4.98 (dd, J = 7.6, 4.9 Hz, 1 H); 4.65-4.59 (m, 1 H); 4.57 (s, 2 H); 3.38-3.27 (m, 2 H); 3.10 (m, 1 H); 2.77-2.50 (m, 9 H); 1.93-1.89 (m, 1 H); 1.72-1.43 (m, 5 H); 1.35-1.28 (m, 1 H). | Diformate |
| 48B | C | (DMSO-$d_6$, 105° C.): δ 8.19-8.15 (m, 3 H); 7.54 (s, 1 H); 7.36-7.18 (m, 11 H); 7.05-6.82 (m, 6 H); 6.56 (d, J = 3.4 Hz, 1 H); 6.46 (d, J = 9.9 Hz, 1 H); 5.82 (d, J = 8.1 Hz, 1 H); 5.06 (s, 2 H); 4.99 (dd, J = 7.5, 4.8 Hz, 1 H); 4.72 (s, 2 H); 4.62-4.59 (m, 1 H); 3.52-3.45 (m, 2 H); 3.08 (m, 1 H); 2.76-2.57 (m, 9 H); 1.90 (d, J = 3.8 Hz, 1 H); 1.77-1.55 (m, 4 H); 1.54-1.41 (m, 1 H); 1.38-1.26 (m, 1 H). | Diformate |
| 49 | C | (DMSO-$d_6$, 110° C.): δ 8.22-8.10 (m, 3 H); 7.50 (s, 1 H); 7.43 (d, J = 7.9 Hz, 2 H); 7.34-7.25 (m, 6 H); 7.25-7.17 (m, 2 H); 7.08-7.00 (m, 2 H); 6.95-6.85 (m, 3 H); 6.45 (d, J = 9.9 Hz, 1 H); 5.81 (d, J = 7.2 Hz, 1 H); 5.09 (s, 2 H); 5.01-4.96 (m, 1 H); 4.62-4.57 (m, 1 H); 3.55-3.30 (m, 6 H); 3.07 (dd, J = 14.4, 8.4 Hz, | Diformate |

| Cpd. | LCMS/HPLC Method | NMR data (400 MHz) | Salt |
|---|---|---|---|
| | | 1 H); 2.79-2.59 (m, 9 H); 1.93-1.86 (m, 1 H); 1.73-1.54 (m, 6 H); 1.52-1.41 (m, 1 H); 1.35-1.22 (m, 1 H); 1.12-1.05 (m, 3 H). | |
| 50 | C | (DMSO-d$_6$, 110° C.): δ 8.19 (d, J = 9.9 Hz, 1 H); 8.15 (s, 2 H); 7.55 (d, J = 9.3 Hz, 1 H); 7.46 (d, J = 7.9 Hz, 2 H); 7.35-7.28 (m, 6 H); 7.27-7.20 (m, 2 H); 7.09-7.00 (m, 2 H); 6.98-6.86 (m, 3 H); 6.48 (d, J = 9.9 Hz, 1 H); 5.84 (d, J = 7.8 Hz, 1 H); 5.11 (s, 2 H); 5.01 (dd, J = 7.5, 4.9 Hz, 1 H); 4.65-4.60 (m, 1 H); 3.84-3.78 (m, 2 H); 3.40-3.24 (m, 6 H); 3.11 (dd, J = 14.4, 8.3 Hz, 1 H); 2.83-2.53 (m, 11 H); 1.94-1.90 (m, 1 H); 1.83.1.73 (m, 1 H); 1.71-1.57 (m, 3 H); 1.57-1.46 (m, 3 H); 1.38-1.30 (m, 1 H); 1.17-1.10 (m, 1 H). | Diformate |
| 51 | C | (DMSO-d$_6$, @ 110° C.): δ 8.23-8.14 (m, 3 H); 7.53 (s, 1 H); 7.45 (d, J = 7.81 Hz, 2 H); 7.34-7.28 (m, 6 H); 7.28-7.20 (m, 2 H); 7.10-7.01 (m, 2 H); 6.98-6.85 (m, 3 H); 6.47 (d, J = 9.91 Hz, 1 H); 5.83 (d, J = 6.70 Hz, 1 H); 5.11 (s, 2 H); 5.03-4.96 (m, 1 H); 4.64-4.59 (m, 1 H); 3.38 (t, J = 7.43 Hz, 2 H); 3.29 (d, J = 7.75 Hz, 2 H); 3.09 (dd, J = 14.48, 8.28 Hz, 1 H); 2.81-2.53 (m, 9 H); 2.25-2.15 (m, 1 H); 1.91 (s, 1 H); 1.83-1.47 (m, 11 H); 1.38-1.26 (m, 1 H); 1.15 (s, 2 H). | Diformate |
| 52 | C | (DMSO-d$_6$, 85° C.): δ 8.23-8.13 (m, 3 H); 7.72 (s, 1 H); 7.47 (d, J = 7.9 Hz, 2 H); 7.39 (d, J = 7.9 Hz, 2 H); 7.33-7.18 (m, 7 H); 7.07-7.01 (m, 2 H); 6.96-6.80 (m, 6 H); 6.47 (d, J = 9.9 Hz, 1 H); 5.82 (d, J = 8.1 Hz, 1 H); 5.10 (s, 2 H); 5.00-4.94 (m, 1 H); 4.63-4.55 (m, 3 H); 3.76 (s, 3 H); 3.38-3.28 (m, 2 H); 3.08 (m, 1 H); 2.74-2.47 (m, 9 H); 1.90 (s, 1 H); 1.73-1.54 (m, 4 H); 1.52-1.43 (m, 1 H); 1.31 (t, J = 10.8 Hz, 1 H). | Diformate |
| 53 | C | (DMSO-d$_6$, @ 105° C.): δ 8.18 (m, 3 H); 7.58 (s, 1 H); 7.49-7.36 (m, 4 H); 7.33-7.26 (m, 3 H); 7.25-7.19 (m, 3 H); 7.11-7.01 (m, 5 H); 6.97-6.85 (m, 4 H); 6.46 (d, J = 4.49 Hz, 1 H); 5.83 (d, J = 7.90 Hz, 1 H); 5.11 (s, 2 H); 4.99 (dd, J = 7.57, 4.84 Hz, 1 H); 4.65-4.59 (m, 1 H); 4.55 (s, 2 H); 3.37-3.29 (m, 2 H); 3.10 (dd, J = 14.45, 8.31 Hz, 1 H); 2.80-2.52 (m, 9 H); 2.31 (s, 3 H); 1.94-1.90 (m, 1 H); 1.75-1.54 (m, 4 H); 1.54-1.44 (m, 1 H); 1.37-1.26 (m, 1 H). | Diformate |
| 54 | C | (DMSO-d$_6$, 110° C.): δ 8.18-8.16 (m, 3 H); 7.55 (m, 1 H); 7.47-7.21 (m, 14 H); 7.06-7.02 (m, 2 H); 6.96-6.88 (m, 3 H); 6.48 (d, J = 9.6 Hz, 1 H); 5.84 (d, J = 8.0 Hz, 1 H); 5.11 (s, 2 H); 4.99-4.96 (m, 1 H); 4.63-4.60 (m, 3 H); 3.35-3.32 (m, 2 H); 3.10-3.06 (m, 1 H); 2.75-2.53 (m, 9 H); 1.92-1.90 (m, 1 H); 1.80-1.60 (m, 4 H); 1.50-1.48 (m, 1 H); 1.40-1.30 (m, 1 H). | Diformate |
| 55 | C | (DMSO 110° C.): δ 8.19 (s, 2 H); 8.14 (d, J = 9.8 Hz, 1 H); 7.59-7.54 (m, 5 H); 7.44 (d, J = 8.1 Hz, 3 H); 7.38-7.33 (m, 2 H); 7.31-7.25 (m, 4 H); 7.24-7.17 (m, 2 H); 7.05-6.98 (m, 2 H); 6.94-6.83 (m, 3 H); 6.44 (d, J = 9.9 Hz, 1 H); 5.81 (s, 1 H); 5.09 (s, 2 H); 4.96-4.91 (m, 1 H); 4.68 (s, 2 H); 4.61-4.56 (m, 1 H); 3.38-3.29 (m, 2 H); 3.05 (dd, J = 14.4, 8.3 Hz, 1 H); 2.73-2.57 (m, 8 H); 1.88 (s, 1 H); 1.73 (s, 1 H); 1.68-1.53 (m, 3 H); 1.50-1.42 (m, 1 H); 1.33-1.24 (m, 1 H). | Diformate |
| 56 | C | (DMSO-d$_6$, @ 110° C.): δ 8.19-8.14 (m, 3 H); 7.53 (s, 1 H); 7.49-7.35 (m, 4 H); 7.33-7.26 (m, 4 H); 7.25-7.14 (m, 6 H); 7.06-7.01 (m, 2 H); 6.96-6.85 (m, 3 H); 6.46 (d, J = 9.90 Hz, 1 H); 5.83 (d, J = 5.94 Hz, 1 H); 5.10 (s, 2 H); 4.96 (dd, J = 7.55, 4.90 Hz, 1 H); 4.65-4.57 (m, 3 H); 3.34-3.27 (m, 2 H); 3.08 (dd, J = 14.46, 8.33 Hz, 1 H); 2.78-2.52 (m, 8 H); 2.21 (s, 3 H); 1.93-1.89 (m, 1 H); 1.76-1.54 (m, 4 H); 1.52-1.46 (m, 1 H); 1.36-1.28 (m, 1 H). | Formate |

-continued

| Cpd. | LCMS/HPLC Method | NMR data (400 MHz) | Salt |
|---|---|---|---|
| 57 | C | (DMSO-d$_6$, @ 110° C.): δ 8.17-8.13 (m, 3 H); 7.71 (t, J = 7.16 Hz, 2 H); 7.56-7.39 (m, 7 H); 7.33-7.27 (m, 4 H); 7.26-7.19 (m, 2 H); 7.07-7.00 (m, 2 H); 6.96-6.85 (m, 3 H); 6.45 (d, J = 9.90 Hz, 1 H); 5.85-5.80 (m, 1 H); 5.10 (s, 2 H); 4.97 (dd, J = 7.63, 4.82 Hz, 1 H); 4.81 (s, 2 H); 4.65-4.60 (m, 1 H); 3.38 (t, J = 7.38 Hz, 2 H); 3.11 (dd, J = 14.40, 8.29 Hz, 1 H); 2.79-2.53 (m, 9 H); 1.94-1.90 (m, 1 H); 1.78-1.56 (m, 4 H); 1.55-1.46 (m, 1 H); 1.38-1.27 (m, 1 H). | Diformate |
| 58 | C | (DMSO-d$_6$, 110° C.): δ 8.17-8.08 (m, 3 H); 7.49 (d, J = 9.5 Hz, 1 H); 7.42-7.08 (m, 12 H); 7.04-6.95 (m, 2 H); 6.93-6.81 (m, 5 H); 6.42 (d, J = 10.0 Hz, 1 H); 5.78 (d, J = 7.6 Hz, 1 H); 5.14-4.99 (m, 2 H); 4.98-4.92 (m, 1 H); 4.59-4.54 (m, 1 H); 4.46 (s, 2 H); 3.78-3.63 (m, 3 H); 3.30-3.20 (m, 2 H); 3.05 (dd, J = 14.4, 8.3 Hz, 1 H); 2.74-2.53 (m, 9 H); 1.89-1.85 (m, 1 H); 1.71 (s, 1 H); 1.65-1.51 (m, 3 H); 1.49-1.40 (m, 1 H); 1.32-1.21 (m, 1 H). | Diformate |
| 59 | C | (DMSO-d$_6$, 110° C.): δ 8.17-8.05 (m, 3 H); 7.48 (s, 1 H); 7.41 (d, J = 8.0 Hz, 2 H); 7.37-7.22 (m, 9 H); 7.18 (t, J = 7.5 Hz, 3 H); 7.04-6.96 (m, 2 H); 6.91-6.80 (m, 3 H); 6.42 (d, J = 9.9 Hz, 1 H); 5.78 (d, J = 7.7 Hz, 1 H); 5.06 (s, 2 H); 4.97-4.90 (m, 1 H); 4.67-4.49 (m, 3 H); 3.32-3.25 (m, 2 H); 3.06 (dd, J = 14.4, 8.3 Hz, 1 H); 2.74-2.55 (m, 9 H); 1.87 (s, 1 H); 1.72 (s, 1 H); 1.65-1.52 (m, 3 H); 1.49-1.43 (m, 1 H); 1.28 (m, 1 H). | Diformate |
| 60 | C | (DMSO-d$_6$, 110° C.): δ 8.14-8.09 (m, 3 H); 7.49 (d, J = 9.2 Hz, 1 H); 7.42-7.29 (m, 4 H); 7.29-7.12 (m, 8 H); 7.04-6.95 (m, 2 H); 6.97-6.81 (m, 5 H); 6.42 (dd, J = 9.9, 4.2 Hz, 1 H); 5.78 (d, J = 7.6 Hz, 1 H); 5.05 (s, 2 H); 4.94 (dd, J = 7.5, 4.9 Hz, 1 H); 4.60-4.54 (m, 1 H); 4.51 (s, 2 H); 3.72 (s, 3 H); 3.33-3.25 (m, 2 H); 3.04 (dd, J = 14.4, 8.2 Hz, 1 H); 2.75-2.48 (m, 9 H); 1.88-1.84 (m, 1 H); 1.76-1.67 (m, 1 H); 1.65-1.50 (m, 3 H); 1.49-1.39 (m, 1 H); 1.32-1.20 (m, 1 H). | Diformate |
| 61 | C | (DMSO-d$_6$, 110° C.): δ 8.21-8.10 (m, 3 H); 7.55 (s, 1 H); 7.48-7.36 (m, 7 H); 7.34-7.19 (m, 7 H); 7.08-6.98 (m, 2 H); 6.96-6.86 (m, 3 H); 6.45 (dd, J = 9.9, 6.4 Hz, 1 H); 5.83 (d, J = 7.7 Hz, 1 H); 5.11 (s, 2 H); 4.98 (dd, J = 7.6, 4.8 Hz, 1 H); 4.70 (s, 2 H); 4.67-4.61 (m, 1 H); 3.39-3.32 (m, 2 H); 3.11 (dd, J = 14.4, 8.3 Hz, 1 H); 2.80-2.52 (m, 9 H); 1.95-1.90 (m, 1 H); 1.84-1.74 (m, 1 H); 1.71-1.56 (m, 3 H); 1.55-1.45 (m, 1 H); 1.38-1.27 (m, 1 H). | Diformate |
| 62 | C | (DMSO-d$_6$, 110° C.): δ 8.16-8.11 (m, 3 H); 7.51 (s, 1 H); 7.44-7.23 (m, 10 H); 7.24-7.08 (m, 4 H); 7.05-6.98 (m, 2 H); 6.94-6.83 (m, 3 H); 6.46-6.42 (m, 1 H); 5.81 (d, J = 7.7 Hz, 1 H); 5.28-4.85 (m, 2 H); 4.96 (dd, J = 7.7, 5.0 Hz, 1 H); 4.64-4.57 (m, 3 H); 3.37-3.28 (m, 2 H); 3.08 (dd, J = 14.4, 8.3 Hz, 1 H); 2.74-2.58 (m, 8 H); 1.92-1.88 (m, 1 H); 1.80-1.61 (m, 1 H); 1.69-1.55 (m, 4 H); 1.52-1.42 (m, 1 H); 1.35-1.25 (m, 1 H). | Diformate |
| 63 | C | (DMSO-d$_6$, 110° C.): δ 8.17-8.11 (m, 3 H); 7.51 (d, J = 9.7 Hz, 1 H); 7.44 (d, J = 7.9 Hz, 2 H); 7.38-7.31 (m, 2 H); 7.30-7.25 (m, 6 H); 7.24-7.18 (m, 2 H); 7.13-7.05 (m, 2 H); 7.05-6.98 (m, 2 H); 6.93-6.82 (m, 3 H); 6.44 (d, J = 9.9 Hz, 1 H); 5.81 (d, J = 7.5 Hz, 1 H); 5.08 (s, 2 H); 4.97-4.93 (m, 1 H); 4.61-4.56 (m, 1 H); 4.55 (s, 2 H); 3.33-3.26 (m, 2 H); 3.11-3.02 (m, 1 H); 2.79-2.55 (m, 9 H); 1.91-1.87 (m, 1 H); 1.81-1.69 (m, 1 H); 1.65-1.56 (m, 3 H); 1.48 (dd, J = 10.1, 5.7 Hz, 1 H); 1.30 (s, 1 H). | Diformate |
| 64 | C | (DMSO-d$_6$, 110° C.): δ 8.19-8.12 (m, 3 H); 7.52 (s, 1 H); 7.48-7.27 (m, 12 H); 7.27-7.19 (m, 2 H); 7.07-7.01 (m, 2 H); 6.97-6.87 (m, 3 | Diformate |

| Cpd. | LCMS/HPLC Method | NMR data (400 MHz) | Salt |
|---|---|---|---|
| | | H); 6.46 (d, J = 9.9 Hz, 1 H); 5.83 (d, J = 6.4 Hz, 1 H); 5.11 (s, 2 H); 5.00-4.94 (m, 1 H); 4.70 (s, 2 H); 4.65-4.59 (m, 1 H); 3.40-3.30 (m, 2 H); 3.09 (dd, J = 14.3, 8.2 Hz, 1 H); 2.77-2.58 (m, 9 H); 1.94-1.86 (m, 1 H); 1.83-1.71 (m, 1 H); 1.70-1.58 (m, 3 H); 1.51-1.47 (m, 1 H); 1.38-1.22 (m, 1 H). | |
| 65 | C | (DMSO-$d_6$, 110° C.): δ 8.19-8.13 (m, 3 H); 7.53 (s, 1 H); 7.50-7.43 (m, 2 H); 7.40-7.19 (m, 12 H); 7.08-7.02 (m, 2 H); 6.96-6.85 (m, 3 H); 6.47 (d, J = 9.9 Hz, 1 H); 5.83 (d, J = 7.9 Hz, 2 H); 5.11 (s, 2 H); 4.99 (dd, J = 7.7, 4.9 Hz, 1 H); 4.68-4.55 (m, 3 H); 3.36-3.29 (m, 2 H); 3.11 (dd, J = 14.4, 8.2 Hz, 1 H); 2.79-2.59 (m, 8 H); 1.94-1.90 (m, 1 H); 1.84-1.71 (m, 1 H); 1.69-1.59 (m, 3 H); 1.52-1.47 (m, 1 H); 1.36-1.29 (m, 1 H). | Diformate |
| 66 | C | (DMSO-$d_6$, 110° C.): δ 8.17 (d, J = 9.9 Hz, 1 H); 7.83 (d, J = 8.5 Hz, 1 H); 7.70 (d, J = 8.0 Hz, 2 H); 7.51-7.40 (m, 6 H); 7.33-7.20 (m, 6 H); 7.14 (d, J = 8.2 Hz, 1 H); 7.06-6.94 (m, 3 H); 6.92 (dd, J = 8.2, 2.5 Hz, 1 H); 6.55 (d, J = 9.9 Hz, 1 H); 5.84 (d, J = 8.6 Hz, 1 H); 5.33 (dd, J = 7.7, 5.3 Hz, 1 H); 5.11 (s, 2 H); 4.95-4.90 (m, 1 H); 4.69 (s, 2 H); 3.66 (ddd, J = 13.9, 8.5, 2.5 Hz, 1 H); 3.49-3.41 (m, 2 H); 3.33-2.98 (m, 9 H); 2.25 (d, J = 4.3 Hz, 1 H); 2.06-1.74 (m, 6 H). | Ditrifluoro-acetate |
| 67 | C | (DMSO-$d_6$, 110° C.): δ 8.17 (d, J = 9.9 Hz, 1 H); 7.82 (d, J = 8.9 Hz, 1 H); 7.48 (d, J = 8.0 Hz, 2 H); 7.43 (d, J = 8.0 Hz, 2 H); 7.32 (d, J = 4.3 Hz, 4 H); 7.30-7.22 (m, 2 H); 7.20-7.10 (m, 5 H); 7.03-6.88 (m, 4 H); 6.56 (d, J = 9.9 Hz, 1 H); 5.84 (d, J = 8.6 Hz, 1 H); 5.33-5.30 (m, 1 H); 5.11 (s, 2 H); 4.95-4.90 (m, 1 H); 4.54 (s, 2 H); 3.66 (ddd, J = 14.0, 8.5, 2.7 Hz, 2 H); 3.46-2.98 (m, 11 H); 2.30 (s, 3 H); 2.25 (m, 1 H); 2.05-1.75 (m, 7 H) | Ditrifluoro-acetate |
| 68 | C | (DMSO-$d_6$, 110° C.): δ 8.19-8.14 (m, 3 H); 7.53 (s, 1 H); 7.45 (d, J = 7.89 Hz, 2 H); 7.38 (t, J = 7.29 Hz, 2 H); 7.33-7.26 (m, 4 H); 7.25-7.18 (m, 2 H); 7.06 (dd, J = 16.23, 8.13 Hz, 3 H); 6.97-6.85 (m, 3 H); 6.57-6.45 (m, 3 H); 5.83 (d, J = 7.27 Hz, 1 H); 5.11 (s, 2 H); 4.99 (dd, J = 7.52, 4.95 Hz, 1 H); 4.64-4.58 (m, 1 H); 4.47 (s, 2 H); 3.82-3.73 (m, 3 H); 3.79-3.71 (m, 3 H); 3.33-3.27 (m, 2 H); 3.09 (dd, J = 14.47, 8.28 Hz, 1 H); 2.78-2.52 (m, 9 H); 1.93-1.89 (m, 1 H); 1.79-1.70 (m, 1 H); 1.68-1.55 (m, 3 H); 1.53-1.44 (m, 1 H); 1.35-1.26 (m, 1 H). | Diformate |
| 69 | C | (DMSO-$d_6$, 110° C.): δ 8.25-8.12 (m, 3 H); 7.53 (s, 1 H); 7.46 (d, J = 7.9 Hz, 2 H); 7.32 (d, J = 5.8 Hz, 6 H); 7.28-7.20 (m, 2 H); 7.09 (d, J = 8.1 Hz, 1 H); 7.04 (s, 1 H); 6.98-6.86 (m, 3 H); 6.48 (d, J = 9.9 Hz, 1 H); 5.84 (d, J = 7.8 Hz, 1 H); 5.11 (s, 2 H); 5.06-4.99 (m, 1 H); 4.65-4.60 (m, 1 H); 4.05 (d, J = 8.6 Hz, 1 H); 3.32-3.21 (, 2 H); 3.10 (dd, J = 14.4, 8.4 Hz, 1 H); 2.82-2.53 (m, 9 H); 1.91 (s, 1 H); 1.78-1.56 (m, 11 H); 1.49-1.43 (m, 2 H); 1.32 (m, 1 H). | Diformate |
| 70 | C | (DMSO-$d_6$, 110° C.): δ 8.22-8.14 (m, 3 H); 7.53 (s, 1 H); 7.45 (d, J = 7.8 Hz, 2 H); 7.33-7.28 (m, 6 H); 7.26-7.19 (m, 2 H); 7.09-7.03 (m, 2 H); 6.97-6.86 (m, 3 H); 6.47 (d, J = 9.9 Hz, 1 H); 5.84 (d, J = 7.2 Hz, 1 H); 5.11 (s, 2 H); 5.02-4.97 (m, 1 H); 4.64-4.59 (m, 1 H); 3.40-3.31 (m, 2 H); 3.25-3.18 (m, 2 H); 3.09 (dd, J = 14.5, 8.3 Hz, 1 H); 2.81-2.54 (m, 8 H); 1.91 (d, J = 4.0 Hz, 1 H); 1.72-1.41 (m, 11 H); 1.34-1.12 (m, 5 H); 0.86 (m, 2 H). | Diformate |
| 71 | C | (DMSO-$d_6$, 110° C.): δ 8.20-8.07 (m, 3 H); 7.51-7.38 (m, 3 H); 7.30-7.15 (m, 8 H); 7.07-6.96 (m, 2 H); 6.93-6.81 (m, 3 H); 6.43 (d, J = 9.9 Hz, 1 H); 5.79 (d, J = 7.9 Hz, 1 H); | Diformate |

-continued

| Cpd. | LCMS/HPLC Method | NMR data (400 MHz) | Salt |
|---|---|---|---|
| | | 5.14-5.01 (m, 2 H); 5.01-4.94 (m, 1 H); 4.60-4.55 (m, 1 H); 3.46-3.32 (m, 2 H); 3.16 (d, J = 6.9 Hz, 2 H); 3.05 (dd, J = 14.5, 8.4 Hz, 1 H); 2.79-2.49 (m, 9 H); 1.87 (s, 1 H); 1.73-1.52 (m, 4 H); 1.45 (m, 1 H); 1.35-1.20 (m, 1 H); 0.97-0.82 (m, 1 H); 0.46-0.39 (m, 2 H); 0.09 (d, J = 5.1 Hz, 2 H). | |
| 72 | C | (DMSO-d$_6$, 110° C.): δ 8.19-8.12 (m, 3 H); 7.52 (s, 1 H); 7.48-7.39 (m, 2 H); 7.32-7.26 (m, 6 H); 7.24-7.17 (m, 2 H); 7.08-6.98 (m, 2 H); 6.95-6.83 (m, 3 H); 6.45 (d, J = 9.9 Hz, 1 H); 5.81 (d, J = 7.5 Hz, 1 H); 5.26-4.93 (m, 2 H); 5.04-4.95 (m, 1 H); 4.60 (ddd, J = 8.3, 3.9, 3.7 Hz, 1 H); 3.38-3.30 (m, 2 H); 3.15 (t, J = 7.4 Hz, 2 H); 3.08 (dd, J = 14.5, 8.3 Hz, 1 H); 2.77-2.57 (m, 8 H); 1.94-1.87 (m, 2 H); 1.81-1.69 (m, 1 H); 1.69-1.54 (m, 4 H); 1.52-1.43 (m, 1 H); 1.35-1.25 (m, 1 H); 0.87-0.76 (m, 6 H). | Diformate |
| 73 | C | (DMSO-d$_6$, 110° C.): δ 8.21-8.13 (m, 2 H); 7.55 (d, J = 9.0 Hz, 1 H); 7.38-7.28 (m, 8 H); 7.28-7.20 (m, 2 H); 7.09 (d, J = 8.1 Hz, 1 H); 6.99-6.89 (m, 3 H); 6.85-6.80 (m, 1 H); 6.46 (d, J = 9.9 Hz, 1 H); 5.83 (d, J = 8.5 Hz, 1 H); 5.08 (dd, J = 7.6, 4.7 Hz, 1 H); 4.67-4.61 (m, 1 H); 4.05 (d, J = 13.2 Hz, 3 H); 3.91-3.85 (m, 2 H); 3.82 (s, 2 H); 3.12 (dd, J = 14.4, 8.3 Hz, 1 H); 3.01-2.92 (m, 2 H); 2.91-2.52 (m, 5 H); 2.09-2.01 (m, 1 H); 1.95-1.91 (m, 1 H); 1.83-1.75 (m, 3 H); 1.69-1.59 (m, 1 H); 1.56-1.46 (m, 1 H); 1.38-1.24 (m, 4 H). | Diformate |
| 74 | C | (DMSO-d$_6$, 110° C.): δ 8.19-8.13 (m, 2 H); 7.56 (d, J = 8.9 Hz, 1 H); 7.36-7.28 (m, 6 H); 7.27-7.19 (m, 2 H); 7.08 (d, J = 8.2 Hz, 1 H); 6.99-6.87 (m, 4 H); 6.83 (dd, J = 8.3, 2.5 Hz, 1 H); 6.47 (d, J = 9.9 Hz, 1 H); 5.85-5.81 (m, 1 H); 5.06 (dd, J = 7.5, 4.9 Hz, 1 H); 4.67-4.61 (m, 1 H); 4.11-4.00 (m, 2 H); 3.91-3.83 (m, 2 H); 3.80 (s, 3 H); 3.78 (s, 2 H); 3.12 (dd, J = 14.4, 8.3 Hz, 1 H); 3.03-2.91 (m, 2 H); 2.88-2.62 (m, 5 H); 2.64-2.44 (m, 2 H); 2.09-2.00 (m, 1 H); 1.95-1.91 (m, 1 H); 1.86-1.76 (m, 3 H); 1.69-1.58 (m, 1 H); 1.56-1.46 (m, 1 H); 1.38-1.25 (m, 3 H). | Formate |
| 75 | C | (DMSO-d$_6$, 110° C.): δ 8.19 (d, J = 9.9 Hz, 1 H); 7.83 (d, J = 8.7 Hz, 1 H); 7.38-7.29 (m, 7 H); 7.30-7.22 (m, 3 H); 7.16 (d, J = 8.2 Hz, 1 H); 7.02 (d, J = 8.1 Hz, 1 H); 6.96-6.89 (m, 2 H); 6.84 (dd, J = 8.2, 2.5 Hz, 1 H); 6.57 (d, J = 9.9 Hz, 1 H); 5.84 (d, J = 8.7 Hz, 1 H); 5.37 (dd, J = 7.9, 5.0 Hz, 1 H); 4.96-4.91 (m, 1 H); 4.05 (d, J = 12.3 Hz, 2 H); 3.88 (d, J = 6.2 Hz, 2 H); 3.66 (ddd, J = 13.9, 8.4, 2.6 Hz, 1 H); 3.36-2.90 (m, 11 H); 2.28-2.24 (m, 1 H); 2.08-1.77 (m, 8 H); 1.37-1.27 (m, 3 H). | Formate |
| 76 | C | (DMSO-d$_6$, 110° C.): δ 8.25-8.12 (m, 3 H); 7.62-7.41 (m, 1 H); 7.56-7.25 (m, 4 H); 7.34-7.28 (m, 4 H); 7.26-7.19 (m, 2 H); 7.08 (d, J = 8.1 Hz, 1 H); 6.99-6.87 (m, 3 H); 6.87-6.79 (m, 1 H); 6.48 (d, J = 9.9 Hz, 1 H); 5.86-5.79 (m, 1 H); 5.05-4.99 (m, 1 H); 4.65-4.60 (m, 1 H); 4.11-4.01 (m, 2 H); 3.89 (d, J = 6.2, 2 H); 3.10 (dd, J = 14.4, 8.5 Hz, 1 H); 3.06-2.89 (m, 4 H); 2.84-2.46 (m, 12 H); 2.11-2.02 (m, 1 H); 1.94-1.90 (m, 1 H); 1.83-1.55 (m, 6 H); 1.54-1.45 (m, 1 H); 1.36-1.25 (m, 3 H). | Diformate |
| 77 | C | (DMSO-d$_6$): δ 8.72 (t, J = 5.6 Hz, 1 H); 8.32 (s, 3 H); 8.26 (d, J = 9.3 Hz, 1 H); 8.19 (d, J = 9.9 Hz, 1 H); 7.90 (d, J = 8.0 Hz, 2 H); 7.46 (d, J = 8.0 Hz, 2 H); 7.35-7.27 (m, 3 H); 7.25-7.18 (m, 2 H); 7.10 (d, J = 8.2 Hz, 1 H); 6.99-6.88 (m, 3 H); 6.83-6.77 (m, 1 H); 6.52 (d, J = 9.9 Hz, 1 H); 5.81 (d, J = 8.9 Hz, 1 H); 5.20 (dd, J = 8.2, 4.4 Hz, 1 H); 4.68-4.43 (m, 2 H); 3.83 (d, J = 6.3 Hz, 2 H); 3.60-3.46 (m, 1 H); 3.37-3.30 (m, 2 H); 3.19-3.05 (m, 2 H); | Formate |

| Cpd. | LCMS/HPLC Method | NMR data (400 MHz) | Salt |
|---|---|---|---|
| | | 2.88-2.52 (m, 9 H); 2.13-1.93 (m, 1 H); 2.03-1.55 (m, 7 H); 1.62-1.35 (m, 2 H); 1.49-1.12 (m, 4 H). | |
| 78 | C | (DMSO-d$_6$, 110° C.): δ 8.10 (d, J = 9.9 Hz, 1 H); 7.83 (d, J = 8.6 Hz, 1 H); 7.45 (d, J = 8.2 Hz, 2 H); 7.35-7.22 (m, 6 H); 7.12 (d, J = 8.2 Hz, 1 H); 7.03-6.96 (m, 5 H); 6.88 (d, J = 8.3 Hz, 1 H); 6.53 (d, J = 9.9 Hz, 1 H); 5.85 (d, J = 8.6 Hz, 1 H); 5.39-5.32 (m, 1 H); 4.94 (d, J = 7.6 Hz, 1 H); 4.38-4.27 (m, 4 H); 4.20 (s, 2 H); 3.70-3.61 (m, 1 H); 3.30-3.07 (m, 7 H); 2.25 (s, 1 H); 2.03 (s, 1 H); 1.97-1.90 (m, 1 H); 1.86 (s, 1 H); 1.76 (s, 1 H). | Trifluoro-acetate |
| 79 | C | (DMSO-d$_6$): δ 10.51 (s, 2 H); 9.69 (br s, 1 H); 9.10 (br s, 2 H); 8.45 (d, J = 9.2 Hz, 1 H); 8.07 (d, J = 9.9 Hz, 1 H); 7.40-7.23 (m, 6 H); 7.19 (s, 1 H); 7.12 (t, J = 7.1 Hz, 2 H); 7.04-6.95 (m, 4 H); 6.88 (d, J = 8.3 Hz, 1 H); 6.56 (dd, J = 9.7, 1.8 Hz, 2 H); 6.20 (br s, 1 H); 5.84 (d, J = 9.1 Hz, 1 H); 5.34 (d, J = 9.5 Hz, 1 H); 4.89-4.84 (m, 1 H); 4.30 (s, 4 H); 4.21 (s, 2 H); 3.66 (t, J = 11.1 Hz, 1 H); 3.32-3.04 (m, 5 H); 3.10-3.00 (m, 2 H); 2.23 (s, 1 H); 2.06 (br s, 1 H); 1.88-1.70 (m, 3 H). | Trifluoro-acetate |
| 80 | C | (DMSO-d$_6$): δ 10.02 (s, 1 H); 8.25 (d, J = 9.3 Hz, 1 H); 8.11 (d, J = 9.9 Hz, 1 H); 7.61 (s, 1 H); 7.49 (d, J = 8.2 Hz, 1 H); 7.35-7.17 (m, 7 H); 7.08-7.01 (m, 3 H); 6.99-6.81 (m, 3 H); 6.46 (d, J = 9.9 Hz, 1 H); 5.83 (d, J = 8.3 Hz, 1 H); 5.06 (dd, J = 8.0, 4.2 Hz, 1 H); 4.66 (s, 2 H); 4.56 (s, 1 H); 3.73 (s, 2 H); 3.07 (t, J = 10.6 Hz, 1 H); 2.73-2.59 (m, 6 H); 1.89 (s, 1 H); 1.78 (s, 1 H); 1.57 (s, 1 H); 1.45 (s, 2 H); 1.31 (s, 1 H). | None |

Biological Characterization

Example 10

M3 Receptor Radioligand Binding Assay

Human M3 receptor membranes (15 ug/well) from Perkin Elmer were incubated with 0.52 nM Scopolamine Methyl Chloride, [N-methyl-3H] with or without test compounds, or a saturating concentration of Atropine (5 μM) for the determination of non-specific binding. The assay was carried out in 96-well polypropylene plates in a volume of 250 ul. The assay buffer used was 50 mM Tris-HCl, 154 mM NaCl (pH 7.4). The final assay concentration of DMSO was 0.5% (v/v). The plates were sealed and incubated for 2 hours at RT on an orbital shaker (slow speed). Membranes were harvested onto 96-well unifilter GF/C filter plates pre-treated with 0.5% polyethyleneimine (v/v), using a filter manifold, washed four times with 200 ul of assay buffer. The plates were dried before addition of 50 μl of microscint-0, sealed then read in a Trilux Microbeta scintillation counter. IC50 values are determined from competition curves using a non-linear curve fitting program. Ki values were calculated from IC50 values by the Cheng and Prusoff equation.

The Ki values of the most of the compounds of the examples are less than 10 nM.

Example 11

β2 Adrenoceptor Radioligand Binding Assay

Human β$_2$ adrenoceptor membranes (7.5 ug/well) from Perkin Elmer were incubated with 0.3 nM 125-I Cyanopin-dolol with or without test compounds, or a saturating concentration of s-propranolol (2 μM) for the determination of non-specific binding. The assay was carried out in 96-well polypropylene plates in a volume of 200 ul. The assay buffer used was 25 mM HEPES, 0.5% BSA (w/v), 1 mM EDTA, 0.02% ascorbic acid (v/v), (pH 7.4). The final assay concentration of DMSO was 0.5% (v/v). The plates were sealed and incubated for 1 h at RT on an orbital shaker (slow speed). Membranes were harvested onto 96-well unifilter GF/C filter plates pre-treated with 0.5% polyethyleneimine (v/v), using a filter manifold, washed six times with 200 ul of wash buffer containing 10 mM HEPES and 500 mM NaCl. The plates were dried before addition of 50 μl of microscint-0, sealed then read in a Trilux Microbeta scintillation counter. IC50 values are determined from competition curves using a non-linear curve fitting program. Ki values were calculated from IC50 values by the Cheng and Prusoff equation.

The Ki values of the most of the compounds of the examples are less than 10 nM.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A compound represented by formula (I):

(I)

wherein
Q is Q1 or Q2,

Q1

Q2

Z is H or OH;
Y is Y' or Y1 which are divalent groups of formula $$\{-A_1-B-(CH_2)_{n'}-A_2-C-D-(CH_2)_m-E-\}$$ Y' or $$\{-A_1-C-B-C'-D-(CH_2)_p-E-\}$$ Y1 wherein
- A1 and A2 are independently absent or are ($C_1$-$C_6$) alkylene, ($C_3$-$C_8$)cycloalkylene, or ($C_3$-$C_8$)heterocycloalkylene optionally substituted by one or more substituents selected from the group consisting of ($C_1$-$C_6$)alkyl, aryl($C_1$-$C_6$)alkyl, and heteroaryl($C_1$-$C_6$)alkyl;
- B is absent or is ($C_3$-$C_8$)cycloalkylene, ($C_3$-$C_8$) heterocycloalkylene, arylene, or heteroarylene, optionally substituted by one or more groups selected from the group consisting of halogen, nitrile, linear or branched ($C_1$-$C_6$)alkyl, linear or branched ($C_1$-$C_6$)haloalkyl, ($C_1$-$C_6$)alkoxy, aryl, aryl($C_1$-$C_6$)alkyl,
- —$NR_7(R_8)$ and heteroaryl;
- C and C' are absent, or are independently —O—, —CO—, —OC(O)—, —C(OO)—, or one of the following groups C1-C14

C1

C2

C3

C4

C5

C6

C7

C8

C9

C10

C11

C12

-continued

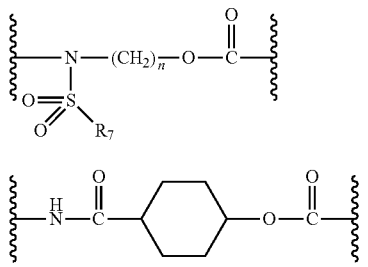
C13

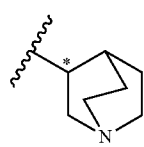
C14 wherein $R_7$, $R_{7'}$ and $R_8$ are independently H or linear or branched $(C_1\text{-}C_6)$alkyl, $(C_3\text{-}C_8)$cycloalkyl, $(C_3\text{-}C_8)$cycloalkyl$(C_1\text{-}C_6)$alkyl, $(C_3\text{-}C_8)$heterocycloalkyl$(C_1\text{-}C_6)$alkyl, aryl, or aryl$(C_1\text{-}C_6)$alkyl, optionally substituted by one or more substituents selected from the group consisting of $(C_1\text{-}C_6)$alkyl, halo$(C_1\text{-}C_6)$alkyl, halogen atom, $(C_1\text{-}C_6)$alkoxy, and halo$(C_1\text{-}C_6)$alkoxy;

D is absent or is $(C_1\text{-}C_6)$alkylene, arylene, heteroarylene, and $(C_3\text{-}C_8)$heterocycloalkylene, optionally substituted by one or more $(C_1\text{-}C_6)$ alkyl groups;

n, n', m and p are independently 0 or an integer from 1 to 3;

E is absent or is —O— or —OC(O)—;

G is arylene optionally substituted by one or more substituents selected from the group consisting of halogen atom, —OH, oxo (=O), —SH, —NO$_2$, —CN, and —NH$_2$;

$R_1$ is H;

$R_2$ is H or $(C_1\text{-}C_6)$alkyl or aryl, optionally substituted by one or more halogen atoms;

M is —N($R_3$)—;

$R_3$ is H or $(C_1\text{-}C_6)$alkyl;

$R_4$ is a group of formula J1

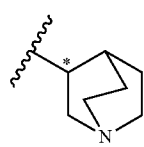
J1 or a pharmaceutically acceptable salt thereof.

2. A compound or pharmaceutically acceptable salt according to claim 1, wherein Q is Q1

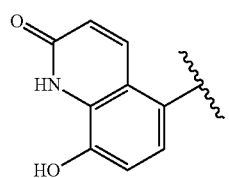
Q1

Z is H or OH;

Y is Y1 which is a divalent group of formula

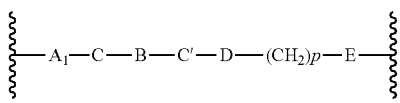
Y1 wherein A1 is absent or is $(C_1\text{-}C_6)$alkylene, $(C_3\text{-}C_8)$cycloalkylene, or $(C_3\text{-}C_8)$heterocycloalkylene, optionally substituted by one or more substituents selected from the group consisting of $(C_1\text{-}C_6)$alkyl, aryl$(C_1\text{-}C_6)$alkyl, and heteroaryl$(C_1\text{-}C_6)$alkyl;

B is absent or is $(C_3\text{-}C_8)$cycloalkylene, $(C_3\text{-}C_8)$heterocycloalkylene, arylene, and heteroarylene, optionally substituted by one or more groups selected from the group consisting of halogen, nitrile, linear or branched $(C_1\text{-}C_6)$alkyl, linear or branched $(C_1\text{-}C_6)$ haloalkyl, $(C_1\text{-}C_6)$alkoxy, aryl, and heteroaryl;

C and C' are absent or are independently —O—, —CO—, —OC(O)—, —C(OO)—, or is one of the following groups C1-C14

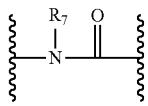
C1

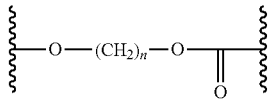
C2

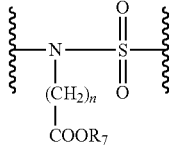
C3

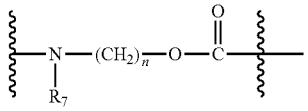
C4

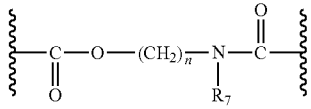
C5

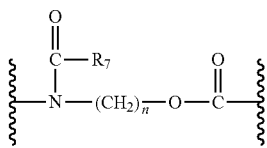
C6

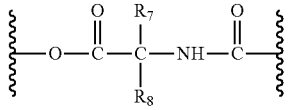
C7

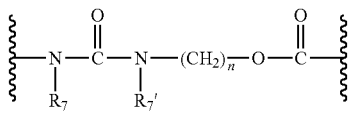
C8

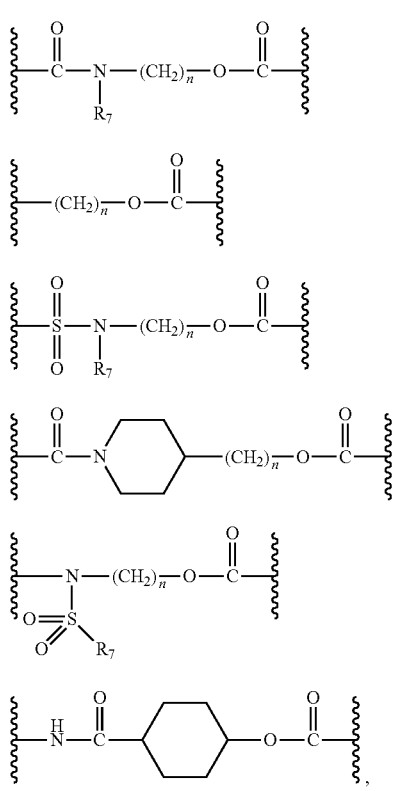

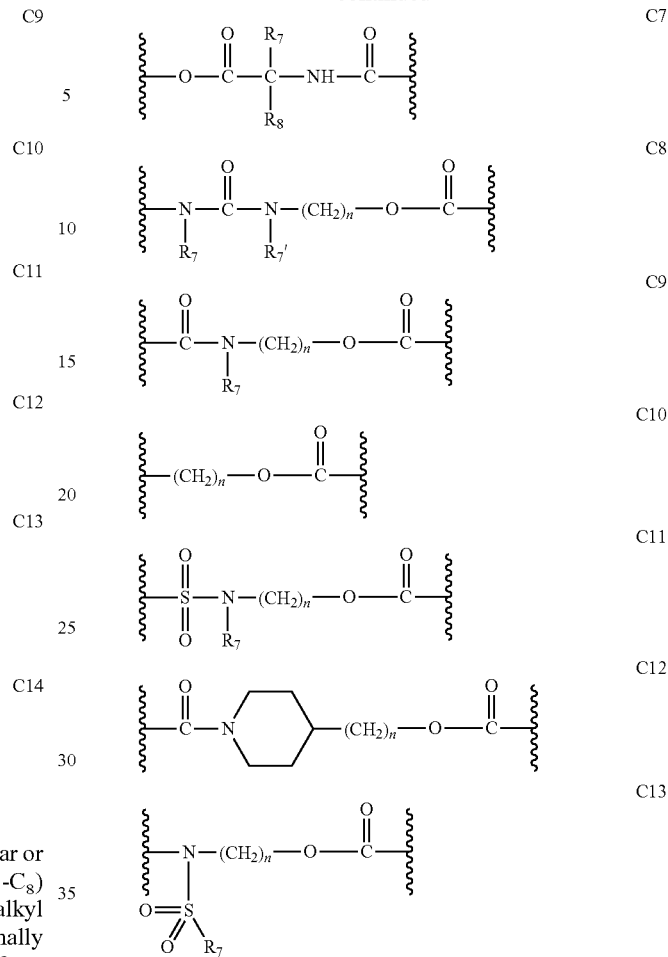

wherein $R_7$, $R_{7'}$ and $R_8$ are independently H or linear or branched $(C_1-C_6)$alkyl, $(C_3-C_8)$cycloalkyl, $(C_3-C_8)$cycloalkyl$(C_1-C_6)$alkyl, $(C_3-C_8)$heterocycloalkyl$(C_1-C_6)$alkyl, aryl, or aryl$(C_1-C_6)$alkyl, optionally substituted by one or more substituents selected from the group consisting of $(C_1-C_6)$alkyl, halo$(C_1-C_6)$alkyl, halogen atoms, $(C_1-C_6)$alkoxy, and halo$(C_1-C_6)$alkoxy;

D is absent or is $(C_1-C_6)$alkylene, arylene, heteroarylene, or $(C_3-C_8)$heterocycloalkylene, optionally substituted by one or more $(C_1-C_6)$alkyl groups;

n and p are independently 0 or an integer from 1 to 3;

E is absent or is —O— or —OC(O)—;

G is arylene optionally substituted by one or more substituents selected from the group consisting of halogen atom, —OH, oxo (=O), —SH, —NO$_2$, —CN, and —NH$_2$.

3. A compound or pharmaceutically acceptable salt according to claim 1, wherein A1 is selected from the group consisting of methylene, propylene, and butylene;

B is absent or is selected from the group consisting of piperidinylene, phenylene, pyridinediyl, furanediyl, thiophenediyl, and cyclohexylene, optionally substituted by one or more groups selected from methoxy, trifluoromethyl, fluorine, and chlorine;

C is absent or is —OC(O)—, or one of C4 and C7-C13

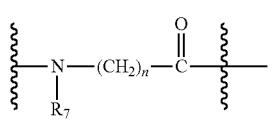

C' is absent or —CO—, wherein $R_7$, $R_{7'}$ and $R_8$ are independently H or linear or branched $(C_1-C_6)$alkyl, $(C_3-C_8)$cycloalkyl, $(C_3-C_8)$cycloalkyl$(C_1-C_6)$alkyl, $(C_3-C_8)$heterocycloalkyl$(C_1-C_6)$alkyl, aryl, or aryl$(C_1-C_6)$alkyl, optionally substituted by one or more substituents selected from the group consisting of $(C_1-C_6)$alkyl, halo$(C_1-C_6)$alkyl, halogen atom, $(C_1-C_6)$alkoxy, and halo$(C_1-C_6)$alkoxy;

D is absent or is $(C_1-C_6)$alkylene, arylene, heteroarylene, or $(C_3-C_8)$heterocycloalkylene, optionally substituted by one or more $(C_1-C_6)$alkyl groups;

n is 2 or 3 and p is 1;

E is —O—; and

G is phenylene.

4. A compound or pharmaceutically acceptable salt according to claim 1, wherein Q is a group of formula Q1 or Q2

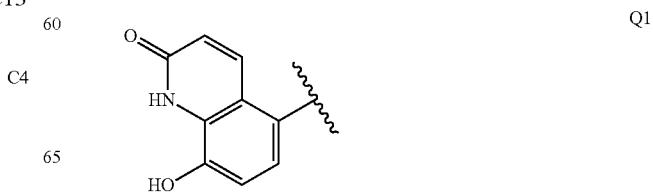

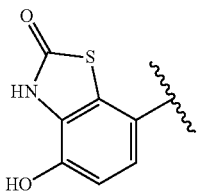

Z is H or OH;
Y is Y' which is a divalent group of formula

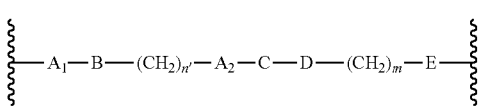

wherein
A1 and A2 are independently absent or are (C$_1$-C$_6$) alkylene, (C$_3$-C$_8$)cycloalkylene, or (C$_3$-C$_8$)heterocycloalkylene, optionally substituted by one or more substituents selected from the group consisting of (C$_1$-C$_6$)alkyl, aryl(C$_1$-C$_6$)alkyl, and heteroaryl(C$_1$-C$_6$)alkyl;

B is absent or is (C$_3$-C$_8$)cycloalkylene, (C$_3$-C$_8$)heterocycloalkylene, arylene, or heteroarylene, optionally substituted by one or more groups selected from the group consisting of halogen, nitrile, linear or branched (C$_1$-C$_6$)alkyl, linear or branched (C$_1$-C$_6$) haloalkyl, (C$_1$-C$_6$)alkoxy, aryl, aryl(C$_1$-C$_6$)alkyl, —NR$_7$(R$_8$), and heteroaryl;

C and C' are absent or are independently —O—, —CO—, —OC(O)—, —C(OO)—, or one of the following groups C1-C14

C1
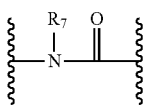

C2
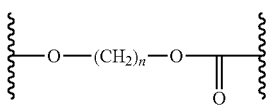

C3
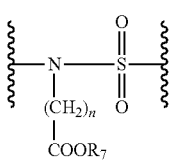

C4
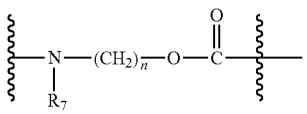

C5
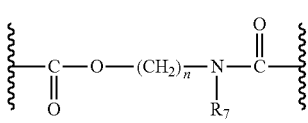

C6
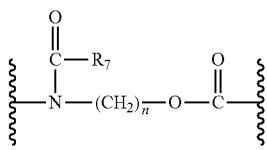

C7
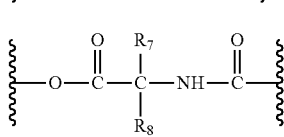

C8
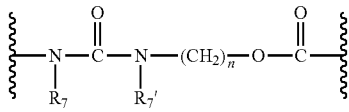

C9
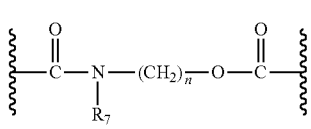

C10
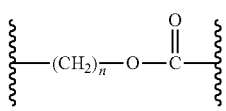

C11
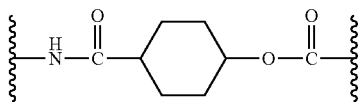

C12

C13
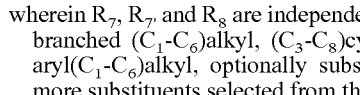

C14
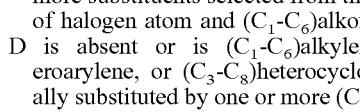

wherein R$_7$, R$_{7'}$ and R$_8$ are independently H or linear or branched (C$_1$-C$_6$)alkyl, (C$_3$-C$_8$)cycloalkyl, aryl, or aryl(C$_1$-C$_6$)alkyl, optionally substituted by one or more substituents selected from the group consisting of halogen atom and (C$_1$-C$_6$)alkoxy;

D is absent or is (C$_1$-C$_6$)alkylene, arylene, heteroarylene, or (C$_3$-C$_8$)heterocycloalkylene, optionally substituted by one or more (C$_1$-C$_6$)alkyl groups;

n, n' and m are independently 0 or an integer from 1 to 3;

E is absent or is —O— or —OC(O)—;

G is arylene optionally substituted by one or more substituents selected from the group consisting of halogen atom, —OH, oxo (═O), —SH, —NO$_2$, —CN, and —NH$_2$; R$_1$.

5. A compound or pharmaceutically acceptable salt according to claim 1, wherein
A1 is selected from the group consisting of methylene, propylene, and butylene;

A2 is absent or is methylene or piperidinylene;

B is absent or is phenylene, pyridinediyl, furanediyl, thiophenediyl, or cyclohexylene, optionally substituted by one or more groups selected from the group consisting of methoxy, trifluoromethyl, fluorine, and chlorine;

C is —O— or —OC(O)— or is one of the groups C4 or C8-C12

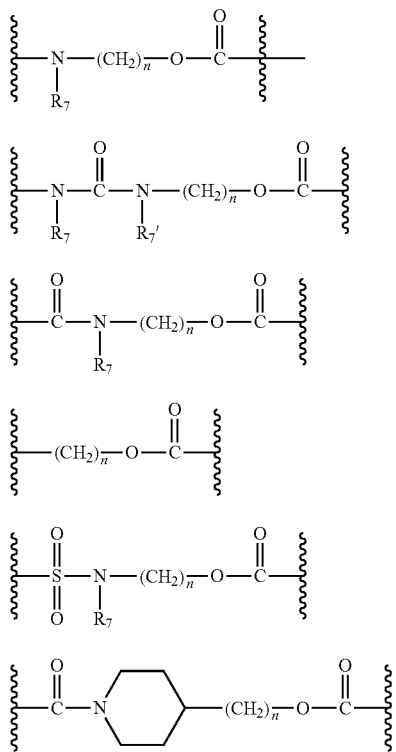

wherein $R_7$ and $R_{7'}$ are independently H or selected from the group consisting of methyl, ethyl, benzyl, phenyl, isopropyl, cyclohexyl, chloro-benzyl, and fluoro-benzyl;

D is absent or is phenyl;

n is 2 or 3;

n' is 1;

m is;

E is absent or is —O—;

and G is phenylene.

6. A pharmaceutical composition, comprising a compound or pharmaceutically acceptable salt according to claim 1, and one or more pharmaceutically acceptable carriers and/or excipients.

7. A method for the treatment of a broncho-obstructive or inflammatory disease, comprising administering an effective amount of a compound or pharmaceutically acceptable salt according to claim 1 to a subject in need thereof, wherein said broncho-obstructive or inflammatory disease is asthma chronic bronchitis, or chronic obstructive pulmonary disease.

8. A combination, comprising a compound or pharmaceutically acceptable salt according to claim 1 one or more active ingredients selected from the group consisting of a beta2-agonist, antimuscarinic agent, mitogen-activated protein kinase (P38 MAP kinase) inhibitor, nuclear factor kappa-B kinase subunit beta (IKK2) inhibitor, human neutrophil elastase (HNE) inhibitor, phosphodiesterase 4 (PDE4) inhibitor, leukotriene modulator, non-steroidal anti-inflammatory agent (NSAID), antitussive agent, mucus regulator, mucolytic, expectorant/mucokinetic modulator, peptide mucolytic, antibiotic, inhibitor of JAK, SYK inhibitor, inhibitor of PI3Kdelta or PI3Kgamma, corticosteroid, and M3-antagonists/PDE4-inhibitor (MAPI).

9. A pharmaceutical composition according to claim 6, which is in a form suitable to be administered by inhalation.

10. A pharmaceutical composition according to claim 9, which is an inhalable powder, a propellant-containing metering aerosol, or a propellant-free inhalable formulation.

11. A device, comprising a pharmaceutical composition according to claim 6 and which is a single- or multi-dose dry powder inhaler, a metered dose inhaler, or a soft mist nebulizer.

12. A method for the treatment of a broncho-obstructive or inflammatory disease, comprising administering an effective amount of a compound or pharmaceutically acceptable salt according to claim 2 to a subject in need thereof, wherein said broncho-obstructive or inflammatory disease is asthma chronic bronchitis, or chronic obstructive pulmonary disease.

13. A method for the treatment of a broncho-obstructive or inflammatory disease, comprising administering an effective amount of a compound or pharmaceutically acceptable salt according to claim 3 to a subject in need thereof, wherein said broncho-obstructive or inflammatory disease is asthma chronic bronchitis, or chronic obstructive pulmonary disease.

14. A method for the treatment of a broncho-obstructive or inflammatory disease, comprising administering an effective amount of a compound or pharmaceutically acceptable salt according to claim 4 to a subject in need thereof, wherein said broncho-obstructive or inflammatory disease is asthma chronic bronchitis, or chronic obstructive pulmonary disease.

15. A method for the treatment of a broncho-obstructive or inflammatory disease, comprising administering an effective amount of a compound or pharmaceutically acceptable salt according to claim 5 to a subject in need thereof, wherein said broncho-obstructive or inflammatory disease is asthma chronic bronchitis, or chronic obstructive pulmonary disease.

16. A method for the treatment of a broncho-obstructive or inflammatory disease, comprising administering an effective amount of a combination according to claim 8 to a subject in need thereof, wherein said broncho-obstructive or inflammatory disease is asthma chronic bronchitis, or chronic obstructive pulmonary disease.

* * * * *